US011596677B2

(12) United States Patent
Curtiss, III et al.

(10) Patent No.: US 11,596,677 B2
(45) Date of Patent: Mar. 7, 2023

(54) INDUCTION OF PROTECTIVE IMMUNITY AGAINST ANTIGENS

(71) Applicant: University of Florida Research Foundation, Incorporated, Gainesville, FL (US)

(72) Inventors: Roy Curtiss, III, Gainesville, FL (US); Shifeng Wang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 37 days.

(21) Appl. No.: 16/636,251

(22) PCT Filed: Aug. 3, 2018

(86) PCT No.: PCT/US2018/045231
§ 371 (c)(1),
(2) Date: Feb. 3, 2020

(87) PCT Pub. No.: WO2019/028396
PCT Pub. Date: Feb. 7, 2019

(65) Prior Publication Data
US 2020/0368339 A1 Nov. 26, 2020

Related U.S. Application Data

(60) Provisional application No. 62/541,293, filed on Aug. 4, 2017.

(51) Int. Cl.
*A61K 39/08* (2006.01)
*A61P 31/04* (2006.01)
*C12N 15/85* (2006.01)
*A61K 39/00* (2006.01)

(52) U.S. Cl.
CPC .............. *A61K 39/08* (2013.01); *A61P 31/04* (2018.01); *C12N 15/85* (2013.01); *A61K 2039/523* (2013.01); *A61K 2039/552* (2013.01)

(58) Field of Classification Search
None
See application file for complete search history.

(56) References Cited

U.S. PATENT DOCUMENTS

| 8,465,755 | B2 | 6/2013 | Curtiss, III et al. |
| 9,040,059 | B2 | 5/2015 | Curtiss, III et al. |
| 9,050,285 | B2 | 6/2015 | Curtiss, III et al. |
| 10,988,729 | B2 | 4/2021 | Curtiss, III et al. |
| 2006/0233825 | A1* | 10/2006 | Jayappa .................. A61P 29/00 424/190.1 |
| 2010/0255022 | A1 | 10/2010 | Prescott et al. |
| 2011/0256181 | A1 | 10/2011 | Curtiss, III et al. |
| 2011/0287052 | A1 | 11/2011 | Curtiss, III et al. |
| 2013/0337013 | A1 | 12/2013 | Mellata |
| 2015/0056232 | A1 | 2/2015 | Curtiss, III |
| 2016/0074440 | A1 | 3/2016 | Brugere et al. |
| 2019/0185520 | A1 | 6/2019 | Curtiss, III |
| 2019/0382717 | A1 | 12/2019 | Curtiss, III et al. |

FOREIGN PATENT DOCUMENTS

| EP | 1874344 A1 | 1/2008 | |
| EP | 1874344 B1 * | 6/2016 | ......... A61K 39/0258 |
| WO | 2006/113772 A1 | 10/2006 | |
| WO | 2009/046449 A1 | 4/2009 | |
| WO | 2009/046451 A1 | 4/2009 | |
| WO | 2010/045620 A1 | 4/2010 | |
| WO | 2011/150421 A2 | 12/2011 | |
| WO | 2015/118541 A1 | 8/2015 | |

OTHER PUBLICATIONS

Coleman et al., Cloning and characterization of a conjugated bile acid hydrolase gene from Clostridium perfringens. Appl Environ Microbiol. Jul. 1995;61(7):2514-20.
International Preliminary Report on Patentability for Application No. PCT/US2018/045231, dated Feb. 13, 2020, 6 pages.
International Search Report and Written Opinion for Application No. PCT/US2018/045231, dated Nov. 5, 2018, 8 pages.
U.S. Appl. No. 16/480,253, filed Jul. 23, 2019, U.S. Pat. No. 10,988,729, Issued.
U.S. Appl. No. 17/213,619, filed Mar. 26, 2021, Filed.
Curtiss et al., New technologies in using recombinant attenuated *Salmonella* vaccine vectors. Crit Rev Immunol. 2010;30(3):255-270.
Czeczulin et al., Cloning, nucleotide sequencing, and expression of the Clostridium perfringens enterotoxin gene in *Escherichia coli*. Infect Immun. Aug. 1993;61(8):3429-39.
Dwivedi et al., Comparative analysis of extractable proteins from Clostridium perfringens type A and type C strains showing varying degree of virulence. Anaerobe. Oct. 2015;35(Pt B):77-91.
Jiang et al., Protection against necrotic enteritis in broiler chickens by regulated delayed lysis *Salmonella* vaccines. Avian Dis. Dec. 2015;59(4):475-85.
Kong et al., Effect of deletion of genes involved in lipopolysaccharide core and O-antigen synthesis on virulence and immunogenicity of *Salmonella enterica* serovar typhimurium. Infect Immun. Oct. 2011;79(10):4227-39.
Kong et al., Turning self-destructing *Salmonella* into a universal DNA vaccine delivery platform. Proc Natl Acad Sci U S A. Nov. 20, 2012;109(47):19414-9. Including supplementary information.
Kulkarni et al., Oral immunization of broiler chickens against necrotic enteritis with an attenuated *Salmonella* vaccine vector expressing Clostridium perfringens antigens. Vaccine. Aug. 5, 2008;26(33):4194-203.

(Continued)

*Primary Examiner* — Jana A Hines
*Assistant Examiner* — Khatol S Shahnan Shah
(74) *Attorney, Agent, or Firm* — McCarter & English, LLP; Marcie B. Clarke

(57) ABSTRACT

Described herein are compositions and methods for making and using recombinant bacteria that are capable of regulated attenuation and/or regulated expression of one or more antigens from *Clostridium Perfringens* as vaccines to prevent necrotic enteritis (NE).

17 Claims, 32 Drawing Sheets
Specification includes a Sequence Listing.

(56) References Cited

OTHER PUBLICATIONS

Zekarias et al., Recombinant attenuated *Salmonella enterica* serovar typhimurium expressing the carboxy-terminal domain of alpha toxin from Clostridium perfringens induces protective responses against necrotic enteritis in chickens. Clin Vaccine Immunol. May 2008;15(5):805-16.
Extended European Search Report for Application No. EP18841409.8, dated May 10, 2021, 11 pages.

* cited by examiner

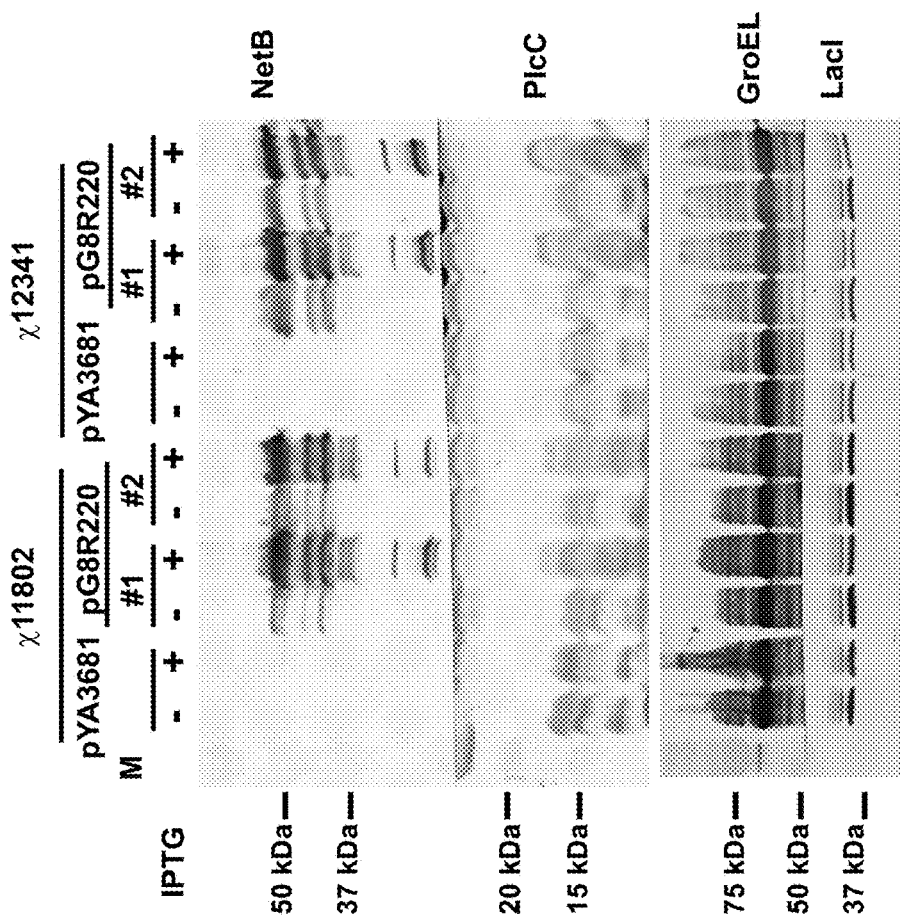
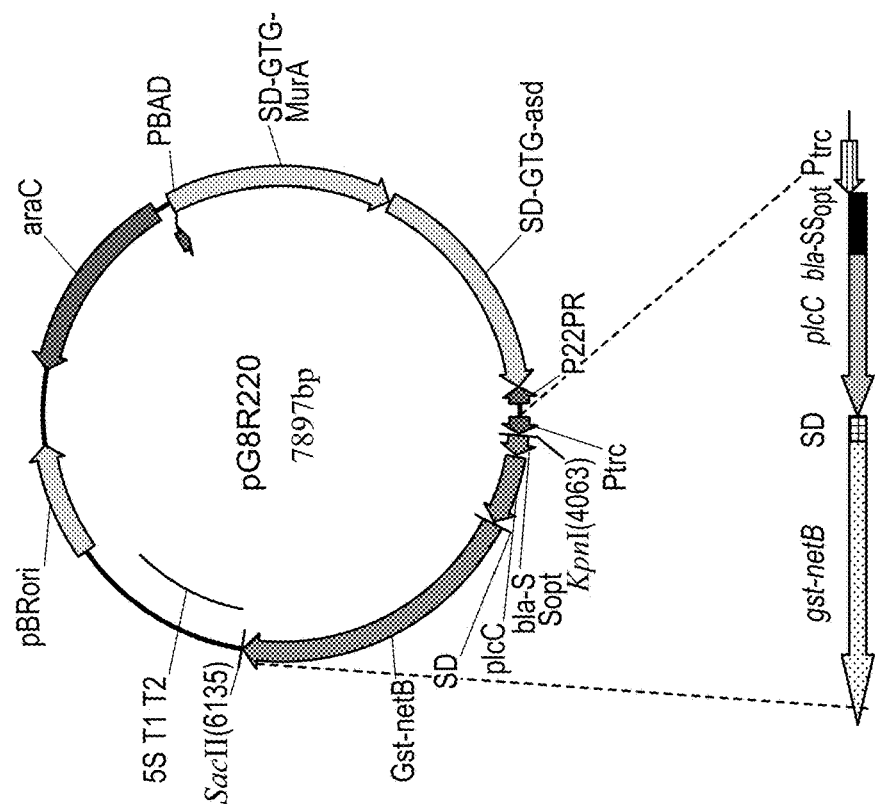
FIG. 1B
FIG. 1A

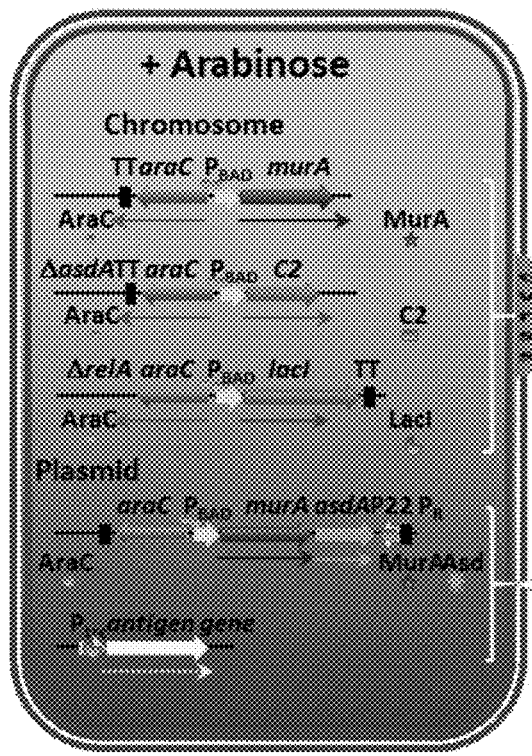
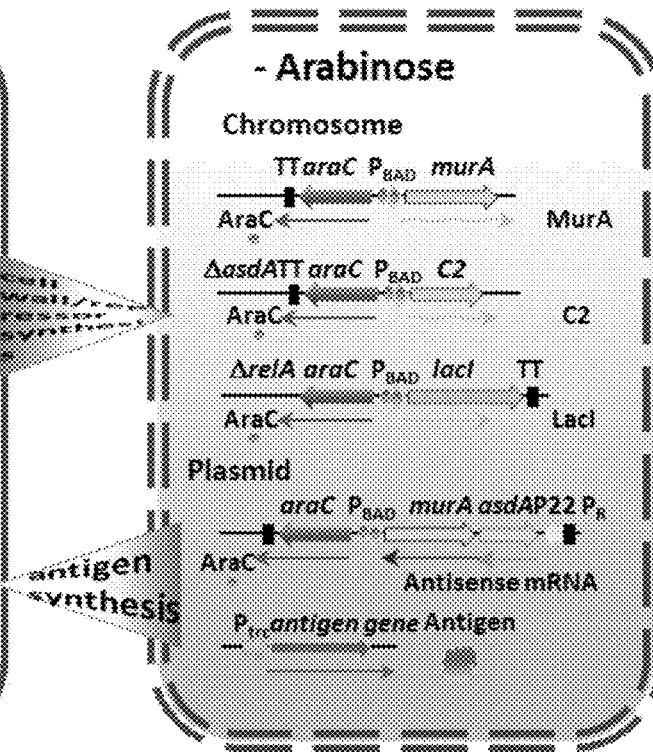
FIG. 2A    FIG. 2B
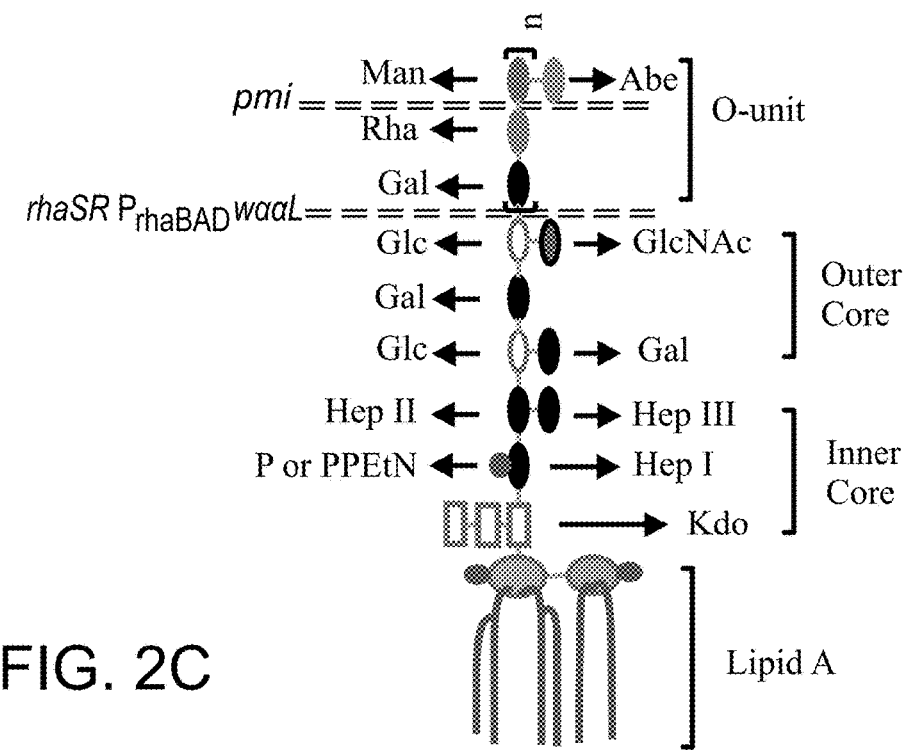
FIG. 2C

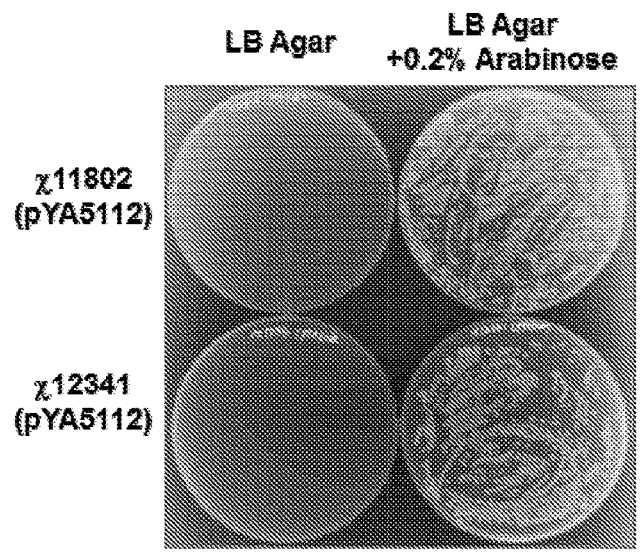
Fig. 3A
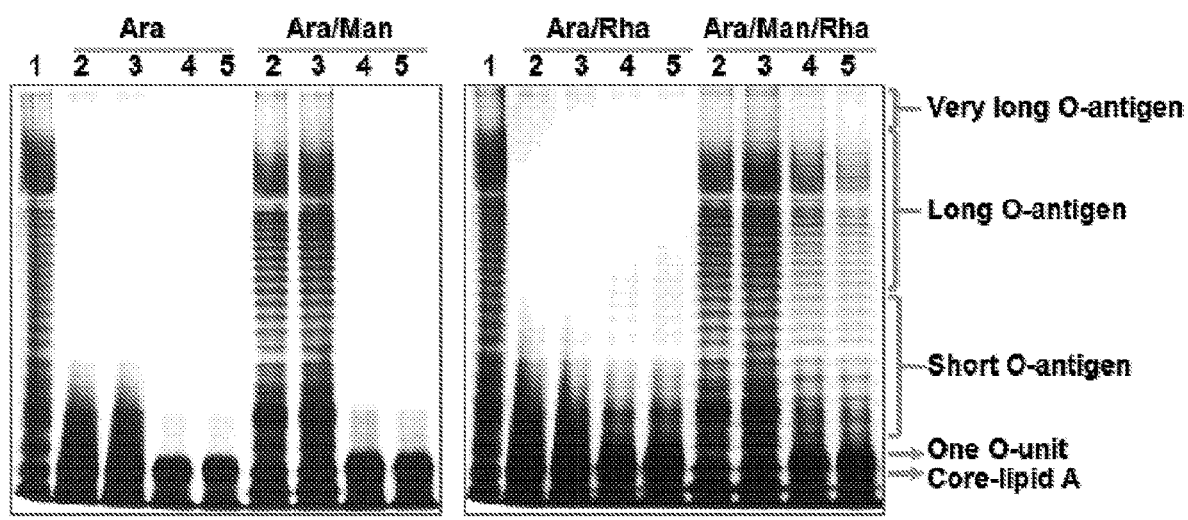
Fig. 3B
Fig. 3C

Fig. 7A

```
       BspEI
       ~~~~~~~~
   1 GGA TCT TCC GGA AGA CCT TCC ATT CTG AAA TGA GCT GTT GAC AAT TAA TCA TCC GGC TCG
                                                                          M   K   K
  61 TAT AAT GTG TGG AAT TGT GAG CGG ATA ACA ATT TCA CAC AGG A AA CAG ACC ATG AAA AAA
       Q   H   F   R   V   A   L   I   P   F   F   A   A   F   C   L   P   V   F   A
 121 CAA CAT TTC CGT GTC GCC CTT ATT CCC TTT TTT GCG GCA TTT TGC CTT CCT GTT TTT GCT
                                                            XhoI
                                                            ~~~~~~~~
                                                                   SacI          KpnI
                                                                   ~~~~~~~~      ~~~~~~~~
       H   P   E   T   L   V   K   V   K   D   A   E                                 M
 181 CAC CCA GAA ACG CTG GTG AAA GTA AAA GAT GCT GAA CTC GAG CTC CAC GTG GGT ACC ATG
       C   T   G   L   A   L   E   T   K   D   G   L   H   L   F   G   R   N   M   D
 241 TGC ACA GGC CTG GCA CTG GAA ACT AAA GAC GGC CTG CAC TTG TTC GGC CGC AAC ATG GAC
       I   E   Y   S   F   N   Q   S   I   I   F   I   P   R   N   F   K   C   V   N
 301 ATC GAA TAT TCT TTC AAT CAA TCT ATT ATT TTC ATT CCG CGC AAC TTC AAG TGC GTG AAC
       K   S   N   K   K   E   L   T   T   K   Y   A   V   L   G   M   G   T   I   F
 361 AAA TCC AAC AAA AAA GAA CTG ACC ACC AAA TAC GCT GTG CTG GGC ATG GGC ACT ATC TTC
       D   D   Y   P   T   F   A   D   G   M   N   E   K   G   L   G   C   A   G   L
 421 GAC GAT TAC CCG ACC TTC GCT GAC GGC ATG AAC GAA AAA GGC CTG GGC TGT GCG GGC CTG
       N   F   P   V   Y   V   S   Y   S   K   E   D   I   E   G   K   T   N   I   P
 481 AAC TTC CCG GTG TAT GTG AGC TAC TCT AAA GAA GAC ATC GAA GGC AAA ACC AAC ATC CCG
       V   Y   N   F   L   L   W   V   L   A   N   F   S   S   V   E   E   V   K   E
 541 GTG TAC AAC TTC CTG CTG TGG GTG CTG GCG AAC TTC AGC TCT GTG GAA GAG GTG AAG GAA
       A   L   K   N   A   N   I   V   D   I   P   I   S   E   N   I   P   N   T   T
 601 GCC CTG AAA AAC GCG AAC ATC GTG GAC ATC CCG ATC TCA GAG AAC ATC CCG AAC ACC ACG
       L   H   W   M   I   S   D   I   T   G   K   S   I   V   V   E   Q   T   K   E
 661 CTG CAC TGG ATG ATC TCC GAC ATC ACC GGC AAA TCC ATC GTG GTG GAA CAG ACC AAG GAA
       K   L   N   V   F   D   N   N   I   G   V   L   T   N   S   P   T   F   D   W
 721 AAA CTG AAC GTG TTC GAC AAC AAC ATC GGC GTG CTG ACC AAC AGC CCG ACG TTC GAC TGG
       H   V   A   N   L   N   Q   Y   V   G   L   R   Y   N   Q   V   P   E   F   K
 781 CAC GTG GCC AAC CTG AAC CAG TAC GTG GGC CTG CGC TAT AAC CAG GTG CCG GAG TTC AAG
       L   G   D   Q   S   L   T   A   L   G   Q   G   T   G   L   V   G   L   P   G
 841 CTG GGC GAC CAG TCT CTG ACT GCT CTG GGC CAG GGC ACT GGC CTG GTG GGC CTG CCG GGC
       D   F   T   P   A   S   R   F   I   R   V   A   F   L   R   D   A   M   I   K
 901 GAC TTC ACA CCG GCG TCT CGC TTC ATC CGC GTA GCG TTT CTG CGT GAC GCG ATG ATC AAA
                                              EcoRI
                                              ~~~~~~~~
       N   D   K   D   S   I   D   L   I   E   F   F   H   I   L   N   N   V   A   M
 961 AAC GAC AAA GAC AGC ATC GAC CTG ATC GAA TTC TTC CAC ATC CTG AAC AAC GTG GCT ATG
       V   R   G   S   T   R   T   V   E   E   K   S   D   L   T   Q   Y   T   S   C
1021 GTA CGC GGC TCC ACT CGC ACA GTG GAA GAG AAA TCC GAC CTG ACA CAG TAC ACG TCT TGC
       M   C   L   E   K   G   I   Y   Y   Y   N   T   Y   E   N   N   Q   I   N   A
1081 ATG TGC CTG GAA AAA GGC ATC TAT TAT TAT AAC ACC TAT GAA AAC AAC CAG ATC AAC GCA
       I   D   M   N   K   E   N   L   D   G   N   E   I   K   T   Y   K   Y   N   K
1141 ATC GAC ATG AAC AAA GAA AAC CTG GAC GGC AAC GAA ATC AAA ACC TAC AAA TAC AAC AAA
       T   L   S   I   N   H   V   N   G   H   H   H
1201 ACC CTG AGC ATC AAC CAC GTG AAC GGT CAC CAT CAT
```

Fig. 7B

```
            BspEI
            ~~~~~~~~
  1 GGA TCT TCC GGA AGA CCT TCC ATT CTG AAA TGA GCT GTT GAC AAT TAA TCA TCC GGC TCG
                                                                               M   K   K
 61 TAT AAT GTG TGG AAT TGT GAG CGG ATA ACA ATT TCA CAC AGG AAA CAG ACC ATG AAA AAA
     Q   H   F   R   V   A   L   I   P   F   F   A   A   F   C   L   P   V   F   A
121 CAA CAT TTC CGT GTC GCC CTT ATT CCC TTT TTT GCG GCA TTT TGC CTT CCT GTT TTT GCT
                                                        XhoI
                                                        ~~~~~~~~
                                            SacI                    KpnI
                                            ~~~~~~~~                ~~~~~~~~
     H   P   E   T   L   V   K   V   K   D   A   E   L   E   L   H   V   G   T   D
181 CAC CCA GAA ACG CTG GTG AAA GTA AAA GAT GCT GAA CTC GAG CTC CAC GTG GGT ACC GAC
     I   E   K   E   I   L   D   L   A   A   A   T   E   R   L   N   L   T   D   A
241 ATC GAA AAA GAA ATC CTG GAC CTG GCG GCG GCG ACC GAA CGT CTG AAC CTG ACC GAC GCG
     L   N   S   N   P   A   G   N   L   Y   D   W   R   S   S   N   S   Y   P   W
301 CTG AAC TCT AAC CCG GCG GGC AAC CTG TAC GAC TGG CGT TCT TCT AAC TCT TAC CCG TGG
     T   Q   K   L   N   L   H   L   T   I   T   A   T   G   Q   K   Y   R   I   L
361 ACC CAG AAA CTG AAC CTG CAC CTG ACC ATC ACC GCG ACC GGT CAG AAA TAC CGT ATC CTG
     A   S   K   I   V   D   F   N   I   Y   S   N   N   F   N   N   L   V   K   L
421 GCG TCT AAA ATC GTT GAC TTC AAC ATC TAC TCT AAC AAC TTC AAC AAC CTG GTT AAA CTG
     E   Q   S   L   G   D   G   V   K   D   H   Y   V   D   I   S   L   D   A   G
481 GAA CAG TCT CTG GGT GAC GGT GTT AAA GAC CAC TAC GTT GAC ATC TCT CTG GAC GCG GGT
     Q   Y   V   L   V   M   K   A   N   S   S   Y   S   G   N   Y   P   Y   S   I
541 CAG TAC GTT CTG GTT ATG AAA GCG AAC TCT TCC TAC TCC GGT AAC TAC CCG TAC TCT ATC
                                                                    PstI
                                                                    ~~~~~~~~
     L   F   Q   K   F           H   H   H   H   H   H   *
601 CTG TTC CAG AAA TTC GCC GGC CAC CAT CAC CAT CAC CAT TAG CCG GCT AAT CTG CAG CCA
                HindIII
                ~~~~~~~~
661 AGC TCC CAA GCT TGG CTG TTT TGG CGG ATG AGA GAA GAT TTT CAG CCT GAT ACA GAT TAA
```

Fig. 7C

```
            BspEI
            ~~~~~~~~
  1 GGA TCT TCC GGA AGA CCT TCC ATT CTG AAA TGA GCT GTT GAC AAT TAA TCA TCC GGC TCG
                                                                               M   K   K
 61 TAT AAT GTG TGG AAT TGT GAG CGG ATA ACA ATT TCA CAC AGG A AA CAG ACC ATG AAA AAA
     Q   H   F   R   V   A   L   I   P   F   F   A   A   F   C   L   P   V   F   A
121 CAA CAT TTC CGT GTC GCC CTT ATT CCC TTT TTT GCG GCA TTT TGC CTT CCT GTT TTT GCT
                                                        XhoI
                                                        ~~~~~~~~
     H   P   E   T   L   V   K   V   K   D   A   E           D   P   S   V   G   N
181 CAC CCA GAA ACG CTG GTG AAA GTA AAA GAT GCT GAA CTC GAG GAC CCG TCC GTG GGC AAC
     N   V   K   E   L   V   A   Y   I   S   T   S   G   E   K   D   A   G   T   D
241 AAC GTG AAA GAA CTG GTG GCT TAC ATC TCC ACT AGC GGC GAA AAA GAC GCT GGC ACC GAC
     D   Y   M   Y   F   G   I   K   T   K   D   G   K   T   Q   E   W   E   M   D
301 GAC TAC ATG TAT TTC GGC ATC AAA ACC AAG GAC GGC AAA ACT CAA GAA TGG GAA ATG GAC
        XmaI
        ~~~~~~~~
        SmaI
        ~~~~~~~~
     N   P   G   N   D   F   M   A   G   S   K   D   T   Y   T   F   K   L   K   D
361 AAC CCG GGC AAC GAC TTC ATG GCT GGC AGC AAA GAC ACT TAT ACT TTC AAA TTA AAA GAC
     E   N   L   K   I   D   D   I   Q   N   M   W   I   R   K   R   K   Y   T   A
421 GAA AAC CTG AAA ATT GAC GAC ATC CAA AAC ATG TGG ATT CGC AAA CGT AAA TAT ACC GCA
     F   P   D   A   Y   K   P   E   N   I   K   V   I   A   N   G   K   V   V   V
481 TTC CCG GAC GCT TAT AAG CCG GAA AAC ATC AAG GTG ATC GCA AAC GGC AAA GTG GTA GTG
                                                                            HindIII
                                                                            ~~~
```

Fig. 7C (continued)

```
          D   K   D   I   N   E   W   I   S   G   N   S   T   Y   N   I   K   *
541 GAC AAG GAC ATC AAC GAG TGG ATT TCC GGC AAC TCC ACT TAT AAC ATC AAA TAA TAA AAG
    HindIII             NcoI
    ~~~~                ~~~~~~~~
                                  M   A   P   I   L   G   Y   W   K   I   K   G   L   V   Q
601 CTT AGG AAA CAG ACC ATG GCC CCT ATA CTA GGT TAT TGG AAA ATT AAG GGC CTT GTG CAA
     P   T   R   L   L   L   E   Y   L   E   E   K   Y   E   E   H   L   Y   E   R
661 CCC ACT CGA CTT CTT TTG GAA TAT CTT GAA GAA AAA TAT GAA GAG CAT TTG TAT GAG CGC
     D   E   G   D   K   W   R   N   K   K   F   E   L   G   L   E   F   P   N   L
721 GAT GAA GGT GAT AAA TGG CGA AAC AAA AAG TTT GAA TTG GGT TTG GAG TTT CCC AAT CTT
     P   Y   Y   I   D   G   D   V   K   L   T   Q   S   M   A   I   I   R   Y   I
781 CCT TAT TAT ATT GAT GGT GAT GTT AAA TTA ACA CAG TCT ATG GCC ATC ATA CGT TAT ATA
     A   D   K   H   N   M   L   G   G   C   P   K   E   R   A   E   I   S   M   L
841 GCT GAC AAG CAC AAC ATG TTG GGT GGT TGT CCA AAA GAG CGT GCA GAG ATT TCA ATG CTT
     E   G   A   V   L   D   I   R   Y   G   V   S   R   I   A   Y   S   K   D   F
901 GAA GGA GCG GTT TTG GAT ATT AGA TAC GGT GTT TCG AGA ATT GCA TAT AGT AAA GAC TTT
     E   T   L   K   V   D   F   L   S   K   L   P   E   M   L   K   M   F   E   D
961 GAA ACT CTC AAA GTT GAT TTT CTT AGC AAG CTA CCT GAA ATG CTG AAA ATG TTC GAA GAT
      R   L   C   H   K   T   Y   L   N   G   D   H   V   T   H   P   D   F   M   L
1021 CGT TTA TGT CAT AAA ACA TAT TTA AAT GGT GAT CAT GTA ACC CAT CCT GAC TTC ATG TTG
      Y   D   A   L   D   V   V   L   Y   M   D   P   M   C   L   D   A   F   P   K
1081 TAT GAC GCT CTT GAT GTT GTT TTA TAC ATG GAC CCA ATG TGC CTG GAT GCG TTC CCA AAA
      L   V   C   F   K   K   R   I   E   A   I   P   Q   I   D   K   Y   L   K   S
1141 TTA GTT TGT TTT AAA AAA CGT ATT GAA GCT ATC CCA CAA ATT GAT AAG TAC TTG AAA TCC
      S   K   Y   I   A   W   P   L   Q   G   W   Q   A   T   F   G   G   G   D   H
1201 AGC AAG TAT ATA GCA TGG CCT TTG CAG GGC TGG CAA GCC ACG TTT GGT GGT GGC GAC CAT
                                   BamHI           EcoRI
                                   ~~~~~~~~        ~~~~~~~~
      P   P   K   S   D   L   V   P   R   G   S   P   G   I   P   S   E   L   N   D
1261 CCT CCA AAA TCG GAT CTG GTT CCG CGT GGA TCC CCA GGA ATT CCA AGC GAA CTG AAC GAC
      I   N   K   I   E   L   K   N   L   S   G   E   I   I   K   E   N   G   K   E
1321 ATC AAC AAA ATT GAG CTG AAA AAC CTG AGC GGC GAA ATC ATC AAA GAA AAC GGC AAG GAA
      A   I   K   Y   T   S   S   D   T   A   S   H   K   G   W   K   A   T   L   S
1381 GCT ATT AAA TAT ACT TCC AGC GAC ACC GCT TCC CAT AAA GGC TGG AAG GCA ACT CTG AGC
      G   T   F   I   E   D   P   H   S   D   K   K   T   A   L   L   N   L   E   G
1441 GGC ACC TTC ATT GAA GAC CCG CAT TCC GAC AAG AAA ACT GCT CTG CTG AAC CTG GAA GGC
      F   I   P   S   D   K   Q   I   F   G   S   K   Y   Y   G   K   M   K   W   P
1501 TTT ATC CCG TCC GAC AAA CAG ATT TTC GGC TCT AAA TAT TAC GGC AAA ATG AAA TGG CCG
      E   T   Y   R   I   N   V   K   S   A   D   V   N   N   N   I   K   I   A   N
1561 GAA ACT TAT CGC ATT AAT GTG AAA AGC GCT GAC GTG AAC AAT AAC ATC AAA ATC GCA AAC
      S   I   P   K   N   T   I   D   K   K   D   V   S   N   S   I   G   Y   S   I
1621 TCC ATT CCG AAA AAT ACT ATC GAC AAA AAA GAC GTG TCC AAT TCC ATT GGC TAT TCC ATC
      G   G   N   I   S   V   E   G   K   T   A   G   A   G   I   N   A   S   Y   N
1681 GGC GGT AAC ATC TCC GTG GAA GGC AAA ACT GCT GGC GCT GGC ATC AAC GCT TCC TAT AAC
      V   Q   N   T   I   S   Y   E   Q   P   D   F   R   T   I   Q   R   K   D   D
1741 GTC CAA AAC ACT ATC AGC TAT GAA CAA CCG GAC TTC CGC ACC ATT CAA CGC AAA GAC GAT
      A   N   L   A   S   W   D   I   K   F   V   E   T   K   D   G   Y   N   I   D
1801 GCA AAC CTG GCA TCC TGG GAC ATC AAA TTC GTT GAG ACT AAG GAC GGC TAT AAC ATC GAC
      S   Y   H   A   I   Y   G   N   Q   L   F   M   K   S   R   L   Y   N   N   G
1861 TCC TAT CAT GCT ATT TAT GGC AAC CAA CTG TTC ATG AAA TCC CGC CTG TAT AAC AAT GGC
      D   K   N   F   T   D   D   R   D   L   S   T   L   I   S   G   G   F   S   P
1921 GAC AAA AAC TTC ACC GAC GAT CGC GAC CTG TCC ACC CTG ATT TCC GGC GGC TTC TCC CCG
      N   M   A   L   A   L   T   A   P   K   N   A   K   E   S   V   I   I   V   E
1981 AAC ATG GCT CTG GCA CTG ACC GCA CCT AAA AAT GCT AAA GAA TCC GTG ATC ATC GTG GAA
      Y   Q   R   F   D   N   D   Y   I   L   N   W   E   T   T   Q   W   R   G   T
2041 TAT CAA CGC TTC GAC AAC GAC TAT ATT CTG AAT TGG GAA ACT ACT CAA TGG CGC GGC ACC
      N   K   L   S   S   T   S   E   Y   N   E   F   M   F   K   I   N   W   Q   D
2101 AAC AAA CTT TCC TCA ACC AGC GAA TAT AAC GAA TTT ATG TTC AAA ATC AAC TGG CAA GAC
                    KpnI             SpeI                                      NotI
                    ~~~~~~~          ~~~~~~~~                                  ~~~~~
```

Fig. 7C (continued)

```
           H   K   I   E   Y   Y   L   *
2161 CAT AAA ATC GAA TAT TAT CTG TAA TGG TAC CAG TAC TAG TTG ATC ATT CGA AGC CGG CGG
             SmaI
             ~~~~~~~~
             XmaI
             ~~~~~~~~
         NotI              PstI                    HindIII
         ~~~~~         ~~~~~~~~                ~~~~~~~~
2221 CCG CCC GGG CCC TGC AGC CAA GCT CCC AAG CTT GGC TGT TTT GGC GGA TGA GAG AAG ATT
```

Fig. 7D

```
           BspEI
           ~~~~~~~~
   1 GGA TCT TCC GGA AGA CCT TCC ATT CTG AAA TGA GCT GTT GAC AAT TAA TCA TCC GGC TCG
                                                                                 M   K   K
  61 TAT AAT GTG TGG AAT TGT GAG CGG ATA ACA ATT TCA CAC AGG AA A CAG ACC ATG AAA AAA
       Q   H   F   R   V   A   L   I   P   F   F   A   A   F   C   L   P   V   F   A
 121 CAA CAT TTC CGT GTC GCC CTT ATT CCC TTT TTT GCG GCA TTT TGC CTT CCT GTT TTT GCT
                                                               XhoI
                                                               ~~~~~~~~
       H   P   E   T   L   V   K   V   K   D   A   E           D   P   S   V   G   N
 181 CAC CCA GAA ACG CTG GTG AAA GTA AAA GAT GCT GAA   CTC GAG GAC CCG TCC GTG GGC AAC
       N   V   K   E   L   V   A   Y   I   S   T   S   G   E   K   D   A   G   T   D
 241 AAC GTG AAA GAA CTG GTG GCT TAC ATC TCC ACT AGC GGC GAA AAA GAC GCT GGC ACC GAC
       D   Y   M   Y   F   G   I   K   T   K   D   G   K   T   Q   E   W   E   M   D
 301 GAC TAC ATG TAT TTC GGC ATC AAA ACC AAG GAC GGC AAA ACT CAA GAA TGG GAA ATG GAC
           XmaI
           ~~~~~~~~
           SmaI
           ~~~~~~~~
       N   P   G   N   D   F   M   A   G   S   K   D   T   Y   T   F   K   L   K   D
 361 AAC CCG GGC AAC GAC TTC ATG GCT GGC AGC AAA GAC ACT TAT ACT TTC AAA TTA AAA GAC
       E   N   L   K   I   D   D   I   Q   N   M   W   I   R   K   R   K   Y   T   A
 421 GAA AAC CTG AAA ATT GAC GAC ATC CAA AAC ATG TGG ATT CGC AAA CGT AAA TAT ACC GCA
       F   P   D   A   Y   K   P   E   N   I   K   V   I   A   N   G   K   V   V   V
 481 TTC CCG GAC GCT TAT AAG CCG GAA AAC ATC AAG GTG ATC GCA AAC GGC AAA GTG GTA GTG
                                                                                 HindIII
                                                                                 ~~~
       D   K   D   I   N   E   W   I   S   G   N   S   T   Y   N   I   K   *
 541 GAC AAG GAC ATC AAC GAG TGG ATT TCC GGC AAC TCC ACT TAT AAC ATC AAA TAA TAA AAG
         HindIII              NcoI
         ~~~~                 ~~~~~~~~
                         M   A   P   I   L   G   Y   W   K   I   K   G   L   V   Q
 601 CTT AGG AAA CAG ACC ATG GCC CCT ATA CTA GGT TAT TGG AAA ATT AAG GGC CTT GTG CAA
       P   T   R   L   L   L   E   Y   L   E   E   K   Y   E   E   H   L   Y   E   R
 661 CCC ACT CGA CTT CTT TTG GAA TAT CTT GAA GAA AAA TAT GAA GAG CAT TTG TAT GAG CGC
       D   E   G   D   K   W   R   N   K   K   F   E   L   G   L   E   F   P   N   L
 721 GAT GAA GGT GAT AAA TGG CGA AAC AAA AAG TTT GAA TTG GGT TTG GAG TTT CCC AAT CTT
       P   Y   Y   I   D   G   D   V   K   L   T   Q   S   M   A   I   I   R   Y   I
 781 CCT TAT TAT ATT GAT GGT GAT GTT AAA TTA ACA CAG TCT ATG GCC ATC ATA CGT TAT ATA
       A   D   K   H   N   M   L   G   G   C   P   K   E   R   A   E   I   S   M   L
 841 GCT GAC AAG CAC AAC ATG TTG GGT GGT TGT CCA AAA GAG CGT GCA GAG ATT TCA ATG CTT
       E   G   A   V   L   D   I   R   Y   G   V   S   R   I   A   Y   S   K   D   F
 901 GAA GGA GCG GTT TTG GAT ATT AGA TAC GGT GTT TCG AGA ATT GCA TAT AGT AAA GAC TTT
```

Fig. 7D (continued)

```
            E   T   L   K   V   D   F   L   S   K   L   P   E   M   L   K   M   F   E   D
 961 GAA ACT CTC AAA GTT GAT TTT CTT AGC AAG CTA CCT GAA ATG CTG AAA ATG TTC GAA GAT
            R   L   C   H   K   T   Y   L   N   G   D   H   V   T   H   P   D   F   M   L
1021 CGT TTA TGT CAT AAA ACA TAT TTA AAT GGT GAT CAT GTA ACC CAT CCT GAC TTC ATG TTG
            Y   D   A   L   D   V   V   L   Y   M   D   P   M   C   L   D   A   F   P   K
1081 TAT GAC GCT CTT GAT GTT GTT TTA TAC ATG GAC CCA ATG TGC CTG GAT GCG TTC CCA AAA
            L   V   C   F   K   K   R   I   E   A   I   P   Q   I   D   K   Y   L   K   S
1141 TTA GTT TGT TTT AAA AAA CGT ATT GAA GCT ATC CCA CAA ATT GAT AAG TAC TTG AAA TCC
            S   K   Y   I   A   W   P   L   Q   G   W   Q   A   T   F   G   G   G   D   H
1201 AGC AAG TAT ATA GCA TGG CCT TTG CAG GGC TGG CAA GCC ACG TTT GGT GGT GGC GAC CAT
                                                BamHI           EcoRI
                                               ~~~~~~~         ~~~~~~~
            P   P   K   S   D   L   V   P   R   G   S   P   G   I   P   S   E   L   N   D
1261 CCT CCA AAA TCG GAT CTG GTT CCG CGT GGA TCC CCA GGA ATT CCA AGC GAA CTG AAC GAC
            I   N   K   I   E   L   K   N   L   S   G   E   I   I   K   E   N   G   K   E
1321 ATC AAC AAA ATT GAG CTG AAA AAC CTG AGC GGC GAA ATC ATC AAA GAA AAC GGC AAG GAA
            A   I   K   Y   T   S   S   D   T   A   S   H   K   G   W   K   A   T   L   S
1381 GCT ATT AAA TAT ACT TCC AGC GAC ACC GCT TCC CAT AAA GGC TGG AAG GCA ACT CTG AGC
            G   T   F   I   E   D   P   H   S   D   K   K   T   A   L   L   N   L   E   G
1441 GGC ACC TTC ATT GAA GAC CCG CAT TCC GAC AAG AAA ACT GCT CTG CTG AAC CTG GAA GGC
            F   I   P   S   D   K   Q   I   F   G   S   K   Y   Y   G   K   M   K   W   P
1501 TTT ATC CCG TCC GAC AAA CAG ATT TTC GGC TCT AAA TAT TAC GGC AAA ATG AAA TGG CCG
            E   T   Y   R   I   N   V   K   S   A   D   V   N   N   N   I   K   I   A   N
1561 GAA ACT TAT CGC ATT AAT GTG AAA AGC GCT GAC GTG AAC AAT AAC ATC AAA ATC GCA AAC
            S   I   P   K   N   T   I   D   K   K   D   V   S   N   S   I   G   Y   S   I
1621 TCC ATT CCG AAA AAT ACT ATC GAC AAA AAA GAC GTG TCC AAT TCC ATT GGC TAT TCC ATC
            G   G   N   I   S   V   E   G   K   T   A   G   A   G   I   N   A   S   Y   N
1681 GGC GGT AAC ATC TCC GTG GAA GGC AAA ACT GCT GGC GCT GGC ATC AAC GCT TCC TAT AAC
            V   Q   N   T   I   S   Y   E   Q   P   D   F   R   T   I   Q   R   K   D   D
1741 GTC CAA AAC ACT ATC AGC TAT GAA CAA CCG GAC TTC CGC ACC ATT CAA CGC AAA GAC GAT
            A   N   L   A   S   W   D   I   K   F   V   E   T   K   D   G   Y   N   I   D
1801 GCA AAC CTG GCA TCC TGG GAC ATC AAA TTC GTT GAG ACT AAG GAC GGC TAT AAC ATC GAC
            S   Y   H   A   I   Y   G   N   Q   L   F   M   K   S   R   L   Y   N   N   G
1861 TCC TAT CAT GCT ATT TAT GGC AAC CAA CTG TTC ATG AAA TCC CGC CTG TAT AAC AAT GGC
            D   K   N   F   T   D   D   R   D   L   S   T   L   I   S   G   G   F   S   P
1921 GAC AAA AAC TTC ACC GAC GAT CGC GAC CTG TCC ACC CTG ATT TCC GGC GGC TTC TCC CCG
            N   M   A   L   A   L   T   A   P   K   N   A   K   E   S   V   I   I   V   E
1981 AAC ATG GCT CTG GCA CTG ACC GCA CCT AAA AAT GCT AAA GAA TCC GTG ATC ATC GTG GAA
            Y   Q   R   F   D   N   D   Y   I   L   N   W   E   T   T   Q   W   R   G   T
2041 TAT CAA CGC TTC GAC AAC GAC TAT ATT CTG AAT TGG GAA ACT ACT CAA TGG CGC GGC ACC
            N   K   L   S   S   T   S   E   Y   N   E   F   M   F   K   I   N   W   Q   D
2101 AAC AAA CTT TCC TCA ACC AGC GAA TAT AAC GAA TTT ATG TTC AAA ATC AAC TGG CAA GAC
                                        KpnI
                                       ~~~~~~~
                                                                    M   K   K   I   W   L ·
            H   K   I   E   Y   Y   L   *
2161 CAT AAA ATC GAA TAT TAT CTG TAA TGG TAC CAG GAA GTT GAT CAT GAA AAA GAT TTG GCT
                                                                                    XhoI
                                                                                   ~~~~~~
          · A   L   A   G   M   V   L   A   F   S   A   S   A   A   Q   I   S   D
2221 GGC GCT GGC TGG TAT GGT TTT AGC TTT TAG CGC CTC GGC AGC ACA GAT CAG CGA CCT CGA
     XhoI
      ~
            M   C   T   G   L   A   L   E   T   K   D   G   L   H   L   F   G   R   N   M ·
2281 GAT GTG CAC AGG CCT GGC ACT GGA AAC TAA AGA CGG CCT GCA CTT GTT CGG CCG CAA CAT
          · D   I   E   Y   S   F   N   Q   S   I   I   F   I   P   R   N   F   K   C   V ·
2341 GGA CAT CGA ATA TTC TTT CAA TCA ATC TAT TAT TTT CAT TCC GCG CAA CTT CAA GTG CGT
```

Fig. 7D (continued)

```
        · N   K   S   N   K   K   E   L   T   T   K   Y   A   V   L   G   M   G   T   I ·
2401    GAA CAA ATC CAA CAA AAA AGA ACT GAC CAC CAA ATA CGC TGT GCT GGG CAT GGG CAC TAT
        · F   D   D   Y   P   T   F   A   D   G   M   N   E   K   G   L   G   C   A   G ·
2461    CTT CGA CGA TTA CCC GAC CTT CGC TGA CGG CAT GAA CGA AAA AGG CCT GGG CTG TGC GGG
        · L   N   F   P   V   Y   V   S   Y   S   K   E   D   I   E   G   K   T   N   I ·
2521    CCT GAA CTT CCC GGT GTA TGT GAG CTA CTC TAA AGA AGA CAT CGA AGG CAA AAC CAA CAT
        · P   V   Y   N   F   L   L   W   V   L   A   N   F   S   S   V   E   E   V   K ·
2581    CCC GGT GTA CAA CTT CCT GCT GTG GGT GCT GGC GAA CTT CAG CTC TGT GGA AGA GGT GAA
        · E   A   L   K   N   A   N   I   V   D   I   P   I   S   E   N   I   P   N   T ·
2641    GGA AGC CCT GAA AAA CGC GAA CAT CGT GGA CAT CCC GAT CTC AGA GAA CAT CCC GAA CAC
        · T   L   H   W   M   I   S   D   I   T   G   K   S   I   V   V   E   Q   T   K ·
2701    CAC GCT GCA CTG GAT GAT CTC CGA CAT CAC CGG CAA ATC CAT CGT GGT GGA ACA GAC CAA
        · E   K   L   N   V   F   D   N   N   I   G   V   L   T   N   S   P   T   F   D ·
2761    GGA AAA ACT GAA CGT GTT CGA CAA CAA CAT CGG CGT GCT GAC CAA CAG CCC GAC GTT CGA
        · W   H   V   A   N   L   N   Q   Y   V   G   L   R   Y   N   Q   V   P   E   F ·
2821    CTG GCA CGT GGC CAA CCT GAA CCA GTA CGT GGG CCT GCG CTA TAA CCA GGT GCC GGA GTT
        · K   L   G   D   Q   S   L   T   A   L   G   Q   G   T   G   L   V   G   L   P ·
2881    CAA GCT GGG CGA CCA GTC TCT GAC TGC TCT GGG CCA GGG CAC TGG CCT GGT GGG CCT GCC
        · G   D   F   T   P   A   S   R   F   I   R   V   A   F   L   R   D   A   M   I ·
2941    GGG CGA CTT CAC ACC GGC GTC TCG CTT CAT CCG CGT AGC GTT TCT GCG TGA CGC GAT GAT
                                                          EcoRI
                                                         ~~~~~~~~
        · K   N   D   K   D   S   I   D   L   I   E   F   F   H   I   L   N   N   V   A ·
3001    CAA AAA CGA CAA AGA CAG CAT CGA CCT GAT CGA ATT CTT CCA CAT CCT GAA CAA CGT GGC
        · M   V   R   G   S   T   R   T   V   E   E   K   S   D   L   T   Q   Y   T   S ·
3061    TAT GGT ACG CGG CTC CAC TCG CAC AGT GGA AGA GAA ATC CGA CCT GAC ACA GTA CAC GTC
        · C   M   C   L   E   K   G   I   Y   Y   N   T   Y   E   N   N   Q   I   N ·
3121    TTG CAT GTG CCT GGA AAA AGG CAT CTA TTA TTA TAA CAC CTA TGA AAA CAA CCA GAT CAA
        · A   I   D   M   N   K   E   N   L   D   G   N   E   I   K   T   Y   K   Y   N ·
3181    CGC AAT CGA CAT GAA CAA AGA AAA CCT GGA CGG CAA CGA AAT CAA AAC CTA CAA ATA CAA
        · K   T   L   S   I   N   H   V   N           H   H   H   H   H                 * ·
3241    CAA AAC CCT GAG CAT CAA CCA CGT GAA CCC GCG GCA CCA CCA CCA TCA TCA TCC GCG GTA
                  PstI                      HindIII
                ~~~~~~~~                   ~~~~~~~~
        . *
3301    ATG GGC CCT GCA GCC AAG CTC CCA AGC TTG GCT GTT TTG GCG GAT GAG AGA AGA TTT TCA
```

Fig. 7E

```
           BspEI
          ~~~~~~~~
    1   GGA TCT TCC GGA AGA CCT TCC ATT CTG AAA TGA GCT GTT GAC AAT TAA TCA TCC GGC TCG
                                                                           M   K   K
   61   TAT AAT GTG TGG AAT TGT GAG CGG ATA ACA ATT TCA CAC AGG A AA CAG ACC ATG AAA AAA
          Q   H   F   R   V   A   L   I   P   F   F   A   A   F   C   L   P   V   F   A
  121   CAA CAT TTC CGT GTC GCC CTT ATT CCC TTT TTT GCG GCA TTT TGC CTT CCT GTT TTT GCT
                                                              XhoI
                                                             ~~~~~~~~
          H   P   E   T   L   V   K   V   K   D   A   E           D   P   S   V   G   N
  181   CAC CCA GAA ACG CTG GTG AAA GTA AAA GAT GCT GAA CTC GAG GAC CCG TCC GTG GGC AAC
          N   V   K   E   L   V   A   Y   I   S   T   S   G   E   K   D   A   G   T   D
  241   AAC GTG AAA GAA CTG GTG GCT TAC ATC TCC ACT AGC GGC GAA AAA GAC GCT GGC ACC GAC
          D   Y   M   Y   F   G   I   K   T   K   D   G   K   T   Q   E   W   E   M   D
  301   GAC TAC ATG TAT TTC GGC ATC AAA ACC AAG GAC GGC AAA ACT CAA GAA TGG GAA ATG GAC
           XmaI
          ~~~~~~~~
           SmaI
          ~~~~~~~~
```

Fig. 7E (continued)

```
          N   P   G   N   D   F   M   A   G   S   K   D   T   Y   T   F   K   L   K   D
 361    AAC CCG GGC AAC GAC TTC ATG GCT GGC AGC AAA GAC ACT TAT ACT TTC AAA TTA AAA GAC
          E   N   L   K   I   D   D   I   Q   N   M   W   I   R   K   R   K   Y   T   A
 421    GAA AAC CTG AAA ATT GAC GAC ATC CAA AAC ATG TGG ATT CGC AAA CGT AAA TAT ACC GCA
          F   P   D   A   Y   K   P   E   N   I   K   V   I   A   N   G   K   V   V   V
 481    TTC CCG GAC GCT TAT AAG CCG GAA AAC ATC AAG GTG ATC GCA AAC GGC AAA GTG GTA GTG
                                                                                HindIII
                                                                                ~~~
          D   K   D   I   N   E   W   I   S   G   N   S   T   Y   N   I   K   *
 541    GAC AAG GAC ATC AAC GAG TGG ATT TCC GGC AAC TCC ACT TAT AAC ATC AAA TAA TAA AAG
        HindIII             NcoI
        ~~~~                ~~~~~~~~
                                    M   A   P   I   L   G   Y   W   K   I   K   G   L   V   Q
 601    CTT AGG AAA CAG ACC ATG GCC CCT ATA CTA GGT TAT TGG AAA ATT AAG GGC CTT GTG CAA
          P   T   R   L   L   L   E   Y   L   E   E   K   Y   E   E   H   L   Y   E   R
 661    CCC ACT CGA CTT CTT TTG GAA TAT CTT GAA GAA AAA TAT GAA GAG CAT TTG TAT GAG CGC
          D   E   G   D   K   W   R   N   K   K   F   E   L   G   L   E   F   P   N   L
 721    GAT GAA GGT GAT AAA TGG CGA AAC AAA AAG TTT GAA TTG GGT TTG GAG TTT CCC AAT CTT
          P   Y   Y   I   D   G   D   V   K   L   T   Q   S   M   A   I   I   R   Y   I
 781    CCT TAT TAT ATT GAT GGT GAT GTT AAA TTA ACA CAG TCT ATG GCC ATC ATA CGT TAT ATA
          A   D   K   H   N   M   L   G   G   C   P   K   E   R   A   E   I   S   M   L
 841    GCT GAC AAG CAC AAC ATG TTG GGT GGT TGT CCA AAA GAG CGT GCA GAG ATT TCA ATG CTT
          E   G   A   V   L   D   I   R   Y   G   V   S   R   I   A   Y   S   K   D   F
 901    GAA GGA GCG GTT TTG GAT ATT AGA TAC GGT GTT TCG AGA ATT GCA TAT AGT AAA GAC TTT
          E   T   L   K   V   D   F   L   S   K   L   P   E   M   L   K   M   F   E   D
 961    GAA ACT CTC AAA GTT GAT TTT CTT AGC AAG CTA CCT GAA ATG CTG AAA ATG TTC GAA GAT
          R   L   C   H   K   T   Y   L   N   G   D   H   V   T   H   P   D   F   M   L
1021    CGT TTA TGT CAT AAA ACA TAT TTA AAT GGT GAT CAT GTA ACC CAT CCT GAC TTC ATG TTG
          Y   D   A   L   D   V   V   L   Y   M   D   P   M   C   L   D   A   F   P   K
1081    TAT GAC GCT CTT GAT GTT GTT TTA TAC ATG GAC CCA ATG TGC CTG GAT GCG TTC CCA AAA
          L   V   C   F   K   K   R   I   E   A   I   P   Q   I   D   K   Y   L   K   S
1141    TTA GTT TGT TTT AAA AAA CGT ATT GAA GCT ATC CCA CAA ATT GAT AAG TAC TTG AAA TCC
          S   K   Y   I   A   W   P   L   Q   G   W   Q   A   T   F   G   G   G   D   H
1201    AGC AAG TAT ATA GCA TGG CCT TTG CAG GGC TGG CAA GCC ACG TTT GGT GGT GGC GAC CAT
                                                        BamHI           EcoRI
                                                        ~~~~~~~~        ~~~~~~~~
          P   P   K   S   D   L   V   P   R   G   S   P   G   I   P   S   E   L   N   D
1261    CCT CCA AAA TCG GAT CTG GTT CCG CGT GGA TCC CCA GGA ATT CCA AGC GAA CTG AAC GAC
          I   N   K   I   E   L   K   N   L   S   G   E   I   I   K   E   N   G   K   E
1321    ATC AAC AAA ATT GAG CTG AAA AAC CTG AGC GGC GAA ATC ATC AAA GAA AAC GGC AAG GAA
          A   I   K   Y   T   S   S   D   T   A   S   H   K   G   W   K   A   T   L   S
1381    GCT ATT AAA TAT ACT TCC AGC GAC ACC GCT TCC CAT AAA GGC TGG AAG GCA ACT CTG AGC
          G   T   F   I   E   D   P   H   S   D   K   K   T   A   L   L   N   L   E   G
1441    GGC ACC TTC ATT GAA GAC CCG CAT TCC GAC AAG AAA ACT GCT CTG CTG AAC CTG GAA GGC
          F   I   P   S   D   K   Q   I   F   G   S   K   Y   Y   G   K   M   K   W   P
1501    TTT ATC CCG TCC GAC AAA CAG ATT TTC GGC TCT AAA TAT TAC GGC AAA ATG AAA TGG CCG
          E   T   Y   R   I   N   V   K   S   A   D   V   N   N   N   I   K   I   A   N
1561    GAA ACT TAT CGC ATT AAT GTG AAA AGC GCT GAC GTG AAC AAT AAC ATC AAA ATC GCA AAC
          S   I   P   K   N   T   I   D   K   K   D   V   S   N   S   I   G   Y   S   I
1621    TCC ATT CCG AAA AAT ACT ATC GAC AAA AAA GAC GTG TCC AAT TCC ATT GGC TAT TCC ATC
          G   G   N   I   S   V   E   G   K   T   A   G   A   G   I   N   A   S   Y   N
1681    GGC GGT AAC ATC TCC GTG GAA GGC AAA ACT GCT GGC GCT GGC ATC AAC GCT TCC TAT AAC
          V   Q   N   T   I   S   Y   E   Q   P   D   F   R   T   I   Q   R   K   D   D
1741    GTC CAA AAC ACT ATC AGC TAT GAA CAA CCG GAC TTC CGC ACC ATT CAA CGC AAA GAC GAT
          A   N   L   A   S   W   D   I   K   F   V   E   T   K   D   G   Y   N   I   D
1801    GCA AAC CTG GCA TCC TGG GAC ATC AAA TTC GTT GAG ACT AAG GAC GGC TAT AAC ATC GAC
          S   Y   H   A   I   Y   G   N   Q   L   F   M   K   S   R   L   Y   N   N   G
1861    TCC TAT CAT GCT ATT TAT GGC AAC CAA CTG TTC ATG AAA TCC CGC CTG TAT AAC AAT GGC
```

Fig. 7E (continued)

```
          D   K   N   F   T   D   D   R   D   L   S   T   L   I   S   G   G   F   S   P
1921 GAC AAA AAC TTC ACC GAC GAT CGC GAC CTG TCC ACC CTG ATT TCC GGC GGC TTC TCC CCG
      N   M   A   L   A   L   T   A   P   K   N   A   K   E   S   V   I   I   V   E
1981 AAC ATG GCT CTG GCA CTG ACC GCA CCT AAA AAT GCT AAA GAA TCC GTG ATC ATC GTG GAA
      Y   Q   R   F   D   N   D   Y   I   L   N   W   E   T   T   Q   W   R   G   T
2041 TAT CAA CGC TTC GAC AAC GAC TAT ATT CTG AAT TGG GAA ACT ACT CAA TGG CGC GGC ACC
      N   K   L   S   S   T   S   E   Y   N   E   F   M   F   K   I   N   W   Q   D
2101 AAC AAA CTT TCC TCA ACC AGC GAA TAT AAC GAA TTT ATG TTC AAA ATC AAC TGG CAA GAC
                                              KpnI
                                              ~~~~~~~~
                                                                  M   K   K   T   A   I·
      H   K   I   E   Y   Y   L   *
2161 CAT AAA ATC GAA TAT TAT CTG TAA TGG TAC CAG GAC GCA AAA AAT GAA AAA GAC AGC TAT
     ·A   I   A   V   A   L   A   G   F   A   T   V   A   Q   A   A   P   K   D   N·
2221 CGC GAT TGC AGT GGC ACT GGC TGG TTT CGC TAC CGT AGC GCA GGC CGC TCC GAA AGA TAA
         SacI
         ~~~~~~~~
     ·N       D   I   E   K   E   I   L   D   L   A   A   A   T   E   R   L   N   L·
2281 CGA GCT CGA CAT CGA AAA AGA AAT CCT GGA CCT GGC GGC GGC GAC CGA ACG TCT GAA CCT
     ·T   D   A   L   N   S   N   P   A   G   N   L   Y   D   W   R   S   S   N   S·
2341 GAC CGA CGC GCT GAA CTC TAA CCC GGC GGG CAA CCT GTA CGA CTG GCG TTC TTC TAA CTC
     ·Y   P   W   T   Q   K   L   N   L   H   L   T   I   T   A   T   G   Q   K   Y·
2401 TTA CCC GTG GAC CCA GAA ACT GAA CCT GCA CCT GAC CAT CAC CGC GAC CGG TCA GAA ATA
     ·R   I   L   A   S   K   I   V   D   F   N   I   Y   S   N   N   F   N   N   L·
2461 CCG TAT CCT GGC GTC TAA AAT CGT TGA CTT CAA CAT CTA CTC TAA CAA CTT CAA CAA CCT
     ·V   K   L   E   Q   S   L   G   D   G   V   K   D   H   Y   V   D   I   S   L·
2521 GGT TAA ACT GGA ACA GTC TCT GGG TGA CGG TGT TAA AGA CCA CTA CGT TGA CAT CTC TCT
     ·D   A   G   Q   Y   V   L   V   M   K   A   N   S   S   Y   S   G   N   Y   P·
2581 GGA CGC GGG TCA GTA CGT TCT GGT TAT GAA AGC GAA CTC TTC CTA CTC CGG TAA CTA CCC
     ·Y   S   I   L   F   Q   K   F       H   H   H   H   H   H                   *
2641 GTA CTC TAT CCT GTT CCA GAA ATT CCC TAG GCA CCA TCA TCA CCA CCA TCC TAG GTA ATG
         PstI                      HindIII
         ~~~~~~~~                  ~~~~~~~~
2701 GGC CCT GCA GCC AAG CTC CCA AGC TTG GCT GTT TTG GCG GAT GAG AGA AGA TTT TCA GCC
```

Fig. 7F

```
         BspEI
         ~~~~~~~~
   1 GGA TCT TCC GGA AGA CCT TCC ATT CTG AAA TGA GCT GTT GAC AAT TAA TCA TCC GGC TCG
                                                                              M   K   K
  61 TAT AAT GTG TGG AAT TGT GAG CGG ATA ACA ATT TCA CAC AGG A AA CAG ACC ATG AAA AAA
      Q   H   F   R   V   A   L   I   P   F   F   A   A   F   C   L   P   V   F   A
 121 CAA CAT TTC CGT GTC GCC CTT ATT CCC TTT TTT GCG GCA TTT TGC CTT CCT GTT TTT GCT
                                                          XhoI
                                                          ~~~~~~~~
                                                      SacI           KpnI
                                                      ~~~~~~~~       ~~~~~~~~
      H   P   E   T   L   V   K   V   K   D   A   E                           M
 181 CAC CCA GAA ACG CTG GTG AAA GTA AAA GAT GCT GAA CTC GAG CTC CAC GTG GGT ACC ATG
      C   T   G   L   A   L   E   T   K   D   G   L   H   L   F   G   R   N   M   D
 241 TGC ACA GGC CTG GCA CTG GAA ACT AAA GAC GGC CTG CAC TTG TTC GGC CGC AAC ATG GAC
      I   E   Y   S   F   N   Q   S   I   I   F   I   P   R   N   F   K   C   V   N
 301 ATC GAA TAT TCT TTC AAT CAA TCT ATT ATT TTC ATT CCG CGC AAC TTC AAG TGC GTG AAC
      K   S   N   K   K   E   L   T   T   K   Y   A   V   L   G   M   G   T   I   F
 361 AAA TCC AAC AAA AAA GAA CTG ACC ACC AAA TAC GCT GTG CTG GGC ATG GGC ACT ATC TTC
      D   D   Y   P   T   F   A   D   G   M   N   E   K   G   L   G   C   A   G   L
 421 GAC GAT TAC CCG ACC TTC GCT GAC GGC ATG AAC GAA AAA GGC CTG GGC TGT GCG GGC TG
```

Fig. 7F (continued)

```
         N   F   P   V   Y   V   S   Y   S   K   E   D   I   E   G   K   T   N   I   P
 481 AAC TTC CCG GTG TAT GTG AGC TAC TCT AAA GAA GAC ATC GAA GGC AAA ACC AAC ATC CCG
         V   Y   N   F   L   L   W   V   L   A   N   F   S   S   V   E   E   V   K   E
 541 GTG TAC AAC TTC CTG CTG TGG GTG CTG GCG AAC TTC AGC TCT GTG GAA GAG GTG AAG GAA
         A   L   K   N   A   N   I   V   D   I   P   I   S   E   N   I   P   N   T   T
 601 GCC CTG AAA AAC GCG AAC ATC GTG GAC ATC CCG ATC TCA GAG AAC ATC CCG AAC ACC ACG
         L   H   W   M   I   S   D   I   T   G   K   S   I   V   V   E   Q   T   K   E
 661 CTG CAC TGG ATG ATC TCC GAC ATC ACC GGC AAA TCC ATC GTG GTG GAA CAG ACC AAG GAA
         K   L   N   V   F   D   N   N   I   G   V   L   T   N   S   P   T   F   D   W
 721 AAA CTG AAC GTG TTC GAC AAC AAC ATC GGC GTG CTG ACC AAC AGC CCG ACG TTC GAC TGG
         H   V   A   N   L   N   Q   Y   V   G   L   R   Y   N   Q   V   P   E   F   K
 781 CAC GTG GCC AAC CTG AAC CAG TAC GTG GGC CTG CGC TAT AAC CAG GTG CCG GAG TTC AAG
         L   G   D   Q   S   L   T   A   L   G   Q   G   T   G   L   V   G   L   P   G
 841 CTG GGC GAC CAG TCT CTG ACT GCT CTG GGC CAG GGC ACT GGC CTG GTG GGC CTG CCG GGC
         D   F   T   P   A   S   R   F   I   R   V   A   F   L   R   D   A   M   I   K
 901 GAC TTC ACA CCG GCG TCT CGC TTC ATC CGC GTA GCG TTT CTG CGT GAC GCG ATG ATC AAA
                                             EcoRI
                                             ~~~~~~~~
         N   D   K   D   S   I   D   L   I   E   F   F   H   I   L   N   N   V   A   M
 961 AAC GAC AAA GAC AGC ATC GAC CTG ATC GAA TTC TTC CAC ATC CTG AAC AAC GTG GCT ATG
         V   R   G   S   T   R   T   V   E   E   K   S   D   L   T   Q   Y   T   S   C
1021 GTA CGC GGC TCC ACT CGC ACA GTG GAA GAG AAA TCC GAC CTG ACA CAG TAC ACG TCT TGC
         M   C   L   E   K   G   I   Y   Y   Y   N   T   Y   E   N   N   Q   I   N   A
1081 ATG TGC CTG GAA AAA GGC ATC TAT TAT TAT AAC ACC TAT GAA AAC AAC CAG ATC AAC GCA
         I   D   M   N   K   E   N   L   D   G   N   E   I   K   T   Y   K   Y   N   K
1141 ATC GAC ATG AAC AAA GAA AAC CTG GAC GGC AAC GAA ATC AAA ACC TAC AAA TAC AAC AAA
         T   L   S   I   N   H   V   N       H   H   H   H   H   H   *
1201 ACC CTG AGC ATC AAC CAC GTG AAC GGT CAC CAT CAC CAT CAC CAT TAG GTC ACC AAT AAT
     PstI
     ~~~~~~~~
                                     M   K   K   T   A   I   A   I   A   V   A   L   A   G
1261 CTG CAG AGG ACG CAA AAA ATG AAA AAG ACA GCT ATC GCG ATT GCA GTG GCA CTG GCT GGT
                                                     SacI
                                                     ~~~~~~~~
         F   A   T   V   A   Q   A   A   P   K   D   N       D   I   E   K   E   I
1321 TTC GCT ACC GTA GCG CAG GCC GCT CCG AAA GAT AAC GAG CTC GAC ATC GAA AAA GAA ATC
         L   D   L   A   A   A   T   E   R   L   N   L   T   D   A   L   N   S   N   P
1381 CTG GAC CTG GCG GCG GCG ACC GAA CGT CTG AAC CTG ACC GAC GCG CTG AAC TCT AAC CCG
         A   G   N   L   Y   D   W   R   S   S   N   S   Y   P   W   T   Q   K   L   N
1441 GCG GGC AAC CTG TAC GAC TGG CGT TCT TCT AAC TCT TAC CCG TGG ACC CAG AAA CTG AAC
         L   H   L   T   I   T   A   T   G   Q   K   Y   R   I   L   A   S   K   I   V
1501 CTG CAC CTG ACC ATC ACC GCG ACC GGT CAG AAA TAC CGT ATC CTG GCG TCT AAA ATC GTT
         D   F   N   I   Y   S   N   N   F   N   N   L   V   K   L   E   Q   S   L   G
1561 GAC TTC AAC ATC TAC TCT AAC AAC TTC AAC AAC CTG GTT AAA CTG GAA CAG TCT CTG GGT
         D   G   V   K   D   H   Y   V   D   I   S   L   D   A   G   Q   Y   V   L   V
1621 GAC GGT GTT AAA GAC CAC TAC GTT GAC ATC TCT CTG GAC GCG GGT CAG TAC GTT CTG GTT
         M   K   A   N   S   S   Y   S   G   N   Y   P   Y   S   I   L   F   Q   K   F
1681 ATG AAA GCG AAC TCT TCC TAC TCC GGT AAC TAC CCG TAC TCT ATC CTG TTC CAG AAA TTC
                                                                 PstI            HindIII
                                                                 ~~~~~~~~        ~~~~~~
         H   H   H   H   H   H                   *
1741 CCT AGG CAC CAT CAT CAC CAC CAT CCT AGG TAA TGG GCC CTG CAG CCA AGC TCC CAA GCT
     HindIII
     ~
1801 TGG CTG TTT TGG CGG ATG AGA GAA GAT TTT CAG CCT GAT ACA GAT TAA ATC AGA ACG CAG
```

Fig. 7G

```
              BspEI
              ~~~~~~~~
   1 GGA TCT TCC GGA AGA CCT TCC ATT CTG AAA TGA GCT GTT GAC AAT TAA TCA TCC GGC TCG
                                                                                 M   K   K
  61 TAT AAT GTG TGG AAT TGT GAG CGG ATA ACA ATT TCA CAC AGG A AA CAG ACC ATG AAA AAA
      Q   H   F   R   V   A   L   I   P   F   F   A   A   F   C   L   P   V   F   A
 121 CAA CAT TTC CGT GTC GCC CTT ATT CCC TTT TTT GCG GCA TTT TGC CTT CCT GTT TTT GCT
                                                             XhoI
                                                             ~~~~~~~~
                                                                  SacI             KpnI
                                                                  ~~~~~~~~         ~~~~~~~~
      H   P   E   T   L   V   K   V   K   D   A   E                                    D
 181 CAC CCA GAA ACG CTG GTG AAA GTA AAA GAT GCT GAA CTC GAG CTC CAC GTG GGT ACC GAC
      I   E   K   E   I   L   D   L   A   A   A   T   E   R   L   N   L   T   D   A
 241 ATC GAA AAA GAA ATC CTG GAC CTG GCG GCG GCG ACC GAA CGT CTG AAC CTG ACC GAC GCG
      L   N   S   N   P   A   G   N   L   Y   D   W   R   S   S   N   S   Y   P   W
 301 CTG AAC TCT AAC CCG GCG GGC AAC CTG TAC GAC TGG CGT TCT TCT AAC TCT TAC CCG TGG
      T   Q   K   L   N   L   H   L   T   I   T   A   T   G   Q   K   Y   R   I   L
 361 ACC CAG AAA CTG AAC CTG CAC CTG ACC ATC ACC GCG ACC GGT CAG AAA TAC CGT ATC CTG
      A   S   K   I   V   D   F   N   I   Y   S   N   N   F   N   N   L   V   K   L
 421 GCG TCT AAA ATC GTT GAC TTC AAC ATC TAC TCT AAC AAC TTC AAC AAC CTG GTT AAA CTG
      E   Q   S   L   G   D   G   V   K   D   H   Y   V   D   I   S   L   D   A   G
 481 GAA CAG TCT CTG GGT GAC GGT GTT AAA GAC CAC TAC GTT GAC ATC TCT CTG GAC GCG GGT
      Q   Y   V   L   V   M   K   A   N   S   S   Y   S   G   N   Y   P   Y   S   I
 541 CAG TAC GTT CTG GTT ATG AAA GCG AAC TCT TCC TAC TCC GGT AAC TAC CCG TAC TCT ATC
                                                                          PstI
                                                                          ~~~~~~~~
      L   F   Q   K   F               H   H   H   H   H   H   *
 601 CTG TTC CAG AAA TTC GCC GGC CAC CAT CAC CAT CAC CAT TAG CCG GCT AAT CTG CAG AGG
                      M   K   K   I   W   L   A   L   A   G   M   V   L   A   F   S   A
 661 AAG TTG ATC ATG AAA AAG ATT TGG CTG GCG CTG GCT GGT ATG GTT TTA GCT TTT AGC GCC
                                   XhoI
                                   ~~~~~~~~
      S   A   A   Q   I   S   D   L   E   M   C   T   G   L   A   L   E   T   K   D
 721 TCG GCA GCA CAG ATC AGC GAC CTC GAG ATG TGC ACA GGC CTG GCA CTG GAA ACT AAA GAC
      G   L   H   L   F   G   R   N   M   D   I   E   Y   S   F   N   Q   S   I   I
 781 GGC CTG CAC TTG TTC GGC CGC AAC ATG GAC ATC GAA TAT TCT TTC AAT CAA TCT ATT ATT
      F   I   P   R   N   F   K   C   V   N   K   S   N   K   K   E   L   T   T   K
 841 TTC ATT CCG CGC AAC TTC AAG TGC GTG AAC AAA TCC AAC AAA AAA GAA CTG ACC ACC AAA
      Y   A   V   L   G   M   G   T   I   F   D   D   Y   P   T   F   A   D   G   M
 901 TAC GCT GTG CTG GGC ATG GGC ACT ATC TTC GAC GAT TAC CCG ACC TTC GCT GAC GGC ATG
      N   E   K   G   L   G   C   A   G   L   N   F   P   V   Y   V   S   Y   S   K
 961 AAC GAA AAA GGC CTG GGC TGT GCG GGC CTG AAC TTC CCG GTG TAT GTG AGC TAC TCT AAA
      E   D   I   E   G   K   T   N   I   P   V   Y   N   F   L   L   W   V   L   A
1021 GAA GAC ATC GAA GGC AAA ACC AAC ATC CCG GTG TAC AAC TTC CTG CTG TGG GTG CTG GCG
      N   F   S   S   V   E   E   V   K   E   A   L   K   N   A   N   I   V   D   I
1081 AAC TTC AGC TCT GTG GAA GAG GTG AAG GAA GCC CTG AAA AAC GCG AAC ATC GTG GAC ATC
      P   I   S   E   N   I   P   N   T   T   L   H   W   M   I   S   D   I   T   G
1141 CCG ATC TCA GAG AAC ATC CCG AAC ACC ACG CTG CAC TGG ATG ATC TCC GAC ATC ACC GGC
      K   S   I   V   V   E   Q   T   K   E   L   N   V   F   D   N   N   I   G
1201 AAA TCC ATC GTG GTG GAA CAG ACC AAG GAA AAA CTG AAC GTG TTC GAC AAC AAC ATC GGC
      V   L   T   N   S   P   T   F   D   W   H   V   A   N   L   N   Q   Y   V   G
1261 GTG CTG ACC AAC AGC CCG ACG TTC GAC TGG CAC GTG GCC AAC CTG AAC CAG TAC GTG GGC
      L   R   Y   N   Q   V   P   E   F   K   L   G   D   Q   S   L   T   A   L   G
1321 CTG CGC TAT AAC CAG GTG CCG GAG TTC AAG CTG GGC GAC CAG TCT CTG ACT GCT CTG GGC
      Q   G   T   G   L   V   G   L   P   G   D   F   T   P   A   S   R   F   I   R
1381 CAG GGC ACT GGC CTG GTG GGC CTG CCG GGC GAC TTC ACA CCG GCG TCT CGC TTC ATC CGC
                                                                                  EcoRI
                                                                                  ~~~
```

Fig. 7G (continued)

```
          V   A   F   L   R   D   A   M   I   K   N   D   K   D   S   I   D   L   I   E
1441 GTA GCG TTT CTG CGT GAC GCG ATG ATC AAA AAC GAC AAA GAC AGC ATC GAC CTG ATC GAA
     EcoRI
     ~~~~
          F   F   H   I   L   N   N   V   A   M   V   R   G   S   T   R   T   V   E   E
1501 TTC TTC CAC ATC CTG AAC AAC GTG GCT ATG GTA CGC GGC TCC ACT CGC ACA GTG GAA GAG
          K   S   D   L   T   Q   Y   T   S   C   M   C   L   E   K   G   I   Y   Y   Y
1561 AAA TCC GAC CTG ACA CAG TAC ACG TCT TGC ATG TGC CTG GAA AAA GGC ATC TAT TAT TAT
          N   T   Y   E   N   N   Q   I   N   A   I   D   M   N   K   E   N   L   D   G
1621 AAC ACC TAT GAA AAC AAC CAG ATC AAC GCA ATC GAC ATG AAC AAA GAA AAC CTG GAC GGC
          N   E   I   K   T   Y   K   Y   N   K   T   L   S   I   N   H   V   N
1681 AAC GAA ATC AAA ACC TAC AAA TAC AAC AAA ACC CTG AGC ATC AAC CAC GTG AAC CCG CGG
                                                             PstI              HindIII
                                                             ~~~~~~~~          ~~~~~~~~
          H   H   H   H   H   H               *
1741 CAC CAC CAC CAT CAT CAT CCG CGG TAA TGG GCC CTG CAG CCA AGC TCC CAA GCT TGG CTG
```

Fig. 7H

```
     BspEI
     ~~~~~~~~
   1 GGA TCT TCC GGA AGA CCT TCC ATT CTG AAA TGA GCT GTT GAC AAT TAA TCA TCC GGC TCG
                                                                          M   K   K
  61 TAT AAT GTG TGG AAT TGT GAG CGG ATA ACA ATT TCA CAC AGG A AA CAG ACC ATG AAA AAA
          Q   H   F   R   V   A   L   I   P   F   F   A   A   F   C   L   P   V   F   A
 121 CAA CAT TTC CGT GTC GCC CTT ATT CCC TTT TTT GCG GCA TTT TGC CTT CCT GTT TTT GCT
                                                             XhoI
                                                             ~~~~~~~~
          H   P   E   T   L   V   K   V   K   D   A   E       D   P   S   V   G   N
 181 CAC CCA GAA ACG CTG GTG AAA GTA AAA GAT GCT GAA CTC GAG GAC CCG TCC GTG GGC AAC
          N   V   K   E   L   V   A   Y   I   S   T   S   G   E   K   D   A   G   T   D
 241 AAC GTG AAA GAA CTG GTG GCT TAC ATC TCC ACT AGC GGC GAA AAA GAC GCT GGC ACC GAC
          D   Y   M   Y   F   G   I   K   T   K   D   G   K   T   Q   E   W   E   M   D
 301 GAC TAC ATG TAT TTC GGC ATC AAA ACC AAG GAC GGC AAA ACT CAA GAA TGG GAA ATG GAC
          XmaI
          ~~~~~~~~
          SmaI
          ~~~~~~~~
          N   P   G   N   D   F   M   A   G   S   K   D   T   Y   T   F   K   L   K   D
 361 AAC CCG GGC AAC GAC TTC ATG GCT GGC AGC AAA GAC ACT TAT ACT TTC AAA TTA AAA GAC
          E   N   L   K   I   D   D   I   Q   N   M   W   I   R   K   R   K   Y   T   A
 421 GAA AAC CTG AAA ATT GAC GAC ATC CAA AAC ATG TGG ATT CGC AAA CGT AAA TAT ACC GCA
          F   P   D   A   Y   K   P   E   N   I   K   V   I   A   N   G   K   V   V   V
 481 TTC CCG GAC GCT TAT AAG CCG GAA AAC ATC AAG GTG ATC GCA AAC GGC AAA GTG GTA GTG
                                                                                HindIII
                                                                                ~~~
          D   K   D   I   N   E   W   I   S   G   N   S   T   Y   N   I   K   *
 541 GAC AAG GAC ATC AAC GAG TGG ATT TCC GGC AAC TCC ACT TAT AAC ATC AAA TAA TAA AAG
          HindIII         NcoI
          ~~~~            ~~~~~~~~
                                M   A   P   I   L   G   Y   W   K   I   K   G   L   V   Q
 601 CTT AGG AAA CAG ACC ATG GCC CCT ATA CTA GGT TAT TGG AAA ATT AAG GGC CTT GTG CAA
          P   T   R   L   L   L   E   Y   L   E   E   K   Y   E   E   H   L   Y   E   R
 661 CCC ACT CGA CTT CTT TTG GAA TAT CTT GAA GAA AAA TAT GAA GAG CAT TTG TAT GAG CGC
          D   E   G   D   K   W   R   N   K   K   F   E   L   G   L   E   F   P   N   L
 721 GAT GAA GGT GAT AAA TGG CGA AAC AAA AAG TTT GAA TTG GGT TTG GAG TTT CCC AAT CTT
```

Fig. 7H (continued)

```
           P   Y   Y   I   D   G   D   V   K   L   T   Q   S   M   A   I   I   R   Y   I
 781 CCT TAT TAT ATT GAT GGT GAT GTT AAA TTA ACA CAG TCT ATG GCC ATC ATA CGT TAT ATA
           A   D   K   H   N   M   L   G   G   C   P   K   E   R   A   E   I   S   M   L
 841 GCT GAC AAG CAC AAC ATG TTG GGT GGT TGT CCA AAA GAG CGT GCA GAG ATT TCA ATG CTT
           E   G   A   V   L   D   I   R   Y   G   V   S   R   I   A   Y   S   K   D   F
 901 GAA GGA GCG GTT TTG GAT ATT AGA TAC GGT GTT TCG AGA ATT GCA TAT AGT AAA GAC TTT
           E   T   L   K   V   D   F   L   S   K   L   P   E   M   L   K   M   F   E   D
 961 GAA ACT CTC AAA GTT GAT TTT CTT AGC AAG CTA CCT GAA ATG CTG AAA ATG TTC GAA GAT
           R   L   C   H   K   T   Y   L   N   G   D   H   V   T   H   P   D   F   M   L
1021 CGT TTA TGT CAT AAA ACA TAT TTA AAT GGT GAT CAT GTA ACC CAT CCT GAC TTC ATG TTG
           Y   D   A   L   D   V   V   L   Y   M   D   P   M   C   L   D   A   F   P   K
1081 TAT GAC GCT CTT GAT GTT GTT TTA TAC ATG GAC CCA ATG TGC CTG GAT GCG TTC CCA AAA
           L   V   C   F   K   K   R   I   E   A   I   P   Q   I   D   K   Y   L   K   S
1141 TTA GTT TGT TTT AAA AAA CGT ATT GAA GCT ATC CCA CAA ATT GAT AAG TAC TTG AAA TCC
           S   K   Y   I   A   W   P   L   Q   G   W   Q   A   T   F   G   G   G   D   H
1201 AGC AAG TAT ATA GCA TGG CCT TTG CAG GGC TGG CAA GCC ACG TTT GGT GGT GGC GAC CAT
                                                   BamHI           EcoRI
                                                   ~~~~~~~~        ~~~~~~~~
           P   P   K   S   D   L   V   P   R   G   S   P   G   I   P   S   E   L   N   D
1261 CCT CCA AAA TCG GAT CTG GTT CCG CGT GGA TCC CCA GGA ATT CCA AGC GAA CTG AAC GAC
           I   N   K   I   E   L   K   N   L   S   G   E   I   I   K   E   N   G   K   E
1321 ATC AAC AAA ATT GAG CTG AAA AAC CTG AGC GGC GAA ATC ATC AAA GAA AAC GGC AAG GAA
           A   I   K   Y   T   S   S   D   T   A   S   H   K   G   W   K   A   T   L   S
1381 GCT ATT AAA TAT ACT TCC AGC GAC ACC GCT TCC CAT AAA GGC TGG AAG GCA ACT CTG AGC
           G   T   F   I   E   D   P   H   S   D   K   K   T   A   L   L   N   L   E   G
1441 GGC ACC TTC ATT GAA GAC CCG CAT TCC GAC AAG AAA ACT GCT CTG CTG AAC CTG GAA GGC
           F   I   P   S   D   K   Q   I   F   G   S   K   Y   Y   G   K   M   K   W   P
1501 TTT ATC CCG TCC GAC AAA CAG ATT TTC GGC TCT AAA TAT TAC GGC AAA ATG AAA TGG CCG
           E   T   Y   R   I   N   V   K   S   A   D   V   N   N   N   I   K   I   A   N
1561 GAA ACT TAT CGC ATT AAT GTG AAA AGC GCT GAC GTG AAC AAT AAC ATC AAA ATC GCA AAC
           S   I   P   K   N   T   I   D   K   K   D   V   S   N   S   I   G   Y   S   I
1621 TCC ATT CCG AAA AAT ACT ATC GAC AAA AAA GAC GTG TCC AAT TCC ATT GGC TAT TCC ATC
           G   G   N   I   S   V   E   G   K   T   A   G   A   G   I   N   A   S   Y   N
1681 GGC GGT AAC ATC TCC GTG GAA GGC AAA ACT GCT GGC GCT GGC ATC AAC GCT TCC TAT AAC
           V   Q   N   T   I   S   Y   E   Q   P   D   F   R   T   I   Q   R   K   D   D
1741 GTC CAA AAC ACT ATC AGC TAT GAA CAA CCG GAC TTC CGC ACC ATT CAA CGC AAA GAC GAT
           A   N   L   A   S   W   D   I   K   F   V   E   T   K   D   G   Y   N   I   D
1801 GCA AAC CTG GCA TCC TGG GAC ATC AAA TTC GTT GAG ACT AAG GAC GGC TAT AAC ATC GAC
           S   Y   H   A   I   Y   G   N   Q   L   F   M   K   S   R   L   Y   N   N   G
1861 TCC TAT CAT GCT ATT TAT GGC AAC CAA CTG TTC ATG AAA TCC CGC CTG TAT AAC AAT GGC
           D   K   N   F   T   D   D   R   D   L   S   T   L   I   S   G   G   F   S   P
1921 GAC AAA AAC TTC ACC GAC GAT CGC GAC CTG TCC ACC CTG ATT TCC GGC GGC TTC TCC CCG
           N   M   A   L   A   L   T   A   P   K   N   A   K   E   S   V   I   I   V   E
1981 AAC ATG GCT CTG GCA CTG ACC GCA CCT AAA AAT GCT AAA GAA TCC GTG ATC ATC GTG GAA
           Y   Q   R   F   D   N   D   Y   I   L   N   W   E   T   T   Q   W   R   G   T
2041 TAT CAA CGC TTC GAC AAC GAC TAT ATT CTG AAT TGG GAA ACT ACT CAA TGG CGC GGC ACC
           N   K   L   S   S   T   S   E   Y   N   E   F   M   F   K   I   N   W   Q   D
2101 AAC AAA CTT TCC TCA ACC AGC GAA TAT AAC GAA TTT ATG TTC AAA ATC AAC TGG CAA GAC
                                                           KpnI
                                                           ~~~~~~~~
                                                                               M   K   K   I   W   L
           H   K   I   E   Y   Y   L   *
2161 CAT AAA ATC GAA TAT TAT CTG TAA TGG TAC CAG GAA GTT GAT CAT GAA AAA GAT TTG GCT
                                                                                       XhoI
                                                                                       ~~~~~~
          ·A   L   A   G   M   V   L   A   F   S   A   S   A   A   Q   I   S   D
2221 GGC GCT GGC TGG TAT GGT TTT AGC TTT TAG CGC CTC GGC AGC ACA GAT CAG CGA CCT CGA
     XhoI
     ~
```

Fig. 7H (continued)

```
              M   C   T   G   L   A   L   E   T   K   D   G   L   H   L   F   G   R   N   M ·
2281 GAT GTG CAC AGG CCT GGC ACT GGA AAC TAA AGA CGG CCT GCA CTT GTT CGG CCG CAA CAT
     · D   I   E   Y   S   F   N   Q   S   I   I   F   I   P   R   N   F   K   C   V ·
2341 GGA CAT CGA ATA TTC TTT CAA TCA ATC TAT TAT TTT CAT TCC GCG CAA CTT CAA GTG CGT
     · N   K   S   N   K   K   E   L   T   T   K   Y   A   V   L   G   M   G   T   I ·
2401 GAA CAA ATC CAA CAA AAA AGA ACT GAC CAC CAA ATA CGC TGT GCT GGG CAT GGG CAC TAT
     · F   D   D   Y   P   T   F   A   D   G   M   N   E   K   G   L   G   C   A   G ·
2461 CTT CGA CGA TTA CCC GAC CTT CGC TGA CGG CAT GAA CGA AAA AGG CCT GGG CTG TGC GGG
     · L   N   F   P   V   Y   V   S   Y   S   K   E   D   I   E   G   K   T   N   I ·
2521 CCT GAA CTT CCC GGT GTA TGT GAG CTA CTC TAA AGA AGA CAT CGA AGG CAA AAC CAA CAT
     · P   V   Y   N   F   L   L   W   V   L   A   N   F   S   S   V   E   E   V   K ·
2581 CCC GGT GTA CAA CTT CCT GCT GTG GGT GCT GGC GAA CTT CAG CTC TGT GGA AGA GGT GAA
     · E   A   L   K   N   A   N   I   V   D   I   P   I   S   E   N   I   P   N   T ·
2641 GGA AGC CCT GAA AAA CGC GAA CAT CGT GGA CAT CCC GAT CTC AGA GAA CAT CCC GAA CAC
     · T   L   H   W   M   I   S   D   I   T   G   K   S   I   V   V   E   Q   T   K ·
2701 CAC GCT GCA CTG GAT GAT CTC CGA CAT CAC CGG CAA ATC CAT CGT GGT GGA ACA GAC CAA
     · E   K   L   N   V   F   D   N   N   I   G   V   L   T   N   S   P   T   F   D ·
2761 GGA AAA ACT GAA CGT GTT CGA CAA CAA CAT CGG CGT GCT GAC CAA CAG CCC GAC GTT CGA
     · W   H   V   A   N   L   N   Q   Y   V   G   L   R   Y   N   Q   V   P   E   F ·
2821 CTG GCA CGT GGC CAA CCT GAA CCA GTA CGT GGG CCT GCG CTA TAA CCA GGT GCC GGA GTT
     · K   L   G   D   Q   S   L   T   A   L   G   Q   G   T   G   L   V   G   L   P ·
2881 CAA GCT GGG CGA CCA GTC TCT GAC TGC TCT GGG CCA GGG CAC TGG CCT GGT GGG CCT GCC
     · G   D   F   T   P   A   S   R   F   I   R   V   A   F   L   R   D   A   M   I ·
2941 GGG CGA CTT CAC ACC GGC GTC TCG CTT CAT CCG CGT AGC GTT TCT GCG TGA CGC GAT GAT
                                                        EcoRI
                                                        ~~~~~~~~
     · K   N   D   K   D   S   I   D   L   I   E   F   F   H   I   L   N   N   V   A ·
3001 CAA AAA CGA CAA AGA CAG CAT CGA CCT GAT CGA ATT CTT CCA CAT CCT GAA CAA CGT GGC
     · M   V   R   G   S   T   R   T   V   E   E   K   S   D   L   T   Q   Y   T   S ·
3061 TAT GGT ACG CGG CTC CAC TCG CAC AGT GGA AGA GAA ATC CGA CCT GAC ACA GTA CAC GTC
     · C   M   L   E   K   G   I   Y   Y   Y   N   T   Y   E   N   N   Q   I   N ·
3121 TTG CAT GTG CCT GGA AAA AGG CAT CTA TTA TTA TAA CAC CTA TGA AAA CAA CCA GAT CAA
     · A   I   D   M   N   K   E   N   L   D   G   N   E   I   K   T   Y   K   Y   N ·
3181 CGC AAT CGA CAT GAA CAA AGA AAA CCT GGA CGG CAA CGA AAT CAA AAC CTA CAA ATA CAA
     · K   T   L   S   I   N   H   V   N   H   H   H   H   H   * 
3241 CAA AAC CCT GAG CAT CAA CCA CGT GAA CGG TCA CCA TCA CCA TCA CCA TTA GGT CAC CAA
          PstI
          ~~~~~~~~
                                      M   K   K   T   A   I   A   I   A   V   A   L   A ·
3301 TAA TCT GCA GAG GAC GCA AAA AAT GAA AAA GAC AGC TAT CGC GAT TGC AGT GGC ACT GGC
                                                       SacI
                                                       ~~~~~~~~
     · G   F   A   T   V   A   Q   A   A   P   K   D   N       D   I   E   K   E ·
3361 TGG TTT CGC TAC CGT AGC GCA GGC CGC TCC GAA AGA TAA CGA GCT CGA CAT CGA AAA AGA
     · I   L   D   L   A   A   A   T   E   R   L   N   L   T   D   A   L   N   S   N ·
3421 AAT CCT GGA CCT GGC GGC GGC GAC CGA ACG TCT GAA CCT GAC CGA CGC GCT GAA CTC TAA
     · P   A   G   N   L   Y   D   W   R   S   S   N   S   Y   P   W   T   Q   K   L ·
3481 CCC GGC GGG CAA CCT GTA CGA CTG GCG TTC TTC TAA CTC TTA CCC GTG GAC CCA GAA ACT
     · N   L   H   L   T   I   T   A   T   G   Q   K   Y   R   I   L   A   S   K   I ·
3541 GAA CCT GCA CCT GAC CAT CAC CGC GAC CGG TCA GAA ATA CCG TAT CCT GGC GTC TAA AAT
     · V   D   F   N   I   Y   S   N   N   F   N   N   L   V   K   L   E   Q   S   L ·
3601 CGT TGA CTT CAA CAT CTA CTC TAA CAA CTT CAA CAA CCT GGT TAA ACT GGA ACA GTC TCT
     · G   D   G   V   K   D   H   Y   V   D   I   S   L   D   A   G   Q   Y   V   L ·
3661 GGG TGA CGG TGT TAA AGA CCA CTA CGT TGA CAT CTC TCT GGA CGC GGG TCA GTA CGT TCT
     · V   M   K   A   N   S   S   Y   S   G   N   Y   P   Y   S   I   L   F   Q   K ·
3721 GGT TAT GAA AGC GAA CTC TTC CTA CTC CGG TAA CTA CCC GTA CTC TAT CCT GTT CCA GAA
                                                                      PstI
HindIII                                                               ~~~~~~~~    ~
     · F       H   H   H   H   H           *
3781 ATT CCC TAG GCA CCA TCA TCA CCA CCA TCC TAG GTA ATG GGC CCT GCA GCC AAG CTC CCA
          HindIII
          ~~~~~~
3841 AGC TTG GCT GTT TTG GCG GAT GAG AGA AGA TTT TCA GCC TGA TAC AGA TTA AAT CAG AAC
```

Fig. 7I

```
      M   A   L   V   N   A   K   E   M   L   N   K   A   R   E   G   K   Y   A   V
  1 ATG GCA CTG GTT AAC GCA AAA GAA ATG CTG AAT AAA GCA CGC GAA GGC AAA TAC GCT GTT
      G   Q   F   N   I   N   N   L   E   W   T   K   A   I   L   L   T   A   Q   E
 61 GGT CAA TTC AAC ATC AAC AAC CTG GAA TGG ACA AAA GCT ATC CTG CTG ACT GCT CAA GAA
      N   N   S   P   V   I   L   G   V   S   E   G   A   A   K   Y   M   C   G   F
121 AAT AAC TCA CCA GTT ATC CTG GGC GTA TCA GAA GGT GCT GCT AAA TAC ATG TGT GGC TTC
      K   T   I   V   G   M   V   N   G   M   L   E   E   L   K   I   T   V   P   V
181 AAA ACA ATC GTT GGC ATG GTT AAC GGC ATG CTG GAA GAA CTG AAA ATC ACT GTT CCT GTA
      A   L   H   L   D   H   G   S   Y   Q   G   A   I   D   A   M   D   A   G   F
241 GCA CTG CAC CTG GAT CAC GGT AGC TAC CAA GGC GCT ATC GAT GCT ATG GAT GCT GGC TTC
      S   S   V   M   F   D   G   S   H   Y   S   I   E   E   N   I   V   K   T   K
301 TCA TCA GTA ATG TTC GAT GGC TCA CAC TAC TCA ATC GAA GAA AAC ATC GTT AAA ACT AAA
      E   I   I   N   L   A   A   A   K   N   V   S   V   E   A   E   V   G   S   I
361 GAA ATC ATC AAC CTG GCT GCT GCT AAA AAC GTA TCA GTT GAA GCT GAA GTT GGC TCA ATC
      G   G   E   E   D   G   V   V   G   A   G   E   I   A   D   P   A   E   C   K
421 GGT GGC GAA GAA GAC GGT GTT GTT GGC GCT GGT GAA ATC GCT GAT CCT GCT GAA TGT AAA
      Q   I   A   E   L   G   V   T   M   L   A   A   G   I   G   N   I   H   G   K
481 CAA ATC GCT GAA CTG GGC GTT ACT ATG CTG GCT GCT GGT ATC GGC AAC ATT CAC GGC AAA
      Y   P   A   N   W   A   G   L   N   F   E   A   L   A   N   I   K   A   A   T
541 TAC CCT GCA AAC TGG GCT GGC CTG AAC TTC GAA GCT CTG GCT AAC ATT AAA GCT GCT ACT
      G   D   M   P   L   V   L   H   G   G   T   G   I   P   S   D   M   I   A   E
601 GGC GAT ATG CCT CTG GTA CTG CAC GGT GGT ACT GGC ATC CCT TCA GAT ATG ATC GCA GAA
      A   I   S   L   G   V   S   K   I   N   V   N   T   E   C   Q   L   S   F   A
661 GCT ATC TCA CTG GGC GTA TCA AAA ATC AAT GTT AAT ACT GAG TGT CAA CTG TCA TTT GCT
      E   A   T   R   K   Y   I   E   A   G   K   D   L   E   G   K   G   F   D   P
721 GAA GCT ACT CGT AAA TAT ATC GAA GCT GGC AAA GAC CTG GAA GGC AAA GGC TTT GAC CCA
      R   K   L   L   N   P   G   F   E   A   I   K   A   T   V   K   E   K   M   E
781 CGC AAA CTG CTG AAT CCT GGC TTC GAA GCT ATC AAA GCT ACA GTT AAA GAA AAA ATG GAA
      L   F   G   S   V   N   R   A   *   *
841 CTG TTC GGT TCA GTA AAC AGA GCT TAA TAG
```

Fig. 7J

```
        BspEI
       ~~~~~~~~
  1 GGA TCT TCC GGA AGA CCT TCC ATT CTG AAA TGA GCT GTT GAC AAT TAA TCA TCC GGC TCG
                                                                           NcoI
                                                                        ~~~~~~~~
                                                                                KpnI
                                                                               ~~~~~~
 61 TAT AAT GTG TGG AAT TGT GAG CGG ATA ACA ATT TCA CAC AGG AAA CAG ACC ATG GGG TAC
    KpnI
    ~
      M   S   I   Q   H   F   R   V   A   L   I   P   F   F   A   A   F   C   L
121 CAG ATG AGT ATT CAA CAT TTC CGT GTC GCC CTT ATT CCC TTT TTT GCG GCA TTT TGC CTT
                                                                   EcoRI
                                                                  ~~~~~~~~
      P   V   F   A   H   P   E   T   L   V   K   V   K   D   A   E   E   F   D   P
181 CCT GTT TTT GCT CAC CCA GAA ACG CTG GTG AAA GTA AAA GAT GCT GAA GAA TTC GAC CCG
      S   V   G   N   N   V   K   E   L   V   A   Y   I   S   T   S   G   E   K   D
241 TCC GTG GGC AAC AAC GTG AAA GAA CTG GTG GCT TAC ATC TCC ACT AGC GGC GAA AAA GAC
      A   G   T   D   D   Y   M   Y   F   G   I   K   T   K   D   G   K   T   Q   E
301 GCT GGC ACC GAC GAC TAC ATG TAT TTC GGC ATC AAA ACC AAG GAC GGC AAA ACT CAA GAA
                                    SmaI
                                   ~~~~~~~~
```

Fig. 7J (continued)

```
         W   E   M   D   N   P   G   N   D   F   M   A   G   S   K   D   T   Y   T   F
    361 TGG GAA ATG GAC AAC CCG GGC AAC GAC TTC ATG GCT GGC AGC AAA GAC ACT TAT ACT TTC
         K   L   K   D   E   N   L   K   I   D   D   I   Q   N   M   W   I   R   K   R
    421 AAA TTA AAA GAC GAA AAC CTG AAA ATT GAC GAC ATC CAA AAC ATG TGG ATT CGC AAA CGT
         K   Y   T   A   F   P   D   A   Y   K   P   E   N   I   K   V   I   A   N   G
    481 AAA TAT ACC GCA TTC CCG GAC GCT TAT AAG CCG GAA AAC ATC AAG GTG ATC GCA AAC GGC
         K   V   V   V   D   K   D   I   N   E   W   I   S   G   N   S   T   Y   N   I
    541 AAA GTG GTA GTG GAC AAG GAC ATC AAC GAG TGG ATT TCC GGC AAC TCC ACT TAT AAC ATC
                         HindIII                 NcoI
                         ~~~~~~~~                ~~~~~~~~
         K   *
    601 AAA TAA TAA AAG CTT AGG AAA CAG ACC ATG GCA CTG GTT AAC GCA AAA GAA ATG CTG AAT
         K   A   R   E   G   K   Y   A   V   G   Q   F   N   I   N   N   L   E   W   T
    661 AAA GCA CGC GAA GGC AAA TAC GCT GTT GGT CAA TTC AAC ATC AAC AAC CTG GAA TGG ACA
         K   A   I   L   L   T   A   Q   E   N   N   S   P   V   I   L   G   V   S   E
    721 AAA GCT ATC CTG CTG ACT GCT CAA GAA AAT AAC TCA CCA GTT ATC CTG GGC GTA TCA GAA
                                                                             SphI
                                                                             ~~~~~~~~
         G   A   A   K   Y   M   C   G   F   K   T   I   V   G   M   V   N   G   M   L
    781 GGT GCT GCT AAA TAC ATG TGT GGC TTC AAA ACA ATC GTT GGC ATG GTT AAC GGC ATG CTG
         E   E   L   K   I   T   V   P   V   A   L   H   L   D   H   G   S   Y   Q   G
    841 GAA GAA CTG AAA ATC ACT GTT CCT GTA GCA CTG CAC CTG GAT CAC GGT AGC TAC CAA GGC
         A   I   D   A   M   D   A   G   F   S   S   V   M   F   D   G   S   H   Y   S
    901 GCT ATC GAT GCT ATG GAT GCT GGC TTC TCA TCA GTA ATG TTC GAT GGC TCA CAC TAC TCA
         I   E   E   N   I   V   K   T   K   E   I   I   N   L   A   A   A   K   N   V
    961 ATC GAA GAA AAC ATC GTT AAA ACT AAA GAA ATC ATC AAC CTG GCT GCT GCT AAA AAC GTA
         S   V   E   A   E   V   G   S   I   G   G   E   E   D   G   V   V   G   A   G
   1021 TCA GTT GAA GCT GAA GTT GGC TCA ATC GGT GGC GAA GAA GAC GGT GTT GTT GGC GCT GGT
         E   I   A   D   P   A   E   C   K   Q   I   A   E   L   G   V   T   M   L   A
   1081 GAA ATC GCT GAT CCT GCT GAA TGT AAA CAA ATC GCT GAA CTG GGC GTT ACT ATG CTG GCT
         A   G   I   G   N   I   H   G   K   Y   P   A   N   W   A   G   L   N   F   E
   1141 GCT GGT ATC GGC AAC ATT CAC GGC AAA TAC CCT GCA AAC TGG GCT GGC CTG AAC TTC GAA
         A   L   A   N   I   K   A   A   T   G   D   M   P   L   V   L   H   G   G   T
   1201 GCT CTG GCT AAC ATT AAA GCT GCT ACT GGC GAT ATG CCT CTG GTA CTG CAC GGT GGT ACT
         G   I   P   S   D   M   I   A   E   A   I   S   L   G   V   S   K   I   N   V
   1261 GGC ATC CCT TCA GAT ATG ATC GCA GAA GCT ATC TCA CTG GGC GTA TCA AAA ATC AAT GTT
         N   T   E   C   Q   L   S   F   A   E   A   T   R   K   Y   I   E   A   G   K
   1321 AAT ACT GAG TGT CAA CTG TCA TTT GCT GAA GCT ACT CGT AAA TAT ATC GAA GCT GGC AAA
         D   L   E   G   K   G   F   D   P   R   K   L   L   N   P   G   F   E   A   I
   1381 GAC CTG GAA GGC AAA GGC TTT GAC CCA CGC AAA CTG CTG AAT CCT GGC TTC GAA GCT ATC
                                                                                 PstI
                                                                                 ~~~
         K   A   T   V   K   E   K   M   E   L   F   G   S   V   N   R   A   *   *
   1441 AAA GCT ACA GTT AAA GAA AAA ATG GAA CTG TTC GGT TCA GTA AAC AGA GCT TAA TAG CTG
         PstI                NcoI
         ~~~~                ~~~~~~~~
                             M   A   P   I   L   G   Y   W   K   I   K   G   L   V   Q
   1501 CAG AGG AAA CAG ACC ATG GCC CCT ATA CTA GGT TAT TGG AAA ATT AAG GGC CTT GTG CAA
         P   T   R   L   L   L   E   Y   L   E   E   K   Y   E   E   H   L   Y   E   R
   1561 CCC ACT CGA CTT CTT TTG GAA TAT CTT GAA GAA AAA TAT GAA GAG CAT TTG TAT GAG CGC
         D   E   G   D   K   W   R   N   K   K   F   E   L   G   L   E   F   P   N   L
   1621 GAT GAA GGT GAT AAA TGG CGA AAC AAA AAG TTT GAA TTG GGT TTG GAG TTT CCC AAT CTT
         P   Y   Y   I   D   G   D   V   K   L   T   Q   S   M   A   I   I   R   Y   I
   1681 CCT TAT TAT ATT GAT GGT GAT GTT AAA TTA ACA CAG TCT ATG GCC ATC ATA CGT TAT ATA
         A   D   K   H   N   M   L   G   G   C   P   K   E   R   A   E   I   S   M   L
   1741 GCT GAC AAG CAC AAC ATG TTG GGT GGT TGT CCA AAA GAG CGT GCA GAG ATT TCA ATG CTT
         E   G   A   V   L   D   I   R   Y   G   V   S   R   I   A   Y   S   K   D   F
   1801 GAA GGA GCG GTT TTG GAT ATT AGA TAC GGT GTT TCG AGA ATT GCA TAT AGT AAA GAC TTT
```

Fig. 7J (continued)

```
           E   T   L   K   V   D   F   L   S   K   L   P   E   M   L   K   M   F   E   D
1861 GAA ACT CTC AAA GTT GAT TTT CTT AGC AAG CTA CCT GAA ATG CTG AAA ATG TTC GAA GAT
           R   L   C   H   K   T   Y   L   N   G   D   H   V   T   H   P   D   F   M   L
1921 CGT TTA TGT CAT AAA ACA TAT TTA AAT GGT GAT CAT GTA ACC CAT CCT GAC TTC ATG TTG
           Y   D   A   L   D   V   V   L   Y   M   D   P   M   C   L   D   A   F   P   K
1981 TAT GAC GCT CTT GAT GTT GTT TTA TAC ATG GAC CCA ATG TGC CTG GAT GCG TTC CCA AAA
           L   V   C   F   K   K   R   I   E   A   I   P   Q   I   D   K   Y   L   K   S
2041 TTA GTT TGT TTT AAA AAA CGT ATT GAA GCT ATC CCA CAA ATT GAT AAG TAC TTG AAA TCC
           S   K   Y   I   A   W   P   L   Q   G   W   Q   A   T   F   G   G   G   D   H
2101 AGC AAG TAT ATA GCA TGG CCT TTG CAG GGC TGG CAA GCC ACG TTT GGT GGT GGC GAC CAT
                                                   BamHI           EcoRI
                                                   ~~~~~~~~        ~~~~~~~~
           P   P   K   S   D   L   V   P   R   G   S   P   G   I   P   S   E   L   N   D
2161 CCT CCA AAA TCG GAT CTG GTT CCG CGT GGA TCC CCA GGA ATT CCA AGC GAA CTG AAC GAC
           I   N   K   I   E   L   K   N   L   S   G   E   I   I   K   E   N   G   K   E
2221 ATC AAC AAA ATT GAG CTG AAA AAC CTG AGC GGC GAA ATC ATC AAA GAA AAC GGC AAG GAA
           A   I   K   Y   T   S   S   D   T   A   S   H   K   G   W   K   A   T   L   S
2281 GCT ATT AAA TAT ACT TCC AGC GAC ACC GCT TCC CAT AAA GGC TGG AAG GCA ACT CTG AGC
           G   T   F   I   E   D   P   H   S   D   K   K   T   A   L   L   N   L   E   G
2341 GGC ACC TTC ATT GAA GAC CCG CAT TCC GAC AAG AAA ACT GCT CTG CTG AAC CTG GAA GGC
           F   I   P   S   D   K   Q   I   F   G   S   K   Y   Y   G   K   M   K   W   P
2401 TTT ATC CCG TCC GAC AAA CAG ATT TTC GGC TCT AAA TAT TAC GGC AAA ATG AAA TGG CCG
           E   T   Y   R   I   N   V   K   S   A   D   V   N   N   N   I   K   I   A   N
2461 GAA ACT TAT CGC ATT AAT GTG AAA AGC GCT GAC GTG AAC AAT AAC ATC AAA ATC GCA AAC
           S   I   P   K   N   T   I   D   K   K   D   V   S   N   S   I   G   Y   S   I
2521 TCC ATT CCG AAA AAT ACT ATC GAC AAA AAA GAC GTG TCC AAT TCC ATT GGC TAT TCC ATC
           G   G   N   I   S   V   E   G   K   T   A   G   A   G   I   N   A   S   Y   N
2581 GGC GGT AAC ATC TCC GTG GAA GGC AAA ACT GCT GGC GCT GGC ATC AAC GCT TCC TAT AAC
           V   Q   N   T   I   S   Y   E   Q   P   D   F   R   T   I   Q   R   K   D   D
2641 GTC CAA AAC ACT ATC AGC TAT GAA CAA CCG GAC TTC CGC ACC ATT CAA CGC AAA GAC GAT
           A   N   L   A   S   W   D   I   K   F   V   E   T   K   D   G   Y   N   I   D
2701 GCA AAC CTG GCA TCC TGG GAC ATC AAA TTC GTT GAG ACT AAG GAC GGC TAT AAC ATC GAC
           S   Y   H   A   I   Y   G   N   Q   L   F   M   K   S   R   L   Y   N   N   G
2761 TCC TAT CAT GCT ATT TAT GGC AAC CAA CTG TTC ATG AAA TCC CGC CTG TAT AAC AAT GGC
           D   K   N   F   T   D   D   R   D   L   S   T   L   I   S   G   G   F   S   P
2821 GAC AAA AAC TTC ACC GAC GAT CGC GAC CTG TCC ACC CTG ATT TCC GGC GGC TTC TCC CCG
           N   M   A   L   A   L   T   A   P   K   N   A   K   E   S   V   I   I   V   E
2881 AAC ATG GCT CTG GCA CTG ACC GCA CCT AAA AAT GCT AAA GAA TCC GTG ATC ATC GTG GAA
           Y   Q   R   F   D   N   D   Y   I   L   N   W   E   T   T   Q   W   R   G   T
2941 TAT CAA CGC TTC GAC AAC GAC TAT ATT CTG AAT TGG GAA ACT ACT CAA TGG CGC GGC ACC
           N   K   L   S   S   T   S   E   Y   N   E   F   M   F   K   I   N   W   Q   D
3001 AAC AAA CTT TCC TCA ACC AGC GAA TAT AAC GAA TTT ATG TTC AAA ATC AAC TGG CAA GAC
           H   K   I   E   Y   Y   L   *
3061 CAT AAA ATC GAA TAT TAT CTG TAA CCG CGG GGC TGT TTT GGC GGA TGA GAG AAG ATT TTC
```

Fig. 8B
blaPlcC: 18.4/14.01
GstnetB: 59.792
dsbA cbh: 39.93/37.18
ompA cpEc: : 17.055/14.259
Fba: 30.432
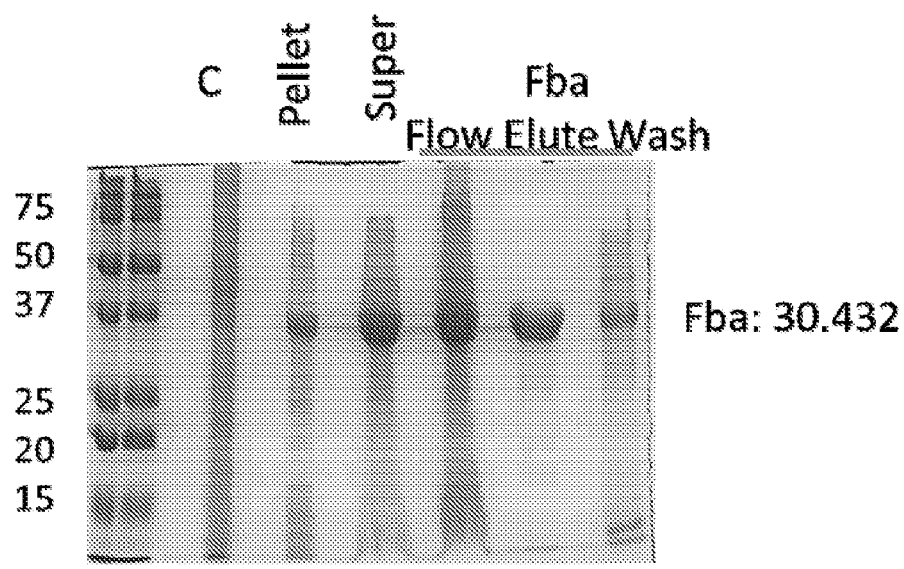
Fig. 8C

SEQUENCE LISTING

```
<160> NUMBER OF SEQ ID NOS: 62

<210> SEQ ID NO 1
<211> LENGTH: 1215
<212> TYPE: DNA
<213> ORGANISM: Salmonella sp.

<400> SEQUENCE: 1
atgctaacca catcattaac gttaaataaa gagaaatgga agccgatctg gaataaagcg      60
ctggtttttc tttttgttgc cacgtatttt ctggatggta ttacgcgtta taaacatttg     120
ataatcatac ttatggttat caccgcgatt tatcaggtct cacgctcacc gaaaagtttc     180
cccctctttt tcaaaaatag cgtattttat agcgtagcag tattatcatt aatccttgtt     240
tattccatac tcatatcgcc agatatgaaa gaaagtttca aggaatttga aaatacggta     300
ctggagggct tcttattata tactttatta attcccgtac tattaaaaga tgaaacaaaa     360
gaaacggttg cgaaaatagt acttttctcc tttttaacaa gtttaggact tcgctgcctt     420
gcagagagta ttctgtatat cgaggactat aataaaggga ttatgccatt cataagctat     480
gcgcatcgac atatgtccga ttccatggtt ttcttatttc cagcattatt gaatatttgg     540
ctgtttagaa aaaatgcaat taagttggtt tttttggtgc ttagcgccat ctacctttc      600 tttatcctgg gaaccctatc gcgagggca tggttggcgg tgcttatagt aggtgttctg      660 tgggcaaatac tgaaccgcca atggaagtta ataggagtta gtgccatttt attagccatt     720
atcggcgctt tggttatcac tcaacataat aacaaaccag acccagaaca tttactgtat     780
aaattacagc agacagatag ctcatatcgt tatactaacg gaacccaggg caccgcgtgg     840
atactgattc aggaaaaccc gatcaagggc tacggctatg gtaatgatgt gtatgatggt     900
gtttataata aacgcgttgt cgattatcca acgtggacct ttaaagaatc tatcggtccg     960
cataatacca ttctgtacat ctggtttagt gcaggcatat tgggtctggc gagcctggtc    1020
tatttatatg gcgctatcat cagggaaaca gccagctcta ccctcaggaa agtagagata    1080
agcccctaca atgctcatct cttgctattt ttatctttcg tcggttttta tatcgttcgt    1140
ggcaattttg aacaggtcga tattgctcaa attggtatca ttaccggttt tctgctggcg    1200
ctaagaaata gataa                                                    1215
```

```
<210> SEQ ID NO 2
<211> LENGTH: 404
<212> TYPE: PRT
<213> ORGANISM: Salmonella sp.

<400> SEQUENCE: 2
```

| | | | | | | | | | | | | | | | |
|---|---|---|---|---|---|---|---|---|---|---|---|---|---|---|---|
| Met | Leu | Thr | Thr | Ser | Leu | Thr | Leu | Asn | Lys | Glu | Lys | Trp | Lys | Pro | Ile |
| 1 | | | | 5 | | | | | 10 | | | | | 15 | |
| Trp | Asn | Lys | Ala | Leu | Val | Phe | Leu | Phe | Val | Ala | Thr | Tyr | Phe | Leu | Asp |
| | | | 20 | | | | | 25 | | | | | 30 | | |
| Gly | Ile | Thr | Arg | Tyr | Lys | His | Leu | Ile | Ile | Ile | Leu | Met | Val | Ile | Thr |
| | | | | 35 | | | | | 40 | | | | | 45 | |
| Ala | Ile | Tyr | Gln | Val | Ser | Arg | Ser | Pro | Lys | Ser | Phe | Pro | Pro | Leu | Phe |
| | 50 | | | | | 55 | | | | | 60 | | | | |
| Lys | Asn | Ser | Val | Phe | Tyr | Ser | Val | Ala | Val | Leu | Ser | Leu | Ile | Leu | Val |
| 65 | | | | | 70 | | | | | 75 | | | | | 80 |
| Tyr | Ser | Ile | Leu | Ile | Ser | Pro | Asp | Met | Lys | Glu | Ser | Phe | Lys | Glu | Phe |
| | | | | 85 | | | | | 90 | | | | | 95 | |
| Glu | Asn | Thr | Val | Leu | Glu | Gly | Phe | Leu | Leu | Tyr | Thr | Leu | Leu | Ile | Pro |
| | | | 100 | | | | | 105 | | | | | 110 | | |
| Val | Leu | Leu | Lys | Asp | Glu | Thr | Lys | Glu | Thr | Val | Ala | Lys | Ile | Val | Leu |
| | | | | 115 | | | | | 120 | | | | | 125 | |
| Phe | Ser | Phe | Leu | Thr | Ser | Leu | Gly | Leu | Arg | Cys | Leu | Ala | Glu | Ser | Ile |
| | 130 | | | | | 135 | | | | | 140 | | | | |
| Leu | Tyr | Ile | Glu | Asp | Tyr | Asn | Lys | Gly | Ile | Met | Pro | Phe | Ile | Ser | Tyr |
| 145 | | | | | 150 | | | | | 155 | | | | | 160 |
| Ala | His | Arg | His | Met | Ser | Asp | Ser | Met | Val | Phe | Leu | Phe | Pro | Ala | Leu |
| | | | | 165 | | | | | 170 | | | | | 175 | |
| Leu | Asn | Ile | Trp | Leu | Phe | Arg | Lys | Asn | Ala | Ile | Lys | Leu | Val | Phe | Leu |
| | | | 180 | | | | | 185 | | | | | 190 | | |
| Val | Leu | Ser | Ala | Ile | Tyr | Leu | Phe | Phe | Ile | Leu | Gly | Thr | Leu | Ser | Arg |
| | | | | 195 | | | | | 200 | | | | | 205 | |
| Gly | Ala | Trp | Leu | Ala | Val | Leu | Ile | Val | Gly | Val | Leu | Trp | Ala | Ile | Leu |
| | 210 | | | | | 215 | | | | | 220 | | | | |
| Asn | Arg | Gln | Trp | Lys | Leu | Ile | Gly | Val | Gly | Ala | Ile | Leu | Leu | Ala | Ile |
| 225 | | | | | 230 | | | | | 235 | | | | | 240 |
| Ile | Gly | Ala | Leu | Val | Ile | Thr | Gln | His | Asn | Asn | Lys | Pro | Asp | Pro | Glu |
| | | | | 245 | | | | | 250 | | | | | 255 | |
| His | Leu | Leu | Tyr | Lys | Leu | Gln | Gln | Thr | Asp | Ser | Ser | Tyr | Arg | Tyr | Thr |
| | | | 260 | | | | | 265 | | | | | 270 | | |
| Asn | Gly | Thr | Gln | Gly | Thr | Ala | Trp | Ile | Leu | Ile | Gln | Glu | Asn | Pro | Ile |
| | | | | 275 | | | | | 280 | | | | | 285 | |
| Lys | Gly | Tyr | Gly | Tyr | Gly | Asn | Asp | Val | Tyr | Asp | Gly | Val | Tyr | Asn | Lys |
| | 290 | | | | | 295 | | | | | 300 | | | | |
| Arg | Val | Val | Asp | Tyr | Pro | Thr | Trp | Thr | Phe | Lys | Glu | Ser | Ile | Gly | Pro |
| 305 | | | | | 310 | | | | | 315 | | | | | 320 |
| His | Asn | Thr | Ile | Leu | Tyr | Ile | Trp | Phe | Ser | Ala | Gly | Ile | Leu | Gly | Leu |
| | | | | 325 | | | | | 330 | | | | | 335 | |
| Ala | Ser | Leu | Val | Tyr | Leu | Tyr | Gly | Ala | Ile | Ile | Arg | Glu | Thr | Ala | Ser |
| | | | 340 | | | | | 345 | | | | | 350 | | |
| Ser | Thr | Leu | Arg | Lys | Val | Glu | Ile | Ser | Pro | Tyr | Asn | Ala | His | Leu | Leu |
| | | | | 355 | | | | | 360 | | | | | 365 | |
| Leu | Phe | Leu | Ser | Phe | Val | Gly | Phe | Tyr | Ile | Val | Arg | Gly | Asn | Phe | Glu |
| | 370 | | | | | 375 | | | | | 380 | | | | |

Gln Val Asp Ile Ala Gln Ile Gly Ile Ile Thr Gly Phe Leu Leu Ala
385                 390                 395                 400

Leu Arg Asn Arg

<210> SEQ ID NO 3
<211> LENGTH: 453
<212> TYPE: DNA
<213> ORGANISM: Salmonella sp.

<400> SEQUENCE: 3
atgactgaca acaataccgc attaaagaag gctggcctga agtaacgct tcctcgttta      60 aaaattctgg aagttcttca ggaaccagat aaccatcacg tcagtgcgga agatttatac   120
aaacgcctga tcgacatggg tgaagaaatc ggtctggcaa ccgtataccg tgtgctgaac   180
cagtttgacg atgccggtat cgtgacccgc cataattttg aaggcggtaa atccgttttt   240
gaactgacgc aacagcatca tcacgaccat cttatctgcc ttgattgcgg aaaagtgatt   300
gaatttagtg atgactctat tgaagcgcgc cagcgtgaaa ttgcggcgaa acacggtatt   360
cgtttaacta atcacagcct ctatctttac ggccactgcg ctgaaggcga ctgccgcgaa   420
gacgagcacg cgcacgatga cgcgactaaa taa                                453

<210> SEQ ID NO 4
<211> LENGTH: 150
<212> TYPE: PRT
<213> ORGANISM: Salmonella sp.

<400> SEQUENCE: 4

Met Thr Asp Asn Asn Thr Ala Leu Lys Lys Ala Gly Leu Lys Val Thr
1               5                   10                  15

Leu Pro Arg Leu Lys Ile Leu Glu Val Leu Gln Glu Pro Asp Asn His
            20                  25                  30

His Val Ser Ala Glu Asp Leu Tyr Lys Arg Leu Ile Asp Met Gly Glu
        35                  40                  45

Glu Ile Gly Leu Ala Thr Val Tyr Arg Val Leu Asn Gln Phe Asp Asp
    50                  55                  60

Ala Gly Ile Val Thr Arg His Asn Phe Glu Gly Gly Lys Ser Val Phe
65                  70                  75                  80

Glu Leu Thr Gln Gln His His His Asp His Leu Ile Cys Leu Asp Cys
                85                  90                  95

Gly Lys Val Ile Glu Phe Ser Asp Asp Ser Ile Glu Ala Arg Gln Arg
            100                 105                 110

Glu Ile Ala Ala Lys His Gly Ile Arg Leu Thr Asn His Ser Leu Tyr
        115                 120                 125

Leu Tyr Gly His Cys Ala Glu Gly Asp Cys Arg Glu Asp Glu His Ala
    130                 135                 140

His Asp Asp Ala Thr Lys
145                 150

<210> SEQ ID NO 5

<400> SEQUENCE: 5

000

<210> SEQ ID NO 6

<400> SEQUENCE: 6

000

<210> SEQ ID NO 7
<211> LENGTH: 1011
<212> TYPE: DNA
<213> ORGANISM: Salmonella sp.

<400> SEQUENCE: 7

| | | |
|---|---|---|
| atgccgatta ctataggggaa tggttttta aaaagtgaaa tccttaccaa ctccccaagg | 60 |
| aatacgaaag aagcatggtg aaagttttta tgggaaaaaa ttaaagactt cttttttct | 120 |
| actggcaaag caaaagcgga ccgttgtcta catgagatgt tgtttgccga acgcgccccc | 180 |
| acacgagagc ggcttacaga dattttttt gagttgaaag agttagcctg cgcatcgcaa | 240 |
| agagatagat tcaggttca taatcctcat gaaaatgatg ccaccattat tcttcgcatc | 300 |
| atggatcaaa acgaagagaa cgaattgtta cgtatcactc aaaataccga taccttagc | 360 |
| tgtgaagtca tggggaatct ttattttta atgaaagatc gcccggatat tttaaaatcg | 420 |
| catccacaaa tgacggccat gattaagaga agatatagcg aaatcgtaga ctaccccctc | 480 |
| ccttcgacat tatgtctcaa tcctgctggc gcgccgatat tatcggttcc attagacaac | 540 |
| atagaggggt atttatatac tgaattgaga aaaggacatt tagatgggtg aaagcgcaa | 600 |
| gaaaaggcaa cctacctggc agcgaaaatt cagtctggga ttgaaaagac aacgcgcatt | 660 |
| ttacaccatg cgaatatatc cgaaagtact cagcaaaacg catttttaga aacaatggcg | 720 |
| atgtgtggat taaacagct tgaaatacca ccaccgcata cccacatacc tattgaaaaa | 780 |
| atggtaaaag aggttttact agcggataag acgtttcagg cgttcctcgt aacggatccc | 840 |
| agcaccagcc aaagtatgtt agctgagata gtcgaagcca tctctgatca ggttttcac | 900 |
| gccatttta gaatagaccc ccaggctata caaaaaatgg cggaagaaca gttaaccacg | 960 |
| ctacacgttc gctcagaaca caaagcggc tgtttatgtt gttttttata a | 1011 |

<210> SEQ ID NO 8
<211> LENGTH: 336
<212> TYPE: PRT
<213> ORGANISM: Salmonella sp.

<400> SEQUENCE: 8

Met Pro Ile Thr Ile Gly Asn Gly Phe Leu Lys Ser Glu Ile Leu Thr
1               5                   10                  15

Asn Ser Pro Arg Asn Thr Lys Glu Ala Trp Trp Lys Val Leu Trp Glu
            20                  25                  30

Lys Ile Lys Asp Phe Phe Phe Ser Thr Gly Lys Ala Lys Ala Asp Arg
        35                  40                  45

Cys Leu His Glu Met Leu Phe Ala Glu Arg Ala Pro Thr Arg Glu Arg
    50                  55                  60

Leu Thr Glu Ile Phe Phe Glu Leu Lys Glu Leu Ala Cys Ala Ser Gln
65                  70                  75                  80

Arg Asp Arg Phe Gln Val His Asn Pro His Glu Asn Asp Ala Thr Ile
                85                  90                  95

Ile Leu Arg Ile Met Asp Gln Asn Glu Glu Asn Glu Leu Leu Arg Ile
            100                 105                 110

Thr Gln Asn Thr Asp Thr Phe Ser Cys Glu Val Met Gly Asn Leu Tyr
        115                 120                 125

Phe Leu Met Lys Asp Arg Pro Asp Ile Leu Lys Ser His Pro Gln Met
    130                 135                 140

Thr Ala Met Ile Lys Arg Arg Tyr Ser Glu Ile Val Asp Tyr Pro Leu
145                 150                 155                 160

Pro Ser Thr Leu Cys Leu Asn Pro Ala Gly Ala Pro Ile Leu Ser Val
                165                 170                 175

Pro Leu Asp Asn Ile Glu Gly Tyr Leu Tyr Thr Glu Leu Arg Lys Gly
            180                 185                 190

His Leu Asp Gly Trp Lys Ala Gln Glu Lys Ala Thr Tyr Leu Ala Ala
        195                 200                 205

Lys Ile Gln Ser Gly Ile Glu Lys Thr Thr Arg Ile Leu His His Ala
210                 215                 220

Asn Ile Ser Glu Ser Thr Gln Gln Asn Ala Phe Leu Glu Thr Met Ala
225                 230                 235                 240

Met Cys Gly Leu Lys Gln Leu Glu Ile Pro Pro His Thr His Ile
                245                 250                 255

Pro Ile Glu Lys Met Val Lys Glu Val Leu Leu Ala Asp Lys Thr Phe
            260                 265                 270

Gln Ala Phe Leu Val Thr Asp Pro Ser Thr Ser Gln Ser Met Leu Ala
        275                 280                 285

Glu Ile Val Glu Ala Ile Ser Asp Gln Val Phe His Ala Ile Phe Arg
        290                 295                 300

Ile Asp Pro Gln Ala Ile Gln Lys Met Ala Glu Gln Leu Thr Thr
305                 310                 315                 320

Leu His Val Arg Ser Glu Gln Gln Ser Gly Cys Leu Cys Cys Phe Leu
                325                 330                 335

<210> SEQ ID NO 9
<211> LENGTH: 1083
<212> TYPE: DNA
<213> ORGANISM: E. coli

<400> SEQUENCE: 9

```
gtgaaaccag taacgttata cgatgtcgca gagtatgccg gtgtctctta tcagaccgtt    60
tcccgcgtgg tgaaccaggc cagccacgtt tctgcgaaaa cgcgggaaaa agtggaagcg   120
gcgatggcgg agctgaatta cattcccaac cgcgtggcac aacaactggc gggcaaacag   180
tcgttgctga ttggcgttgc cacctccagt ctggccctgc acgcgccgtc gcaaattgtc   240
gcggcgatta aatctcgcgc cgatcaactg ggtgccagcg tggtggtgtc gatggtagaa   300
cgaagcggcg tcgaagcctg taaagcggcg gtgcacaatc ttctcgcgca acgcgtcagt   360
gggctgatca ttaactatcc gctggatgac caggatgcca ttgctgtgga agctgcctgc   420
actaatgttc cggcgttatt tcttgatgtc tctgaccaga cacccatcaa cagtattatt   480
ttctcccatg aagacggtac gcgactgggc gtggagcatc tggtcgcatt gggtcaccag   540
caaatcgcgc tgttagcggg cccattaagt tctgtctcgg cgcgtctgcg tctggctggc   600
tggcataaat atctcactcg caatcaaatt cagccgatag cggaacggga aggcgactgg   660
agtgccatgt ccggttttca acaaaccatg caaatgctga atgagggcat cgttcccact   720
gcgatgctgg ttgccaacga tcagatggcg ctgggcgcaa tgcgcgccat taccgagtcc   780
gggctgcgcg ttggtgcgga tatctcggta gtgggatacg acgataccga agacagctca   840
tgttatatcc cgccgttaac caccatcaaa caggattttc gcctgctggg gcaaaccagc   900
gtggaccgct tgctgcaact ctctcagggc caggcggtga aggcaatca gctgttgccc   960 gtctcactgg tgaaaagaaa aaccaccctg gcgcccaata cgcaaaccgc ctctccccgc  1020
```

```
gcgttggccg attcattaat gcagctggca cgacaggttt cccgactgga aagcgggcag    1080
tga                                                                  1083
```

<210> SEQ ID NO 10
<211> LENGTH: 360
<212> TYPE: PRT
<213> ORGANISM: E. coli

<400> SEQUENCE: 10

```
Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360
```

355					360

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14
<211> LENGTH: 368
<212> TYPE: PRT
<213> ORGANISM: Artificial Sequence
<220> FEATURE:
<223> OTHER INFORMATION: Synthetic

<400> SEQUENCE: 14

Met Lys Lys Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Met Cys Thr Gly Leu Ala Leu Glu Thr Lys Asp Gly Leu
        35                  40                  45

His Leu Phe Gly Arg Asn Met Asp Ile Glu Tyr Ser Phe Asn Gln Ser
    50                  55                  60

Ile Ile Phe Ile Pro Arg Asn Phe Lys Cys Val Asn Lys Ser Asn Lys
65                  70                  75                  80

Lys Glu Leu Thr Thr Lys Tyr Ala Val Leu Gly Met Gly Thr Ile Phe
                85                  90                  95

Asp Asp Tyr Pro Thr Phe Ala Asp Gly Met Asn Glu Lys Gly Leu Gly
            100                 105                 110

Cys Ala Gly Leu Asn Phe Pro Val Tyr Val Ser Tyr Ser Lys Glu Asp
        115                 120                 125

Ile Glu Gly Lys Thr Asn Ile Pro Val Tyr Asn Phe Leu Leu Trp Val
    130                 135                 140

Leu Ala Asn Phe Ser Ser Val Glu Glu Val Lys Glu Ala Leu Lys Asn
145                 150                 155                 160

Ala Asn Ile Val Asp Ile Pro Ile Ser Glu Asn Ile Pro Asn Thr Thr
                165                 170                 175

Leu His Trp Met Ile Ser Asp Ile Thr Gly Lys Ser Ile Val Val Glu
            180                 185                 190

Gln Thr Lys Glu Lys Leu Asn Val Phe Asp Asn Ile Gly Val Leu
        195                 200                 205

Thr Asn Ser Pro Thr Phe Asp Trp His Val Ala Asn Leu Asn Gln Tyr
    210                 215                 220

Val Gly Leu Arg Tyr Asn Gln Val Pro Glu Phe Lys Leu Gly Asp Gln
225                 230                 235                 240

Ser Leu Thr Ala Leu Gly Gln Gly Thr Gly Leu Val Gly Leu Pro Gly

```
                    245                 250                 255
Asp Phe Thr Pro Ala Ser Arg Phe Ile Arg Val Ala Phe Leu Arg Asp
                260                 265                 270

Ala Met Ile Lys Asn Asp Lys Asp Ser Ile Asp Leu Ile Glu Phe Phe
            275                 280                 285

His Ile Leu Asn Asn Val Ala Met Val Arg Gly Ser Thr Arg Thr Val
        290                 295                 300

Glu Glu Lys Ser Asp Leu Thr Gln Tyr Thr Ser Cys Met Cys Leu Glu
305                 310                 315                 320

Lys Gly Ile Tyr Tyr Tyr Asn Thr Tyr Glu Asn Asn Gln Ile Asn Ala
                325                 330                 335

Ile Asp Met Asn Lys Glu Asn Leu Asp Gly Asn Glu Ile Lys Thr Tyr
            340                 345                 350

Lys Tyr Asn Lys Thr Leu Ser Ile Asn His Val Asn Gly His His His
        355                 360                 365
```

<210> SEQ ID NO 15
<211> LENGTH: 1236
<212> TYPE: DNA
<213> ORGANISM: Artificial Sequence
<220> FEATURE:
<223> OTHER INFORMATION: Synthetic

<400> SEQUENCE: 15

```
ggatcttccg aagaccttc cattctgaaa tgagctgttg acaattaatc atccggctcg      60
tataatgtgt ggaattgtga gcggataaca atttcacaca ggaaacagac catgaaaaaa    120
caacatttcc gtgtcgccct tattcccttt tttgcggcat tttgccttcc tgttttttgct   180
cacccagaaa cgctggtgaa agtaaaagat gctgaactcg agctccacgt gggtaccatg    240
tgcacaggcc tggcactgga actaaagac ggcctgcact tgttcggccg caacatggac     300
atcgaatatt ctttcaatca atctattatt ttcattccgc gcaacttcaa gtgcgtgaac    360
aaatccaaca aaaagaact gaccaccaaa tacgctgtgc tgggcatggg cactatcttc     420
gacgattacc cgaccttcgc tgacggcatg aacgaaaaag gcctgggctg tgcgggcctg    480
aacttcccgg tgtatgtgag ctactctaaa gaagacatcg aaggcaaaac caacatcccg    540
gtgtacaact tcctgctgtg ggtgctggcg aacttcagct ctgtggaaga ggtgaaggaa    600
gccctgaaaa acgcgaacat cgtggacatc ccgatctcag agaacatccc gaacaccacg    660
ctgcactgga tgatctccga catcaccggc aaatccatcg tggtggaaca gaccaaggaa    720
aaactgaacg tgttcgacaa caacatcggc gtgctgacca cagcccgac gttcgactgg    780
cacgtggcca acctgaacca gtacgtgggc ctgcgctata accaggtgcc ggagttcaag    840
ctgggcgacc agtctctgac tgctctgggc cagggcactg gcctggtggg cctgccgggc    900
gacttcacac cggcgtctcg cttcatccgc gtagcgtttc tgcgtgacgc gatgatcaaa    960
aacgacaaag acagcatcga cctgatcgaa ttcttccaca tcctgaacaa cgtggctatg   1020
gtacgcggct ccactcgcac agtggaagag aaatccgacc tgacacagta cacgtcttgc   1080
atgtgcctgg aaaaaggcat ctattattat aacacctatg aaaacaacca gatcaacgca   1140
atcgacatga caaagaaaa cctggacggc aacgaaatca aacctacaa atacaacaaa    1200
accctgagca tcaaccacgt gaacggtcac catcat                             1236
```

<210> SEQ ID NO 16
<211> LENGTH: 174
<212> TYPE: PRT

<213> ORGANISM: Artificial Sequence
<220> FEATURE:
<223> OTHER INFORMATION: Synthetic

<400> SEQUENCE: 16

```
Met Lys Lys Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Leu Glu Leu His Val Gly Thr Asp Ile Glu Lys Glu Ile
            35                  40                  45

Leu Asp Leu Ala Ala Ala Thr Glu Arg Leu Asn Leu Thr Asp Ala Leu
50                  55                  60

Asn Ser Asn Pro Ala Gly Asn Leu Tyr Asp Trp Arg Ser Ser Asn Ser
65                  70                  75                  80

Tyr Pro Trp Thr Gln Lys Leu Asn Leu His Leu Thr Ile Thr Ala Thr
                85                  90                  95

Gly Gln Lys Tyr Arg Ile Leu Ala Ser Lys Ile Val Asp Phe Asn Ile
            100                 105                 110

Tyr Ser Asn Asn Phe Asn Asn Leu Val Lys Leu Glu Gln Ser Leu Gly
        115                 120                 125

Asp Gly Val Lys Asp His Tyr Val Asp Ile Ser Leu Asp Ala Gly Gln
130                 135                 140

Tyr Val Leu Val Met Lys Ala Asn Ser Ser Tyr Ser Gly Asn Tyr Pro
145                 150                 155                 160

Tyr Ser Ile Leu Phe Gln Lys Phe His His His His His
                165                 170
```

<210> SEQ ID NO 17
<211> LENGTH: 720
<212> TYPE: DNA
<213> ORGANISM: Artificial Sequence
<220> FEATURE:
<223> OTHER INFORMATION: Synthetic

<400> SEQUENCE: 17

```
ggatcttccg aagaccttc cattctgaaa tgagctgttg acaattaatc atccggctcg     60
tataatgtgt ggaattgtga gcggataaca atttcacaca ggaaacagac catgaaaaaa    120
caacatttcc gtgtcgccct tattccctttt tttgcggcat tttgccttcc tgttttttgct    180 cacccagaaa cgctggtgaa agtaaaagat gctgaactcg agctccacgt gggtaccgac    240
atcgaaaaag aaatcctgga cctggcggcg gcgaccgaac gtctgaacct gaccgacgcg    300
ctgaactcta acccggcggg caacctgtac gactggcgtt cttctaactc ttacccgtgg    360
acccagaaac tgaacctgca cctgaccatc accgcgaccg gtcagaaata ccgtatcctg    420
gcgtctaaaa tcgttgactt caacatctac tctaacaact caacaacct ggttaaactg     480 gaacagtctc tgggtgacgg tgttaaagac cactacgttg acatctctct ggacgcgggt    540
cagtacgttc tggttatgaa agcgaactct cctactccg taactaccc gtactctatc     600 ctgttccaga aattcgccgg ccaccatcac catcaccatt agccggctaa tctgcagcca    660
agctcccaag cttggctgtt ttggcggatg agagaagatt ttcagcctga tacagattaa    720
```

<210> SEQ ID NO 18
<211> LENGTH: 680
<212> TYPE: PRT
<213> ORGANISM: Artificial Sequence
<220> FEATURE:

<223> OTHER INFORMATION: Synthetic

<400> SEQUENCE: 18

Met Lys Lys Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Pro Ser Val Gly Asn Asn Val Lys Glu Leu Val Ala
        35                  40                  45

Tyr Ile Ser Thr Ser Gly Glu Lys Asp Ala Gly Thr Asp Asp Tyr Met
    50                  55                  60

Tyr Phe Gly Ile Lys Thr Lys Asp Gly Lys Thr Gln Glu Trp Glu Met
65                  70                  75                  80

Asp Asn Pro Gly Asn Asp Phe Met Ala Gly Ser Lys Asp Thr Tyr Thr
                85                  90                  95

Phe Lys Leu Lys Asp Glu Asn Leu Lys Ile Asp Asp Ile Gln Asn Met
            100                 105                 110

Trp Ile Arg Lys Arg Lys Tyr Thr Ala Phe Pro Asp Ala Tyr Lys Pro
        115                 120                 125

Glu Asn Ile Lys Val Ile Ala Asn Gly Lys Val Val Asp Lys Asp
    130                 135                 140

Ile Asn Glu Trp Ile Ser Gly Asn Ser Thr Tyr Asn Ile Lys Met Ala
145                 150                 155                 160

Pro Ile Leu Gly Tyr Trp Lys Ile Lys Gly Leu Val Gln Pro Thr Arg
                165                 170                 175

Leu Leu Leu Glu Tyr Leu Glu Glu Lys Tyr Glu Glu His Leu Tyr Glu
            180                 185                 190

Arg Asp Glu Gly Asp Lys Trp Arg Asn Lys Lys Phe Glu Leu Gly Leu
        195                 200                 205

Glu Phe Pro Asn Leu Pro Tyr Tyr Ile Asp Gly Asp Val Lys Leu Thr
    210                 215                 220

Gln Ser Met Ala Ile Ile Arg Tyr Ile Ala Asp Lys His Asn Met Leu
225                 230                 235                 240

Gly Gly Cys Pro Lys Glu Arg Ala Glu Ile Ser Met Leu Glu Gly Ala
                245                 250                 255

Val Leu Asp Ile Arg Tyr Gly Val Ser Arg Ile Ala Tyr Ser Lys Asp
            260                 265                 270

Phe Glu Thr Leu Lys Val Asp Phe Leu Ser Lys Leu Pro Glu Met Leu
        275                 280                 285

Lys Met Phe Glu Asp Arg Leu Cys His Lys Thr Tyr Leu Asn Gly Asp
    290                 295                 300

His Val Thr His Pro Asp Phe Met Leu Tyr Asp Ala Leu Asp Val Val
305                 310                 315                 320

Leu Tyr Met Asp Pro Met Cys Leu Asp Ala Phe Pro Lys Leu Val Cys
                325                 330                 335

Phe Lys Lys Arg Ile Glu Ala Ile Pro Gln Ile Asp Lys Tyr Leu Lys
            340                 345                 350

Ser Ser Lys Tyr Ile Ala Trp Pro Leu Gln Gly Trp Gln Ala Thr Phe
        355                 360                 365

Gly Gly Gly Asp His Pro Pro Lys Ser Asp Leu Val Pro Arg Gly Ser
    370                 375                 380

Pro Gly Ile Pro Ser Glu Leu Asn Asp Ile Asn Lys Ile Glu Leu Lys
385                 390                 395                 400

Asn Leu Ser Gly Glu Ile Ile Lys Glu Asn Gly Lys Glu Ala Ile Lys
                405                 410                 415
Tyr Thr Ser Ser Asp Thr Ala Ser His Lys Gly Trp Lys Ala Thr Leu
            420                 425                 430
Ser Gly Thr Phe Ile Glu Asp Pro His Ser Asp Lys Lys Thr Ala Leu
        435                 440                 445
Leu Asn Leu Glu Gly Phe Ile Pro Ser Asp Lys Gln Ile Phe Gly Ser
450                 455                 460
Lys Tyr Tyr Gly Lys Met Lys Trp Pro Glu Thr Tyr Arg Ile Asn Val
465                 470                 475                 480
Lys Ser Ala Asp Val Asn Asn Asn Ile Lys Ile Ala Asn Ser Ile Pro
                485                 490                 495
Lys Asn Thr Ile Asp Lys Lys Asp Val Ser Asn Ser Ile Gly Tyr Ser
            500                 505                 510
Ile Gly Gly Asn Ile Ser Val Glu Gly Lys Thr Ala Gly Ala Gly Ile
        515                 520                 525
Asn Ala Ser Tyr Asn Val Gln Asn Thr Ile Ser Tyr Glu Gln Pro Asp
530                 535                 540
Phe Arg Thr Ile Gln Arg Lys Asp Asp Ala Asn Leu Ala Ser Trp Asp
545                 550                 555                 560
Ile Lys Phe Val Glu Thr Lys Asp Gly Tyr Asn Ile Asp Ser Tyr His
                565                 570                 575
Ala Ile Tyr Gly Asn Gln Leu Phe Met Lys Ser Arg Leu Tyr Asn Asn
            580                 585                 590
Gly Asp Lys Asn Phe Thr Asp Asp Arg Asp Leu Ser Thr Leu Ile Ser
        595                 600                 605
Gly Gly Phe Ser Pro Asn Met Ala Leu Ala Leu Thr Ala Pro Lys Asn
610                 615                 620
Ala Lys Glu Ser Val Ile Ile Val Glu Tyr Gln Arg Phe Asp Asn Asp
625                 630                 635                 640
Tyr Ile Leu Asn Trp Glu Thr Thr Gln Trp Arg Gly Thr Asn Lys Leu
                645                 650                 655
Ser Ser Thr Ser Glu Tyr Asn Glu Phe Met Phe Lys Ile Asn Trp Gln
            660                 665                 670
Asp His Lys Ile Glu Tyr Tyr Leu
        675                 680

<210> SEQ ID NO 19
<211> LENGTH: 2280
<212> TYPE: DNA
<213> ORGANISM: Artificial Sequence
<220> FEATURE:
<223> OTHER INFORMATION: Synthetic

<400> SEQUENCE: 19
ggatcttccg gaagaccttc cattctgaaa tgagctgttg acaattaatc atccggctcg      60
tataatgtgt ggaattgtga gcggataaca atttcacaca ggaaacagac catgaaaaaa     120
caacatttcc gtgtcgccct tattcccttt tttgcggcat tttgccttcc tgttttttgct    180 cacccagaaa cgctggtgaa agtaaaagat gctgaactcg aggacccgtc cgtgggcaac    240
aacgtgaaag aactggtggc ttacatctcc actagcggcg aaaagacgc tggcaccgac    300 gactacatgt attcggcat caaaaccaag gacggcaaaa ctcaagaatg gaaatggac     360 aacccgggca cgacttcat ggctggcagc aagacactt tactttcaa attaaaagac     420 gaaaacctga aaattgacga catccaaaac atgtggattc gcaaacgtaa atataccgca    480

```
ttcccggacg cttataagcc ggaaaacatc aaggtgatcg caaacggcaa agtggtagtg    540
gacaaggaca tcaacgagtg gatttccggc aactccactt ataacatcaa ataataaaag    600
cttaggaaac agaccatggc ccctatacta ggttattgga aaattaaggg ccttgtgcaa    660
cccactcgac ttcttttgga atatcttgaa gaaaaatatg aagagcattt gtatgagcgc    720
gatgaaggtg ataaatggcg aaacaaaaag tttgaattgg gtttggagtt cccaatctt     780 ccttattata ttgatggtga tgttaaatta acacagtcta tggccatcat acgttatata    840
gctgacaagc acaacatgtt gggtggttgt ccaaagagc gtgcagagat ttcaatgctt     900
gaaggagcgg ttttggatat tagatacggt gtttcgagaa ttgcatatag taaagacttt    960
gaaactctca agttgatttt cttagcaag ctacctgaaa tgctgaaaat gttcgaagat     1020 cgttatgtc ataaaacata tttaaatggt gatcatgtaa cccatcctga cttcatgttg      1080
tatgacgctc ttgatgttgt tttatacatg gacccaatgt gcctggatgc gttcccaaaa    1140
ttagtttgtt ttaaaaaacg tattgaagct atcccacaaa ttgataagta cttgaaatcc    1200
agcaagtata tagcatggcc tttgcagggc tggcaagcca cgtttggtgg tggcgaccat    1260
cctccaaaat cggatctggt tccgcgtgga tccccaggaa ttccaagcga actgaacgac    1320
atcaacaaaa ttgagctgaa aaacctgagc ggcgaaatca tcaaagaaaa cggcaaggaa    1380
gctattaaat atacttccag cgacaccgct tcccataaag gctggaaggc aactctgagc    1440
ggcaccttca ttgaagaccc gcattccgac aagaaaactg ctctgctgaa cctggaaggc    1500
tttatcccgt ccgacaaaca gattttcggc tctaaatatt acggcaaaat gaaatggccg    1560
gaaacttatc gcattaatgt gaaaagcgct gacgtgaaca taacatcaa atcgcaaac     1620 tccattccga aaatactat cgacaaaaaa gacgtgtcca attccattgg ctattccatc    1680
ggcggtaaca tctccgtgga aggcaaaact gctggcgctg catcaacgc ttcctataac     1740 gtccaaaaca ctatcagcta tgaacaaccg gacttccgca ccattcaacg caaagacgat    1800
gcaaacctgg catcctggga catcaaattc gttgagacta aggacggcta taacatcgac    1860
tcctatcatg ctatttatgg caaccaactg ttcatgaaat cccgcctgta taacaatggc    1920
gacaaaaact tcaccgacga tcgcgacctg tccaccctga tttccggcgg cttctccccg    1980
aacatggctc tggcactgac cgcacctaaa aatgctaaag aatccgtgat catcgtggaa    2040
tatcaacgct tcgacaacga ctatattctg aattgggaaa ctactcaatg gcgcggcacc    2100
aacaaacttt cctcaaccag cgaatataac gaatttatgt tcaaaatcaa ctggcaagac    2160
cataaaatcg aatattatct gtaatggtac cagtactagt tgatcattcg aagcggcgg    2220 ccgcccgggc cctgcagcca agctcccaag cttggctgtt ttggcggatg agagaagatt    2280
```

<210> SEQ ID NO 20
<211> LENGTH: 1039
<212> TYPE: PRT
<213> ORGANISM: Artificial Sequence
<220> FEATURE:
<223> OTHER INFORMATION: Synthetic

<400> SEQUENCE: 20

Met Lys Lys Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Pro Ser Val Gly Asn Asn Val Lys Glu Leu Val Ala
        35                  40                  45

```
Tyr Ile Ser Thr Ser Gly Glu Lys Asp Ala Gly Thr Asp Asp Tyr Met
         50                  55                  60

Tyr Phe Gly Ile Lys Thr Lys Asp Gly Lys Thr Gln Glu Trp Glu Met
 65                  70                  75                  80

Asp Asn Pro Gly Asn Asp Phe Met Ala Gly Ser Lys Asp Thr Tyr Thr
                     85                  90                  95

Phe Lys Leu Lys Asp Glu Asn Leu Lys Ile Asp Asp Ile Gln Asn Met
                100                 105                 110

Trp Ile Arg Lys Arg Lys Tyr Thr Ala Phe Pro Asp Ala Tyr Lys Pro
            115                 120                 125

Glu Asn Ile Lys Val Ile Ala Asn Gly Lys Val Val Asp Lys Asp
            130                 135                 140

Ile Asn Glu Trp Ile Ser Gly Asn Ser Thr Tyr Asn Ile Lys Met Ala
145                 150                 155                 160

Pro Ile Leu Gly Tyr Trp Lys Ile Lys Gly Leu Val Gln Pro Thr Arg
                165                 170                 175

Leu Leu Leu Glu Tyr Leu Glu Glu Lys Tyr Glu Glu His Leu Tyr Glu
                180                 185                 190

Arg Asp Glu Gly Asp Lys Trp Arg Asn Lys Lys Phe Glu Leu Gly Leu
            195                 200                 205

Glu Phe Pro Asn Leu Pro Tyr Tyr Ile Asp Gly Asp Val Lys Leu Thr
210                 215                 220

Gln Ser Met Ala Ile Ile Arg Tyr Ile Ala Asp Lys His Asn Met Leu
225                 230                 235                 240

Gly Gly Cys Pro Lys Glu Arg Ala Glu Ile Ser Met Leu Glu Gly Ala
                245                 250                 255

Val Leu Asp Ile Arg Tyr Gly Val Ser Arg Ile Ala Tyr Ser Lys Asp
                260                 265                 270

Phe Glu Thr Leu Lys Val Asp Phe Leu Ser Lys Leu Pro Glu Met Leu
            275                 280                 285

Lys Met Phe Glu Asp Arg Leu Cys His Lys Thr Tyr Leu Asn Gly Asp
290                 295                 300

His Val Thr His Pro Asp Phe Met Leu Tyr Asp Ala Leu Asp Val Val
305                 310                 315                 320

Leu Tyr Met Asp Pro Met Cys Leu Asp Ala Phe Pro Lys Leu Val Cys
                325                 330                 335

Phe Lys Lys Arg Ile Glu Ala Ile Pro Gln Ile Asp Lys Tyr Leu Lys
                340                 345                 350

Ser Ser Lys Tyr Ile Ala Trp Pro Leu Gln Gly Trp Gln Ala Thr Phe
            355                 360                 365

Gly Gly Gly Asp His Pro Pro Lys Ser Asp Leu Val Pro Arg Gly Ser
370                 375                 380

Pro Gly Ile Pro Ser Glu Leu Asn Asp Ile Asn Lys Ile Glu Leu Lys
385                 390                 395                 400

Asn Leu Ser Gly Glu Ile Ile Lys Glu Asn Gly Lys Glu Ala Ile Lys
                405                 410                 415

Tyr Thr Ser Ser Asp Thr Ala Ser His Lys Gly Trp Lys Ala Thr Leu
                420                 425                 430

Ser Gly Thr Phe Ile Glu Asp Pro His Ser Asp Lys Lys Thr Ala Leu
            435                 440                 445

Leu Asn Leu Glu Gly Phe Ile Pro Ser Asp Lys Gln Ile Phe Gly Ser
450                 455                 460
```

Lys Tyr Tyr Gly Lys Met Lys Trp Pro Glu Thr Tyr Arg Ile Asn Val
465                 470                 475                 480

Lys Ser Ala Asp Val Asn Asn Asn Ile Lys Ile Ala Asn Ser Ile Pro
            485                 490                 495

Lys Asn Thr Ile Asp Lys Lys Asp Val Ser Asn Ser Ile Gly Tyr Ser
        500                 505                 510

Ile Gly Gly Asn Ile Ser Val Glu Gly Lys Thr Ala Gly Ala Gly Ile
    515                 520                 525

Asn Ala Ser Tyr Asn Val Gln Asn Thr Ile Ser Tyr Glu Gln Pro Asp
530                 535                 540

Phe Arg Thr Ile Gln Arg Lys Asp Ala Asn Leu Ala Ser Trp Asp
545                 550                 555                 560

Ile Lys Phe Val Glu Thr Lys Asp Gly Tyr Asn Ile Asp Ser Tyr His
                565                 570                 575

Ala Ile Tyr Gly Asn Gln Leu Phe Met Lys Ser Arg Leu Tyr Asn Asn
            580                 585                 590

Gly Asp Lys Asn Phe Thr Asp Asp Arg Asp Leu Ser Thr Leu Ile Ser
        595                 600                 605

Gly Gly Phe Ser Pro Asn Met Ala Leu Ala Leu Thr Ala Pro Lys Asn
    610                 615                 620

Ala Lys Glu Ser Val Ile Ile Val Glu Tyr Gln Arg Phe Asp Asn Asp
625                 630                 635                 640

Tyr Ile Leu Asn Trp Glu Thr Thr Gln Trp Arg Gly Thr Asn Lys Leu
                645                 650                 655

Ser Ser Thr Ser Glu Tyr Asn Glu Phe Met Phe Lys Ile Asn Trp Gln
            660                 665                 670

Asp Met Lys Lys Ile Trp Leu His Lys Ile Glu Tyr Tyr Leu Ala Leu
        675                 680                 685

Ala Gly Met Val Leu Ala Phe Ser Ala Ser Ala Ala Gln Ile Ser Asp
    690                 695                 700

Met Cys Thr Gly Leu Ala Leu Glu Thr Lys Asp Gly Leu His Leu Phe
705                 710                 715                 720

Gly Arg Asn Met Asp Ile Glu Tyr Ser Phe Asn Gln Ser Ile Ile Phe
                725                 730                 735

Ile Pro Arg Asn Phe Lys Cys Val Asn Lys Ser Asn Lys Lys Glu Leu
            740                 745                 750

Thr Thr Lys Tyr Ala Val Leu Gly Met Gly Thr Ile Phe Asp Asp Tyr
        755                 760                 765

Pro Thr Phe Ala Asp Gly Met Asn Glu Lys Gly Leu Gly Cys Ala Gly
    770                 775                 780

Leu Asn Phe Pro Val Tyr Val Ser Tyr Ser Lys Glu Asp Ile Glu Gly
785                 790                 795                 800

Lys Thr Asn Ile Pro Val Tyr Asn Phe Leu Leu Trp Val Leu Ala Asn
                805                 810                 815

Phe Ser Ser Val Glu Glu Val Lys Glu Ala Leu Lys Asn Ala Asn Ile
            820                 825                 830

Val Asp Ile Pro Ile Ser Glu Asn Ile Pro Asn Thr Thr Leu His Trp
        835                 840                 845

Met Ile Ser Asp Ile Thr Gly Lys Ser Ile Val Val Glu Gln Thr Lys
    850                 855                 860

Glu Lys Leu Asn Val Phe Asp Asn Asn Ile Gly Val Leu Thr Asn Ser
865                 870                 875                 880

Pro Thr Phe Asp Trp His Val Ala Asn Leu Asn Gln Tyr Val Gly Leu 885                 890                 895
Arg Tyr Asn Gln Val Pro Glu Phe Lys Leu Gly Asp Gln Ser Leu Thr
                900                 905                 910

Ala Leu Gly Gln Gly Thr Gly Leu Val Gly Leu Pro Gly Asp Phe Thr
            915                 920                 925

Pro Ala Ser Arg Phe Ile Arg Val Ala Phe Leu Arg Asp Ala Met Ile
        930                 935                 940

Lys Asn Asp Lys Asp Ser Ile Asp Leu Ile Glu Phe Phe His Ile Leu
945                 950                 955                 960

Asn Asn Val Ala Met Val Arg Gly Ser Thr Arg Thr Val Glu Glu Lys
                965                 970                 975

Ser Asp Leu Thr Gln Tyr Thr Ser Cys Met Cys Leu Glu Lys Gly Ile
            980                 985                 990

Tyr Tyr Tyr Asn Thr Tyr Glu Asn  Asn Gln Ile Asn Ala  Ile Asp Met
        995                 1000                1005

Asn Lys  Glu Asn Leu Asp Gly  Asn Glu Ile Lys Thr  Tyr Lys Tyr
    1010                1015                1020

Asn Lys  Thr Leu Ser Ile Asn  His Val Asn His  His His His
    1025                1030                1035

His

<210> SEQ ID NO 21
<211> LENGTH: 3360
<212> TYPE: DNA
<213> ORGANISM: Artificial Sequence
<220> FEATURE:
<223> OTHER INFORMATION: Synthetic

<400> SEQUENCE: 21
ggatcttccg aagaccttc cattctgaaa tgagctgttg acaattaatc atccggctcg      60
tataatgtgt ggaattgtga gcggataaca atttcacaca ggaaacagac catgaaaaaa    120
caacatttcc gtgtcgccct tattcccttt tttgcggcat tttgccttcc tgttttttgct   180 cacccagaaa cgctggtgaa agtaaaagat gctgaactcg aggacccgtc cgtgggcaac    240
aacgtgaaag aactggtggc ttacatctcc actagcggcg aaaagacgc tggcaccgac     300 gactacatgt atttcggcat caaaaccaag gacggcaaaa ctcaagaatg gaaatggac     360 aacccgggca cgacttcat ggctggcagc aaagacactt tactttcaa attaaaagac     420 gaaaacctga aaattgacga catccaaaac atgtggattc gcaaacgtaa atataccgca    480
ttcccggacg cttataagcc ggaaaacatc aaggtgatcg caaacggcaa agtggtagtg    540
gacaaggaca tcaacgagtg gatttccggc aactccactt ataacatcaa ataataaaag   600
cttaggaaac agaccatggc ccctatacta ggttattgga aaattaaggg ccttgtgcaa    660
cccactcgac ttcttttgga atatcttgaa gaaaaatatg aagagcattt gtatgagcgc    720
gatgaaggtg ataatggcg aaacaaaaag tttgaattgg gtttggagtt tcccaatctt    780
ccttattata ttgatggtga tgttaaatta acacagtcta tggccatcat acgttatata    840
gctgacaagc acaacatgtt gggtggttgt ccaaaagagc gtgcagagat ttcaatgctt    900
gaaggagcgg ttttggatat tagatacggt gtttcgagaa ttgcatatag taaagacttt   960
gaaactctca agttgatttt cttagcaag ctacctgaaa tgctgaaaat gttcgaagat   1020
cgtttatgtc ataaaacata tttaaatggt gatcatgtaa cccatcctga cttcatgttg    1080
tatgacgctc ttgatgttgt tttatacatg gacccaatgt gcctggatgc gttcccaaaa   1140

```
ttagtttgtt ttaaaaaacg tattgaagct atcccacaaa ttgataagta cttgaaatcc    1200
agcaagtata tagcatggcc tttgcagggc tggcaagcca cgtttggtgg tggcgaccat    1260
cctccaaaat cggatctggt tccgcgtgga tccccaggaa ttccaagcga actgaacgac    1320
atcaacaaaa ttgagctgaa aaacctgagc ggcgaaatca tcaaagaaaa cggcaaggaa    1380
gctattaaat atacttccag cgacaccgct tcccataaag gctggaaggc aactctgagc    1440
ggcaccttca ttgaagaccc gcattccgac aagaaaactg ctctgctgaa cctgaaggc    1500
tttatcccgt ccgacaaaca gattttcggc tctaaatatt acggcaaaat gaatggccg    1560
gaaacttatc gcattaatgt gaaaagcgct gacgtgaaca ataacatcaa atcgcaaac    1620
tccattccga aaatactat cgacaaaaaa gacgtgtcca attccattgg ctattccatc    1680
ggcggtaaca tctccgtgga aggcaaaact gctggcgctg gcatcaacgc ttcctataac    1740
gtccaaaaca ctatcagcta tgaacaaccg gacttccgca ccattcaacg caaagacgat    1800
gcaaacctgg catcctggga catcaaattc gttgagacta aggacggcta taacatcgac    1860
tcctatcatg ctatttatgg caaccaactg ttcatgaaat cccgcctgta taacaatggc    1920
gacaaaaact tcaccgacga tcgcgacctg tccaccctga tttccggcgg cttctccccg    1980
aacatggctc tggcactgac cgcacctaaa aatgctaaag aatccgtgat catcgtggaa    2040
tatcaacgct tcgacaacga ctatattctg aattgggaaa ctactcaatg gcgcggcacc    2100
aacaaacttt cctcaaccag cgaatataac gaatttatgt tcaaaatcaa ctggcaagac    2160
cataaaatcg aatattatct gtaatggtac caggaagttg atcatgaaaa agatttggct    2220
ggcgctggct ggtatggttt tagcttttag cgcctcggca gcacagatca gcgacctcga    2280
gatgtgcaca ggcctggcac tggaaactaa agacggcctg cacttgttcg ccgcaacat    2340
ggacatcgaa tattctttca atcaatctat tattttcatt ccgcgcaact tcaagtgcgt    2400
gaacaaatcc aacaaaaaag aactgaccac caaatacgct gtgctgggca tgggcactat    2460
cttcgacgat taccegaccct tcgctgacgg catgaacgaa aaaggcctgg gctgtgcggg    2520
cctgaacttc ccggtgtatg tgagctactc taaagaagac atcgaaggca aaaccaacat    2580
cccggtgtac aacttcctgc tgtgggtgct ggcgaacttc agctctgtgg aagaggtgaa    2640
ggaagccctg aaaaacgcga acatcgtgga catcccgatc tcagagaaca tcccgaacac    2700
cacgctgcac tggatgatct ccgacatcac cggcaaatcc atcgtggtgg aacagaccaa    2760
ggaaaaactg aacgtgttcg acaacaacat cggcgtgctg accaacagcc cgacgttcga    2820
ctggcacgtg gccaacctga accagtacgt ggggcctgcgc tataaccagg tgccggagtt    2880
caagctgggc gaccagtctc tgactgctct gggccagggc actggcctgg tgggcctgcc    2940
gggcgacttc acaccggcgt ctcgcttcat ccgcgtagcg tttctgcgtg acgcgatgat    3000
caaaaacgac aaagacagca tcgacctgat cgaattcttc cacatcctga caacgtggc    3060
tatggtacgc ggctccactc gcacagtgga agagaaatcc gacctgacac agtacacgtc    3120
ttgcatgtgc ctggaaaaag gcatctatta ttataacacc tatgaaaaca accagatcaa    3180
cgcaatcgac atgaacaaag aaaacctgga cggcaacgaa atcaaaacct acaaatacaa    3240
caaaacctg agcatcaacc acgtgaaccc gcggcaccac caccatcatc atccgcggta    3300
atgggccctg cagccaagct cccaagcttg gctgttttgg cggatgagag aagattttca    3360
```

<210> SEQ ID NO 22
<211> LENGTH: 839
<212> TYPE: PRT
<213> ORGANISM: Artificial Sequence
<220> FEATURE:
<223> OTHER INFORMATION: Synthetic

<400> SEQUENCE: 22

Met Lys Lys Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Pro Ser Val Gly Asn Asn Val Lys Glu Leu Val Ala
            35                  40                  45

Tyr Ile Ser Thr Ser Gly Glu Lys Asp Ala Gly Thr Asp Asp Tyr Met
50                  55                  60

Tyr Phe Gly Ile Lys Thr Lys Asp Gly Lys Thr Gln Glu Trp Glu Met
65                  70                  75                  80

Asp Asn Pro Gly Asn Asp Phe Met Ala Gly Ser Lys Thr Tyr Thr
                85                  90                  95

Phe Lys Leu Lys Asp Glu Asn Leu Lys Ile Asp Asp Ile Gln Asn Met
                100                 105                 110

Trp Ile Arg Lys Arg Lys Tyr Thr Ala Phe Pro Asp Ala Tyr Lys Pro
            115                 120                 125

Glu Asn Ile Lys Val Ile Ala Asn Gly Lys Val Val Asp Lys Asp
            130                 135                 140

Ile Asn Glu Trp Ile Ser Gly Asn Ser Thr Tyr Asn Ile Lys Met Ala
145                 150                 155                 160

Pro Ile Leu Gly Tyr Trp Lys Ile Lys Gly Leu Val Gln Pro Thr Arg
                165                 170                 175

Leu Leu Leu Glu Tyr Leu Glu Glu Lys Tyr Glu Glu His Leu Tyr Glu
                180                 185                 190

Arg Asp Glu Gly Asp Lys Trp Arg Asn Lys Lys Phe Glu Leu Gly Leu
            195                 200                 205

Glu Phe Pro Asn Leu Pro Tyr Tyr Ile Asp Gly Asp Val Lys Leu Thr
    210                 215                 220

Gln Ser Met Ala Ile Ile Arg Tyr Ile Ala Asp Lys His Asn Met Leu
225                 230                 235                 240

Gly Gly Cys Pro Lys Glu Arg Ala Glu Ile Ser Met Leu Glu Gly Ala
                245                 250                 255

Val Leu Asp Ile Arg Tyr Gly Val Ser Arg Ile Ala Tyr Ser Lys Asp
                260                 265                 270

Phe Glu Thr Leu Lys Val Asp Phe Leu Ser Lys Leu Pro Glu Met Leu
    275                 280                 285

Lys Met Phe Glu Asp Arg Leu Cys His Lys Thr Tyr Leu Asn Gly Asp
290                 295                 300

His Val Thr His Pro Asp Phe Met Leu Tyr Asp Ala Leu Asp Val Val
305                 310                 315                 320

Leu Tyr Met Asp Pro Met Cys Leu Asp Ala Phe Pro Lys Leu Val Cys
                325                 330                 335

Phe Lys Lys Arg Ile Glu Ala Ile Pro Gln Ile Asp Lys Tyr Leu Lys
                340                 345                 350

Ser Ser Lys Tyr Ile Ala Trp Pro Leu Gln Gly Trp Gln Ala Thr Phe
                355                 360                 365

Gly Gly Gly Asp His Pro Pro Lys Ser Asp Leu Val Pro Arg Gly Ser
            370                 375                 380

Pro Gly Ile Pro Ser Glu Leu Asn Asp Ile Asn Lys Ile Glu Leu Lys
385                 390                 395                 400

```
Asn Leu Ser Gly Glu Ile Ile Lys Glu Asn Gly Lys Glu Ala Ile Lys
                405                 410                 415
Tyr Thr Ser Ser Asp Thr Ala Ser His Lys Gly Trp Lys Ala Thr Leu
            420                 425                 430
Ser Gly Thr Phe Ile Glu Asp Pro His Ser Asp Lys Lys Thr Ala Leu
        435                 440                 445
Leu Asn Leu Glu Gly Phe Ile Pro Ser Asp Lys Gln Ile Phe Gly Ser
    450                 455                 460
Lys Tyr Tyr Gly Lys Met Lys Trp Pro Glu Thr Tyr Arg Ile Asn Val
465                 470                 475                 480
Lys Ser Ala Asp Val Asn Asn Ile Lys Ile Ala Asn Ser Ile Pro
                485                 490                 495
Lys Asn Thr Ile Asp Lys Lys Asp Val Ser Asn Ser Ile Gly Tyr Ser
                500                 505                 510
Ile Gly Gly Asn Ile Ser Val Glu Gly Lys Thr Ala Gly Ala Gly Ile
                515                 520                 525
Asn Ala Ser Tyr Asn Val Gln Asn Thr Ile Ser Tyr Glu Gln Pro Asp
            530                 535                 540
Phe Arg Thr Ile Gln Arg Lys Asp Ala Asn Leu Ala Ser Trp Asp
545                 550                 555                 560
Ile Lys Phe Val Glu Thr Lys Asp Gly Tyr Asn Ile Asp Ser Tyr His
                565                 570                 575
Ala Ile Tyr Gly Asn Gln Leu Phe Met Lys Ser Arg Leu Tyr Asn Asn
            580                 585                 590
Gly Asp Lys Asn Phe Thr Asp Asp Arg Asp Leu Ser Thr Leu Ile Ser
        595                 600                 605
Gly Gly Phe Ser Pro Asn Met Ala Leu Ala Leu Thr Ala Pro Lys Asn
    610                 615                 620
Ala Lys Glu Ser Val Ile Ile Val Glu Tyr Gln Arg Phe Asp Asn Asp
625                 630                 635                 640
Tyr Ile Leu Asn Trp Glu Thr Thr Gln Trp Arg Gly Thr Asn Lys Leu
                645                 650                 655
Ser Ser Thr Ser Glu Tyr Asn Glu Phe Met Phe Lys Ile Asn Trp Gln
            660                 665                 670
Asp Met Lys Lys Thr Ala Ile His Lys Ile Glu Tyr Tyr Leu Ala Ile
        675                 680                 685
Ala Val Ala Leu Ala Gly Phe Ala Thr Val Ala Gln Ala Ala Pro Lys
    690                 695                 700
Asp Asn Asn Asp Ile Glu Lys Glu Ile Leu Asp Leu Ala Ala Ala Thr
705                 710                 715                 720
Glu Arg Leu Asn Leu Thr Asp Ala Leu Asn Ser Asn Pro Ala Gly Asn
                725                 730                 735
Leu Tyr Asp Trp Arg Ser Ser Asn Ser Tyr Pro Trp Thr Gln Lys Leu
            740                 745                 750
Asn Leu His Leu Thr Ile Thr Ala Thr Gly Gln Lys Tyr Arg Ile Leu
        755                 760                 765
Ala Ser Lys Ile Val Asp Phe Asn Ile Tyr Ser Asn Asn Phe Asn Asn
    770                 775                 780
Leu Val Lys Leu Glu Gln Ser Leu Gly Asp Gly Val Lys Asp His Tyr
785                 790                 795                 800
Val Asp Ile Ser Leu Asp Ala Gly Gln Tyr Val Leu Val Met Lys Ala
                805                 810                 815
```

```
Asn Ser Ser Tyr Ser Gly Asn Tyr Pro Tyr Ser Ile Leu Phe Gln Lys
        820                 825                 830

Phe His His His His His His
        835

<210> SEQ ID NO 23
<211> LENGTH: 2760
<212> TYPE: DNA
<213> ORGANISM: Artificial Sequence
<220> FEATURE:
<223> OTHER INFORMATION: Synthetic

<400> SEQUENCE: 23
ggatcttccg aagaccttc cattctgaaa tgagctgttg acaattaatc atccggctcg      60
tataatgtgt ggaattgtga gcggataaca atttcacaca ggaaacagac catgaaaaaa    120
caacatttcc gtgtcgccct tattccctt tttgcggcat tttgccttcc tgttttgct     180 cacccagaaa cgctggtgaa agtaaaagat gctgaactcg aggacccgtc cgtgggcaac    240
aacgtgaaag aactggtggc ttacatctcc actagcggcg aaaagacgc tggcaccgac    300 gactacatgt atttcggcat caaaaccaag gacggcaaaa ctcaagaatg gaaatggac    360 aacccgggca cgacttcat ggctggcagc aaagacactt atactttcaa attaaaagac    420
gaaaacctga aaattgacga catccaaaac atgtggattc gcaaacgtaa ataaccgca    480 ttcccggacg cttataagcc ggaaaacatc aaggtgatcg caaacggcaa agtggtagtg    540
gacaaggaca tcaacgagtg gatttccggc aactccactt ataacatcaa ataataaaag    600
cttaggaaac agaccatggc ccctatacta ggttattgga aaattaaggg ccttgtgcaa    660
cccactcgac ttctttttgga atatcttgaa gaaaaatatg aagagcattt gtatgagcgc    720
gatgaaggtg ataaatggcg aaacaaaaag tttgaattgg gtttggagtt tcccaatctt    780
ccttattata ttgatggtga tgttaaatta acacagtcta tggccatcat acgttatata    840
gctgacaagc acaacatgtt gggtggttgt ccaaaagagc gtgcagagat ttcaatgctt    900
gaaggagcgg ttttggatat tagatacggt gtttcgagaa ttgcatatag taaagacttt    960
gaaactctca agttgatttt tcttagcaag ctacctgaaa tgctgaaaat gttcgaagat   1020
cgtttatgtc ataaaacata tttaaatggt gatcatgtaa cccatcctga cttcatgttg   1080
tatgacgctc ttgatgttgt tttatacatg gacccaatgt gcctggatgc gttcccaaaa   1140
ttagtttgtt ttaaaaaacg tattgaagct atcccacaaa ttgataagta cttgaaatcc   1200
agcaagtata tagcatggcc tttgcagggc tggcaagcca cgtttggtgg tggcgaccat   1260
cctccaaaat cggatctggt tccgcgtgga tccccaggaa ttccaagcga actgaacgac   1320
atcaacaaaa ttgagctgaa aaacctgagc ggcgaaatca tcaaagaaaa cggcaaggaa   1380
gctattaaat atacttccag cgacaccgct tcccataaag gctggaaggc aactctgagc   1440
ggcaccttca ttgaagaccc gcattccgac aagaaaactg ctctgctgaa cctggaaggc   1500
tttatcccgt ccgacaaaca gatttttcggc tctaaatatt acggcaaaat gaatggccg    1560 gaaacttatc gcattaatgt gaaaagcgct gacgtgaaca taacatcaa atcgcaaac    1620 tccattccga aaaatactat cgacaaaaaa gacgtgtcca attccattgg ctattccatc   1680
ggcggtaaca tctccgtgga aggcaaaact gctggcgctg catcaacgc ttcctataac    1740 gtccaaaaca ctatcagcta tgaacaaccg gacttccgca ccattcaacg caaagacgat   1800
gcaaacctgg catcctggga catcaaattc gttgagacta aggacggcta taacatcgac   1860
tcctatcatg ctatttatgg caaccaactg ttcatgaaat cccgcctgta taacaatggc   1920
```

```
gacaaaaact tcaccgacga tcgcgacctg tccaccctga tttccggcgg cttctccccg   1980
aacatggctc tggcactgac cgcacctaaa aatgctaaag aatccgtgat catcgtggaa   2040
tatcaacgct tcgacaacga ctatattctg aattgggaaa ctactcaatg cgcggcacc    2100 aacaaacttt cctcaaccag cgaatataac gaatttatgt tcaaaatcaa ctggcaagac   2160
cataaaatcg aatattatct gtaatggtac caggacgcaa aaaatgaaaa agacagctat   2220
cgcgattgca gtggcactgg ctggtttcgc taccgtagcg caggccgctc cgaaagataa   2280
cgagctcgac atcgaaaaag aaatcctgga cctggcggcg gcgaccgaac gtctgaacct   2340
gaccgacgcg ctgaactcta acccggcggg caacctgtac gactggcgtt cttctaactc   2400
ttacccgtgg acccagaaac tgaacctgca cctgaccatc accgcgaccg gtcagaaata   2460
ccgtatcctg gcgtctaaaa tcgttgactt caacatctac tctaacaact tcaacaacct   2520
ggttaaactg gaacagtctc tgggtgacgg tgttaaagac cactacgttg acatctctct   2580
ggacgcgggt cagtacgttc tggttatgaa agcgaactct tcctactccg gtaactaccc   2640
gtactctatc ctgttccaga aattccctag gcaccatcat caccaccatc ctaggtaatg   2700
ggccctgcag ccaagctccc aagcttggct gttttggcgg atgagagaag attttcagcc   2760
```

<210> SEQ ID NO 24
<211> LENGTH: 528
<212> TYPE: PRT
<213> ORGANISM: Artificial Sequence
<220> FEATURE:
<223> OTHER INFORMATION: Synthetic

<400> SEQUENCE: 24

```
Met Lys Lys Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Met Cys Thr Gly Leu Ala Leu Glu Thr Lys Asp Gly Leu
        35                  40                  45

His Leu Phe Gly Arg Asn Met Asp Ile Glu Tyr Ser Phe Asn Gln Ser
    50                  55                  60

Ile Ile Phe Ile Pro Arg Asn Phe Lys Cys Val Asn Lys Ser Asn Lys
65                  70                  75                  80

Lys Glu Leu Thr Thr Lys Tyr Ala Val Leu Gly Met Gly Thr Ile Phe
                85                  90                  95

Asp Asp Tyr Pro Thr Phe Ala Asp Gly Met Asn Glu Lys Gly Leu Gly
            100                 105                 110

Cys Ala Gly Leu Asn Phe Pro Val Tyr Val Ser Tyr Ser Lys Glu Asp
        115                 120                 125

Ile Glu Gly Lys Thr Asn Ile Pro Val Tyr Asn Phe Leu Leu Trp Val
    130                 135                 140

Leu Ala Asn Phe Ser Ser Val Glu Glu Val Lys Glu Ala Leu Lys Asn
145                 150                 155                 160

Ala Asn Ile Val Asp Ile Pro Ile Ser Glu Asn Ile Pro Asn Thr Thr
                165                 170                 175

Leu His Trp Met Ile Ser Asp Ile Thr Gly Lys Ser Ile Val Val Glu
            180                 185                 190

Gln Thr Lys Glu Lys Leu Asn Val Phe Asp Asn Asn Ile Gly Val Leu
        195                 200                 205

Thr Asn Ser Pro Thr Phe Asp Trp His Val Ala Asn Leu Asn Gln Tyr
```

```
                    210                 215                 220
Val Gly Leu Arg Tyr Asn Gln Val Pro Glu Phe Lys Leu Gly Asp Gln
225                 230                 235                 240

Ser Leu Thr Ala Leu Gly Gln Gly Thr Gly Leu Val Gly Leu Pro Gly
                245                 250                 255

Asp Phe Thr Pro Ala Ser Arg Phe Ile Arg Val Ala Phe Leu Arg Asp
                260                 265                 270

Ala Met Ile Lys Asn Asp Lys Asp Ser Ile Asp Leu Ile Glu Phe Phe
                275                 280                 285

His Ile Leu Asn Asn Val Ala Met Val Arg Gly Ser Thr Arg Thr Val
                290                 295                 300

Glu Glu Lys Ser Asp Leu Thr Gln Tyr Thr Ser Cys Met Cys Leu Glu
305                 310                 315                 320

Lys Gly Ile Tyr Tyr Tyr Asn Thr Tyr Glu Asn Asn Gln Ile Asn Ala
                325                 330                 335

Ile Asp Met Asn Lys Glu Asn Leu Asp Gly Asn Glu Ile Lys Thr Tyr
                340                 345                 350

Lys Tyr Asn Lys Thr Leu Ser Ile Asn His Val Asn His His His
                355                 360                 365

His His Met Lys Lys Thr Ala Ile Ala Ile Ala Val Ala Leu Ala Gly
                370                 375                 380

Phe Ala Thr Val Ala Gln Ala Ala Pro Lys Asp Asn Asp Ile Glu Lys
385                 390                 395                 400

Glu Ile Leu Asp Leu Ala Ala Ala Thr Glu Arg Leu Asn Leu Thr Asp
                405                 410                 415

Ala Leu Asn Ser Asn Pro Ala Gly Asn Leu Tyr Asp Trp Arg Ser Ser
                420                 425                 430

Asn Ser Tyr Pro Trp Thr Gln Lys Leu Asn Leu His Leu Thr Ile Thr
                435                 440                 445

Ala Thr Gly Gln Lys Tyr Arg Ile Leu Ala Ser Lys Ile Val Asp Phe
                450                 455                 460

Asn Ile Tyr Ser Asn Asn Phe Asn Asn Leu Val Lys Leu Glu Gln Ser
465                 470                 475                 480

Leu Gly Asp Gly Val Lys Asp His Tyr Val Asp Ile Ser Leu Asp Ala
                485                 490                 495

Gly Gln Tyr Val Leu Val Met Lys Ala Asn Ser Ser Tyr Ser Gly Asn
                500                 505                 510

Tyr Pro Tyr Ser Ile Leu Phe Gln Lys Phe His His His His His
                515                 520                 525

<210> SEQ ID NO 25
<211> LENGTH: 1860
<212> TYPE: DNA
<213> ORGANISM: Artificial Sequence
<220> FEATURE:
<223> OTHER INFORMATION: Synthetic

<400> SEQUENCE: 25
ggatcttccg gaagaccttc cattctgaaa tgagctgttg acaattaatc atccggctcg      60
tataatgtgt ggaattgtga gcggataaca atttcacaca ggaaacagac catgaaaaaa     120
caacatttcc gtgtcgccct tattcccttt tttgcggcat tttgccttcc tgttttttgct    180 cacccagaaa cgctggtgaa agtaaaagat gctgaactcg agctccacgt gggtaccatg     240
tgcacaggcc tggcactgga aactaaagac ggcctgcact tgttcggccg caacatggac     300
```

-continued

```
atcgaatatt ctttcaatca atctattatt ttcattccgc gcaacttcaa gtgcgtgaac      360
aaatccaaca aaaagaact gaccaccaaa tacgctgtgc tgggcatggg cactatcttc       420
gacgattacc cgaccttcgc tgacggcatg aacgaaaaag gcctgggctg tgcgggcctg      480
aacttcccgg tgtatgtgag ctactctaaa gaagacatcg aaggcaaaac caacatcccg      540
gtgtacaact tcctgctgtg ggtgctggcg aacttcagct ctgtggaaga ggtgaaggaa      600
gccctgaaaa acgcgaacat cgtggacatc ccgatctcag agaacatccc gaacaccacg      660
ctgcactgga tgatctccga catcaccggc aaatccatcg tggtggaaca gaccaaggaa      720
aaactgaacg tgttcgacaa caacatcggc gtgctgacca cagcccgac gttcgactgg       780 cacgtggcca acctgaacca gtacgtgggc ctgcgctata accaggtgcc ggagttcaag      840
ctgggcgacc agtctctgac tgctctgggc cagggcactg gctggtggg cctgccgggc       900 gacttcacac cggcgtctcg cttcatccgc gtagcgtttc tgcgtgacgc gatgatcaaa     960
aacgacaaag acagcatcga cctgatcgaa ttcttccaca tcctgaacaa cgtggctatg    1020
gtacgcggct ccactcgcac agtggaagag aaatccgacc tgacacagta cacgtcttgc    1080
atgtgcctgg aaaaaggcat ctattattat aacacctatg aaaacaacca gatcaacgca    1140
atcgacatga acaaagaaaa cctggacggc aacgaaatca aaacctacaa atacaacaaa    1200
accctgagca tcaaccacgt gaacggtcac catcaccatc accattaggt caccaataat    1260
ctgcagagga cgcaaaaaat gaaaaagaca gctatcgcga ttgcagtggc actggctggt    1320
ttcgctaccg tagcgcaggc cgctccgaaa gataacgagc tcgacatcga aaaagaaatc    1380
ctggacctgg cggcggcgac cgaacgtctg aacctgaccg acgcgctgaa ctctaacccg    1440
gcgggcaacc tgtacgactg gcgttcttct aactcttacc cgtggaccca gaaactgaac    1500
ctgcacctga ccatcaccgc gaccggtcag aaataccgta tcctggcgtc taaaatcgtt    1560
gacttcaaca tctactctaa caacttcaac aacctggtta actggaaca gtctctgggt    1620 gacggtgtta agaccactac cgttgacatc tctctggacg cgggtcagta cgttctggtt    1680
atgaaagcga actcttccta ctccggtaac tacccgtact ctatcctgtt ccagaaattc    1740
cctaggcacc atcatcacca ccatcctagg taatgggccc tgcagccaag ctcccaagct    1800
tggctgtttt ggcggatgag agaagatttt cagcctgata cagattaaat cagaacgcag    1860
```

<210> SEQ ID NO 26
<211> LENGTH: 526
<212> TYPE: PRT
<213> ORGANISM: Artificial Sequence
<220> FEATURE:
<223> OTHER INFORMATION: Synthetic

<400> SEQUENCE: 26

```
Met Lys Lys Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Ile Glu Lys Glu Ile Leu Asp Leu Ala Ala Ala Thr
        35                  40                  45

Glu Arg Leu Asn Leu Thr Asp Ala Leu Asn Ser Asn Pro Ala Gly Asn
    50                  55                  60

Leu Tyr Asp Trp Arg Ser Ser Asn Ser Tyr Pro Trp Thr Gln Lys Leu
65                  70                  75                  80

Asn Leu His Leu Thr Ile Thr Ala Thr Gly Gln Lys Tyr Arg Ile Leu
                85                  90                  95
```

```
Ala Ser Lys Ile Val Asp Phe Asn Ile Tyr Ser Asn Phe Asn Asn
            100                 105                 110

Leu Val Lys Leu Glu Gln Ser Leu Gly Asp Gly Val Lys Asp His Tyr
        115                 120                 125

Val Asp Ile Ser Leu Asp Ala Gly Gln Tyr Val Leu Val Met Lys Ala
    130                 135                 140

Asn Ser Ser Tyr Ser Gly Asn Tyr Pro Tyr Ser Ile Leu Phe Gln Lys
145                 150                 155                 160

Phe His His His His His Met Lys Lys Ile Trp Leu Ala Leu Ala
                    165                 170                 175

Gly Met Val Leu Ala Phe Ser Ala Ser Ala Gln Ile Ser Asp Met
            180                 185                 190

Cys Thr Gly Leu Ala Leu Glu Thr Lys Asp Gly Leu His Leu Phe Gly
        195                 200                 205

Arg Asn Met Asp Ile Glu Tyr Ser Phe Asn Gln Ser Ile Ile Phe Ile
    210                 215                 220

Pro Arg Asn Phe Lys Cys Val Asn Lys Ser Asn Lys Lys Glu Leu Thr
225                 230                 235                 240

Thr Lys Tyr Ala Val Leu Gly Met Gly Thr Ile Phe Asp Asp Tyr Pro
                    245                 250                 255

Thr Phe Ala Asp Gly Met Asn Glu Lys Gly Leu Gly Cys Ala Gly Leu
            260                 265                 270

Asn Phe Pro Val Tyr Val Ser Tyr Ser Lys Glu Asp Ile Glu Gly Lys
        275                 280                 285

Thr Asn Ile Pro Val Tyr Asn Phe Leu Leu Trp Val Leu Ala Asn Phe
    290                 295                 300

Ser Ser Val Glu Glu Val Lys Glu Ala Leu Lys Asn Ala Asn Ile Val
305                 310                 315                 320

Asp Ile Pro Ile Ser Glu Asn Ile Pro Asn Thr Thr Leu His Trp Met
                    325                 330                 335

Ile Ser Asp Ile Thr Gly Lys Ser Ile Val Val Glu Gln Thr Lys Glu
            340                 345                 350

Lys Leu Asn Val Phe Asp Asn Asn Ile Gly Val Leu Thr Asn Ser Pro
        355                 360                 365

Thr Phe Asp Trp His Val Ala Asn Leu Asn Gln Tyr Val Gly Leu Arg
    370                 375                 380

Tyr Asn Gln Val Pro Glu Phe Lys Leu Gly Asp Gln Ser Leu Thr Ala
385                 390                 395                 400

Leu Gly Gln Gly Thr Gly Leu Val Gly Leu Pro Gly Asp Phe Thr Pro
                    405                 410                 415

Ala Ser Arg Phe Ile Arg Val Ala Phe Leu Arg Asp Ala Met Ile Lys
            420                 425                 430

Asn Asp Lys Asp Ser Ile Asp Leu Ile Glu Phe Phe His Ile Leu Asn
        435                 440                 445

Asn Val Ala Met Val Arg Gly Ser Thr Arg Thr Val Glu Glu Lys Ser
    450                 455                 460

Asp Leu Thr Gln Tyr Thr Ser Cys Met Cys Leu Glu Lys Gly Ile Tyr
465                 470                 475                 480

Tyr Tyr Asn Thr Tyr Glu Asn Gln Ile Asn Ala Ile Asp Met Asn
                    485                 490                 495

Lys Glu Asn Leu Asp Gly Asn Glu Ile Lys Thr Tyr Lys Tyr Asn Lys
            500                 505                 510
```

Thr Leu Ser Ile Asn His Val Asn His His His His His His
            515                 520                 525

<210> SEQ ID NO 27
<211> LENGTH: 1800
<212> TYPE: DNA
<213> ORGANISM: Artificial Sequence
<220> FEATURE:
<223> OTHER INFORMATION: Synthetic

<400> SEQUENCE: 27

| | | | | |
|---|---|---|---|---|
| ggatcttccg | gaagaccttc | cattctgaaa | tgagctgttg | acaattaatc atccggctcg | 60 |
| tataatgtgt | ggaattgtga | gcggataaca | atttcacaca | ggaaacagac catgaaaaaa | 120 |
| caacatttcc | gtgtcgccct | tattccctttt | tttgcggcat | tttgccttcc tgttttttgct | 180 |
| cacccagaaa | cgctggtgaa | agtaaaagat | gctgaactcg | agctccacgt gggtaccgac | 240 |
| atcgaaaaag | aaatcctgga | cctggcggcg | gcgaccgaac | gtctgaacct gaccgacgcg | 300 |
| ctgaactcta | acccggcggg | caacctgtac | gactggcgtt | cttctaactc ttacccgtgg | 360 |
| acccagaaac | tgaacctgca | cctgaccatc | accgcgaccg | gtcagaaata ccgtatcctg | 420 |
| gcgtctaaaa | tcgttgactt | caacatctac | tctaacaact | tcaacaacct ggttaaactg | 480 |
| gaacagtctc | tgggtgacgg | tgttaaagac | cactacgttg | acatctctct ggacgcgggt | 540 |
| cagtacgttc | tggttatgaa | agcgaactct | tcctactccg | gtaactaccc gtactctatc | 600 |
| ctgttccaga | aattcgccgg | ccaccatcac | catcaccatt | agccggctaa tctgcagagg | 660 |
| aagttgatca | tgaaaaagat | ttggctggcg | ctggctggta | tggttttagc ttttagcgcc | 720 |
| tcggcagcac | agatcagcga | cctcgagatg | tgcacaggcc | tggcactgga aactaaagac | 780 |
| ggcctgcact | tgttcggccg | caacatggac | atcgaatatt | ctttcaatca atctattatt | 840 |
| ttcattccgc | gcaacttcaa | gtgcgtgaac | aaatccaaca | aaaagaact gaccaccaaa | 900 |
| tacgctgtgc | tgggcatggg | cactatcttc | gacgattacc | cgaccttcgc tgacggcatg | 960 |
| aacgaaaaag | gcctgggctg | tgcgggcctg | aacttcccgg | tgtatgtgag ctactctaaa | 1020 |
| gaagacatcg | aaggcaaaac | caacatcccg | gtgtacaact | tcctgctgtg ggtgctggcg | 1080 |
| aacttcagct | ctgtggaaga | ggtgaaggaa | gccctgaaaa | cgcgaacat cgtggacatc | 1140 |
| ccgatctcag | agaacatccc | gaacaccacg | ctgcactgga | tgatctccga catcaccggc | 1200 |
| aaatccatcg | tggtggaaca | gaccaaggaa | aaactgaacg | tgttcgacaa caacatcggc | 1260 |
| gtgctgacca | cagcccgac | gttcgactgg | cacgtggcca | acctgaacca gtacgtgggc | 1320 |
| ctgcgctata | accaggtgcc | ggagttcaag | ctgggcgacc | agtctctgac tgctctgggc | 1380 |
| cagggcactg | gcctggtggg | cctgccgggc | gacttcacac | cggcgtctcg cttcatccgc | 1440 |
| gtagcgtttc | tgcgtgacgc | gatgatcaaa | acgacaaag | acagcatcga cctgatcgaa | 1500 |
| ttcttccaca | tcctgaacaa | cgtggctatg | gtacgcggct | ccactcgcac agtggaagag | 1560 |
| aaatccgacc | tgacacagta | cacgtcttgc | atgtgcctgg | aaaaggcat ctattattat | 1620 |
| aacacctatg | aaaacaacca | gatcaacgca | atcgacatga | caaagaaaa cctggacggc | 1680 |
| aacgaaatca | aaacctacaa | atacaacaaa | accctgagca | tcaaccacgt gaacccgcgg | 1740 |
| caccaccacc | atcatcatcc | gcggtaatgg | gccctgcagc | aagctcccca agcttggctg | 1800 |

<210> SEQ ID NO 28
<211> LENGTH: 1197
<212> TYPE: PRT
<213> ORGANISM: Artificial Sequence
<220> FEATURE:

<223> OTHER INFORMATION: Synthetic

<400> SEQUENCE: 28

```
Met Lys Lys Gln His Phe Arg Val Ala Leu Ile Pro Phe Phe Ala Ala
1               5                   10                  15
Phe Cys Leu Pro Val Phe Ala His Pro Glu Thr Leu Val Lys Val Lys
                20                  25                  30
Asp Ala Glu Asp Pro Ser Val Gly Asn Asn Val Lys Glu Leu Val Ala
            35                  40                  45
Tyr Ile Ser Thr Ser Gly Glu Lys Asp Ala Gly Thr Asp Asp Tyr Met
        50                  55                  60
Tyr Phe Gly Ile Lys Thr Lys Asp Gly Lys Thr Gln Glu Trp Glu Met
65                  70                  75                  80
Asp Asn Pro Gly Asn Asp Phe Met Ala Gly Ser Lys Asp Thr Tyr Thr
                85                  90                  95
Phe Lys Leu Lys Asp Glu Asn Leu Lys Ile Asp Ile Gln Asn Met
                100                 105                 110
Trp Ile Arg Lys Arg Lys Tyr Thr Ala Phe Pro Asp Ala Tyr Lys Pro
            115                 120                 125
Glu Asn Ile Lys Val Ile Ala Asn Gly Lys Val Val Asp Lys Asp
            130                 135                 140
Ile Asn Glu Trp Ile Ser Gly Asn Ser Thr Tyr Asn Ile Lys Met Ala
145                 150                 155                 160
Pro Ile Leu Gly Tyr Trp Lys Ile Lys Gly Leu Val Gln Pro Thr Arg
                165                 170                 175
Leu Leu Leu Glu Tyr Leu Glu Glu Lys Tyr Glu Glu His Leu Tyr Glu
                180                 185                 190
Arg Asp Glu Gly Asp Lys Trp Arg Asn Lys Lys Phe Glu Leu Gly Leu
            195                 200                 205
Glu Phe Pro Asn Leu Pro Tyr Tyr Ile Asp Gly Asp Val Lys Leu Thr
        210                 215                 220
Gln Ser Met Ala Ile Ile Arg Tyr Ile Ala Asp Lys His Asn Met Leu
225                 230                 235                 240
Gly Gly Cys Pro Lys Glu Arg Ala Glu Ile Ser Met Leu Glu Gly Ala
                245                 250                 255
Val Leu Asp Ile Arg Tyr Gly Val Ser Arg Ile Ala Tyr Ser Lys Asp
                260                 265                 270
Phe Glu Thr Leu Lys Val Asp Phe Leu Ser Lys Leu Pro Glu Met Leu
            275                 280                 285
Lys Met Phe Glu Asp Arg Leu Cys His Lys Thr Tyr Leu Asn Gly Asp
            290                 295                 300
His Val Thr His Pro Asp Phe Met Leu Tyr Asp Ala Leu Asp Val Val
305                 310                 315                 320
Leu Tyr Met Asp Pro Met Cys Leu Asp Ala Phe Pro Lys Leu Val Cys
                325                 330                 335
Phe Lys Lys Arg Ile Glu Ala Ile Pro Gln Ile Asp Lys Tyr Leu Lys
            340                 345                 350
Ser Ser Lys Tyr Ile Ala Trp Pro Leu Gln Gly Trp Gln Ala Thr Phe
        355                 360                 365
Gly Gly Gly Asp His Pro Pro Lys Ser Asp Leu Val Pro Arg Gly Ser
        370                 375                 380
Pro Gly Ile Pro Ser Glu Leu Asn Asp Ile Asn Lys Ile Glu Leu Lys
385                 390                 395                 400
```

```
Asn Leu Ser Gly Glu Ile Ile Lys Glu Asn Gly Lys Glu Ala Ile Lys
                405                 410                 415

Tyr Thr Ser Ser Asp Thr Ala Ser His Lys Gly Trp Lys Ala Thr Leu
            420                 425                 430

Ser Gly Thr Phe Ile Glu Asp Pro His Ser Asp Lys Lys Thr Ala Leu
        435                 440                 445

Leu Asn Leu Glu Gly Phe Ile Pro Ser Asp Lys Gln Ile Phe Gly Ser
    450                 455                 460

Lys Tyr Tyr Gly Lys Met Lys Trp Pro Glu Thr Tyr Arg Ile Asn Val
465                 470                 475                 480

Lys Ser Ala Asp Val Asn Asn Asn Ile Lys Ile Ala Asn Ser Ile Pro
                485                 490                 495

Lys Asn Thr Ile Asp Lys Lys Asp Val Ser Asn Ser Ile Gly Tyr Ser
            500                 505                 510

Ile Gly Gly Asn Ile Ser Val Glu Gly Lys Thr Ala Gly Ala Gly Ile
        515                 520                 525

Asn Ala Ser Tyr Asn Val Gln Asn Thr Ile Ser Tyr Glu Gln Pro Asp
    530                 535                 540

Phe Arg Thr Ile Gln Arg Lys Asp Asp Ala Asn Leu Ala Ser Trp Asp
545                 550                 555                 560

Ile Lys Phe Val Glu Thr Lys Asp Gly Tyr Asn Ile Asp Ser Tyr His
                565                 570                 575

Ala Ile Tyr Gly Asn Gln Leu Phe Met Lys Ser Arg Leu Tyr Asn Asn
            580                 585                 590

Gly Asp Lys Asn Phe Thr Asp Asp Arg Asp Leu Ser Thr Leu Ile Ser
        595                 600                 605

Gly Gly Phe Ser Pro Asn Met Ala Leu Ala Leu Thr Ala Pro Lys Asn
    610                 615                 620

Ala Lys Glu Ser Val Ile Ile Val Glu Tyr Gln Arg Phe Asp Asn Asp
625                 630                 635                 640

Tyr Ile Leu Asn Trp Glu Thr Thr Gln Trp Arg Gly Thr Asn Lys Leu
                645                 650                 655

Ser Ser Thr Ser Glu Tyr Asn Glu Phe Met Phe Lys Ile Asn Trp Gln
            660                 665                 670

Asp Met Lys Lys Ile Trp Leu His Lys Ile Glu Tyr Tyr Leu Ala Leu
        675                 680                 685

Ala Gly Met Val Leu Ala Phe Ser Ala Ser Ala Ala Gln Ile Ser Asp
    690                 695                 700

Met Cys Thr Gly Leu Ala Leu Glu Thr Lys Asp Gly Leu His Leu Phe
705                 710                 715                 720

Gly Arg Asn Met Asp Ile Glu Tyr Ser Phe Asn Gln Ser Ile Ile Phe
                725                 730                 735

Ile Pro Arg Asn Phe Lys Cys Val Asn Lys Ser Asn Lys Lys Glu Leu
            740                 745                 750

Thr Thr Lys Tyr Ala Val Leu Gly Met Gly Thr Ile Phe Asp Asp Tyr
        755                 760                 765

Pro Thr Phe Ala Asp Gly Met Asn Glu Lys Gly Leu Gly Cys Ala Gly
    770                 775                 780

Leu Asn Phe Pro Val Tyr Val Ser Tyr Ser Lys Glu Asp Ile Glu Gly
785                 790                 795                 800

Lys Thr Asn Ile Pro Val Tyr Asn Phe Leu Leu Trp Val Leu Ala Asn
                805                 810                 815

Phe Ser Ser Val Glu Glu Val Lys Glu Ala Leu Lys Asn Ala Asn Ile
```

```
                    820                 825                 830
Val Asp Ile Pro Ile Ser Glu Asn Ile Pro Asn Thr Thr Leu His Trp
            835                 840                 845

Met Ile Ser Asp Ile Thr Gly Lys Ser Ile Val Val Glu Gln Thr Lys
850                 855                 860

Glu Lys Leu Asn Val Phe Asp Asn Asn Ile Gly Val Leu Thr Asn Ser
865                 870                 875                 880

Pro Thr Phe Asp Trp His Val Ala Asn Leu Asn Gln Tyr Val Gly Leu
                885                 890                 895

Arg Tyr Asn Gln Val Pro Glu Phe Lys Leu Gly Asp Gln Ser Leu Thr
            900                 905                 910

Ala Leu Gly Gln Gly Thr Gly Leu Val Gly Leu Pro Gly Asp Phe Thr
            915                 920                 925

Pro Ala Ser Arg Phe Ile Arg Val Ala Phe Leu Arg Asp Ala Met Ile
            930                 935                 940

Lys Asn Asp Lys Asp Ser Ile Asp Leu Ile Glu Phe His Ile Leu
945                 950                 955                 960

Asn Asn Val Ala Met Val Arg Gly Ser Thr Arg Thr Val Glu Glu Lys
                965                 970                 975

Ser Asp Leu Thr Gln Tyr Thr Ser Cys Met Cys Leu Glu Lys Gly Ile
            980                 985                 990

Tyr Tyr Tyr Asn Thr Tyr Glu Asn Asn Gln Ile Asn Ala Ile Asp Met
            995                 1000                1005

Asn Lys Glu Asn Leu Asp Gly Asn Glu Ile Lys Thr Tyr Lys Tyr
    1010                1015                1020

Asn Lys Thr Leu Ser Ile Asn His Val Asn His His His His
    1025                1030                1035

His Met Lys Lys Thr Ala Ile Ala Ile Ala Val Ala Leu Ala Gly
    1040                1045                1050

Phe Ala Thr Val Ala Gln Ala Ala Pro Lys Asp Asn Asp Ile Glu
    1055                1060                1065

Lys Glu Ile Leu Asp Leu Ala Ala Ala Thr Glu Arg Leu Asn Leu
    1070                1075                1080

Thr Asp Ala Leu Asn Ser Asn Pro Ala Gly Asn Leu Tyr Asp Trp
    1085                1090                1095

Arg Ser Ser Asn Ser Tyr Pro Trp Thr Gln Lys Leu Asn Leu His
    1100                1105                1110

Leu Thr Ile Thr Ala Thr Gly Gln Lys Tyr Arg Ile Leu Ala Ser
    1115                1120                1125

Lys Ile Val Asp Phe Asn Ile Tyr Ser Asn Asn Phe Asn Asn Leu
    1130                1135                1140

Val Lys Leu Glu Gln Ser Leu Gly Asp Gly Val Lys Asp His Tyr
    1145                1150                1155

Val Asp Ile Ser Leu Asp Ala Gly Gln Tyr Val Leu Val Met Lys
    1160                1165                1170

Ala Asn Ser Ser Tyr Ser Gly Asn Tyr Pro Tyr Ser Ile Leu Phe
    1175                1180                1185

Gln Lys Phe His His His His His His
    1190                1195

<210> SEQ ID NO 29
<211> LENGTH: 3900
<212> TYPE: DNA
<213> ORGANISM: Artificial Sequence
```

<220> FEATURE:
<223> OTHER INFORMATION: Synthetic

<400> SEQUENCE: 29

```
ggatcttccg gaagaccttc cattctgaaa tgagctgttg acaattaatc atccggctcg      60
tataatgtgt ggaattgtga gcggataaca atttcacaca ggaaacagac catgaaaaaa     120
caacatttcc gtgtcgccct tattcccttt tttgcggcat tttgccttcc tgttttgct      180
cacccagaaa cgctggtgaa agtaaaagat gctgaactcg aggacccgtc cgtgggcaac     240
aacgtgaaag aactggtggc ttacatctcc actagcggcg aaaagacgc tggcaccgac      300
gactacatgt atttcggcat caaaaccaag gacggcaaaa ctcaagaatg ggaaatggac     360
aacccgggca acgacttcat ggctggcagc aaagacactt atactttcaa attaaaagac     420
gaaaacctga aaattgacga catccaaaac atgtggattc gcaaacgtaa ataccgca       480
ttcccggacg cttataagcc ggaaaacatc aaggtgatcg caaacggcaa agtggtagtg     540
gacaaggaca tcaacgagtg gatttccggc aactccactt ataacatcaa ataataaaag    600
cttaggaaac agaccatggc ccctatacta ggttattgga aaattaaggg ccttgtgcaa    660
cccactcgac ttcttttgga atatcttgaa gaaaaatatg aagagcattt gtatgagcgc    720
gatgaaggtg ataaatggcg aaacaaaaag tttgaattgg gtttggagtt tcccaatctt    780
ccttattata ttgatggtga tgttaaatta acacagtcta tggccatcat acgttatata    840
gctgacaagc acaacatgtt gggtggttgt ccaaagagc gtgcagagat ttcaatgctt     900
gaaggagcgg ttttggatat tagatacggt gtttcgagaa ttgcatatag taaagacttt    960
gaaactctca agttgatttt cttagcaag ctacctgaaa tgctgaaaat gttcgaagat    1020
cgtttatgtc ataaaacata tttaaatggt gatcatgtaa cccatcctga cttcatgttg   1080
tatgacgctc ttgatgttgt tttatacatg gacccaatgt gcctggatgc gttcccaaaa   1140
ttagtttgtt ttaaaaaacg tattgaagct atcccacaaa ttgataagta cttgaaatcc   1200
agcaagtata tagcatggcc tttgcagggc tggcaagcca cgtttggtgg tggcgaccat   1260
cctccaaaat cggatctggt tccgcgtgga tccccaggaa ttccaagcga actgaacgac   1320
atcaacaaaa ttgagctgaa aaacctgagc ggcgaaatca tcaaagaaaa cggcaaggaa   1380
gctattaaat atacttccag cgacaccgct tcccataaag gctggaaggc aactctgagc   1440
ggcaccttca ttgaagaccc gcattccgac aagaaaactg ctctgctgaa cctggaaggc   1500
tttatcccgt ccgacaaaca gatttttcggc tctaaatatt acggcaaaat gaaatggccg   1560
gaaacttatc gcattaatgt gaaaagcgct gacgtgaaca ataacatcaa aatcgcaaac   1620
tccattccga aaaatactat cgacaaaaaa gacgtgtcca attccattgg ctattccatc   1680
ggcggtaaca tctccgtgga aggcaaaact gctggcgctg gcatcaacgc ttcctataac   1740
gtccaaaaca ctatcagcta tgaacaaccg gacttccgca ccattcaacg caaagacgat   1800
gcaaacctgg catcctggga catcaaattc gttgagacta aggacggcta taacatcgac   1860
tcctatcatg ctatttatgg caaccaactg ttcatgaaat cccgcctgta taacaatggc   1920
gacaaaaact tcaccgacga tcgcgacctg tccacccctga tttccggcgg cttctccccg   1980
aacatggctc tggcactgac cgcacctaaa atgctaaag aatccgtgat catcgtggaa    2040
tatcaacgct tcgacaacga ctatattctg aattgggaaa ctactcaatg gcgcggcacc   2100
aacaaacttt cctcaaccag cgaatataac gaatttatgt tcaaaatcaa ctggcaagac   2160
cataaaatcg aatattatct gtaatggtac caggaagttg atcatgaaaa agatttggct   2220
```

```
ggcgctggct ggtatggttt tagcttttag cgcctcggca gcacagatca gcgacctcga    2280
gatgtgcaca ggcctggcac tggaaactaa agacggcctg cacttgttcg gccgcaacat    2340
ggacatcgaa tattctttca atcaatctat tattttcatt ccgcgcaact tcaagtgcgt    2400
gaacaaatcc aacaaaaaag aactgaccac caaatacgct gtgctgggca tgggcactat    2460
cttcgacgat tacccgacct tcgctgacgg catgaacgaa aaaggcctgg gctgtgcggg    2520
cctgaacttc ccggtgtatg tgagctactc taaagaagac atcgaaggca aaaccaacat    2580
cccggtgtac aacttcctgc tgtgggtgct ggcgaacttc agctctgtgg aagaggtgaa    2640
ggaagccctg aaaaacgcga acatcgtgga catcccgatc tcagagaaca tcccgaacac    2700
cacgctgcac tggatgatct ccgacatcac cggcaaatcc atcgtggtgg aacagaccaa    2760
ggaaaaactg aacgtgttcg acaacaacat cggcgtgctg accaacagcc cgacgttcga    2820
ctggcacgtg gccaacctga accagtacgt gggcctgcgc tataaccagg tgccggagtt    2880
caagctgggc gaccagtctc tgactgctct gggccagggc actggcctgg tgggcctgcc    2940
gggcgacttc acaccggcgt ctcgcttcat ccgcgtagcg tttctgcgtg acgcgatgat    3000
caaaaacgac aaagacagca tcgacctgat cgaattcttc cacatcctga caacgtggc    3060 tatggtacgc ggctccactc gcacagtgga agagaaatcc gacctgacac agtacacgtc    3120
ttgcatgtgc ctggaaaaag gcatctatta ttataacacc tatgaaaaca accagatcaa    3180
cgcaatcgac atgaacaaag aaaacctgga cggcaacgaa atcaaaacct acaaatacaa    3240 caaaacccctg agcatcaacc acgtgaacgg tcaccatcac catcaccatt aggtcaccaa    3300
taatctgcag aggacgcaaa aaatgaaaaa gacagctatc gcgattgcag tggcactggc    3360
tggtttcgct accgtagcgc aggccgctcc gaaagataac gagctcgaca tcgaaaaaga    3420
aatcctggac ctggcggcgg cgaccgaacg tctgaacctg accgacgcgc tgaactctaa    3480
cccggcgggc aacctgtacg actggcgttc ttctaactct tacccgtgga cccagaaact    3540
gaacctgcac ctgaccatca ccgcgaccgg tcagaaatac cgtatcctgg cgtctaaaat    3600
cgttgacttc aacatctact ctaacaactt caacaacctg gttaaactgg aacagtctct    3660
gggtgacggt gttaaagacc actacgttga catctctctg gacgcgggtc agtacgttct    3720
ggttatgaaa gcgaactctt cctactccgg taactacccg tactctatcc tgttccagaa    3780
attccctagg caccatcatc accaccatcc taggtaatgg gccctgcagc caagctccca    3840
agcttggctg ttttggcgga tgagagaaga ttttcagcct gatacagatt aaatcagaac    3900
```

<210> SEQ ID NO 30
<211> LENGTH: 18
<212> TYPE: DNA
<213> ORGANISM: Artificial Sequence
<220> FEATURE:
<223> OTHER INFORMATION: Synthetic

<400> SEQUENCE: 30
caccaccacc atcatcat                                                    18

<210> SEQ ID NO 31
<211> LENGTH: 18
<212> TYPE: DNA
<213> ORGANISM: Artificial Sequence
<220> FEATURE:
<223> OTHER INFORMATION: Synthetic

<400> SEQUENCE: 31
caccatcatc accaccat                                                    18

<210> SEQ ID NO 32
<211> LENGTH: 372
<212> TYPE: DNA
<213> ORGANISM: Clostridium perfringens

<400> SEQUENCE: 32

```
gacccgtccg tgggcaacaa cgtgaaagaa ctggtggctt acatctccac tagcggcgaa      60
aaagacgctg gcaccgacga ctacatgtat ttcggcatca aaaccaagga cggcaaaact     120
caagaatggg aaatggacaa cccgggcaac gacttcatgg ctggcagcaa agacacttat     180
actttcaaat aaaagacga aaacctgaaa attgacgaca tccaaaacat gtggattcgc     240
aaacgtaaat ataccgcatt cccggacgct tataagccgg aaaacatcaa ggtgatcgca     300
aacggcaaag tggtagtgga caaggacatc aacgagtgga tttccggcaa ctccacttat     360
aacatcaaat aa                                                         372
```

<210> SEQ ID NO 33
<211> LENGTH: 123
<212> TYPE: PRT
<213> ORGANISM: Clostridium perfringens

<400> SEQUENCE: 33

Asp Pro Ser Val Gly Asn Asn Val Lys Glu Leu Val Ala Tyr Ile Ser
1               5                   10                  15
Thr Ser Gly Glu Lys Asp Ala Gly Thr Asp Asp Tyr Met Tyr Phe Gly
            20                  25                  30
Ile Lys Thr Lys Asp Gly Lys Thr Gln Glu Trp Glu Met Asp Asn Pro
        35                  40                  45
Gly Asn Asp Phe Met Ala Gly Ser Lys Asp Thr Tyr Thr Phe Lys Leu
    50                  55                  60
Lys Asp Glu Asn Leu Lys Ile Asp Asp Ile Gln Asn Met Trp Ile Arg
65                  70                  75                  80
Lys Arg Lys Tyr Thr Ala Phe Pro Asp Ala Tyr Lys Pro Glu Asn Ile
                85                  90                  95
Lys Val Ile Ala Asn Gly Lys Val Val Val Asp Lys Asp Ile Asn Glu
            100                 105                 110
Trp Ile Ser Gly Asn Ser Thr Tyr Asn Ile Lys
        115                 120

<210> SEQ ID NO 34
<211> LENGTH: 1569
<212> TYPE: DNA
<213> ORGANISM: Clostridium perfringens

<400> SEQUENCE: 34

```
atggcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acgtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
```

-continued

```
gttgttttat acatggaccc aatgtgcctg gatgcgttcc caaaattagt ttgttttaaa    540
aaacgtattg aagctatccc acaaattgat aagtacttga aatccagcaa gtatatagca    600
tggcctttgc agggctggca agccacgttt ggtggtggcg accatcctcc aaaatcggat    660
ctggttccgc gtggatcccc aggaattcca agcgaactga acgacatcaa caaaattgag    720
ctgaaaaacc tgagcggcga aatcatcaaa gaaaacggca aggaagctat taaatatact    780
tccagcgaca ccgcttccca taaaggctgg aaggcaactc tgagcggcac cttcattgaa    840
gacccgcatt ccgacaagaa aactgctctg ctgaacctgg aaggctttat cccgtccgac    900
aaacagattt tcggctctaa atattacggc aaaatgaaat ggccggaaac ttatcgcatt    960
aatgtgaaaa gcgctgacgt gaacaataac atcaaaatcg caaactccat tccgaaaaat   1020
actatcgaca aaaaagacgt gtccaattcc attggctatt ccatcggcgg taacatctcc   1080
gtggaaggca aaactgctgg cgctggcatc aacgcttcct ataacgtcca aaacactatc   1140
agctatgaac aaccggactt ccgcaccatt caacgcaaag acgatgcaaa cctggcatcc   1200
tgggacatca aattcgttga gactaaggac ggctataaca tcgactccta tcatgctatt   1260
tatggcaacc aactgttcat gaaatcccgc ctgtataaca atggcgacaa aaacttcacc   1320
gacgatcgcg acctgtccac cctgatttcc ggcggcttct ccccgaacat ggctctggca   1380
ctgaccgcac ctaaaaatgc taaagaatcc gtgatcatcg tggaatatca acgcttcgac   1440
aacgactata ttctgaattg ggaaactact caatggcgcg gcaccaacaa actttcctca   1500
accagcgaat ataacgaatt tatgttcaaa atcaactggc aagaccataa aatcgaatat   1560
tatctgtaa                                                           1569
```

<210> SEQ ID NO 35
<211> LENGTH: 522
<212> TYPE: PRT
<213> ORGANISM: Clostridium perfringens

<400> SEQUENCE: 35

```
Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Ser Glu Leu Asn Asp Ile Asn Lys Ile Glu
225                 230                 235                 240

Leu Lys Asn Leu Ser Gly Glu Ile Ile Lys Glu Asn Gly Lys Glu Ala
                245                 250                 255

Ile Lys Tyr Thr Ser Ser Asp Thr Ala Ser His Lys Gly Trp Lys Ala
            260                 265                 270

Thr Leu Ser Gly Thr Phe Ile Glu Asp Pro His Ser Asp Lys Lys Thr
        275                 280                 285

Ala Leu Leu Asn Leu Glu Gly Phe Ile Pro Ser Asp Lys Gln Ile Phe
    290                 295                 300

Gly Ser Lys Tyr Tyr Gly Lys Met Lys Trp Pro Glu Thr Tyr Arg Ile
305                 310                 315                 320

Asn Val Lys Ser Ala Asp Val Asn Asn Ile Lys Ile Ala Asn Ser
                325                 330                 335

Ile Pro Lys Asn Thr Ile Asp Lys Lys Asp Val Ser Asn Ser Ile Gly
            340                 345                 350

Tyr Ser Ile Gly Gly Asn Ile Ser Val Glu Gly Lys Thr Ala Gly Ala
        355                 360                 365

Gly Ile Asn Ala Ser Tyr Asn Val Gln Asn Thr Ile Ser Tyr Glu Gln
    370                 375                 380

Pro Asp Phe Arg Thr Ile Gln Arg Lys Asp Asp Ala Asn Leu Ala Ser
385                 390                 395                 400

Trp Asp Ile Lys Phe Val Glu Thr Lys Asp Gly Tyr Asn Ile Asp Ser
                405                 410                 415

Tyr His Ala Ile Tyr Gly Asn Gln Leu Phe Met Lys Ser Arg Leu Tyr
            420                 425                 430

Asn Asn Gly Asp Lys Asn Phe Thr Asp Asp Arg Asp Leu Ser Thr Leu
        435                 440                 445

Ile Ser Gly Gly Phe Ser Pro Asn Met Ala Leu Ala Leu Thr Ala Pro
    450                 455                 460

Lys Asn Ala Lys Glu Ser Val Ile Val Glu Tyr Gln Arg Phe Asp
465                 470                 475                 480

Asn Asp Tyr Ile Leu Asn Trp Glu Thr Thr Gln Trp Arg Gly Thr Asn
                485                 490                 495

Lys Leu Ser Ser Thr Ser Glu Tyr Asn Glu Phe Met Phe Lys Ile Asn
            500                 505                 510

Trp Gln Asp His Lys Ile Glu Tyr Tyr Leu
        515                 520

<210> SEQ ID NO 36
<211> LENGTH: 987
<212> TYPE: DNA
<213> ORGANISM: Clostridium perfringens

<400> SEQUENCE: 36
atgtgcacag gcctggcact ggaaactaaa gacggcctgc acttgttcgg ccgcaacatg    60
gacatcgaat attctttcaa tcaatctatt attttcattc cgcgcaactt caagtgcgtg   120
aacaaatcca acaaaaaaga actgaccacc aaatacgctg tgctgggcat gggcactatc   180
```

```
ttcgacgatt acccgacctt cgctgacggc atgaacgaaa aaggcctggg ctgtgcgggc    240
ctgaacttcc cggtgtatgt gagctactct aaagaagaca tcgaaggcaa aaccaacatc    300
ccggtgtaca acttcctgct gtgggtgctg gcgaacttca gctctgtgga gaggtgaag     360 gaagccctga aaaacgcgaa catcgtggac atcccgatct cagagaacat cccgaacacc    420
acgctgcact ggatgatctc cgacatcacc ggcaaatcca tcgtggtgga acagaccaag    480
gaaaaactga acgtgttcga caacaacatc ggcgtgctga ccaacagccc gacgttcgac    540
tggcacgtgg ccaacctgaa ccagtacgtg ggcctgcgct ataaccaggt gccggagttc    600
aagctgggcg accagtctct gactgctctg ggccagggca ctggcctggt gggcctgccg    660
ggcgacttca caccggcgtc tcgcttcatc cgcgtagcgt ttctgcgtga cgcgatgatc    720
aaaaacgaca agacagcat cgacctgatc gaattcttcc acatcctgaa caacgtggct    780
atggtacgcg gctccactcg cacagtggaa gagaaatccg acctgacaca gtacacgtct    840
tgcatgtgcc tggaaaaagg catctattat tataacacct atgaaaacaa ccagatcaac    900
gcaatcgaca tgaacaaaga aaacctggac ggcaacgaaa tcaaaaccta caaatacaac    960
aaaaccctga gcatcaacca cgtgaac                                        987

<210> SEQ ID NO 37
<211> LENGTH: 329
<212> TYPE: PRT
<213> ORGANISM: Clostridium perfringens

<400> SEQUENCE: 37

Met Cys Thr Gly Leu Ala Leu Glu Thr Lys Asp Gly Leu His Leu Phe
1               5                   10                  15

Gly Arg Asn Met Asp Ile Glu Tyr Ser Phe Asn Gln Ser Ile Ile Phe
            20                  25                  30

Ile Pro Arg Asn Phe Lys Cys Val Asn Lys Ser Asn Lys Lys Glu Leu
        35                  40                  45

Thr Thr Lys Tyr Ala Val Leu Gly Met Gly Thr Ile Phe Asp Asp Tyr
    50                  55                  60

Pro Thr Phe Ala Asp Gly Met Asn Glu Lys Gly Leu Gly Cys Ala Gly
65                  70                  75                  80

Leu Asn Phe Pro Val Tyr Val Ser Tyr Ser Lys Glu Asp Ile Glu Gly
                85                  90                  95

Lys Thr Asn Ile Pro Val Tyr Asn Phe Leu Leu Trp Val Leu Ala Asn
            100                 105                 110

Phe Ser Ser Val Glu Glu Val Lys Glu Ala Leu Lys Asn Ala Asn Ile
        115                 120                 125

Val Asp Ile Pro Ile Ser Glu Asn Ile Pro Asn Thr Thr Leu His Trp
    130                 135                 140

Met Ile Ser Asp Ile Thr Gly Lys Ser Ile Val Val Glu Gln Thr Lys
145                 150                 155                 160

Glu Lys Leu Asn Val Phe Asp Asn Asn Ile Gly Val Leu Thr Asn Ser
                165                 170                 175

Pro Thr Phe Asp Trp His Val Ala Asn Leu Asn Gln Tyr Val Gly Leu
            180                 185                 190

Arg Tyr Asn Gln Val Pro Glu Phe Lys Leu Gly Asp Gln Ser Leu Thr
        195                 200                 205

Ala Leu Gly Gln Gly Thr Gly Leu Val Gly Leu Pro Gly Asp Phe Thr
    210                 215                 220
```

```
Pro Ala Ser Arg Phe Ile Arg Val Ala Phe Leu Arg Asp Ala Met Ile
225                 230                 235                 240

Lys Asn Asp Lys Asp Ser Ile Asp Leu Ile Glu Phe Phe His Ile Leu
                245                 250                 255

Asn Asn Val Ala Met Val Arg Gly Ser Thr Arg Thr Val Glu Glu Lys
                260                 265                 270

Ser Asp Leu Thr Gln Tyr Thr Ser Cys Met Cys Leu Glu Lys Gly Ile
            275                 280                 285

Tyr Tyr Tyr Asn Thr Tyr Glu Asn Asn Gln Ile Asn Ala Ile Asp Met
        290                 295                 300

Asn Lys Glu Asn Leu Asp Gly Asn Glu Ile Lys Thr Tyr Lys Tyr Asn
305                 310                 315                 320

Lys Thr Leu Ser Ile Asn His Val Asn
                325

<210> SEQ ID NO 38
<211> LENGTH: 378
<212> TYPE: DNA
<213> ORGANISM: Clostridium perfringens

<400> SEQUENCE: 38
gacattgaaa aagaaatcct ggacctggcc gctgctaccg aacgtctgaa cctgaccgac      60
gcgctgaact caaacccggc tgcaacctg tacgactggc gttcttctaa ctcctacccg      120
tggacccaga aactgaacct gcacctgacc atcaccgcga ctggccagaa ataccgtatc      180
ctggcgagca aaatcgttga cttcaacatc tattcaaaca acttcaacaa cctggtgaaa      240
ctggaacagt ccctgggcga cggcgtgaaa gaccactacg ttgacattag cctggacgcg      300
ggccagtatg ttctggtgat gaaagcgaac tcctcctata gcggcaacta cccgtattcc      360
attctgttcc agaaattc                                                   378

<210> SEQ ID NO 39
<211> LENGTH: 378
<212> TYPE: DNA
<213> ORGANISM: Clostridium perfringens

<400> SEQUENCE: 39
gacatcgaaa aagaaatcct ggacctggcg gcggcgaccg aacgtctgaa cctgaccgac      60
gcgctgaact ctaacccggc gggcaacctg tacgactggc gttcttctaa ctcttacccg      120
tggacccaga aactgaacct gcacctgacc atcaccgcga ccggtcagaa ataccgtatc      180
ctggcgtcta aaatcgttga cttcaacatc tactctaaca acttcaacaa cctggttaaa      240
ctggaacagt ctctgggtga cggtgttaaa gaccactacg ttgacatctc tctggacgcg      300
ggtcagtacg ttctggttat gaaagcgaac tcttcctact ccggtaacta cccgtactct      360
atcctgttcc agaaattc                                                   378

<210> SEQ ID NO 40
<211> LENGTH: 126
<212> TYPE: PRT
<213> ORGANISM: Clostridium perfringens

<400> SEQUENCE: 40

Asp Ile Glu Lys Glu Ile Leu Asp Leu Ala Ala Ala Thr Glu Arg Leu
1               5                   10                  15

Asn Leu Thr Asp Ala Leu Asn Ser Asn Pro Ala Gly Asn Leu Tyr Asp
                20                  25                  30
```

```
Trp Arg Ser Ser Asn Ser Tyr Pro Trp Thr Gln Lys Leu Asn Leu His
            35                  40                  45

Leu Thr Ile Thr Ala Thr Gly Gln Lys Tyr Arg Ile Leu Ala Ser Lys
 50                  55                  60

Ile Val Asp Phe Asn Ile Tyr Ser Asn Asn Phe Asn Asn Leu Val Lys
 65                  70                  75                  80

Leu Glu Gln Ser Leu Gly Asp Gly Val Lys Asp His Tyr Val Asp Ile
            85                  90                  95

Ser Leu Asp Ala Gly Gln Tyr Val Leu Val Met Lys Ala Asn Ser Ser
            100                 105                 110

Tyr Ser Gly Asn Tyr Pro Tyr Ser Ile Leu Phe Gln Lys Phe
            115                 120                 125

<210> SEQ ID NO 41
<211> LENGTH: 870
<212> TYPE: DNA
<213> ORGANISM: Clostridium perfringens

<400> SEQUENCE: 41
```

| | | | | | |
|---|---|---|---|---|---|
| atggcactgg | ttaacgcaaa | agaaatgctg | aataaagcac | gcgaaggcaa | atacgctgtt | 60 |
| ggtcaattca | acatcaacaa | cctggaatgg | acaaaagcta | tcctgctgac | tgctcaagaa | 120 |
| aataactcac | cagttatcct | gggcgtatca | gaaggtgctg | ctaaatacat | gtgtggcttc | 180 |
| aaaacaatcg | ttggcatggt | taacggcatg | ctggaagaac | tgaaaatcac | tgttcctgta | 240 |
| gcactgcacc | tggatcacgg | tagctaccaa | ggcgctatcg | atgctatgga | tgctggcttc | 300 |
| tcatcagtaa | tgttcgatgg | ctcacactac | tcaatcgaag | aaaacatcgt | taaaactaaa | 360 |
| gaaatcatca | acctggctgc | tgctaaaaac | gtatcagttg | aagctgaagt | tggctcaatc | 420 |
| ggtggcgaag | aagacggtgt | tgttggcgct | ggtgaaatcg | ctgatcctgc | tgaatgtaaa | 480 |
| caaatcgctg | aactgggcgt | tactatgctg | gctgctggta | tcggcaacat | tcacggcaaa | 540 |
| taccctgcaa | actgggctgg | cctgaacttc | gaagctctgg | ctaacattaa | agctgctact | 600 |
| ggcgatatgc | tctctggtact | gcacggtggt | actggcatcc | cttcagatat | gatcgcagaa | 660 |
| gctatctcac | tgggcgtatc | aaaaatcaat | gttaatactg | agtgtcaact | gtcatttgct | 720 |
| gaagctactc | gtaaatatat | cgaagctggc | aaagacctgg | aaggcaaagg | ctttgaccca | 780 |
| cgcaaactgc | tgaatcctgg | cttcgaagct | atcaaagcta | cagttaaaga | aaaaatggaa | 840 |
| ctgttcggtt | cagtaaacag | agcttaatag | | | | 870 |

```
<210> SEQ ID NO 42
<211> LENGTH: 288
<212> TYPE: PRT
<213> ORGANISM: Clostridium perfringens

<400> SEQUENCE: 42

Met Ala Leu Val Asn Ala Lys Glu Met Leu Asn Lys Ala Arg Glu Gly
 1               5                  10                  15

Lys Tyr Ala Val Gly Gln Phe Asn Ile Asn Asn Leu Glu Trp Thr Lys
            20                  25                  30

Ala Ile Leu Leu Thr Ala Gln Glu Asn Asn Ser Pro Val Ile Leu Gly
            35                  40                  45

Val Ser Glu Gly Ala Ala Lys Tyr Met Cys Gly Phe Lys Thr Ile Val
 50                  55                  60

Gly Met Val Asn Gly Met Leu Glu Glu Leu Lys Ile Thr Val Pro Val
 65                  70                  75                  80
```

Ala Leu His Leu Asp His Gly Ser Tyr Gln Gly Ala Ile Asp Ala Met
            85                  90                  95

Asp Ala Gly Phe Ser Ser Val Met Phe Asp Gly Ser His Tyr Ser Ile
        100                 105                 110

Glu Glu Asn Ile Val Lys Thr Lys Glu Ile Ile Asn Leu Ala Ala Ala
        115                 120                 125

Lys Asn Val Ser Val Glu Ala Glu Val Gly Ser Ile Gly Gly Glu Glu
        130                 135                 140

Asp Gly Val Val Gly Ala Gly Glu Ile Ala Asp Pro Ala Glu Cys Lys
145                 150                 155                 160

Gln Ile Ala Glu Leu Gly Val Thr Met Leu Ala Ala Gly Ile Gly Asn
                165                 170                 175

Ile His Gly Lys Tyr Pro Ala Asn Trp Ala Gly Leu Asn Phe Glu Ala
            180                 185                 190

Leu Ala Asn Ile Lys Ala Ala Thr Gly Asp Met Pro Leu Val Leu His
            195                 200                 205

Gly Gly Thr Gly Ile Pro Ser Asp Met Ile Ala Glu Ala Ile Ser Leu
        210                 215                 220

Gly Val Ser Lys Ile Asn Val Asn Thr Glu Cys Gln Leu Ser Phe Ala
225                 230                 235                 240

Glu Ala Thr Arg Lys Tyr Ile Glu Ala Gly Lys Asp Leu Glu Gly Lys
                245                 250                 255

Gly Phe Asp Pro Arg Lys Leu Leu Asn Pro Gly Phe Glu Ala Ile Lys
            260                 265                 270

Ala Thr Val Lys Glu Lys Met Glu Leu Phe Gly Ser Val Asn Arg Ala
            275                 280                 285

<210> SEQ ID NO 43
<211> LENGTH: 31
<212> TYPE: DNA
<213> ORGANISM: Artificial Sequence
<220> FEATURE:
<223> OTHER INFORMATION: Synthetic

<400> SEQUENCE: 43
atatctcgag gacccgtccg tgggcaacaa c                                    31

<210> SEQ ID NO 44
<211> LENGTH: 39
<212> TYPE: DNA
<213> ORGANISM: Artificial Sequence
<220> FEATURE:
<223> OTHER INFORMATION: Synthetic

<400> SEQUENCE: 44
tggccggtac cattacagat aatattcgat tttatggtc                            39

<210> SEQ ID NO 45
<211> LENGTH: 36
<212> TYPE: DNA
<213> ORGANISM: Artificial Sequence
<220> FEATURE:
<223> OTHER INFORMATION: Synthetic

<400> SEQUENCE: 45
gcgcggtacc tgcagaggaa gttgatcatg aaaaag                               36

<210> SEQ ID NO 46
<211> LENGTH: 30
<212> TYPE: DNA

<213> ORGANISM: Artificial Sequence
<220> FEATURE:
<223> OTHER INFORMATION: Synthetic

<400> SEQUENCE: 46
tatactcgag gtcgctgatc tgtgctgccg                                    30

<210> SEQ ID NO 47
<211> LENGTH: 31
<212> TYPE: DNA
<213> ORGANISM: Artificial Sequence
<220> FEATURE:
<223> OTHER INFORMATION: Synthetic

<400> SEQUENCE: 47
ctgactcgag atgtgcacag gcctggcact g                                  31

<210> SEQ ID NO 48
<211> LENGTH: 52
<212> TYPE: DNA
<213> ORGANISM: Artificial Sequence
<220> FEATURE:
<223> OTHER INFORMATION: Synthetic

<400> SEQUENCE: 48
cattaccgcg gatgatgatg gtggtggtgc cgcgggttca cgtggttgat gc           52

<210> SEQ ID NO 49
<211> LENGTH: 34
<212> TYPE: DNA
<213> ORGANISM: Artificial Sequence
<220> FEATURE:
<223> OTHER INFORMATION: Synthetic

<400> SEQUENCE: 49
attactgcag ggcccattac cgcggatgat gatg                               34

<210> SEQ ID NO 50
<211> LENGTH: 41
<212> TYPE: DNA
<213> ORGANISM: Artificial Sequence
<220> FEATURE:
<223> OTHER INFORMATION: Synthetic

<400> SEQUENCE: 50
atatggtacc tgcagaggac gcaaaaaatg aaaaagacag c                       41

<210> SEQ ID NO 51
<211> LENGTH: 32
<212> TYPE: DNA
<213> ORGANISM: Artificial Sequence
<220> FEATURE:
<223> OTHER INFORMATION: Synthetic

<400> SEQUENCE: 51
cttagagctc gttatctttc ggagcggcct gc                                 32

<210> SEQ ID NO 52
<211> LENGTH: 34
<212> TYPE: DNA
<213> ORGANISM: Artificial Sequence
<220> FEATURE:
<223> OTHER INFORMATION: Synthetic

<400> SEQUENCE: 52
gccggagctc gacatcgaaa agaaatcct ggac                                34

```
<210> SEQ ID NO 53
<211> LENGTH: 54
<212> TYPE: DNA
<213> ORGANISM: Artificial Sequence
<220> FEATURE:
<223> OTHER INFORMATION: Synthetic

<400> SEQUENCE: 53
attacctagg atggtggtga tgatggtgcc tagggaattt ctggaacagg atag      54

<210> SEQ ID NO 54
<211> LENGTH: 34
<212> TYPE: DNA
<213> ORGANISM: Artificial Sequence
<220> FEATURE:
<223> OTHER INFORMATION: Synthetic

<400> SEQUENCE: 54
gtgactgcag ggcccattac ctaggatggt ggtg                            34

<210> SEQ ID NO 55
<211> LENGTH: 31
<212> TYPE: DNA
<213> ORGANISM: Artificial Sequence
<220> FEATURE:
<223> OTHER INFORMATION: Synthetic

<400> SEQUENCE: 55
ctgactcgag atgtgcacag gcctggcact g                               31

<210> SEQ ID NO 56
<211> LENGTH: 34
<212> TYPE: DNA
<213> ORGANISM: Artificial Sequence
<220> FEATURE:
<223> OTHER INFORMATION: Synthetic

<400> SEQUENCE: 56
gtgactgcag ggcccattac ctaggatggt ggtg                            34

<210> SEQ ID NO 57
<211> LENGTH: 36
<212> TYPE: DNA
<213> ORGANISM: Artificial Sequence
<220> FEATURE:
<223> OTHER INFORMATION: Synthetic

<400> SEQUENCE: 57
gcgcggtacc tgcagaggaa gttgatcatg aaaaag                          36

<210> SEQ ID NO 58
<211> LENGTH: 30
<212> TYPE: DNA
<213> ORGANISM: Artificial Sequence
<220> FEATURE:
<223> OTHER INFORMATION: Synthetic

<400> SEQUENCE: 58
tatactcgag gtcgctgatc tgtgctgccg                                 30

<210> SEQ ID NO 59

<400> SEQUENCE: 59

000
```

<210> SEQ ID NO 60

<400> SEQUENCE: 60

000

<210> SEQ ID NO 61
<211> LENGTH: 970
<212> TYPE: PRT
<213> ORGANISM: Artificial Sequence
<220> FEATURE:
<223> OTHER INFORMATION: Synthetic

<400> SEQUENCE: 61

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Glu Phe Asp Pro Ser Val Gly Asn Asn Val Lys Glu Leu
            35                  40                  45

Val Ala Tyr Ile Ser Thr Ser Gly Glu Lys Asp Ala Gly Thr Asp Asp
        50                  55                  60

Tyr Met Tyr Phe Gly Ile Lys Thr Lys Asp Gly Lys Thr Gln Glu Trp
65                  70                  75                  80

Glu Met Asp Asn Pro Gly Asn Asp Phe Met Ala Gly Ser Lys Asp Thr
                85                  90                  95

Tyr Thr Phe Lys Leu Lys Asp Glu Asn Leu Lys Ile Asp Asp Ile Gln
            100                 105                 110

Asn Met Trp Ile Arg Lys Arg Lys Tyr Thr Ala Phe Pro Asp Ala Tyr
        115                 120                 125

Lys Pro Glu Asn Ile Lys Val Ile Ala Asn Gly Lys Val Val Val Asp
130                 135                 140

Lys Asp Ile Asn Glu Trp Ile Ser Gly Asn Ser Thr Tyr Asn Ile Lys
145                 150                 155                 160

Met Ala Leu Val Asn Ala Lys Glu Met Leu Asn Lys Ala Arg Glu Gly
                165                 170                 175

Lys Tyr Ala Val Gly Gln Phe Asn Ile Asn Asn Leu Glu Trp Thr Lys
            180                 185                 190

Ala Ile Leu Leu Thr Ala Gln Glu Asn Asn Ser Pro Val Ile Leu Gly
        195                 200                 205

Val Ser Glu Gly Ala Ala Lys Tyr Met Cys Gly Phe Lys Thr Ile Val
    210                 215                 220

Gly Met Val Asn Gly Met Leu Glu Glu Leu Lys Ile Thr Val Pro Val
225                 230                 235                 240

Ala Leu His Leu Asp His Gly Ser Tyr Gln Gly Ala Ile Asp Ala Met
                245                 250                 255

Asp Ala Gly Phe Ser Ser Val Met Phe Asp Gly Ser His Tyr Ser Ile
            260                 265                 270

Glu Glu Asn Ile Val Lys Thr Lys Glu Ile Ile Asn Leu Ala Ala Ala
        275                 280                 285

Lys Asn Val Ser Val Glu Ala Glu Val Gly Ser Ile Gly Gly Glu Glu
    290                 295                 300

Asp Gly Val Val Gly Ala Gly Glu Ile Ala Asp Pro Ala Glu Cys Lys
305                 310                 315                 320

Gln Ile Ala Glu Leu Gly Val Thr Met Leu Ala Ala Gly Ile Gly Asn
```

-continued

```
            325                 330                 335
Ile His Gly Lys Tyr Pro Ala Asn Trp Ala Gly Leu Asn Phe Glu Ala
            340                 345                 350
Leu Ala Asn Ile Lys Ala Ala Thr Gly Asp Met Pro Leu Val Leu His
            355                 360                 365
Gly Gly Thr Gly Ile Pro Ser Asp Met Ile Ala Glu Ala Ile Ser Leu
            370                 375                 380
Gly Val Ser Lys Ile Asn Val Asn Thr Glu Cys Gln Leu Ser Phe Ala
385                 390                 395                 400
Glu Ala Thr Arg Lys Tyr Ile Glu Ala Gly Lys Asp Leu Glu Gly Lys
                405                 410                 415
Gly Phe Asp Pro Arg Lys Leu Leu Asn Pro Gly Phe Glu Ala Ile Lys
                420                 425                 430
Ala Thr Val Lys Glu Lys Met Glu Leu Phe Gly Ser Val Asn Arg Ala
                435                 440                 445
Met Ala Pro Ile Leu Gly Tyr Trp Lys Ile Lys Gly Leu Val Gln Pro
            450                 455                 460
Thr Arg Leu Leu Leu Glu Tyr Leu Glu Glu Lys Tyr Glu Glu His Leu
465                 470                 475                 480
Tyr Glu Arg Asp Glu Gly Asp Lys Trp Arg Asn Lys Lys Phe Glu Leu
                485                 490                 495
Gly Leu Glu Phe Pro Asn Leu Pro Tyr Tyr Ile Asp Gly Asp Val Lys
                500                 505                 510
Leu Thr Gln Ser Met Ala Ile Ile Arg Tyr Ile Ala Asp Lys His Asn
            515                 520                 525
Met Leu Gly Gly Cys Pro Lys Glu Arg Ala Glu Ile Ser Met Leu Glu
            530                 535                 540
Gly Ala Val Leu Asp Ile Arg Tyr Gly Val Ser Arg Ile Ala Tyr Ser
545                 550                 555                 560
Lys Asp Phe Glu Thr Leu Lys Val Asp Phe Leu Ser Lys Leu Pro Glu
                565                 570                 575
Met Leu Lys Met Phe Glu Asp Arg Leu Cys His Lys Thr Tyr Leu Asn
            580                 585                 590
Gly Asp His Val Thr His Pro Asp Phe Met Leu Tyr Asp Ala Leu Asp
            595                 600                 605
Val Val Leu Tyr Met Asp Pro Met Cys Leu Asp Ala Phe Pro Lys Leu
            610                 615                 620
Val Cys Phe Lys Lys Arg Ile Glu Ala Ile Pro Gln Ile Asp Lys Tyr
625                 630                 635                 640
Leu Lys Ser Ser Lys Tyr Ile Ala Trp Pro Leu Gln Gly Trp Gln Ala
                645                 650                 655
Thr Phe Gly Gly Gly Asp His Pro Pro Lys Ser Asp Leu Val Pro Arg
            660                 665                 670
Gly Ser Pro Gly Ile Pro Ser Glu Leu Asn Asp Ile Asn Lys Ile Glu
            675                 680                 685
Leu Lys Asn Leu Ser Gly Glu Ile Ile Lys Glu Asn Gly Lys Glu Ala
            690                 695                 700
Ile Lys Tyr Thr Ser Ser Asp Thr Ala Ser His Lys Gly Trp Lys Ala
705                 710                 715                 720
Thr Leu Ser Gly Thr Phe Ile Glu Asp Pro His Ser Asp Lys Lys Thr
                725                 730                 735
Ala Leu Leu Asn Leu Glu Gly Phe Ile Pro Ser Asp Lys Gln Ile Phe
            740                 745                 750
```

```
Gly Ser Lys Tyr Tyr Gly Lys Met Lys Trp Pro Glu Thr Tyr Arg Ile
            755                 760                 765
Asn Val Lys Ser Ala Asp Val Asn Asn Asn Ile Lys Ile Ala Asn Ser
770                 775                 780
Ile Pro Lys Asn Thr Ile Asp Lys Lys Asp Val Ser Asn Ser Ile Gly
785                 790                 795                 800
Tyr Ser Ile Gly Gly Asn Ile Ser Val Glu Gly Lys Thr Ala Gly Ala
                805                 810                 815
Gly Ile Asn Ala Ser Tyr Asn Val Gln Asn Thr Ile Ser Tyr Glu Gln
            820                 825                 830
Pro Asp Phe Arg Thr Ile Gln Arg Lys Asp Ala Asn Leu Ala Ser
            835                 840                 845
Trp Asp Ile Lys Phe Val Glu Thr Lys Asp Gly Tyr Asn Ile Asp Ser
850                 855                 860
Tyr His Ala Ile Tyr Gly Asn Gln Leu Phe Met Lys Ser Arg Leu Tyr
865                 870                 875                 880
Asn Asn Gly Asp Lys Asn Phe Thr Asp Asp Arg Asp Leu Ser Thr Leu
                885                 890                 895
Ile Ser Gly Gly Phe Ser Pro Asn Met Ala Leu Ala Leu Thr Ala Pro
            900                 905                 910
Lys Asn Ala Lys Glu Ser Val Ile Val Glu Tyr Gln Arg Phe Asp
            915                 920                 925
Asn Asp Tyr Ile Leu Asn Trp Glu Thr Thr Gln Trp Arg Gly Thr Asn
            930                 935                 940
Lys Leu Ser Ser Thr Ser Glu Tyr Asn Glu Phe Met Phe Lys Ile Asn
945                 950                 955                 960
Trp Gln Asp His Lys Ile Glu Tyr Tyr Leu
                965                 970

<210> SEQ ID NO 62
<211> LENGTH: 3120
<212> TYPE: DNA
<213> ORGANISM: Artificial Sequence
<220> FEATURE:
<223> OTHER INFORMATION: Synthetic

<400> SEQUENCE: 62
ggatcttccg aagaccttc cattctgaaa tgagctgttg acaattaatc atccggctcg      60
tataatgtgt ggaattgtga gcggataaca atttcacaca ggaaacagac catggggtac    120
cagatgagta ttcaacattt ccgtgtcgcc cttattccct tttttgcggc attttgcctt    180 cctgttttg ctcacccaga aacgctggtg aaagtaaaag atgctgaaga ttcgacccg      240 tccgtgggca caacgtgaa agaactgtg gcttacatct ccactagcgg cgaaaaagac      300
gctggcaccg acgactacat gtatttcggc atcaaaacca aggacggcaa aactcaagaa    360
tgggaaatgg acaacccggg caacgacttc atggctggca gcaaagacac ttatactttc    420
aaattaaaag acgaaaacct gaaaattgac gacatccaaa acatgtggat cgcaaacgt    480 aaatataccg cattcccgga cgcttataag ccggaaaaca tcaaggtgat cgcaaacggc    540
aaagtggtag tggacaagga catcaacgag tggatttccg gcaactccac ttataacatc    600
aaataataaa agcttaggaa acagaccatg gcactggtta acgcaaaaga aatgctgaat    660
aaagcacgcg aaggcaaata cgctgttggt caattcaaca tcaacaacct ggaatggaca    720
aaagctatcc tgctgactgc tcaagaaaat aactcaccag ttatcctggg cgtatcagaa    780
```

```
ggtgctgcta aatacatgtg tggcttcaaa acaatcgttg gcatggttaa cggcatgctg    840
gaagaactga aaatcactgt tcctgtagca ctgcacctgg atcacggtag ctaccaaggc    900
gctatcgatg ctatggatgc tggcttctca tcagtaatgt tcgatggctc acactactca    960
atcgaagaaa acatcgttaa aactaaagaa atcatcaacc tggctgctgc taaaaacgta   1020
tcagttgaag ctgaagttgg ctcaatcggt ggcgaagaag acggtgttgt tggcgctggt   1080
gaaatcgctg atcctgctga atgtaaacaa atcgctgaac tgggcgttac tatgctggct   1140
gctggtatcg gcaacattca cggcaaatac cctgcaaact gggctggcct gaacttcgaa   1200
gctctggcta acattaaagc tgctactggc gatatgcctc tggtactgca cggtggtact   1260
ggcatccctt cagatatgat cgcagaagct atctcactgg gcgtatcaaa atcaatgtt    1320 aatactgagt gtcaactgtc atttgctgaa gctactcgta aatatatcga agctggcaaa   1380
gacctggaag gcaaaggctt tgacccacgc aaactgctga atcctggctt cgaagctatc   1440
aaagctacag ttaaagaaaa aatggaactg ttcggttcag taaacagagc ttaatagctg   1500
cagaggaaac agaccatggc ccctatacta ggttattgga aaattaaggg ccttgtgcaa   1560
cccactcgac ttcttttgga atatcttgaa gaaaaatatg aagagcattt gtatgagcgc   1620
gatgaaggtg ataaatggcg aaacaaaaag tttgaattgg gtttggagtt tcccaatctt   1680
ccttattata ttgatggtga tgttaaatta acacagtcta tggccatcat acgttatata   1740
gctgacaagc acaacatgtt gggtggttgt ccaaaagagc gtgcagagat ttcaatgctt   1800
gaaggagcgg ttttggatat tagatacggt gtttcgagaa ttgcatatag taaagacttt   1860
gaaactctca agttgatttt cttagcaagc tacctgaaa tgctgaaaat gttcgaagat   1920
cgtttatgtc ataaaacata tttaaatggt gatcatgtaa cccatcctga cttcatgttg   1980
tatgacgctc ttgatgttgt tttatacatg gacccaatgt gcctggatgc gttcccaaaa   2040
ttagtttgtt ttaaaaaacg tattgaagct atcccacaaa ttgataagta cttgaaatcc   2100
agcaagtata tagcatggcc tttgcagggc tggcaagcca cgtttggtgg tggcgaccat   2160
cctccaaaat cggatctggt tccgcgtgga tccccaggaa ttccaagcga actgaacgac   2220
atcaacaaaa ttgagctgaa aaacctgagc ggcgaaatca tcaaagaaaa cggcaaggaa   2280
gctattaaat atacttccag cgacaccgct tcccataaag gctggaaggc aactctgagc   2340
ggcaccttca ttgaagaccc gcattccgac aagaaaactg ctctgctgaa cctggaaggc   2400
tttatcccgt ccgacaaaca gattttcggc tctaaatatt acggcaaaat gaaatggccg   2460
gaaacttatc gcattaatgt gaaaagcgct gacgtgaaca ataacatcaa aatcgcaaac   2520
tccattccga aaaatactat cgacaaaaaa gacgtgtcca attccattgg ctattccatc   2580
ggcggtaaca tctccgtgga aggcaaaact gctggcgctg gcatcaacgc ttcctataac   2640
gtccaaaaca ctatcagcta tgaacaaccg gacttccgca ccattcaacg caaagacgat   2700
gcaaacctgg catcctggga catcaaattc gttgagacta aggacggcta taacatcgac   2760
tcctatcatg ctatttatgg caaccaactg ttcatgaaat cccgcctgta taacaatggc   2820
gacaaaaact tcaccgacga tcgcgacctg tccaccctga tttccggcgg cttctccccg   2880
aacatggctc tggcactgac cgcacctaaa aatgctaaag aatccgtgat catcgtggaa   2940
tatcaacgct tcgacaacga ctatattctg aattgggaaa ctactcaatg gcgcggcacc   3000
aacaaacttt cctcaaccag cgaatataac gaatttatgt tcaaaatcaa ctggcaagac   3060
cataaaatcg aatattatct gtaaccgcgg ggctgttttg gcggatgaga aagattttc    3120
```

INDUCTION OF PROTECTIVE IMMUNITY AGAINST ANTIGENS

RELATED APPLICATION

This application is a 35 U.S.C. § 371 national stage filing of International Application No. PCT/US2018/045231, filed on Aug. 3, 2018, which in turn claims priority to U.S. Provisional Application No. 62/541,293, filed on Aug. 4, 2017. The entire contents of each of the foregoing applications is expressly incorporated by reference herein.

GOVERNMENT SUPPORT CLAUSE

This invention was made with government support under Grant No. 2017-67017-26179 awarded by the United States Department of Agriculture, National Institute of Food and Agriculture, and Grant Nos. AI056289 and AI26172 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 27, 2020, is named 130667-00302_SL.txt and is 122,224 bytes in size.

BACKGROUND

*Clostridium perfringens* Type A is a Gram-positive, spore-forming, anaerobe that is traditionally controlled by the addition of antibiotics in the feed for livestock and poultry as growth promoters, Antimicrobial Growth Promoters (AGP). However, development of antibiotic resistance has led to a decline in the use of antibiotics as AGP, and there is considerable effort by the government and the poultry industry to cease the use of AGP. Consequentially, there has been an increase in necrotic enteritis incidence in poultry.

*C. perfringens*-associated necrotic enteritis (NE) is a widespread disease in broilers. Afflicted poultry exhibit diarrhea, high morbidity with poor feed conversion, weight loss, and 10-40% mortality. NE affects the mucosa and causes epithelial degeneration, necrosis, inflammatory leukocytes in lamina propria, enterocyte sloughing, villi fusion and shortening. NE affects the chicken throughout its life cycle, and is on the rise with elimination/reduction of antibiotic use. In addition, severe NE is often associated with infections by *Eimeria* species, causing coccidiosis to result in mortality of broilers sometimes reaching as high as 50%.

Each year, Cp infection and NE cause great economic loss to the poultry industry and poses a significant threat to public health. There are currently no necrotic enteritis vaccines available for use in poultry. Accordingly, there is a need for a safe, effective vaccine to prevent NE in poultry.

SUMMARY

The instant disclosure provides vaccines for protecting poultry and other animals from necrotic enteritis (NE) due to Cp infection. Surprisingly, the instant invention provides for the delivery of protective antigens, Cbh and/or CpeC, alone or in combination with Fba, PlcC, and/or GST-NetB. The disclosed protective antigens and combinations of protective antigens provide improved *Salmonella* vaccines which exhibit significantly improved protection against *C. perfringens*-induced necrotic enteritis in animals, such as broiler chickens and other poultry.

When delivered in a recombinant bacterium, the PlcC and GST-NetB antigens induce antibodies to counteract and prevent the toxicities caused by the Cp alpha toxin and the NetB toxin that damage the intestinal mucosa of a host, e.g., poultry, to cause it to thicken and be less able to absorb nutrients. This damage and thickening reduces the ability of the host to convert food to muscle, e.g., meat, in broilers, or to eggs in laying hens. Overall, this reduces performance and is an economic loss to poultry producers.

However, immune response against toxins would not contribute to diminishing levels of Cp colonization in poultry. In *Listeria*, production of bile hydrolase is attenuating, most likely due to reduced ability to colonize the intestinal tract. The inventors of the disclosure thus postulated that, if Cp produced a bile hydrolase, its loss might also diminish the ability to of Cp to colonize the gastrointestinal (GI) tract. The instant inventors, therefore, performed a bioinformatic search and identified a DNA sequence encoding a protein Cbh from *C. perfringens*. They next postulated that antibodies against Cbh would block its enzymatic activity and, thus, reduce the ability of Cp to colonize the GI tract.

The Cp enterotoxin CpeC is also a surface-localized protein that is responsible for disease in some animals, such as dogs and horses, but is the primary cause of food poisoning in humans if Cp gets into food, for example, potato salad. Cp is likely transmitted through the food chain from Cp colonizing poultry, similar to how *Salmonella* is transmitted through the food chain from poultry to humans. The inventors thus reasoned that induction of antibodies to CpeC would also reduce ability of Cp strains to colonize poultry.

These surprising ideas led the inventors to design codon-optimized sequences encoding synthesis of Cbh, the non-toxic C-terminal portion of the enterotoxin gene CpeC and Fba as antigens to induce immune responses that would be effective in reducing NE by reducing the ability of Cp to colonize the GI tract of poultry. Cp has a 28.6% GC content of DNA very different than the 52% GC of *Salmonella*. Thus, the redesign of coding sequences to fit *Salmonella* and permit synthesis of the antigens by the RASVs disclosed herein was surprising in terms of their success and is disclosed in more detail herein.

Recently, it has been found that the Fba antigen of *C. perfringens* also decreases colonization of *C. perfringens* in the intestinal tract of chickens (see, for example, U.S. Pat. No. 9,040,059, the entire contents of which are described herein). Therefore, the instant inventors also cloned the gene encoding Fba into plasmids encoding two other antigens encoding non-toxic derivatives of two *C. perfringens* toxins, alpha toxin and netB toxin, responsible for the tissue damage caused by *C. perfringens* to contribute the pathologies associated with NE in poultry. Thus, the combination of the genes encoding synthesis of Cbh, CpeC and Fba in a vaccine to prevent *C. perfringens* colonization have a maximal effect in reducing *C. perfringens* caused NE when delivered with a vaccine encoding synthesis of PlcC and a GST-NetB fusion to induce antibodies to neutralize the effects of the two *C. perfringens* toxins.

In one aspect, disclosed herein is a recombinant bacterium comprising a nucleic acid comprising: a sequence encoding a choloylglycine hydrolase (Cbh) antigen, or fragment thereof. In another aspect, disclosed herein is a recombinant bacterium comprising a nucleic acid comprising a sequence encoding a *Clostridium perfringens* enterotoxin (CpeC) antigen, or fragment thereof.

In one aspect, disclosed herein is a recombinant bacterium comprising a nucleic acid comprising a sequence encoding a choloylglycine hydrolase (Cbh) antigen, or fragment thereof, and a sequence encoding a *Clostridium perfringens* enterotoxin (CpeC) antigen, or fragment thereof. In one embodiment, the sequence encoding the Cbh antigen, or fragment thereof, and the sequence encoding the CpeC antigen, or fragment thereof, are operably linked. In one embodiment, the sequence encoding the Cbh antigen, or fragment thereof, and the sequence encoding the CpeC antigen, or fragment thereof, are operably linked to a repressor-regulatable promoter. In one embodiment, the sequence encoding the Cbh antigen, or fragment thereof, and the sequence encoding the CpeC antigen, or fragment thereof, are not operably linked. In one embodiment, the sequence encoding the Cbh antigen, or fragment thereof, is linked to a first repressor-regulatable promoter, and wherein the sequence encoding the CpeC antigen, or fragment thereof, is linked to a second repressor-regulatable promoter. In one embodiment, the repressor-regulatable promoter is selected from the group consisting of $P_{trc}$, $P_{lac}$, $P_{T7lac}$, $P_{tac}$, $P_{ompA\ lacO}$, and $P_{lpp\ lacO}$.

In one embodiment, wherein the Cbh antigen, or fragment thereof, is a fusion protein. In one embodiment, the CpeC antigen, or fragment thereof, is a fusion protein. In one embodiment, both the Cbh antigen, or fragment thereof, and the CpeC antigen, or fragment thereof, are fusion proteins.

In one embodiment, the Cbh antigen, or fragment thereof, comprises a signal sequence. In one embodiment, the CpeC antigen, or fragment thereof, comprises a signal sequence. In one embodiment, both the Cbh antigen, or fragment thereof, and the CpeC antigen, or fragment thereof, comprise a signal sequence. In one embodiment, the signal sequences are the same signal sequence. In one embodiment, the signal sequences are different signal sequences.

In one embodiment, the sequence encoding the Cbh antigen is codon-optimized for expression in the bacterium. In one embodiment, the sequence encoding the CpeC antigen is codon-optimized for expression in the bacterium. In one embodiment, both the sequence encoding the Cbh antigen, or fragment thereof, and the sequence encoding the CpeC antigen, or fragment thereof, are codon-optimized for expression in the bacterium. In one embodiment, the CpeC antigen is encoded by a cpeC-max sequence.

In one embodiment, the recombinant bacterium further comprises a sequence encoding a C-terminal domain of *C. perfringens* alpha toxin (PlcC) antigen, or fragment thereof. In one embodiment, the PlcC antigen, or fragment thereof, is a fusion protein. In one embodiment, the sequence encoding the PlcC antigen, or fragment thereof, is codon optimized for expression in the bacterium. In one embodiment, the sequence encoding the PlcC antigen, or fragment thereof, is operably linked to the sequence encoding the Cbh antigen. In one embodiment, the sequence encoding the PlcC antigen, or fragment thereof, is operably linked to the sequence encoding the CpeC antigen. In one embodiment, the sequence encoding the PlcC antigen, or fragment thereof, is operably linked to both the sequence encoding the Cbh antigen and the sequence encoding the CpeC antigen.

In one embodiment, the recombinant bacterium further comprises a sequence encoding a non-toxic necrotic enteritis B-like toxin (NetB) antigen, or fragment thereof. In one embodiment, the NetB antigen, or fragment thereof, is a fusion protein. In one embodiment, the fusion protein is a GST-NetB fusion protein. In one embodiment, the sequence encoding the NetB antigen, or fragment thereof, is codon optimized for expression in the bacterium. In one embodiment, the sequence encoding the NetB antigen, or fragment thereof, is operably linked to the sequence encoding the Cbh antigen, or fragment thereof. In one embodiment, the sequence encoding the NetB antigen, or fragment thereof, is operably linked to the sequence encoding the CpeC antigen, or fragment thereof. In one embodiment, the sequence encoding the NetB antigen, or fragment thereof is operably linked to both the sequence encoding the Cbh antigen, or fragment thereof and the sequence encoding the CpeC antigen, or fragment thereof. In one embodiment, the sequence encoding the NetB antigen, or fragment thereof, is operably linked to the sequence encoding the PlcC antigen, or fragment thereof. In one embodiment, the sequence encoding the NetB antigen, or fragment thereof, is operably linked to both the sequence encoding the Cbh antigen, or fragment thereof, and the sequence encoding the PlcC antigen, or fragment thereof. In one embodiment, the sequence encoding the NetB antigen, or fragment thereof, is operably linked to both the sequence encoding the CpeC antigen, or fragment thereof, and the sequence encoding the PlcC antigen, or fragment thereof. In one embodiment, the sequence encoding the NetB antigen, or fragment thereof, is operably linked to or all three of the sequences encoding the Cbh antigen, or fragment thereof, the CpeC antigen, or fragment thereof, and the PlcC antigen, or fragment thereof.

In one embodiment, the recombinant bacterium further comprises a sequence encoding a Fba antigen, or a fragment thereof. In one embodiment, the sequence encoding the Fba antigen, or fragment thereof, is codon optimized for expression in the bacterium. In one embodiment, the sequence encoding the Fba antigen, or fragment thereof, is operably linked to the sequence encoding the Cbh antigen, or fragment thereof. In one embodiment, the sequence encoding the Fba antigen, or fragment thereof, is operably linked to the sequence encoding the CpeC antigen, or fragment thereof. In one embodiment, the sequence encoding the Fba antigen, or fragment thereof, is operably linked to both the sequence encoding the Cbh antigen, or fragment thereof and the sequence encoding the CpeC antigen, or fragment thereof. In one embodiment, the sequence encoding the Fba antigen, or fragment thereof, is operably linked to the sequence encoding the PlcC antigen, or fragment thereof. In one embodiment, the sequence encoding the Fba antigen, or fragment thereof, is operably linked to both the sequence encoding the Cbh antigen, or fragment thereof, and the sequence encoding the PlcC antigen, or fragment thereof. In one embodiment, the sequence encoding the Fba antigen, or fragment thereof, is operably linked to both the sequence encoding the CpeC antigen, or fragment thereof, and the sequence encoding the PlcC antigen, or fragment thereof. In one embodiment, the sequence encoding the Fba antigen, or fragment thereof, is operably linked to all three of the sequences encoding the Cbh antigen, or fragment thereof, the CpeC antigen, or fragment thereof, and the PlcC antigen, or fragment thereof. In one embodiment, the sequence encoding the Fba antigen, or fragment thereof, is operably linked to the sequence encoding the NetB antigen, or fragment thereof. In one embodiment, the sequence encoding the Fba antigen, or fragment thereof, is operably linked to both the sequence encoding the CpeC antigen, or fragment thereof, and the sequence encoding the NetB antigen. In one embodiment, the sequence encoding the Fba antigen, or fragment thereof, is operably linked to both the sequence encoding the Cbh antigen, or fragment thereof, and the sequence encoding the NetB antigen. In one embodiment, the sequence encoding the Fba antigen, or fragment thereof, is operably linked to all three of the sequences encoding the Cbh antigen, or fragment thereof, the sequence encoding the CpeC antigen, or fragment thereof, and the sequence encoding the Fba antigen, or fragment thereof. In one embodiment, the sequence encoding the Fba antigen, or fragment thereof, is operably linked to all four of the sequences encoding the Cbh antigen, or fragment thereof, the sequence encoding the CpeC antigen, or fragment thereof, the sequence encoding the PlcC antigen, or fragment thereof, and the sequence encoding the Fba antigen, or fragment thereof.

In one embodiment, the nucleic acid is present in a plasmid in the bacterium, or in the chromosome of the bacterium.

For any of the antigens, or fragments thereof, disclosed herein, the antigen or fragment thereof may further comprise a signal sequence. In one embodiment, the signal sequence is a bla signal sequence. In one embodiment, the signal sequence is a bla-opt signal sequence. In one embodiment, the signal sequence is a dsbA signal sequence. In one embodiment, the signal sequence is an ompA signal sequence.

In one embodiment, the recombinant bacterium further comprises a deletion in gene encoding an aspartate-semialdehyde dehydrogenase. In one embodiment, the aspartate-semialdehyde dehydrogenase comprises an asd gene. In one embodiment, the gene encoding the aspartate-semialdehyde dehydrogenase comprises an asdA gene.

In one embodiment, the recombinant bacterium further comprises a deletion in a sifA gene.

In one embodiment, the recombinant bacterium comprises a balanced-lethal vector-host system.

In one embodiment, the bacterium is a Gram-negative bacterium. In one embodiment, the bacterium belongs to the family Enterobacteriaceae. In one embodiment, the bacterium is of the genus *Salmonella*. In one embodiment, the bacterium is a *Salmonella enterica* bacterium. In one embodiment, the bacterium is a *Salmonella enterica* subsp. *enterica* serovar Paratyphi A bacterium, a *Salmonella enterica* subsp. *enterica* serovar Enteritidis bacterium, a *Salmonella enterica* subsp. *enterica* serovar Typhi bacterium, a *Salmonella enterica* subsp. *enterica* serovar Typhimurium *bacterium*, *Salmonella enterica* subsp. *enterica* serovar Dublin, *Salmonella* Pullorum, *Salmonella* Gallinarum, or *Salmonella enterica* subsp. *enterica* serovar Choleraesuis.

In one embodiment, the bacterium is an attenuated derivative of a pathogenic *bacterium*.

In one aspect, disclosed herein is a pharmaceutical composition comprising a recombinant bacterium disclosed herein, and a pharmaceutically acceptable carrier.

In one aspect, disclosed herein is a pharmaceutical composition comprising at least a first recombinant bacterium disclosed herein, and at least a second recombinant bacterium disclosed herein, wherein the first recombinant bacterium and the second recombinant bacterium express different antigen(s), or fragments thereof, or different combinations of antigens, or fragments thereof. For example, in one embodiment, a composition may comprise a first recombinant bacterium comprising a nucleic acid encoding Cbh, or a fragment thereof, and a second recombinant bacterium comprising a nucleic acid encoding CpeC, or a fragment thereof. In one embodiment, the composition may further comprise a third recombinant bacterium which comprises a nucleic acid encoding PlcC. In one embodiment, the composition may further comprise a third recombinant bacterium which comprises a nucleic acid encoding NetB. In one embodiment, the composition may further comprise a third recombinant bacterium which comprises a nucleic acid encoding Fba. In one embodiment, the composition may further comprise a third recombinant bacterium which comprises a nucleic acid encoding PlcC and NetB. In one embodiment, the composition may further comprise a third recombinant bacterium which comprises a nucleic acid encoding PlcC and Fba. In one embodiment, the composition may further comprise a third recombinant bacterium which comprises a nucleic acid encoding NetB and Fba. In one embodiment, the composition may further comprise a third recombinant bacterium which comprises a nucleic acid encoding PlcC, NetB and Fba.

In one embodiment, a composition may comprise a first recombinant bacterium comprising a nucleic acid encoding Cbh, or a fragment thereof, and CpeC, or a fragment thereof, and at least a second recombinant bacterium comprising a nucleic acid encoding either PlcC; NetB; Fba; PlcC and NetB; PlcC and Fba; NetB and Fba; or PlcC, NetB and Fba. Any combination of the five antigens CpeC, Cbh, PlcC, NetB, and Fba in two or more recombinant bacterium, e.g., three recombinant bacterium, four recombinant bacterium, five recombinant bacterium, etc., in a composition, e.g., pharmaceutical composition, are contemplated herein.

In one aspect, disclosed herein is a vaccine comprising the recombinant bacterium disclosed herein or a composition, or pharmaceutical composition, disclosed herein.

In one aspect, disclosed herein is a method for eliciting an immune response against an antigen, or fragment thereof, in a subject, the method comprising administering to the subject an effective amount of the composition, or pharmaceutical composition disclosed herein, or the vaccine disclosed herein. In one embodiment, the subject is a chicken, turkey, goose, or duck.

Other aspects and iterations of the invention are described more thoroughly below.

BRIEF DESCRIPTION OF THE FIGURES

FIGS. 1A-1B illustrate the plasmid construct carrying the plcC and netB operon fusion (FIG. 1A) for antigen delivery and western blot evidence of PlcC and NetB expression (FIG. 1B).

FIGS. 2A-2C are schematic illustrations of constructs in the presence of arabinose (FIG. 2A) and in the absence of arabinose (FIG. 2B), as well as lipopolysaccharide structures corresponding to in vivo regulated antigenic phenotypes (FIG. 2C). Arabinose-regulated expression of murA and asdA, two genes required for peptidoglycan synthesis, achieves in vivo regulated delayed lysis, attenuation, and antigen synthesis. Mannose is used to regulate synthesis of LPS O-antigen side chains by pmi mutation to achieve in vivo regulated delayed attenuation. Rhamnose regulated O-antigen ligase waaL expression achieves in vivo regulated delayed attenuation.

FIGS. 3A-3C illustrate the phenotype of a triple-sugar regulated *Salmonella* vaccine exhibiting arabinose-dependent growth and regulated cell lysis in the absence of arabinose and mannose- and rhamnose-dependent O-antigen synthesis.

FIGS. 4A-4B depict the synthesis of additional protective antigens in the triple-sugar regulated vaccine strain χ12341. Shown are LPS profile (FIG. 4A) and western blot (FIG. 4B) evidence demonstrating the synthesis of additional protective antigens in triple-sugar regulated vaccine strain χ12341. Ag 1 is Cbh, and Ag 2 is CpeC.

Figure 4B:
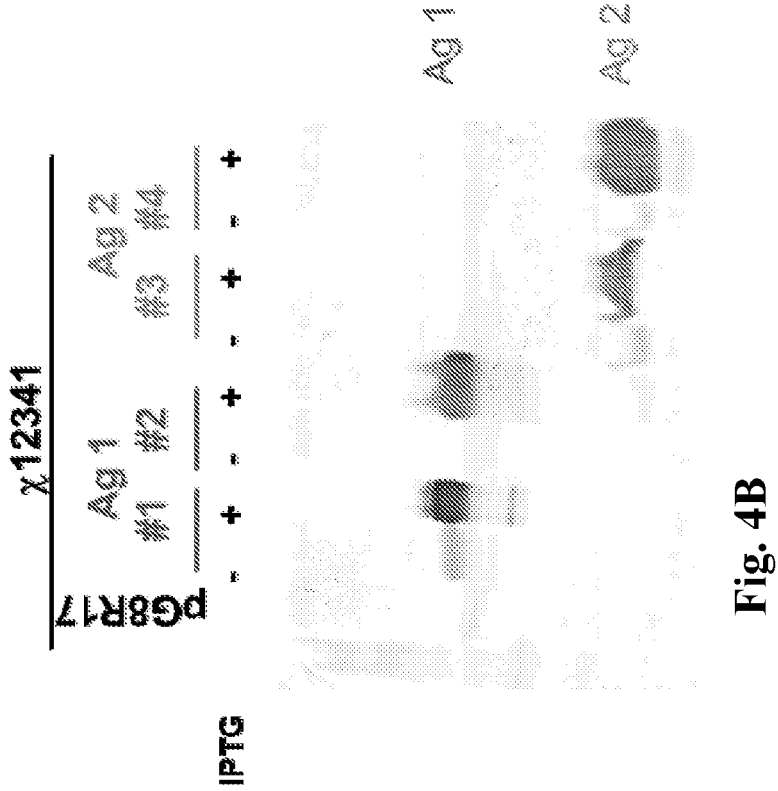

In some embodiments, the promoter for use as described herein may be regulated directly or indirectly by a sugar. For example, in some embodiments, the promoter is responsive to the level of arabinose, otherwise referred to herein as an "arabinose-regulatable promoter". Generally speaking, arabinose may be present during the in vitro growth of a bacterium, while typically absent from host tissue. In one embodiment, the promoter is derived from an araC-$P_{araBAD}$ system from *Escherichia coli*. The araC $P_{araBAD}$ system is a tightly regulated expression system, which has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction.

For convenience, the portion of the araC-araBAD promoter that mediates expression of the araBAD nucleic acid sequences, and which is controlled by the araC nucleic acid sequence product, is referred to herein as $P_{araBAD}$. For use as described herein, a cassette with the araC nucleic acid sequence and the araC-araBAD promoter may be used. This cassette is referred to herein as araC $P_{araBAD}$. The AraC protein is both a positive and negative regulator of $P_{araBAD}$. In the presence of arabinose, the AraC protein is a positive regulatory element that allows expression from $P_{araBAD}$. In the absence of arabinose, the AraC protein represses expression from $P_{ParaBAD}$. Other enteric bacteria contain arabinose regulatory systems homologous to the araC-araBAD system from *E. coli*, including, for example, *S. Typhimurium*. For example, the *E. coli* AraC protein only activates *E. coli* $P_{araBAD}$ (in the presence of arabinose) and not *S. Typhimurium* $P_{araBAD}$. Thus, an arabinose regulated promoter may be used in a recombinant bacterium that possesses a similar arabinose operon, without substantial interference between the two, if the promoter and the operon are derived from two different species of bacteria. Generally speaking, the concentration of arabinose necessary to induce expression is typically less than about 2% (w/w) in a culture media. In some embodiments, the concentration is less than about 1.5%, 1%, 0.5%, 0.2%, 0.1%, or 0.05% (w/w) in a culture media. In other embodiments, the concentration is 0.05% or below, e.g. about 0.04%, 0.03%, 0.02%, or 0.01% (w/w). In an exemplary embodiment, the concentration is about 0.05% (w/w) in a culture media.

In other embodiments, the promoter may be responsive to the level of maltose in the environment, otherwise referred to herein as a "maltose-regulatable promoter". In some embodiments, the recombinant bacteria described herein are cultured in a medium comprising maltose. The malT gene encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced in the presence of maltose. Unlike the araC-$P_{araBAD}$ system, malT expression is regulated by a promoter (i.e., $P_T$) that is functionally unrelated to the other mal promoters. $P_T$ is not regulated by MalT. The malEFG-malKBM promoter is a bidirectional promoter that controls expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by MalT, is referred to herein as $P_{KBM}$, and the portion of the malEFG-malKBM promoter that mediates expression of the malEFG nucleic acid sequence, and which is controlled by MalT, is referred to herein as $P_{EFG}$. Full induction of $P_{KBM}$ requires the presence of the MalT binding sites of $P_{EFG}$. For use in the vectors and systems described herein, a gene cassette comprising a nucleic acid sequence encoding MalT and a mal promoter may be used. This gene cassette is referred to herein as malT-$P_{mal}$. In the presence of maltose, the MalT is a positive regulatory element that allows for expression mediated by $P_{mal}$. Generally speaking, the concentration of maltose necessary to induce expression is typically less than about 1% (w/w) in a culture media. In some embodiments, the concentration is less than about 1.0%, 0.9%, 0.8%, 0.7%, 0.6%, 0.5%, 0.4%, 0.3% 0.2%, 0.1%, or 0.05% (w/w) in a culture media. In other embodiments, the concentration is 0.05% or below, e.g. about 0.04%, 0.03%, 0.02%, or 0.01% (w/w). In an exemplary embodiment, the concentration is about 0.2% to about 0.4% (w/w) in a culture media.

In still other embodiments, the promoter used herein is responsive to the level of rhamnose in the environment, otherwise referred to herein as a "rhamnose-regulatable promoter". Analogous to the araC-$P_{araBAD}$ system described above, the rhaRS-$P_{rhaBAD}$ activator-promoter system is tightly regulated by rhamnose. Expression from the rhamnose promoter ($P_{rhaBAD}$) is induced to high levels in the presence of rhamnose. In some embodiments, the bacteria are cultured in the presence of rhamnose. Rhamnose is commonly found in bacteria but rarely found in human subjects. The rhaBAD operon is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. In the presence of L-rhamnose, RhaR binds to the $P_{rhaRS}$ promoter and activates the production of RhaR and RhaS RhaS together with L-rhamnose, in turn, bind to the $P_{rhaBAD}$ and the $P_{rhaT}$ promoters and activates the transcription of the structural nucleic acid sequences. Full induction of the arabinose, maltose and rhamnose regulated promoters described herein requires binding of the Crp-cAMP complex, which is a key regulator of catabolite repression.

Although both L-arabinose and L-rhamnose act directly as inducers of the expression of regulons that mediate their catabolism, important differences exist in regard to the regulatory mechanisms. L-Arabinose acts as an inducer with the activator AraC in the positive control of the arabinose regulon. However, the L-rhamnose regulon is subject to a regulatory cascade, and is therefore subject to even tighter control than the araC-$P_{araBAD}$ system. L-Rhamnose acts as an inducer with the activator RhaR for synthesis of RhaS, which in turn acts as an activator in the positive control of the rhamnose regulon. In the present disclosure, rhamnose may be used to interact with the RhaR protein and then the RhaS protein may activate transcription of a nucleic acid sequence operably-linked to the $P_{rhaBAD}$ promoter.

In still other embodiments, the promoter may be responsive to the level of xylose in the environment, referred to herein as a "xylose-regulatable promoter". Generally, xylose concentrations of between 0.0002% to 0.63% (w/w) in the environment activate the expression of a xylose inducible promoter described herein (see, e.g., Bhaysar et al. (2001) App. Environ. Microbiol. 67(1): 403-10 (34)). The xylR-$P_{xylA}$ system is another well-established inducible activator-promoter system. Xylose induces xylose-specific operons (e.g., xylE, xylFGHR, and xylAB) that are regulated by XylR and the cyclic AMP-Crp system. The XylR protein serves as a positive regulator by binding to two distinct regions of the xyl nucleic acid sequence promoters. As with the araC-$P_{araBAD}$ system described above, the xylR-$P_{xylAB}$ and/or xylR-$P_{xylFGH}$ regulatory systems may be used. In these embodiments, xylose interacting with the XylR protein activates transcription of nucleic acid sequences operably-linked to either of the two $P_{xyl}$ promoters.

As used herein, the term "exogenous" refers to a substance (e.g., a nucleic acid or polypeptide) present in a cell other than its native source. The term exogenous can refer to a nucleic acid or a protein that has been introduced by a process involving the hand of man into a biological system such as a cell or organism in which it is not normally found or in which it is found in undetectable amounts. A substance can be considered exogenous if it is introduced into a cell or an ancestor of the cell that inherits the substance. In contrast, the term "endogenous" refers to a substance that is native to the biological system or cell.

A "pharmaceutical composition," as used herein, refers to a composition comprising an active ingredient (e.g., a recombinant bacterium described herein) with other components such as a physiologically suitable carrier and/or excipient.

As used herein, the term "pharmaceutically acceptable carrier" or a "pharmaceutically acceptable excipient" refers to a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline (e.g., phosphate-buffered saline (PBS)); (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; and (25) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

A "plasmid" or "vector" includes a nucleic acid construct designed for delivery to a host cell or transfer between different host cells. The nucleic acid incorporated into the plasmid can be operatively linked to an expression control sequence when the expression control sequence controls and regulates the transcription and translation of that polynucleotide sequence.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. The terms "protein" and "polypeptide" as used herein refer to both large polypeptides and small peptides. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA, rRNA, and tRNA.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (35); Bauer et al. (36); Craik (37); Smith et al. (38); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

The term "statistically significant" or "significantly" refers to statistical significance and generally means a two standard deviation (2SD) or greater difference.

As used herein, the term "host cell" refers to a cell in an organism to which the recombinant bacterium is being administered in order to, for example, induce an immune response. In one embodiment, a host is a bird, equine, or human and a host cell refers, respectively, to a bird cell, an equine cell, or a human cell.

Other than in the operating examples, or where otherwise indicated, all numbers expressing quantities of ingredients or reaction conditions used herein should be understood as modified in all instances by the term "about." The term "about" when used in connection with percentages can mean ±1%.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

I. Recombinant Bacteria

The present disclosure provides, in some embodiments, a recombinant bacterium capable of regulated expression of at least one nucleic acid sequence encoding an antigen of interest, e.g., CpeC, and/or Cbh, alone or in combination with Fba, PlcC, and/or GST-NetB. The recombinant bacterium described herein is particularly effective in eliciting an immune response (e.g., protective immunity) against the antigen(s) of interest because the bacterium comprise multiple recombinant regulatory systems that permit the bacterium to replicate upon administration and to colonize lymphoid tissues in a subject in order to elicit potent immune responses. However, after multiple replication cycles in vivo, the bacterium ultimately exhibits an attenuated phenotype which allows for safe administration to a subject, for example as a vaccine composition. Thus, using the phenotype of the recombinant bacteria described herein can be altered upon administration to a subject.

In some embodiments, the recombinant bacterium described herein can be regulated for delayed attenuation in vivo. In some embodiments, the recombinant bacterium described herein is capable of regulated delayed expression of a nucleic acid encoding an antigen of interest. In some embodiments, the recombinant bacterium described herein is capable of both regulated expression of at least one nucleic acid encoding at least one antigen of interest and regulated attenuation. In some embodiments, each of these properties is directly or indirectly regulated by the abundance of at least one sugar (e.g., arabinose, rhamnose, mannose, xylose, maltose, and galactose).

In some embodiments, the bacterium described herein is a Gram negative bacterium. In some embodiments, the bacterium is a pathogenic bacterium. In some embodiments, the bacterium is an avirulent bacterium. In some embodiments, the bacterium belongs to the *Enterobaceteriaceae*. In some embodiments, the bacterium belongs to a genus selected from: *Alterococcus, Aquamonas, Aranicola, Arsenophonus, Brenneria, Budvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus*, or *Yersinia, Yokenella*. In some embodiments, the bacterium is a pathogenic species of *Enterobaceteriaceae*. In some embodiments, the bacterium is selected from the group consisting of *Escherichia coli, Shigella, Edwardsiella, Salmonella, Citrobacter, Klebsiella, Enterobacter, Serratia, Proteus, Morganella, Providencia* and *Yersinia*. In some embodiments, the bacterium is of the genus *Salmonella*. In some embodiments, the bacterium is of the genus *Yersinia*. In some embodiments, the bacterium is of the genus *Edwardsiella*. In some embodiments, the bacterium is of a genus, species, or strain commonly used as a live or attenuated vaccine.

Some embodiments of the instant disclosure comprise a species or subspecies of the *Salmonella* genera (e.g., *S. enterica* or *S. bongori*). For instance, the recombinant bacterium may be a *Salmonella enterica* serovar, including, for example, Paratyphi A, Enteritidis, Typhi, and Typhimurium. In some embodiments, the recombinant bacterium is of the serovar *S. Typhimurium, S. Typhi*, S. Paratyphi, S. Gallinarum, *S. Enteritidis*, S. Choleraesius, S. Arizonae, S. Newport, S. Heidelberg, S. Infantis, S. Cholerasiuis, S. Pullorum, or S. Dublin A recombinant bacterium derived from *Salmonella* may be particularly suited to use as a vaccine. For example, oral infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus, the use of recombinant *Salmonella* for oral immunization stimulates all three branches of the immune system, which is particularly important for immunizing against infectious disease agents that colonize on and/or invade through mucosal surfaces. In some embodiments, the recombinant bacterium described herein is used to induce an immune response in poultry (e.g., as a vaccine). When used in poultry, the recombinant bacterium may be administered by course spray and thereby inoculate the conjunctiva-associated lymphoid tissue (CALT) via eye exposure, the nasal-associated lymphoid tissue (NALT) and bronchus-associated lymphoid tissue (BALT) via respiratory exposure and the GALT via oral exposure. In some embodiments, the recombinant bacterium described herein is administered to newly-hatched chicks.

A. Antigens

The recombinant bacterium disclosed herein comprises a nucleic acid encoding at least one antigen of interest, e.g., two antigens of interest, three antigens of interest, four antigens of interest, or five antigens of interest.

In another aspect, disclosed herein are compositions comprising more than one recombinant bacterium, each recombinant bacterium comprising a nucleic acid encoding at least one antigen of interest, e.g., two antigens of interest, three antigens of interest, four antigens of interest, or five antigens of interest. For example, in one embodiment, a composition may comprise a first recombinant bacterium comprising a nucleic acid encoding Cbh, or a fragment thereof, and a second recombinant bacterium comprising a nucleic acid encoding CpeC, or a fragment thereof. In one embodiment, the composition may further comprise a third recombinant bacterium which comprises a nucleic acid encoding either PlcC; NetB; Fba; PlcC and NetB; PlcC and Fba; NetB and Fba; or PlcC, NetB and Fba. In one embodiment, a composition may comprise a first recombinant bacterium comprising a nucleic acid encoding Cbh, or a fragment thereof, and CpeC, or a fragment thereof, and a second recombinant bacterium comprising a nucleic acid encoding either PlcC; NetB; Fba; PlcC and NetB; PlcC and Fba; NetB and Fba; or PlcC, NetB and Fba. Any combination of the five antigens CpeC, Cbh, PlcC, NetB, and Fba in two or more recombinant bacterium, e.g., three recombinant bacterium, four recombinant bacterium, five recombinant bacterium, etc., in a composition are contemplated herein.

As used herein, "antigen" refers to a biomolecule capable of eliciting an immune response in a host. In some embodiments, the antigen of interest is derived from C. perfringens. In some embodiments, an antigen may be a protein, or fragment of a protein, e.g., an antigenic fragment of a protein.

In one embodiment, the antigen of interest is Cbh. In one embodiment, the antigen of interest is CpeC. In one embodiment, the antigens of interest are Cbh and CpeC. In one embodiment, the antigens of interest are Cbh and Fba. In one embodiment, the antigens of interest are CpeC and Fba. In one embodiment, the antigens of interest are Cbh, CpeC, and Fba. In one embodiment, the antigens of interest are Cbh and PlcC. In one embodiment, the antigens of interest are CpeC and PlcC. In one embodiment, the antigens of interest are Cbh, CpeC, and PlcC. In one embodiment, the antigens of interest are Cbh, CpeC, PlcC, and Fba. In one embodiment, the antigens of interest are Cbh and NetB. In one embodiment, the antigens of interest are CpeC and NetB. In one embodiment, the antigens of interest are Cbh, CpeC, and NetB. In one embodiment, the antigens of interest are Cbh, CpeC, NetB, and Fba. In one embodiment, the antigens of interest are Cbh, CpeC, NetB, Fba, and PlcC.

In one embodiment, the antigen(s) of interest are expressed in a recombinant bacterium disclosed herein. In another embodiment, the antigen(s) of interest, or combinations of the antigen(s) of interest are expressed in a first recombinant bacterium disclosed herein and at least a second recombinant bacterium disclosed herein.

In some embodiments, the nucleic acid comprises a plc gene, or fragment thereof, e.g., C-terminal fragment thereof (also known as PlcC). Plc is a member of a class of membrane-associated enzymes that cleave phospholipids just before the phosphate group. plc is present in Clostridium perfringens, Bacillus cereus, Staphylococcus aureus, Bacillus thuringiensis, Listeria monocytogenes, and Pseudomonas aeruginosa. See, for example, U.S. Pat. No. 9,040,059, the entire contents of which are expressly incorporated herein by reference in their entirety.

The nucleic acid sequence of the gene encoding the C-terminal fragment of PlcC from C. perfringens is provided below:

```
                                              (SEQ ID NO: 32)
GACCCGTCCGTGGGCAACAACGTGAAAGAACTGGTGGCTTACATCTCCAC

TAGCGGCGAAAAAGACGCTGGCACCGACGACTACATGTATTTCGGCATCA

AAACCAAGGACGGCAAAACTCAAGAATGGGAAATGGACAACCCGGGCAAC

GACTTCATGGCTGGCAGCAAAGACACTTATACTTTCAAATTAAAAGACGA

AAACCTGAAAATTGACGACATCCAAAACATGTGGATTCGCAAACGTAAAT

ATACCGCATTCCCGGACGCTTATAAGCCGGAAAACATCAAGGTGATCGCA

AACGGCAAAGTGGTAGTGGACAAGGACATCAACGAGTGGATTTCCGGCAA

CTCCACTTATAACATCAAATAA.
```

The amino acid sequence of the C. perfringens PlcC protein encoded by the nucleic acid of SEQ ID NO: 32 is provided below:

```
                                              (SEQ ID NO: 33)
DPSVGNNVKELVAYISTSGEKDAGTDDYMYFGIKTKDGKTQEWEMDNPGN

DFMAGSKDTYTFKLKDENLKIDDIQNMWIRKRKYTAFPDAYKPENIKVIA

NGKVVVDKDINEWISGNSTYNIK.
```

In some embodiments, the nucleic acid comprises a gene, wherein the gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 32. In some embodiments, the nucleic acid comprises a gene, wherein the gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 32.

In some embodiments, the nucleic acid comprises a nucleic acid sequence encoding a PlcC protein, wherein said PlcC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 33. In some embodiments, the nucleic acid comprises a nucleic acid sequence encoding a PlcC protein, wherein said PlcC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 33.

In some embodiments, the nucleic acid comprises a gene that is operably-linked to a regulatable promoter. In some embodiments, the regulatable promoter is $P_{trc}$ or another promoter regulated by LacI.

In some embodiments, the nucleic acid comprises a netB gene, e.g., a non-toxic netB fusion, e.g., a NetB-GST fusion (see, for example, Jiang et al., 2015). NetB is a pore-forming toxin produced by *C. perfringens* and plays a major role in the pathogenesis of avian necrotic enteritis.

The nucleic acid sequence of the *C. perfringens* GST-netB gene fusion is provided below, with the GST coding region underlined:

(SEQ ID NO: 34)
ATGGCCCCTATACTAGGTTATTGGAAAATTAAGGGCCTTGTGCAACCCAC

TCGACTTCTTTTGGAATATCTTGAAGAAAAATATGAAGAGCATTTGTATG

AGCGCGATGAAGGTGATAAATGGCGAAACAAAAAGTTTGAATTGGGTTTG

GAGTTTCCCAATCTTCCTTATTATATTGATGGTGATGTTAAATTAACACA

GTCTATGGCCATCATACGTTATATAGCTGACAAGCACAACATGTTGGGTG

GTTGTCCAAAAGAGCGTGCAGAGATTTCAATGCTTGAAGGAGCGGTTTTG

GATATTAGATACGGTGTTTCGAGAATTGCATATAGTAAAGACTTTGAAAC

TCTCAAAGTTGATTTTCTTAGCAAGCTACCTGAAATGCTGAAAATGTTCG

AAGATCGTTTATGTCATAAAACATATTTAAATGGTGATCATGTAACCCAT

CCTGACTTCATGTTGTATGACGCTCTTGATGTTGTTTTATACATGGACCC

AATGTGCCTGGATGCGTTCCCAAAATTAGTTTGTTTTAAAAAACGTATTG

AAGCTATCCCACAAATTGATAAGTACTTGAAATCCAGCAAGTATATAGCA

TGGCCTTTGCAGGGCTGGCAAGCCACGTTTGGTGGTGGCGACCATCCTCC

AAAATCGGATCTGGTTCCGCGTGGATCCCCAGGAATTCCAAGCGAACTGA

ACGACATCAACAAAATTGAGCTGAAAAACCTGAGCGGCGAAATCATCAAA

GAAAACGGCAAGGAAGCTATTAAATATACTTCCAGCGACACCGCTTCCCA

TAAAGGCTGGAAGGCAACTCTGAGCGGCACCTTCATTGAAGACCCGCATT

CCGACAAGAAAACTGCTCTGCTGAACCTGGAAGGCTTTATCCCGTCCGAC

AAACAGATTTTCGGCTCTAAATATTACGGCAAAATGAAATGGCCGGAAAC

TTATCGCATTAATGTGAAAAGCGCTGACGTGAACAATAACATCAAAATCG

CAAACTCCATTCCGAAAAATACTATCGACAAAAAAGACGTGTCCAATTCC

ATTGGCTATTCCATCGGCGGTAACATCTCCGTGGAAGGCAAAACTGCTGG

CGCTGGCATCAACGCTTCCTATAACGTCCAAAACACTATCAGCTATGAAC

AACCGGACTTCCGCACCATTCAACGCAAAGACGATGCAAACCTGGCATCC

TGGGACATCAAATTCGTTGAGACTAAGGACGGCTATAACATCGACTCCTA

TCATGCTATTTATGGCAACCAACTGTTCATGAAATCCCGCCTGTATAACA

ATGGCGACAAAAACTTCACCGACGATCGCGACCTGTCCACCCTGATTTCC

GGCGGCTTCTCCCCGAACATGGCTCTGGCACTGACCGCACCTAAAAATGC

TAAAGAATCCGTGATCATCGTGGAATATCAACGCTTCGACAACGACTATA

TTCTGAATTGGGAAACTACTCAATGGCGCGGCACCAACAAACTTTCCTCA

ACCAGCGAATATAACGAATTTATGTTCAAAATCAACTGGCAAGACCATAA

AATCGAATATTATCTGTAA.

The amino acid sequence of the *C. perfringens* GST-NetB fusion protein encoded by the nucleic acid of SEQ ID NO: 34 is provided below, with the GST portion underlined:

(SEQ ID NO: 35)
MAPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLVPRGSPGIPSELNDINKIELKNLSGEIIK

ENGKEAIKYTSSDTASHKGWKATLSGTFIEDPHSDKKTALLNLEGFIPSD

KQIFGSKYYGKMKWPETYRINVKSADVNNNIKIANSIPKNTIDKKDVSNS

IGYSIGGNISVEGKTAGAGINASYNVQNTISYEQPDFRTIQRKDDANLAS

WDIKFVETKDGYNIDSYHAIYGNQLFMKSRLYNNGDKNFTDDRDLSTLIS

GGFSPNMALALTAPKNAKESVIIVEYQRFDNDYILNWETTQWRGTNKLSS

TSEYNEFMFKINWQDHKIEYYL.

In some embodiments, the nucleic acid comprises a netB gene fusion, wherein the netB gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 34. In some embodiments, the nucleic acid comprises a netB gene fusion, wherein the netB gene fusion comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 34.

In some embodiments, the nucleic acid comprises a nucleic acid sequence encoding a NetB fusion protein, wherein said NetB fusion protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 35. In some embodiments, the nucleic acid comprises a nucleic acid sequence encoding a NetB fusion protein, wherein said NetB fusion protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 35.

In some embodiments, the nucleic acid comprises a netB gene fusion that is operably-linked to a regulatable promoter. In some embodiments, the regulatable promoter is $P_{trc}$ or another promoter regulated by LacI.

In some embodiments, the nucleic acid comprises a cbh gene. Cbh is an enzyme belongs to a family of hydrolases, which act on carbon-nitrogen bonds other than peptide bonds, specifically in linear amides.

The nucleic acid sequence of the *C. perfringens* cbh gene is provided below:

(SEQ ID NO: 36)
```
ATGTGCACAGGCCTGGCACTGGAAACTAAAGACGGCCTGCACTTGTTCGG

CCGCAACATGGACATCGAATATTCTTTCAATCAATCTATTATTTTCATTC

CGCGCAACTTCAAGTGCGTGAACAAATCCAACAAAAAAGAACTGACCACC

AAATACGCTGTGCTGGGCATGGGCACTATCTTCGACGATTACCCGACCTT

CGCTGACGGCATGAACGAAAAAGGCCTGGGCTGTGCGGGCCTGAACTTCC

CGGTGTATGTGAGCTACTCTAAAGAAGACATCGAAGGCAAAACCAACATC

CCGGTGTACAACTTCCTGCTGTGGGTGCTGGCGAACTTCAGCTCTGTGGA

AGAGGTGAAGGAAGCCCTGAAAAACGCGAACATCGTGGACATCCCGATCT

CAGAGAACATCCCGAACACCACGCTGCACTGGATGATCTCCGACATCACC

GGCAAATCCATCGTGGTGGAACAGACCAAGGAAAAACTGAACGTGTTCGA

CAACAACATCGGCGTGCTGACCAACAGCCCGACGTTCGACTGGCACGTGG

CCAACCTGAACCAGTACGTGGGCCTGCGCTATAACCAGGTGCCGGAGTTC

AAGCTGGGCGACCAGTCTCTGACTGCTCTGGGCCAGGGCACTGGCCTGGT

GGGCCTGCCGGGCGACTTCACACCGGCGTCTCGCTTCATCCGCGTAGCGT

TTCTGCGTGACGCGATGATCAAAAACGACAAAGACAGCATCGACCTGATC

GAATTCTTCCACATCCTGAACAACGTGGCTATGGTACGCGGCTCCACTCG

CACAGTGGAAGAGAAATCCGACCTGACACAGTACACGTCTTGCATGTGCC

TGGAAAAAGGCATCTATTATTATAACACCTATGAAAACAACCAGATCAAC

GCAATCGACATGAACAAAGAAAACCTGGACGGCAACGAAATCAAAACCTA

CAAATACAACAAAACCCTGAGCATCAACCACGTGAAC.
```

The amino acid sequence of the *C. perfringens* Cbh protein encoded by the nucleic acid of SEQ ID NO: 36 is provided below:

(SEQ ID NO: 37)
```
MCTGLALETKDGLHLFGRNMDIEYSFNQSIIFIPRNFKCVNKSNKKELTT

KYAVLGMGTIFDDYPTFADGMNEKGLGCAGLNFPVYVSYSKEDIEGKTNI

PVYNFLLWVLANFSSVEEVKEALKNANIVDIPISENIPNTTLHWMISDIT

GKSIVVEQTKEKLNVFDNNIGVLTNSPTFDWHVANLNQYVGLRYNQVPEF

KLGDQSLTALGQGTGLVGLPGDFTPASRFIRVAFLRDAMIKNDKDSIDLI

EFFHILNNVAMVRGSTRTVEEKSDLTQYTSCMCLEKGIYYYNTYENNQIN

AIDMNKENLDGNEIKTYKYNKTLSINHVN.
```

In some embodiments, the nucleic acid comprises a cbh gene, wherein the cbh gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 36. In some embodiments, the nucleic acid comprises a cbh gene, wherein the cbh gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 36.

In some embodiments, the nucleic acid comprises a nucleic acid sequence encoding a Cbh protein, wherein said Cbh protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 37. In some embodiments, the nucleic acid comprises a nucleic acid sequence encoding a Cbh protein, wherein said Cbh protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 37.

In some embodiments, the nucleic acid comprises a cbh gene that is operably-linked to a regulatable promoter. In some embodiments, the regulatable promoter is $P_{trc}$ or another promoter regulated by LacI.

In some embodiments, the nucleic acid comprises a non-toxic cpe gene, or antigenic fragment thereof, such as the non-toxic receptor part of the toxin, also called CpeC. Cpe is an enzyme that binds to claudin family proteins, and alters the membrane permeability of cells. cpe is present in all of the species in the *Clostridium* genus.

The nucleic acid sequence encoding the non-toxic receptor part of the *C. perfringens* cpe gene, which has been 5% codon optimized and is also known as cpeC, is provided below:

(SEQ ID NO: 38)
```
GACATTGAAAAAGAAATCCTGGACCTGGCCGCTGCTACCGAACGTCTGAA

CCTGACCGACGCGCTGAACTCAAACCCGGCTGGCAACCTGTACGACTGGC

GTTCTTCTAACTCCTACCCGTGGACCCAGAAACTGAACCTGCACCTGACC

ATCACCGCGACTGGCCAGAAATACCGTATCCTGGCGAGCAAAATCGTTGA

CTTCAACATCTATTCAAACAACTTCAACAACCTGGTGAAACTGGAACAGT

CCCTGGGCGACGGCGTGAAAGACCACTACGTTGACATTAGCCTGGACGCG

GGCCAGTATGTTCTGGTGATGAAAGCGAACTCCTCCTATAGCGGCAACTA

CCCGTATTCCATTCTGTTCCAGAAATTC.
```

The nucleic acid sequence encoding the non-toxic receptor part of the *C. perfringens* cpe gene, which has been codon optimized and is also known as cpeC-max, is provided below:

(SEQ ID NO: 39)
```
GACATCGAAAAAGAAATCCTGGACCTGGCGGCGGCGACCGAACGTCTGAA

CCTGACCGACGCGCTGAACTCTAACCCGGCGGGCAACCTGTACGACTGGC

GTTCTTCTAACTCTTACCCGTGGACCCAGAAACTGAACCTGCACCTGACC

ATCACCGCGACCGGTCAGAAATACCGTATCCTGGCGTCTAAAATCGTTGA

CTTCAACATCTACTCTAACAACTTCAACAACCTGGTTAAACTGGAACAGT

CTCTGGGTGACGGTGTTAAAGACCACTACGTTGACATCTCTCTGGACGCG
```

-continued
```
GGTCAGTACGTTCTGGTTATGAAAGCGAACTCTTCCTACTCCGGTAACTA

CCCGTACTCTATCCTGTTCCAGAAATTC.
```

The amino acid sequence of the *C. perfringens* CpeC protein encoded by the nucleic acid of SEQ ID NOs: 38 and 39 is provided below:

```
                                         (SEQ ID NO: 40)
DIEKEILDLAAATERLNLTDALNSNPAGNLYDWRSSNSYPWTQKLNLHLT

ITATGQKYRILASKIVDFNIYSNNFNNLVKLEQSLGDGVKDHYVDISLDA

GQYVLVMKANSSYSGNYPYSILFQKF.
```

In some embodiments, the nucleic acid comprises a gene, wherein the gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 38 or SEQ ID NO:39. In some embodiments, the nucleic acid comprises a gene, wherein the gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 38 or SEQ ID NO:39.

In some embodiments, the nucleic acid comprises a nucleic acid sequence encoding a CpeC protein, wherein said CpeC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 40. In some embodiments, the nucleic acid comprises a nucleic acid sequence encoding a CpeC protein, wherein said CpeC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 40.

In some embodiments, the nucleic acid comprises a cpeC gene that is operably-linked to a regulatable promoter. In some embodiments, the regulatable promoter is $P_{trc}$ or another promoter regulated by LacI.

In some embodiments, the nucleic acid comprises a *C. perfringens* fba gene, or a fragment thereof. The nucleic acid sequence of a codon-optimized *C. perfringens* fba gene is provided below:

```
                                         (SEQ ID NO: 41)
ATGGCACTGGTTAACGCAAAAGAAATGCTGAATAAAGCACGCGAAGGCAA

ATACGCTGTTGGTCAATTCAACATCAACAACCTGGAATGGACAAAAGCTA

TCCTGCTGACTGCTCAAGAAAATAACTCACCAGTTATCCTGGGCGTATCA

GAAGGTGCTGCTAAATACATGTGTGGCTTCAAAACAATCGTTGGCATGGT

TAACGGCATGCTGGAAGAACTGAAAATCACTGTTCCTGTAGCACTGCACC

TGGATCACGGTAGCTACCAAGGCGCTATCGATGCTATGGATGCTGGCTTC

TCATCAGTAATGTTCGATGGCTCACACTACTCAATCGAAGAAAACATCGT

TAAAACTAAAGAAATCATCAACCTGGCTGCTGCTAAAAACGTATCAGTTG

AAGCTGAAGTTGGCTCAATCGGTGGCGAAGAAGACGGTGTTGTTGGCGCT

GGTGAAATCGCTGATCCTGCTGAATGTAAACAAATCGCTGAACTGGGCGT

TACTATGCTGGCTGCTGGTATCGGCAACATTCACGGCAAATACCCTGCAA

ACTGGGCTGGCCTGAACTTCGAAGCTCTGGCTAACATTAAAGCTGCTACT

GGCGATATGCCTCTGGTACTGCACGGTGGTACTGGCATCCCTTCAGATAT

GATCGCAGAAGCTATCTCACTGGGCGTATCAAAAATCAATGTTAATACTG

AGTGTCAACTGTCATTTGCTGAAGCTACTCGTAAATATATCGAAGCTGGC

ALAGACCTGGAAGGCAAAGGCTTTGACCCACGCAAACTGCTGAATCCTGG

CTTCGAAGCTATCAAAGCTACAGTTAAAGAAAAAATGGAACTGTTCGGTT

CAGTAAACAGAGCTTAATAG.
```

The amino acid sequence of the *C. perfringens* Fba protein encoded by the nucleic acid of SEQ ID NO: 41 is provided below

```
                                         (SEQ ID NO: 42)
MALVNAKEMLNKAREGKYAVGQFNINNLEWTKAILLTAQENNSPVILGVS

EGAAKYMCGFKTIVGMVNGMLEELKITVPVALHLDHGSYQGAIDAMDAGF

SSVMFDGSHYSIEENIVKTKEIINLAAAKNVSVEAEVGSIGGEEDGVVGA

GEIADPAECKQIAELGVTMLAAGIGNIHGKYPANWAGLNFEALANIKAAT

GDMPLVLHGGIGIPSDMIAEAISLGVSKINVNTECQLSFAEATRKYIEAG

KDLEGKGFDPRKLLNPGFEAIKATVKEKMELFGSVNRA.
```

In some embodiments, the nucleic acid comprises fba gene, wherein the fba gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 41. In some embodiments, the nucleic acid comprises a fba gene, wherein the fba gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 41.

In some embodiments, the nucleic acid comprises a nucleic acid sequence encoding a Fba protein, wherein said Fba protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 42. In some embodiments, the nucleic acid comprises a nucleic acid sequence encoding a Fba protein, wherein said Fba protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 42.

In some embodiments, the nucleic acid comprises fba gene that is operably-linked to a regulatable promoter. In some embodiments, the regulatable promoter is $P_{trc}$.

In an exemplary embodiment, the antigen elicits a protective immune response in a subject. As used herein, "protective" means that the immune response contributes to the lessening of any symptoms associated with infection of a host with the pathogen the antigen was derived from or designed to elicit a response against. For example, a protective antigen from a pathogen, such as *Clostridium*, may induce an immune response that helps to ameliorate symptoms associated with *Clostridium* infection or reduce the morbidity and mortality associated with infection with the pathogen or may reduce the ability of *Clostridium* to infect and colonize the host. The use of the term "protective" in this disclosure does not necessarily require that the host is completely protected from the effects of the pathogen.

In one embodiment, protection can be achieved by reducing the ability of the pathogen to colonize or persist in an animal host, as would be the case of induced immune responses against Cbh and/or CpeC; or inhibit the virulence aspects of the pathogen by neutralizing toxins, such as the alpha toxin and NetB toxin that cause damage to the intestinal epithelium of the host.

Immunogenicity of the bacterium may be augmented and/or modulated by constructing strains that also express sequences for cytokines, adjuvants, and other immunomodulators.

In further embodiments, a nucleic acid sequence encoding an antigen may comprise a secretion signal. In one embodiment of the invention, a signal sequence can be a blaSS signal sequence or an optimized blaSS signal sequence, as described in more detail herein.

As stated above, the level of synthesis of an antigen of interest may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding any of the proteins described herein may be codon-optimized, i.e., altered so as to mimic the codons from highly synthesized proteins of a particular organism. In a further embodiment, modify may refer to altering the GC content of the nucleic acid sequence encoding the repressor to change the level of translation of the mRNA encoding the repressor. Methods of modifying a nucleic acid sequence are known in the art.

In some embodiments, more than one modification or type of modification may be performed to optimize the expression level of a nucleic acid described herein (e.g., a nucleic acid encoding a repressor or antigen of interest). For instance, at least one, two, three, four, five, six, seven, eight, or nine modifications, or types of modifications, may be performed to optimize the expression level of a nucleic acid described herein. By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lacI may be altered, the SD sequence may be altered, and the codons of lacI may be optimized.

In some embodiments, the recombinant bacterium comprises a nucleic acid that is located in a plasmid or vector. As used herein, "vector" refers to an autonomously replicating nucleic acid unit. The present disclosure can be practiced with any known type of vector, including viral, cosmid, phasmid, and plasmid vectors. The most preferred type of vector is a plasmid vector. In some embodiments, the plasmid or vector is a high copy plasmid. In some embodiments, the plasmid or vector is a low copy plasmid or vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In some embodiments, the plasmid comprises a nucleic acid sequence encoding an aspartate-semialdehyde dehydrogenase gene (e.g., asdA). These plasmids may be advantageously used to complement a bacterium that comprises an aspartate-semialdehyde dehydrogenase gene mutation (e.g., asdA). In some embodiments, the plasmid is selected from the group consisting of pYA3342, pYA3337, and pYA3332.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

Promoters for use in the embodiments described herein are known in the art. One of skill in the art would recognize that the selection of a repressor dictates, in part, the selection of the promoter to be used to regulate the expression of a nucleic acid described herein. For instance, if the repressor is LacI, then the promoter may be selected from the group consisting of LacI responsive promoters, such as $P_{trc}$, $P_{lac}$, $P_{T7lac}$, $P_{tac}$, $P_{ompA\ lacO}$, and $P_{lpp\ lacO}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence. In some embodiments, the promoter comprises a regulatory sequence controlled by a repressor, such that expression of the nucleic acid sequence is repressed when the repressor is synthesized (e.g., during in vitro growth of the bacterium), but expression of the nucleic acid sequence encoding an antigen is high when the repressor is not synthesized (e.g., in vivo). Generally speaking, the concentration of the repressor will decrease with every cell division after expression of the gene encoding the repressor ceases. In some embodiments, the concentration of the repressor decreases such that high levels of expression of the nucleic acid sequence that is being regulated is achieved after about 2, 3, 4, 5, 6, 7, 8, 9, 10, 11, or 12 divisions of the bacterium. In an exemplary embodiment, the concentration of the repressor decreases enough to allow high-level expression of the nucleic acid sequence encoding an antigen after about 5 divisions of the bacterium in vivo.

In certain embodiments, the promoter may comprise other regulatory elements. For instance, the promoter may comprise lacO if the repressor is LacI. This is the case with the lipoprotein promoter $P_{lpp\ lacO}$ that is regulated by LacI since it possesses the LacI binding domain lacO. In one embodiment, the repressor is a LacI repressor and the promoter is $P_{trc}$.

In some embodiments, the expression of the nucleic acid sequence regulated by a repressor is repressed in vivo. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the repressor is repressed. For instance, if the repressor is not synthesized during growth of the recombinant bacterium in a host, the expression of the nucleic acid under the control of the repressor will be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependent T cell populations or antigen-dependent cytokine levels are known in the art, and methods of measuring levels of expression of antigen encoding sequences by measuring levels of mRNA transcribed or by quantitating the expression level of a protein are also known in the art.

In each of the above embodiments, a recombinant bacterium capable of regulated expression may also be attenuated. "Attenuated" refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the gut (in the case of *Salmonella*) and induce immune responses is, preferably, not substantially compromised.

In an exemplary embodiment, a recombinant bacterium may be attenuated as described above. In which case, both regulated attenuation and regulated expression of an antigen encoding sequence may be dependent upon a sugar regulatable system. Consequently, the concentration of sugar (e.g., arabinose) needed for optimal expression of the regulated antigen encoding sequence may not be the same as the concentration for optimal expression of attenuation. In an exemplary embodiment, the concentration of arabinose for the optimization of both regulated attenuation and regulated expression of sequences encoding antigen will be substantially the same. Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fur and phoPQ, so that the production levels of Fur and PhoPQ are optimal for both the regulated attenuation phenotype and the regulated expression when growing strains with a given concentration of arabinose. One of skill in the art will appreciate that other nucleic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

B. Attenuation

In some embodiments, the recombinant bacterium described herein is modified such that the expression of one or more genes, e.g., virulence genes, can be regulated in a sugar-responsive manner. In some embodiments, one or more endogenous genes, e.g., virulence genes, are deleted from the bacterial chromosome. In some embodiments, the deletion is a partial deletion of the endogenous gene. In some embodiments, the deletion is a full-length deletion of the endogenous gene. In some embodiments, the gene, e.g., virulence gene, is genetically-altered to prevent transcription and/or translation of the gene encoding the protein. In some embodiments, the endogenous gene is genetically altered to insert a transcriptional terminator in the open reading frame of the gene. In some embodiments, a regulatory region of the gene, e.g., virulence gene, is genetically-modified to alter (e.g., decrease) the expression of the gene. In some embodiments, the promoter of a gene, e.g., virulence gene, is altered to include one or more regulatory elements (e.g., a sugar-responsive promoter).

Triple-sugar regulated *Salmonella* vaccines are also disclosed in PCT/US18/14860, filed on Jan. 23, 2018 and published as WO18/136938, the entire contents of which are expressly incorporated herein by reference in their entirety.

In some embodiments, the recombinant bacterium described herein is modified to comprise a nucleic acid comprising a gene. In some embodiments, the recombinant bacterium is modified to comprise a nucleic acid comprising a gene, whereby an endogenous copy of the gene in the bacterial chromosome has been altered and/or deleted. In some embodiments, the nucleic acid comprises a gene that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an endogenous gene in the bacterial chromosome that has been deleted and/or altered. In some embodiments, the nucleic acid comprises a gene that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to an endogenous gene in the bacterial chromosome that has been deleted and/or altered. In some embodiments, the nucleic acid comprises a gene from a bacterial species, subspecies, serovar, or strain that is different than the bacterial species of the recombinant *bacterium*.

In some embodiments, the nucleic acid comprises a gene from a bacterial species, subspecies, serovar, or strain that is the same as the bacterial species of the recombinant bacterium. In some embodiments, the nucleic acid comprises a gene that is operably-linked to a regulatable promoter (e.g., a sugar-regulatable promoter). In some embodiments, the nucleic acid comprises a gene that is operably-linked to a rhamnose-regulatable promoter, a xylose-regulatable promoter, a galactose-regulatable promoter, an arabinose-regulatable promoter, or a maltose-regulatable promoter. In some embodiments, the nucleic acid comprising the gene is located in a plasmid in the bacterium. In some embodiments, the nucleic acid comprising the gene is located in the bacterial chromosome. In some embodiments, the nucleic acid comprising the gene is located at the chromosomal locus corresponding to the locus of an endogenous gene that has been deleted or altered in the bacterial chromosome. In some embodiments, the nucleic acid is codon-optimized (e.g., to improve expression of the nucleic acid in the recombinant bacterium).

1. O-Antigen Synthesis Genes

In some embodiments, the recombinant bacterium comprises a deletion in an endogenous O-antigen synthesis gene. In some embodiments, the recombinant bacterium comprises a deletion in an endogenous O-antigen ligase gene. In some embodiments, the deletion is a partial deletion of the endogenous O-antigen ligase gene. In some embodiments, the deletion is a full-length deletion of the endogenous O-antigen ligase gene. In some embodiments, the endogenous O-antigen ligase gene is genetically altered to insert a transcriptional terminator in the open reading frame of the gene. In some embodiments, a regulatory region of the endogenous O-antigen ligase gene is genetically-modified to alter (e.g., decrease) the expression of the gene. In some embodiments, the promoter of an endogenous O-antigen ligase gene is altered to include one or more regulatory elements (e.g., a sugar-responsive promoter). In some embodiments, the promoter of an endogenous O-antigen ligase gene is altered to increase the spacing between the Shine-Delgarno sequence and the start codon of the gene. In some embodiments, the promoter of an endogenous O-antigen ligase gene is altered to decrease the spacing between the Shine-Delgarno sequence and the start codon of the gene. In some embodiments, the Shine-Delgarno (SD) sequence, the start codon, the second codon and/or third codons of the O-antigen ligase gene is altered to increase the frequency of adenine nucleobases in order to enhance the translation efficiency of the gene. In some embodiments, the Shine-Delgarno (SD) sequence, the start codon, the second codon and/or third codons of the O-antigen ligase gene is altered to reduce the frequency of adenine nucleobases in order to decrease the translation efficiency of the gene. In some embodiments, the O-antigen ligase gene is waaL (also known as rfaL). The O-antigen ligase WaaL is necessary to ligate polysaccharide to the lipid A-LPS core moiety. Deletion of waaL results in an intact lipid A-LPS core with no O-antigen or individual sugars attached to it. In some embodiments, the O-antigen ligase gene is selected from the group consisting of waaG (also known as rfaG), waaI (also known as rfaI), rfaH, waaJ (also known as rfaJ), wbaP (also known as rfbP), wzy (also known as rfc), waaP, waaQ, waaF, waaP, waaC, and waaA.

In some embodiments, the recombinant bacterium described herein is modified to comprise a nucleic acid comprising an O-antigen ligase gene. In some embodiments, the nucleic acid comprising an O-antigen ligase gene is located on a plasmid in the bacterium. In some embodiments, the nucleic acid comprising an O-antigen ligase gene is located on a chromosome of the bacterium. In some embodiments, the nucleic acid comprising an O-antigen ligase gene is located at the chromosomal locus corresponding to the locus of an endogenous O-antigen ligase gene that has been deleted or altered in the bacterial chromosome. In some embodiments, the recombinant bacterium is modified to comprise a nucleic acid comprising an O-antigen ligase gene, whereby an endogenous copy of the gene in the bacterial chromosome has been altered and/or deleted. In some embodiments, the nucleic acid comprises a *Salmonella* O-antigen ligase gene.

The nucleic acid sequence of an exemplary *Salmonella* waaL gene is provided below:

(SEQ ID NO: 1)
atgctaaccacatcattaacgttaaataaagagaaatggaagccgatctg gaataaagcgctggcgttgccacgtactggatggtattacgcgttataaa catttgataatcatacttatggttatcaccgcgatttatcaggtctcacg ctcaccgaaaagtttccccctcattcaaaaatagcgtattttatagcgt agcagtattatcattaatccttgtttattccatactcatatcgccagata tgaaagaaagtttcaaggaatttgaaaatacggtactggagggcttctta -continued
```
ttatatactttattaattcccgtactattaaaagatgaaacaaaagaaac ggttgcgaaaatagtacttttctccttttaacaagtttaggacttcgctg ccttgcagagagtattctgtatatcgaggactataataaagggattatgc cattcataagctatgcgcatcgacatatgtccgattccatggttttactt atttccagcattattgaatatttggctgtttagaaaaaatgcaattaagt tggttttttggtgcttagcgccatctaccttatctttatcctgggaaccc tatcgcgaggggcatggttggcggtgcttatagtaggtgttctgtgggca atactgaaccgccaatggaagttaataggagttggtgccattttattagc cattatcggcgctttggttatcactcaacataataacaaaccagacccag aacatttactgtataaattacagcagacagatagctcatatcgttatact aacggaacccagggcaccgcgtggatactgattcaggaaaacccgatcaa gggctacggctatggtaatgatgtgtatgatggtgtttataataaacgcg ttgtcgattatccaacgtggacctttaaagaatctatcggtccgcataat accattctgtacatctggtttagtgcaggcatattgggtctggcgagcct ggtctatttatatggcgctatcatcagggaaacagccagctctaccctca ggaaagtagagataagcccctacaatgctcatctcttgctattttatct ttcgtcggttttatatcgttcgtggcaattttgaacaggtcgatattgc tcaaattggtatcattaccggttactgctggcgctaagaaatagataa.
```

The amino acid sequence of the WaaL protein encoded by the nucleic acid of SEQ ID NO: 1 is provided below:

```
                                              (SEQ ID NO: 2)
MLTTSLTLNKEKWKPIWNKALVFLFVATYFLDGITRYKHLIIILMVITAI

YQVSRSPKSFPPLFKNSVFYSVAVLSLILVYSILISPDMKESFKEFENTV

LEGFLLYTLLIPVLLKDETKETVAKIVLFSFLTSLGLRCLAESILYIEDY

NKGIMPFISYAHRHMSDSMVFLFPALLNIWLFRKNAIKLVFLVLSAIYLF

FILGTLSRGAWLAVLIVGVLWAILNRQWKLIGVGAILLAIIGALVITQHN

NKPDPEHLLYKLQQTDSSYRYTNGTQGTAWILIQENPIKGYGYGNDVYDG

VYNKRVVDYPTWTFKESIGPHNTILYIWFSAGILGLASLVYLYGAIIRET

ASSTLRKVEISPYNAHLLLFLSFVGFYIVRGNFEQVDIAQIGIITGFLLA

LRNR.
```

In some embodiments, the nucleic acid comprises a *Salmonella* waaL gene (provided as SEQ ID NO: 1). In some embodiments, the nucleic acid comprises a waaL gene, wherein the waaL gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 1. In some embodiments, the nucleic acid comprises a waaL gene, wherein the waaL gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 1.

In some embodiments, the nucleic acid comprises a nucleic acid sequence encoding an O-antigen ligase, wherein said O-antigen ligase comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 2. In some embodiments, the nucleic acid comprises a nucleic acid sequence encoding an O-antigen ligase, wherein said O-antigen ligase comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 2.

In some embodiments, the nucleic acid comprises an O-antigen ligase gene from a bacterial species, subspecies, serovar, or strain that is different than the bacterial species of the recombinant bacterium. In some embodiments, the nucleic acid comprises an O-antigen ligase gene from a bacterial species, subspecies, serovar, or strain that is the same as the bacterial species of the recombinant *bacterium*.

In some embodiments, the nucleic acid comprises an O-antigen ligase gene that is operably-linked to a regulatable promoter (e.g., a sugar-regulatable promoter). In some embodiments, the nucleic acid comprises an O-antigen ligase gene (e.g., waaL) that is operably-linked to a sugar-regulatable promoter. Advantageously, recombinant bacterial strains comprising a nucleic acid comprising an O-antigen ligase gene (e.g., waaL) that is operably linked to a sugar regulatable promoter will synthesize normal LPS in the presence of the sugar (e.g., rhamnose) in vitro, but will form rough LPS in vivo due to the absence of the sugar that activates the promoter and therefore, the expression of the O-antigen ligase. Without wishing to be bound by any particular theory, using this strategy, the bacterium will expose conserved LPS core oligosaccharide and have enhanced production of conserved outer membrane proteins (OMPs; e.g., porins) which may lead to improved immunogenicity and aid in the production of a cross-protective immune response against an antigen of interest synthesized in the bacterium in vivo. In some embodiments, the sugar regulatable promoter exhibits increased activity (e.g., increased transcription) in the presence of a specific sugar and decreased activity in the absence of a sugar. In some embodiments, the nucleic acid comprises an O-antigen ligase gene that is operably-linked to a rhamnose-regulatable promoter (e.g., a sugar-regulatable promoter). In some embodiments, the nucleic acid comprises an O-antigen ligase gene that is operably-linked to an arabinose-regulatable promoter (e.g., a sugar-regulatable promoter). In some embodiments, the use of a rhamnose-regulatable promoter (e.g., rhaSR $P_{rhaBAD}$) may be preferable to an arabinose-regulatable promoter because a relatively higher concentration is required to activate an arabinose-regulatable promoter as compared to a rhamnose-regulatable promoter (see, e.g., Giacalone et al. (2006) *BioTechniques* 40(3): 355-366 (39), the entire contents of which are incorporated herein by reference). In some embodiments, the recombinant bacterium comprises the mutation ΔwaaL/ΔpagL:TT rhaSR $P_{rhaBAD}$ waaL.

2. Lipid A Deacylase Genes

In some embodiments, the recombinant bacterium comprises a deletion in an endogenous lipid A deacylase gene. In some embodiments, the deletion is a partial deletion of the endogenous lipid A deacylase gene. In some embodiments, the deletion is a full-length deletion of the endogenous lipid A deacylase gene. In some embodiments, the endogenous lipid A deacylase gene is genetically altered to insert a transcriptional terminator in the open reading frame of the gene. In some embodiments, a regulatory region of the endogenous lipid A deacylase gene is genetically-modified to alter (e.g., decrease) the expression of the gene. In some embodiments, the promoter of an endogenous lipid A deacylase gene is altered to include one or more regulatory elements (e.g., a sugar-responsive promoter). In some embodiments, the lipid A deacylase gene is pagL. Bacterial comprising a deletion of the lipid A deacylase gene pagL have been found to produced increased amounts of outer membrane vesicles (see, e.g., Elhenawy et al. (2016) mBio 7(4): e00940-16 (40)). Deletion of the pagL gene of Salmonella does not impair bacterial virulence (see, e.g., Man et al. Proc. Nat'l. Acad. Sci. USA 111: 7403-8 (41)). Without wishing to be bound by any particular theory, in some embodiments, the recombinant bacterium described herein comprise one or more genetic modifications which results in increased vesiculation (i.e., increased vesicle production) which may be particularly advantageous in inducing an immune response in the host against an antigen of interest that is expressed by the *bacterium*.

3. Phosphomannose Isomerase Genes

In some embodiments, the recombinant bacterium comprises a deletion in an endogenous phosphomannose isomerase gene. Phosphomannose isomerase, also known as mannose-6 phosphate isomerase, catalyzes the reversible interconversion of fructose 6-phosphate to mannose 6-phosphate. Mannose 6-phosphate is then converted to GDP-mannose and used for the synthesis of O-antigen side chains. Bacteria with deletions of the phosphomannose isomerase gene pmi are not mannose sensitive and are partially attenuated (see, e.g., Collins et al. (1991) Infect. Immun. 59(3): 1079-85 (42)). These pmi mutants synthesize wild-type levels of LPS O-antigen side chains when grown in media containing mannose, and are both attenuated but highly immunogenic (see, e.g., Curtiss et al. (2007) "Induction of host immune responses using *Salmonella*-vectored vaccines." In: Brogden K A, Minion F C, Cornick N, Stanton T B, Zhang Q, Nolan L K, Wannemuehler M J, ed. Virulence Mechanisms of Bacterial Pathogens. 4th ed. Washington D.C.: ASM Press (43)). In some embodiments, the deletion of the endogenous phosphoisomerase gene is a partial deletion. In some embodiments, the deletion of the endogenous phosphomannose isomerase gene is a full-length deletion. In some embodiments, the endogenous phosphomannose isomerase gene is genetically altered to insert a transcriptional terminator in the open reading frame of the gene. In some embodiments, a regulatory region of the endogenous phosphomannose isomerase gene is genetically-modified to alter (e.g., decrease) the expression of the phosphomannose isomerase gene. In some embodiments, the promoter of an endogenous phosphomannose isomerase gene is altered to include one or more regulatory elements (e.g., a sugar-responsive promoter). In some embodiments, the phosphomannose isomerase gene is pmi.

In some embodiments, the bacterium comprises a deletion of a pmi gene. In some embodiments, the bacterium comprises a Δpmi-2426 mutation. A bacterium comprising a Δpmi-2426 mutation, grown in the presence of mannose, is capable of synthesizing a complete LPS O-antigen. Non-phosphorylated mannose, which is the form required for bacterial uptake, is unavailable in vivo. Hence, a bacterium comprising a Δpmi-2426 mutation loses the ability to synthesize LPS O-antigen serotype specific side chains in vivo and the number of O-antigen side chains attached to the LPS core decreases by about half after each cell division in vivo. The LPS that is synthesized comprises a core structure that is substantially similar across all *Salmonella enterica* serotypes except S. Arizona. This results in a bacterium that is capable of eliciting an immune response against at least two *Salmonella* serotypes without substantially inducing an immune response specific to the serotype of the bacterial vector. In some embodiments, the bacterium is capable of eliciting an immune response against all *Salmonella* serotypes without substantially inducing an immune response specific to the serotype of the bacterial vector.

A recombinant bacterium described herein that comprises a deletion in apmi mutation may also comprise other mutations that ensure that mannose available to the bacterium during in vitro growth is used for LPS O-antigen synthesis. For instance, a bacterium may comprise a Δ(gmd-fcl)-26 mutation. This mutation deletes two nucleic acid sequences that encode enzymes for conversion of GDP-mannose to GDP-fucose, ensuring that mannose available to the bacterium during in vitro growth is used for LPS O-antigen synthesis and not colanic acid production. Similarly, a bacterium may comprise the Δ(wcaM-wza)-8 mutation, which deletes all 20 nucleic acid sequences necessary for colanic acid production, and also precludes conversion of GDP-mannose to GDP-fucose.

4. UDP-Galactose Epimerase Genes

UDP-Gal is the precursor for the assembly of the LPS O-antigen side chains, the LPS outer core, for colanic acid and other polysaccharide polymers having galactose as a constituent (44). UDP-Gal is synthesized by conversion of glucose-1-P to UDP-Glu by the enzyme glucose-1-P uridylyltransferase encoded by the galU gene with UDP-Glu converted to UDP-Gal by the enzyme UDP-galactose epimerase encoded by the galE gene (45, 46). Strains grown in the presence of galactose can synthesize UDP-Gal by a different pathway in which galactose after uptake is converted to galactose-1-P by galactose kinase encoded by the galK gene which in tern is converted to UDP-Gal by the enzyme UDP-Gal transferase encoded by the galT gene (45). Strains with a galE mutation are unable to synthesize LPS outer core and LPS O-antigen unless galactose is supplied in the growth medium (47). Because of these facts and properties *Salmonella* strains with galE mutations can synthesize LPS when grown with galactose and are invasive to colonize lyphoid tissues, but loose this ability in vivo due to the unavailability of free galactose such that they gradualy loose LPS components as they multiply in the infected or immunized animal host. Just like pmi mutants, they gradually become attenuated due to increasing susceptibility to complement-mediated cytotoxicity and enhanced phagocytosis and killing my macrophages. However, the supply of galactose to such galE mutants can lead to cell death by lysis since the accummunlation of Gal-1-P and UDP-Gal is toxic (30, 48, 49). Because of this, growth of galE mutants in the presence of galactose selects for mutations in genes for galactose uptake or in the galK and galT genes so that toxic products are not synthesized. Unfortunately, such galactose-resistant mutants are no longer able to make LPS and are totally attenuated, non-invasive and non-immunogenic (30, 50). To circumvent these problems to enable use of galE mutations in *Salmonella* vaccine strains, we have devised a means to generate galE mutants with the potential for reversable synthesis of LPS dependent on the presence or absence of galactose that are resistant to galactose with no selection of mutants unable to synthesize UDP-Gal for LPS synthesis.

5. Iron Acquisition Regulatory Genes

In some embodiments, the recombinant bacterium comprises a deletion in the endogenous promoter $P_{fur}$, which regulates the expression of the fur gene. Fur represses the transcription of genes involved in iron acquisition in the presence of free iron. When iron concentrations become low in the bacterium, Fur ceases to be synthesized which leads to the constitutive expression of genes encoding iron acquisition proteins (e.g., iron-regulated outer membrane proteins (IROMPs). In some embodiments, the deletion is a partial deletion of the endogenous $P_{fur}$ promoter. In some embodiments, the deletion is a full-length deletion of the endogenous $P_{fur}$ promoter. In some embodiments, the endogenous $P_{fur}$ promoter is genetically-modified to alter (e.g., decrease) the expression of the fur gene. In some embodiments, the endogenous $P_{fur}$ promoter is genetically altered to comprise a transcriptional terminator.

In some embodiments, the recombinant bacterium comprises a nucleic acid comprising a fur gene (e.g., a fur gene from the same bacterial species as the recombinant *bacterium*).

In some embodiments, the nucleic acid comprising a fur gene is located on a plasmid in the bacterium. In some embodiments, the nucleic acid comprising a fur gene is located on a chromosome of the bacterium. In some embodiments, the nucleic acid comprising a fur gene is located at the chromosomal locus corresponding to the locus of an endogenous fur gene that has been deleted or altered in the bacterial chromosome. In some embodiments, the recombinant bacterium is modified to comprise a nucleic acid comprising a fur gene, whereby an endogenous copy of the fur gene in the bacterial chromosome has been altered and/or deleted.

The nucleic acid sequence of an exemplary *Salmonella* fur gene is provided below:

(SEQ ID NO: 3)
atgactgacaacaataccgcattaaagaaggctggcctgaaagtaacgct tcctcgtttaaaaattctggaagttcttcaggaaccagataaccatcacg tcagtgcggaagatttatacaaacgcctgatcgacatgggtgaagaaatc ggtctggcaaccgtataccgtgtgctgaaccagtttgacgatgccggtat cgtgacccgccataattttgaaggcggtaaatccgttttttgaactgacgc aacagcatcatcacgaccatcttatctgccttgattgcggaaaagtgatt gaatttagtgatgactctattgaagcgcgccagcgtgaaattgcggcgaa acacggtattcgtttaactaatcacagcctctatctttacggccactgcg ctgaaggcgactgccgcgaagacgagcacgcgcacgatgacgcgactaaa taa.

The amino acid sequence of the Fur protein encoded by the nucleic acid of SEQ ID NO: 3 is provided below:

(SEQ ID NO: 4)
MTDNNTALKKAGLKVTLPRLKILEVLQEPDNHIIVSAEDLYKRLIDMGEE

IGLATVYRVLNQFDDAGIVTRHNFEGGKSVFELTQQHHHDHLICLDCGKV

IEFSDDSIEARQREIAAKHGIRLTNHSLYLYGHCAEGDCREDEHAHDDAT

K.

In some embodiments, the nucleic acid comprises a *Salmonella* fur gene (provided as SEQ ID NO: 3). In some embodiments, the nucleic acid comprises a fur gene, wherein the fur gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 3. In some embodiments, the nucleic acid comprises a fur gene, wherein the fur gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 3.

In some embodiments, the nucleic acid comprises a nucleic acid sequence encoding a Fur protein, wherein said Fur protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 4. In some embodiments, the nucleic acid comprises a nucleic acid sequence encoding a Fur protein, wherein said Fur protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 4.

In some embodiments, the nucleic acid comprises a fur gene from a bacterial species, subspecies, serovar, or strain that is the same as the bacterial species of the recombinant *bacterium*.

In some embodiments, the nucleic acid comprises a fur gene that is operably-linked to a regulatable promoter (e.g., a sugar-regulatable promoter). In some embodiments, the nucleic acid comprises a fur gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a fur gene that is operably-linked to a rhamnose-regulatable promoter (e.g., a sugar-regulatable promoter). In some embodiments, the nucleic acid comprises a fur gene that is operably-linked to an arabinose-regulatable promoter (e.g., a sugar-regulatable promoter). In some embodiments, the arabinose-regulatable promoter is araCP$_{araBAD}$. In some embodiments, the recombinant bacterium comprises the mutation ΔP$_{fur}$::TT araC P$_{araBAD}$ fur.

6. Endosomal Escape Genes

In some embodiments, the recombinant bacterium has been genetically-altered such that the bacterium is capable of escaping the endosomal compartment of a host cell. A recombinant bacterium may exhibit a temporal delay in escaping an endosome following invasion of the host cell. Methods of detecting escape from an endosomal compartment of a host cell are well known in the art, and include, for example, microscopic analysis.

In some embodiments, the recombinant bacterium comprises a deletion in an endogenous sifA gene. In some embodiments, the recombinant bacterium comprises a mutation that alters the function of SifA. SifA is an effector protein necessary for the formation of *Salmonella*-induced filaments and for the maintenance of the vacuolar membrane enclosing the bacterium. Bacteria comprising a deletion of sifA are capable of escaping the host cell endosome (also called the *Salmonella*-containing vesicle, or SCV) following cellular invasion. In some embodiments, the deletion of the endogenous sifA gene is a partial deletion. In some embodiments, the deletion of the endogenous sifA gene is a full-length deletion. In some embodiments, the endogenous sifA gene is genetically altered to insert a transcriptional terminator in the open reading frame of the gene. In some embodiments, a regulatory region of the endogenous sifA gene is genetically-modified to alter (e.g., decrease) the expression of the sifA gene. In some embodiments, the promoter of an endogenous sifA gene is altered to include one or more regulatory elements (e.g., a sugar-responsive promoter).

In some embodiments, the recombinant bacterium described herein is modified to comprise a nucleic acid comprising a sifA gene. In some embodiments, the nucleic acid comprising a sifA gene is located on a plasmid in the bacterium. In some embodiments, the nucleic acid comprising a sifA gene is located on a chromosome of the bacterium. In some embodiments, the nucleic acid comprising a sifA gene is located at the chromosomal locus corresponding to the locus of an endogenous a sifA that has been deleted or altered in the bacterial chromosome. In some embodiments, the recombinant bacterium is modified to comprise a nucleic acid comprising a sifA gene, whereby an endogenous copy of the sifA gene in the bacterial chromosome has been altered and/or deleted.

The nucleic acid sequence of an exemplary *Salmonella* sifA gene is provided below:

(SEQ ID NO: 7)
Atgccgattactatagggaatggttttttaaaaagtgaaatccttaccaa ctccccaaggaatacgaaagaagcatggtggaaagttttatgggaaaaaa ttaaagacttcttttttctactggcaaagcaaaagcggaccgttgtcta catgagatgttgtttgccgaacgcgccccacacgagagcggcttacaga gatttttttgagttgaaagagttagcctgcgcatcgcaaagagatagat ttcaggttcataatcctcatgaaatgatgccaccattattcttcgcatc atggatcaaaacgaagagaacgaattgttacgtatcactcaaaataccga taccttagctgtgaagtcatgggaatctttatttttttaatgaaagatc gcccggatattttaaaatcgcatccacaaatgacggccatgattaagaga agatatagcgaaatcgtagactaccccctcccttcgacattatgtctcaa tcctgctggcgcgccgatattatcggttccattagacaacatagagggt atttatatactgaattgagaaaaggacatttagatgggtggaaagcgcaa gaaaaggcaacctacctggcagcgaaaattcagtctgggattgaaaagac aacgcgcattttacaccatgcgaatatatccgaaagtactcagcaaaacg cattttagaaacaatggcgatgtgtggattaaaacagcttgaaatacca ccaccgcatacccacatacctattgaaaaaatggtaaaagaggttttact agcggataagacgtttcaggcgttcctcgtaacggatcccagcaccagcc aaagtatgttagctgagatagtcgaagccatctctgatcaggtttttcac gccattttagaatagaccccaggctatacaaaaaatggcggaagaaca gttaaccacgctacacgttcgctcagaacaacaaagcggctgtttatgtt gttttttataa.

The amino acid sequence of the SifA protein encoded by the nucleic acid of SEQ ID NO: 7 is provided below:

(SEQ ID NO: 8)
MPITIGNGFLKSEILTNSPRNTKEAWWKVLWEKIKDFFFSTGKAKADRCL

HEMLFAERAPTRERLTEIFFELKELACASQRDRFQVHNPHENDATIILRI

MDQNEENELLRITQNTDTFSCEVMGNLYFLMKDRPDILKSHPQMTAMIKR

RYSEIVDYPLPSTLCLNPAGAPILSVPLDNIEGYLYTELRKGHLDGWKAQ

EKATYLAAKIQSGIEKTTRILHHANISESTQQNAFLETMAMCGLKQLEIP

PPHTHIPIEKMVKEVLLADKTFQAFLVTDPSTSQSMLAEIVEAISDQVFH

AIFRIDPQAIQKMAEEQLTTLHVRSEQQSGCLCCFL.

In some embodiments, the nucleic acid comprises a *Salmonella* sifA gene (provided as SEQ ID NO: 7). In some embodiments, the nucleic acid comprises a sifA gene, wherein the sifA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 7. In some embodiments, the nucleic acid comprises a sifA gene, wherein the sifA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 7.

In some embodiments, the nucleic acid comprises a nucleic acid sequence encoding a SifA protein, wherein said SifA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 8. In some embodiments, the nucleic acid comprises a nucleic acid sequence encoding a SifA protein, wherein said SifA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 8.

In some embodiments, the nucleic acid comprises a sifA gene from a bacterial species, subspecies, serovar, or strain that is different than the bacterial species of the recombinant bacterium. In some embodiments, the nucleic acid comprises a sifA gene from a bacterial species, subspecies, serovar, or strain that is the same as the bacterial species of the recombinant *bacterium*.

In some embodiments, the nucleic acid comprises a sifA gene that is operably-linked to a regulatable promoter (e.g., a sugar-regulatable promoter). In some embodiments, the nucleic acid comprises a sifA gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a sifA gene that is operably-linked to a rhamnose-regulatable promoter (e.g., a sugar-regulatable promoter). In some embodiments, the nucleic acid comprises a sifA gene that is operably-linked to an arabinose-regulatable promoter. In some embodiments, the arabinose-regulatable promoter is $P_{BAD}$. In some embodiments, the recombinant bacterium comprises the mutation ΔsifA::TT araC $P_{BAD}$ sifA. In some embodiments, the recombinant bacterium comprises the mutation $\Delta P_{sifA}$:: TT araC $P_{araBAD}$ sifA. When the expression of the nucleic acid comprising a sifA gene is under the control of an arabinose-regulated promoter, the bacterial escape from the host endosome can be delayed. Since arabinose is absent in host cells, arabinose cannot induce the expression of the sifA gene. Thus, if the recombinant bacterium is cultured in the presence of arabinose prior to administration to the subject, the expression of sifA will gradually decrease with each round of bacterial cell division thereby allowing escape of the bacterium from the host cell endosome during the initial cell division cycles. Similar delayed-escape mutations may be constructed using other regulatable promoters, such as from the xylose-regulatable or rhamnose-regulatable promoter systems.

7. GTP Pyrophosphokinase Genes

In some embodiments, the recombinant bacterium comprises a deletion in an endogenous relA gene, which encodes the GTP pyrophosphokinase RelA. The inclusion of a relA deletion in the recombinant bacterium uncouples the occurrence of growth-dependent lysis to the need for continued protein synthesis. In some embodiments, the deletion of the endogenous relA gene is a partial deletion. In some embodiments, the deletion of the endogenous relA gene is a full-length deletion.

8. Other Attenuation Methods

Other methods of attenuation are known in the art. For instance, attenuation may be accomplished by altering (e.g., deleting) native nucleic acid sequences found in the wild-type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, gal U, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

C. Additional Mutations

In some embodiments, the recombinant bacterium comprises a deletion in an endogenous recF gene, which encodes the DNA replication and repair protein RecF. In some embodiments, the deletion of the endogenous recF gene is a partial deletion. In some embodiments, the deletion of the endogenous recF gene is a full-length deletion. In some embodiments, the endogenous recF gene is genetically altered to insert a transcriptional terminator in the open reading frame of the gene.

In some embodiments, the recombinant bacterium comprises a deletion in an endogenous recJ gene, which encodes the exonuclease RecJ. In some embodiments, the deletion of the endogenous recJ gene is a partial deletion. In some embodiments, the deletion of the endogenous recJ gene is a full-length deletion. In some embodiments, the endogenous recJ gene is genetically altered to insert a transcriptional terminator in the open reading frame of the gene.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP.

In some embodiments, the recombinant bacterium comprises a deletion in an endogenous asd gene. In some embodiments, the deletion of the endogenous asd gene is a partial deletion. In some embodiments, the deletion of the endogenous asd gene is a full-length deletion. In some embodiments, the endogenous asd gene is genetically altered to insert a transcriptional terminator in the open reading frame of the gene. In some embodiments, the promoter of an endogenous asd gene is altered to include one or more regulatory elements (e.g., a sugar-responsive promoter). In one example, the bacterium is modified by using a ΔasdA mutation to eliminate the bacterium's ability to produce β-aspartate semialdehyde dehydrogenase, an enzyme essential for the synthesis of DAP. Other mutations that result in the abolition of the synthesis of DAP include, but are not limited to, dapA, dapB, dapC, dapD, dapE, dapF, and asd (see, e.g., U.S. Pat. No. 6,872,547, incorporated herein by reference). Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall. Thus, the bacterium can be modified by manipulating expression of genes involved in peptidoglycan biosynthesis such as genes encoding peptidoglycan biosynthetic enzymes. Peptidoglycan biosynthetic enzymes are known in the art. See, for example, Otten et al., Molecular Microbiology 107:142:63 (2018), the contents of which is incorporated by reference.

Similarly, various embodiments may comprise the araC P$_{araBAD}$ c2 gene cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows for stable maintenance of plasmids in vivo in the absence of any drug resistance attributes that are not permissible in live bacterial vaccines. In some of these embodiments, the wild-type asd nucleic acid sequence may be encoded by the vector described herein. The vector enables the regulated expression of an antigen encoding sequence through the repressible promoter.

D. Repressor Regulatory Systems

In some embodiments, the recombinant bacterium comprises a nucleic acid (e.g., a gene) that is operably linked to a repressor-regulatable promoter to facilitate the regulatable expression of the gene. Thus, in some embodiments, the recombinant bacterium comprises a nucleic acid comprising a gene encoding a repressor. In some embodiments, the gene encoding the repressor is operably-linked to a regulatable promoter. Methods of chromosomally integrating a nucleic acid sequence encoding a repressor operably-linked to a regulatable promoter are known in the art and detailed in the examples. In some embodiments, the nucleic acid sequence encoding a repressor is not integrated into a chromosomal locus such that the ability of the bacterium to colonize a host cell is disrupted. In some embodiments, the recombinant bacterium comprises a nucleic acid encoding a repressor that is integrated into the relA locus of the bacterial chromosome. In some embodiments, the recombinant bacterium comprises a nucleic acid encoding a repressor that is integrated into the endA locus of the bacterial chromosome. In some embodiments, the recombinant bacterium comprises at least one nucleic acid sequence encoding a repressor. In some embodiments, the recombinant bacterium comprises at least two, at least three, at least four, at least five, at least six or more nucleic acids encoding a repressor. In some embodiments, the nucleic acid encoding the repressor is present on a plasmid in the bacterium. In some embodiments, the nucleic acid encoding the repressor is located in the bacterial chromosome. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

As used herein, a "repressor" refers to a biomolecule that represses the transcriptional activity of a promoter. In some embodiments, the repressor is synthesized by the recombinant bacterium in high enough quantities during in vitro culture, such that the transcription of a nucleic acid that is operably linked to a repressor-regulatable promoter is repressed. This may be particularly advantageous if, for example, expression of the product encoded by said nucleic acid impedes the in vitro growth of the bacterium, and/or the ability of the bacterium to infect and/or colonize a subject. In some embodiments, the nucleic acid that is operably-linked to the repressor-regulatable promoter expresses an antigen of interest. In some embodiments, the concentration of the repressor within the cell gradually decreases with each cell division cycle after transcription of the gene encoding the repressor decreases or ceases (e.g., in vivo). The use of a particular repressor, as described herein, may depend, in part, on the species, subspecies, strain or serovar of the recombinant bacterium being used. In some embodiments, the repressor is derived from the same species (e.g., the same bacterial species or the same phage) from which the repressor-regulatable promoter is derived. In some embodiments the repressor is not derived from the same bacterial species as the bacterial species in which the repressor is expressed. For example, in some embodiments, the repressor is derived from *E. coli* if the recombinant bacterium is of the genus *Salmonella*. Other suitable repressors include repressors derived from a bacteriophage.

A nucleic acid sequence encoding a repressor and regulatable promoter detailed above may be modified so as to optimize the expression level of the nucleic acid sequence encoding the repressor. The optimal level of expression of the nucleic acid sequence encoding the repressor may be estimated, or may be determined by experimentation. Such a determination should take into consideration whether the repressor acts as a monomer, dimer, trimer, tetramer, or higher multiple, and should also take into consideration the copy number of the vector encoding the antigen of interest. In an exemplary embodiment, the level of expression is optimized so that the repressor is synthesized while in a permissive environment (i.e., in vitro growth) at a level that substantially inhibits the expression of the nucleic acid encoding an antigen of interest, and is substantially not synthesized in a non-permissive environment, thereby allowing expression of the nucleic acid encoding an antigen of interest.

In some embodiments, the recombinant bacterium described herein is modified to comprise a nucleic acid comprising a lacI gene, which encodes the LacI repressor protein. The expression of the lacI-encoded repressor in the recombinant bacterium described herein may be used to regulate the expression of a gene encoding an antigen of interest expressed by the bacterium. For example, in some embodiments, the expression of the lacI gene is regulated by a sugar-regulatable promoter (e.g., an arabinose-regulatable promoter). When cultured in the presence of arabinose, the recombinant bacterium will synthesize the LacI repressor protein, which in turn will repress the expression of a gene encoding an antigen of interest that is operably-linked to a LacI-responsive promoter (e.g., P$_{trc}$, P$_{lac}$, P$_{T7lac}$ and Pt$_{lac}$). Upon administration to the subject and in the absence of a source of arabinose, the synthesis of LacI repressor ceases, leading to de-repression of the LacI-responsive promoter and the subsequence causing expression of the antigen of interest. The concentration of LacI in the cell decreases by about half at each cell division in vivo, leading to a gradual decreased level of repression and gradual increased synthesis of the antigen of interest.

In some embodiments, the nucleic acid comprising a lacI gene is located on a plasmid in the bacterium. In some embodiments, the nucleic acid comprising a lacI gene is located on a chromosome of the bacterium. In some embodiments, the nucleic acid comprising a lacI gene is located at the chromosomal locus corresponding to the locus of an endogenous relA gene that has been deleted or altered in the bacterial chromosome. In some embodiments, the recombinant bacterium is modified to comprise a nucleic acid comprising a lacI gene, whereby an endogenous copy of the lacI gene in the bacterial chromosome has been altered and/or deleted.

In some embodiments, the nucleic acid comprises an *Escherichia coli* lacI gene. The nucleic acid sequence of the *E. coli* lacI gene is provided below:

(SEQ ID NO: 9)
```
gtgaaaccagtaacgttatacgatgtcgcagagtatgccggtgtctttta
tcagaccgtttcccgcgtggtgaaccaggccagccacgtttctgcgaaaa
cgcgggaaaagtggaagcggcgatggcggagttgaattacattcccaac
cgcgtggcacaacaactggtgggcaaacagtcgttgctgattggcgttgc
cacctccagtttggccttgcacgcgccgttgcaaattgtcgtggcgatta
aatcttgcgccgatcaactgggtgccagcgtggtggtgtcgatggtagaa
cgaagcggcgtcgaagcctgtaaagcggcggtgcacaatcttctcgcgca
acgcgtcagtgggctgatcattaactatccgctggatgaccaggatgcca
ttgctgtggaagctgcctgcactaatgttccggcgttatttcttgatgtc
tctgaccagacacccatcaacagtattattttctcccatgaagacggtac
gcgactgggcgtggagcatctggtcgcattgggtcaccagcaaatcgcgc
tgttagcgggcccattaagttctgtctcggcgcgtctgcgtctggctggc
tggcataaatatctcactcgcaatcaaattcagccgatagcggaacggga
aggcgactggagtgccatgtccggttttcaacaaaccatgcaaatgctga
atgagggcatcgttcccactgcgatgctggttgccaacgatcagatggcg
ctgggcgcaatgcgcgccattaccgagtccgggctgcgcgttggtgcgga
tatctcggtagtgggatacgacgataccgaagacagctcatgttatatcc
cgccgttaaccaccatcaaacaggattttcgcctgctggggcaaaccagc
gtggaccgcttgctgcaactctctcagggccaggcggtgaagggcaatca
gctgttgcccgtctcactggtgaaaagaaaaaccaccctggcgcccaata
cgcaaaccgcctctcccgcgcgttggccgattcattaatgcagctggca
cgacaggtttcccgactggaaagcgggcagtga.
```

The amino acid sequence of the *E. coli* LacI protein encoded by the nucleic acid of SEQ ID NO: 9 is provided below:

(SEQ ID NO: 10)
MKPVTLYDVAEYAGVSYQTVSRVVNQASHVSAKTREKVEAAMAELNYIPN

RVAQQLAGKQSLLIGVATSSLALHAPSQIVAAIKSRADQLGASVVVSMVE

RSGVEACKAAVHNLLAQRVSGLIINYPLDDQDAIAVEAACTNVPALFLDV

SDQTPINSIIFSHEDGTRLGVEHLVALGHQQIALLAGPLSSVSARLRLAG

WHKYLTRNQIQPIAEREGDWSAMSGFQQTMQMLNEGIVPTAMLVANDQMA

LGAMRAITESGLRVGADISVVGYDDTEDSSCYIPPLTTIKQDFRLLGQTS

VDRLLQLSQGQAVKGNQLLPVSLVKRKTTLAPNTQTASPRALADSLMQLA

RQVSRLESGQ.

In some embodiments, the nucleic acid comprises a lacI gene, wherein the lacI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 9. In some embodiments, the nucleic acid comprises a lacI gene, wherein the lacI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 9.

In some embodiments, the nucleic acid comprises a nucleic acid sequence encoding a LacI protein, wherein said LacI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 10. In some embodiments, the nucleic acid comprises a nucleic acid sequence encoding a LacI protein, wherein said LacI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 10.

In some embodiments, the nucleic acid comprises a lacI gene that is operably-linked to a regulatable promoter (e.g., a sugar-regulatable promoter). In some embodiments, the nucleic acid comprises a lacI gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a lacI gene that is operably-linked to a rhamnose-regulatable promoter (e.g., a sugar-regulatable promoter). In some embodiments, the nucleic acid comprises a lacI gene that is operably-linked to an arabinose-regulatable promoter. In some embodiments, the arabinose-regulatable promoter is $P_{araBAD}$. In some embodiments, the recombinant bacterium comprises the mutation ΔrelA::araC $P_{araBAD}$ lacI TT.

II. Pharmaceutical Compositions

A recombinant bacterium may be administered to a host as a pharmaceutical composition. In some embodiments, the pharmaceutical composition may be used as a vaccine to elicit an immune response to the recombinant bacterium, including any antigens that may be synthesized and delivered by the bacterium. In an exemplary embodiment, the immune response is protective. Immune responses to antigens are well studied and widely reported.

In one embodiment, a pharmaceutical composition may comprise at least two strains of recombinant bacterium. For example, a pharmaceutical composition may comprise a first strain synthesizing at least a first antigen of interest, e.g., PlcC, Fba, and/or NetB, and a second strain synthesizing at least a second antigen of interest, e.g., Cbh, CpeC, or both Cbh and CpeC, etc. The pharmaceutical composition may comprise two or more recombinant bacterium, each expressing any subcombination of the antigens of interest described herein.

Pharmaceutical compositions may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. In one embodiment, the host is a cow. In some embodiments, the host is an equine. In another embodiment, the host is an avian. In another embodiment, the host is a human. The pharmaceutical composition can be administered to the subject as a prophylactic or for treatment purposes.

In some embodiments, the recombinant bacterium is alive when administered to a host in a pharmaceutical composition described herein. Suitable vaccine composition formulations and methods of administration are detailed below.

A pharmaceutical composition comprising a recombinant bacterium may optionally comprise one or more possible additives, such as carriers, preservatives, stabilizers, adjuvants, and other substances.

In one embodiment, the pharmaceutical composition comprises an adjuvant. Adjuvants are optionally added to increase the ability of the vaccine to trigger, enhance, or prolong an immune response. In exemplary embodiments, the use of a live attenuated recombinant bacterium may act as a natural adjuvant. In some embodiments, the recombinant bacterium synthesizes and secretes an immune modulator. Additional materials, such as cytokines, chemokines, and bacterial nucleic acid sequences naturally found in bacteria, like CpG, are also potential vaccine adjuvants.

In some embodiments, the pharmaceutical composition comprises buffered saline (e.g., phosphate-buffered saline (PBS)).

In some embodiments, the pharmaceutical composition comprises a food product.

In another embodiment, the pharmaceutical may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the pharmaceutical composition is preferably presented in the form of an aerosol.

In some embodiments, the pharmaceutical composition is delivered to a farm animal (e.g., poultry). In some embodiments, the pharmaceutical composition is delivered as a course spray (e.g., for use in hatcheries for delivery to poultry). In some embodiments, the pharmaceutical composition is delivered in the drinking water.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the pharmaceutical composition against a variety of conditions, such as temperature variations or a freeze-drying process. The recombinant bacterium may also be co-administered with glutamate and/or arginine as described herein.

The dosages of a pharmaceutical composition can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

In order to stimulate a preferred response of the GALT, NALT or BALT cells, administration of the pharmaceutical composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible, e.g., for anti-cancer applications.

In some embodiments, these compositions are formulated for administration by injection (e.g., intraperitoneally, intravenously, subcutaneously, intradermally, intramuscularly, etc.).

In another embodiment, the disclosure provides a method for eliciting an immune response against an antigen in a host. The method comprises administering to the host an effective amount of a pharmaceutical composition comprising a recombinant bacterium described herein.

In still another embodiment, a recombinant bacterium may be used in a method for eliciting an immune response against a pathogen in an individual in need thereof. The method comprises administrating to the host an effective amount of a pharmaceutical composition comprising a recombinant bacterium as described herein. In a further embodiment, a recombinant bacterium described herein may be used in a method for ameliorating one or more symptoms of an infectious disease in a host in need thereof. The method comprises administering an effective amount of a pharmaceutical composition comprising a recombinant bacterium as described herein.

EXAMPLES

The present invention is further illustrated by the following examples that should not be construed as limiting in any way. The contents of all cited references, including literature references, issued patents, and published patent applications, as cited throughout this application are hereby expressly incorporated herein by reference. It should further be understood that the contents of all the figures and tables attached hereto are also expressly incorporated herein by reference.

Example 1: Introduction

Figure 4A:
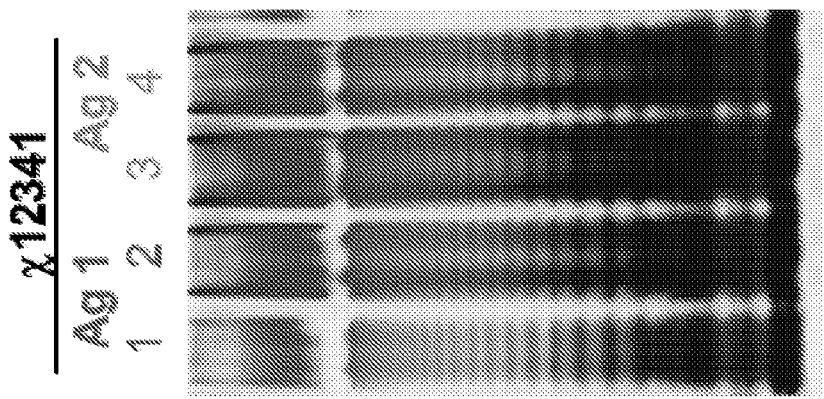

When delivered in a recombinant bacterium of the disclosure, the PlcC and GST-NetB antigens induce antibodies to counteract and prevent the toxicities caused by the Cp alpha toxin and the NetB toxin that damage the intestinal mucosa of a host, e.g., poultry, to cause it to thicken and be less able to absorb nutrients. This damage and thickening reduces the ability of the host to convert food to muscle, e.g., meat, in broilers, or to eggs in laying hens. Overall, this reduces performance and is an economic loss to poultry producers.

However, immune response against toxins would not contribute to diminishing levels of Cp colonization in poultry. In *Listeria*, production of bile hydrolase is attenuating, most likely due to reduced ability to colonize the intestinal tract. The inventors of the disclosure thus postulated that, if Cp produced a bile hydrolase, its loss might also diminish the ability to of Cp to colonize the gastrointestinal (GI) tract. The instant inventors, therefore, performed a bioinformatic search and identified a DNA sequence encoding a protein Cbh from *C. perfringens*. They next postulated that antibodies against Cbh would block its enzymatic activity and, thus, reduce the ability of Cp to colonize the GI tract.

The Cp enterotoxin CpeC is also a surface-localized protein that is responsible for disease in some animals, such as dogs and horses, but is the primary cause of food poisoning in humans if Cp gets into food, for example, potato salad. Cp is likely transmitted through the food chain from Cp colonizing poultry, similar to how *Salmonella* is transmitted through the food chain from poultry to humans. The inventors thus reasoned that induction of antibodies to CpeC would also reduce ability of Cp strains to colonize poultry.

These surprising ideas led the inventors to design codon-optimized sequences encoding synthesis of the C-terminal portions of the Cbh and CpeC antigens to induce immune responses that would be effective in reducing NE by reducing the ability of Cp to colonize the GI tract of poultry. Cp has a 28.6% GC content of DNA very different than the 52% GC of *Salmonella*. Thus, the redesign of coding sequences to fit *Salmonella* and permit synthesis of the antigens by the RASVs disclosed herein was surprising in terms of their success and is disclosed in more detail herein.

Example 2: Materials and Methods

Bacterial strains, media and bacterial growth: Strain construction is performed in virulent *S. Typhimurium* strain χ3761 (75) and *S. Enteritidis* χ3550 (136). Different virulent wild-type *Salmonella* serovars, including *S. Typhimurium* χ3761 (B), *S. Enteritidis* χ3550 (D), S. Heidelberg χ3749 (B) (137), *S. Choleraesuis* χ3246 (C1) (138), S. Infantis χ3213 (C1) (139), S. Newport χ3240 (C2) (139), S. Dublin χ12323 (D) (140), are used for challenges. The $LD_{50}$s of most of these strains are between$10^3$ and $10^5$ in mice and chickens except that S. Heidelberg, S. Infantis and S. Newport do not often cause lethal disease in either mice or chickens. LB media or plates with appropriate supplements when needed are used for growth of *Salmonella* (141, 142). χ12341 has the following genotype: $\Delta P_{murA25}$::TT araC $P_{araBAD}$ murA ΔasasdA27:TT araC $P_{araBAD}$ c2 Δpmi-2426 ΔwaaL46 ΔpagL64::TT rhaRS $P_{rhaBAD}$ waaL Δ(wza-wcaM)-8 ΔrelA197::araC $P_{araBAD}$ lacI TT ΔrecF126 ΔsifA26.

Molecular and genetic procedures. Methods for DNA manipulations and PCR are standard (143). DNA sequence analysis is performed at the UFL DNA Sequence Laboratory while oligonucleotide and/or gene segment syntheses will be obtained commercially.

Strain characterization. Vaccine strains are fully characterized at each step in their construction of introducting recombinant plasmids encoding Cp protective antigens and before immunization studies for the presence of all phenotypes and genotypes. Genetic attributes are confirmed by PCR with appropriate probes and/or phenotype analyses. Strains are compared with vector control strains for stability of plasmid maintenance and antigen synthesis when strains are grown in the presence of arabinose or other sugars and/or DAP over a 50 generation period (147). LPS is checked by silver staining (148). Growth curves will be determined for each strain. Other experiments include determining OMP (147) and IROMPs profiles (149), OMV (80) and GMMA characterization (87, 150, 151), serum (152), bile and microbial peptides resistance (136), and attachment/invasion to epithelial INT-407 cells (153, 154). Each strain with antigen-specifying plasmid is evaluated for synthesis of the heterologous antigen by western blot.

Antigen preparation. Protective antigens CpeC, CpeC-Max, GST-NetB, Cbh, Fba, and/or PlcC with C-terminal His-tag, are cloned into pBAD-His or pET vectors for synthesis in *E. coli* Top10 or BL21 and isolated by nickel chromatography (Sigma). Purified proteins are used for ELISA and ELISPOT assays and for preparing antiserum in New Zealand female rabbits. *Salmonella* LPS O-antigens are obtained commercially. *S. Typhimurium* outer membrane proteins (SOMPs) are purified from strain χ9424 that has been engineered to be unable to produce flagella, all in vitro-expressed pilus antigens, LPS O-antigen and several capsules.

Statistics: The SAS program is used to do statistical tests and power analysis to evaluate animal numbers.

Example 3: Generation of a Triple-Sugar Regulated *Salmonella* Vaccine

The following describes the generation of a triple-sugar regulated *Salmonella* vaccine that offers effective protection against *C. perfringens*-induced NE.

FIGS. 1A-1B illustrate the plasmid construct carrying the plcC GST-netB operon fusion (FIG. 1A) for specifying antigen delivery and western blot evidence of PlcC and GST-NetB synthesis (FIG. 1B). The construction of the progenitor of the pG8R220 plasmid is pYA5112 whose construction was described by Jiang et al., 2015. The important feature is the improved bla signal sequence which increases synthesis and secretion of the two antigens.

FIGS. 2A-2C are schematic illustrations of constructs in the presence of arabinose (FIG. 2A) and in the absence of arabinose (FIG. 2B), as well as lipopolysaccharide structures corresponding to in vivo regulated antigenic phenotypes (FIG. 2C). Arabinose-regulated expression of murA and asdA, two genes required for peptidoglycan synthesis, achieves in vivo regulated delayed lysis, attenuation, and antigen synthesis. Mannose is used to regulate synthesis of LPS O-antigen side chains by pmi mutation to achieve in vivo regulated delayed attenuation. Rhamnose regulated O-antigen ligase waaL expression achieves in vivo regulated delayed attenuation.

Experimental evidence demonstrating the phenotypes of triple-sugar regulated *Salmonella* vaccines are provided in FIGS. 3A-3C. Genotypes of the two host-vector strains used were as follows: (1) χ11802: $\Delta P_{murA}$25::TT araC $P_{BAD}$ murA ΔasdA27::TT araC $P_{BAD}$ c2 Δ(wza-wcaM)-8 ΔrelA198::araC $P_{BAD}$ lacI TT Δpmi-2426 ΔrecF126; and (2) χ12341: $\Delta P_{murA25}$::TTaraC $P_{BAD}$ murA ΔasdA27::TT araC $P_{BAD}$ c2 Δ(wza-wcaM)-8 ΔrelA197::araC $P_{BAD}$ lacI TT Δpmi-2426 ΔrecF126 ΔsifA26 ΔwaaL46 ΔpagL64::TT rhaRS $P_{rhaBAD}$ waaL. Growth of the two host-vector strains in the presence or absence of arabinose is shown in FIG. 3A, and expression of various O-antigens in the presense of arabinose, arabinose/mannose, arabinose/rhamnose, and arabinaose/mannose/rhamnose are shown in FIGS. 3B and 3C.

Example 4: *Salmonella* Vaccine Induces Protection Against *C. perfringens* Challenge FIGS. 4A-4B depict the synthesis of protective antigens in the triple-sugar regulated vaccine strain χ12341. Shown are SDS-PAGE (FIG. 4A) and western blot (FIG. 4B) evidence demonstrating the synthesis of additional protective antigens in triple-sugar regulated vaccine strain χ12341. Ag 1 is Cbh, and Ag 2 is CpeC.

Figure 6A:
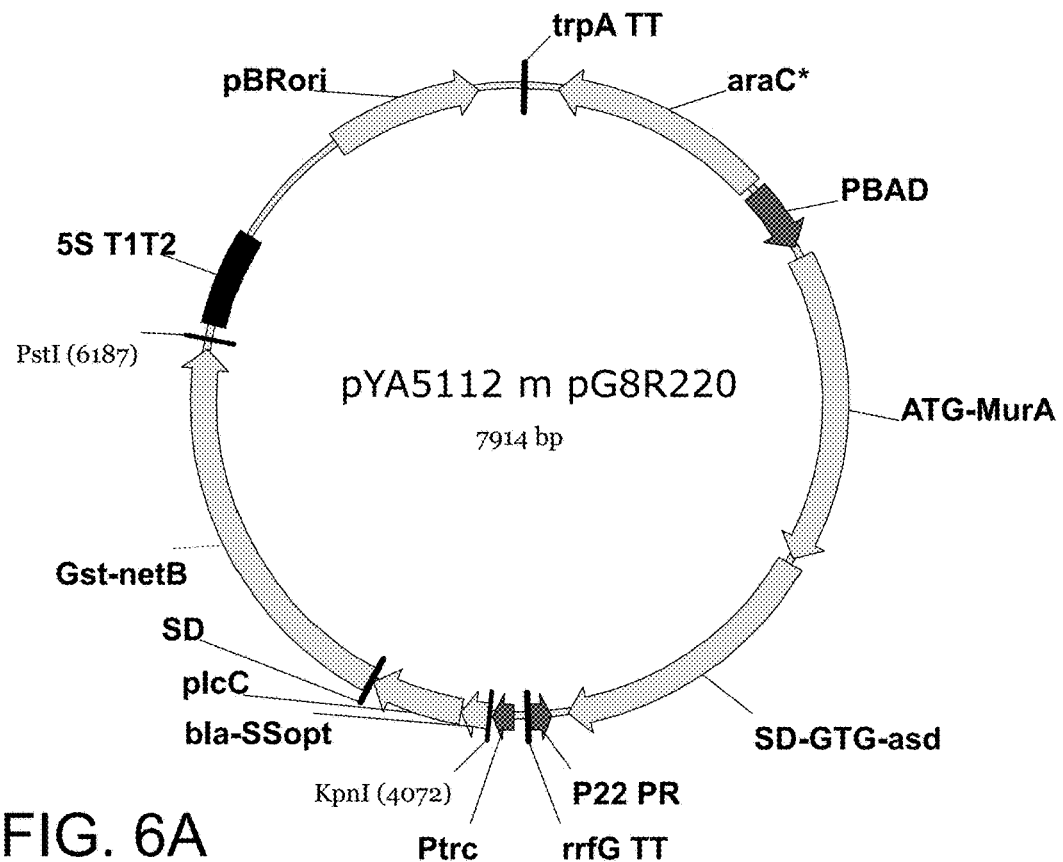
Figure 6B:
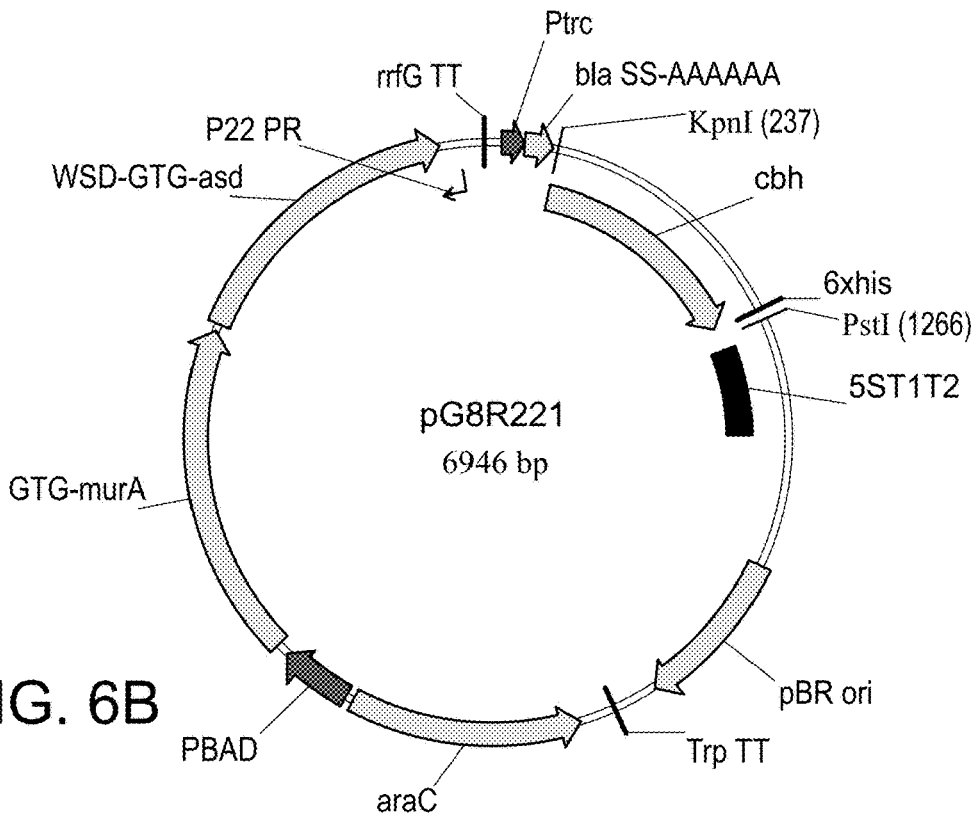
Figure 6C:
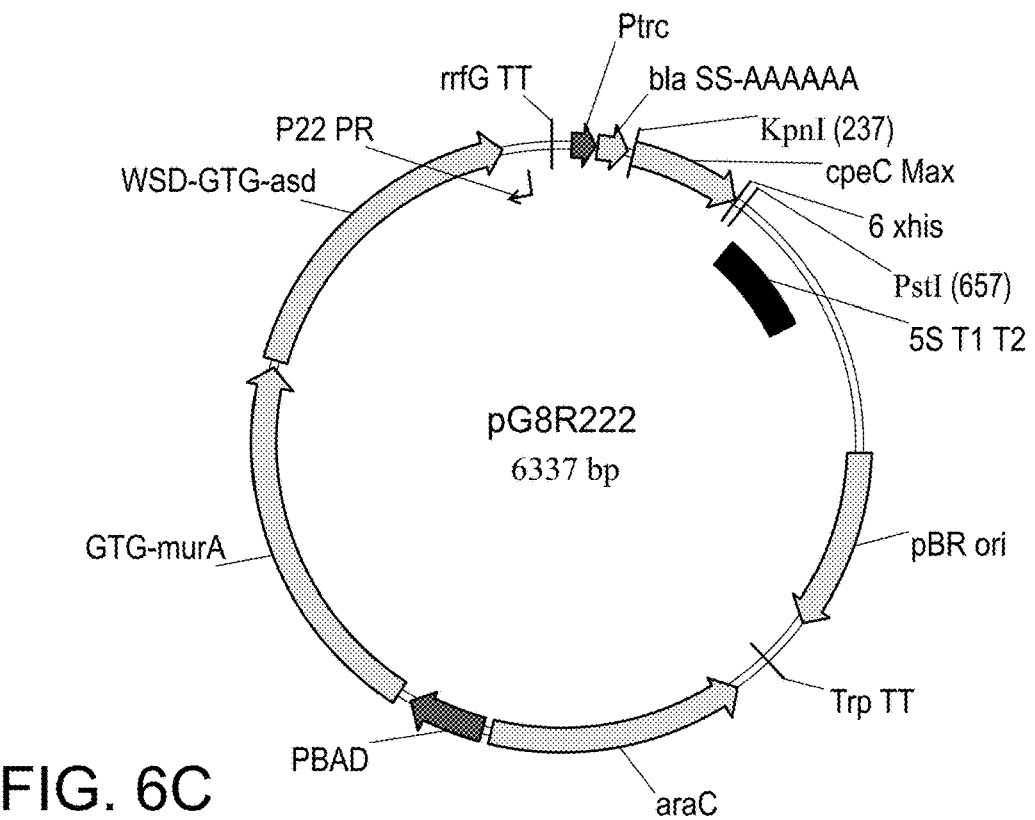
Figure 6D:
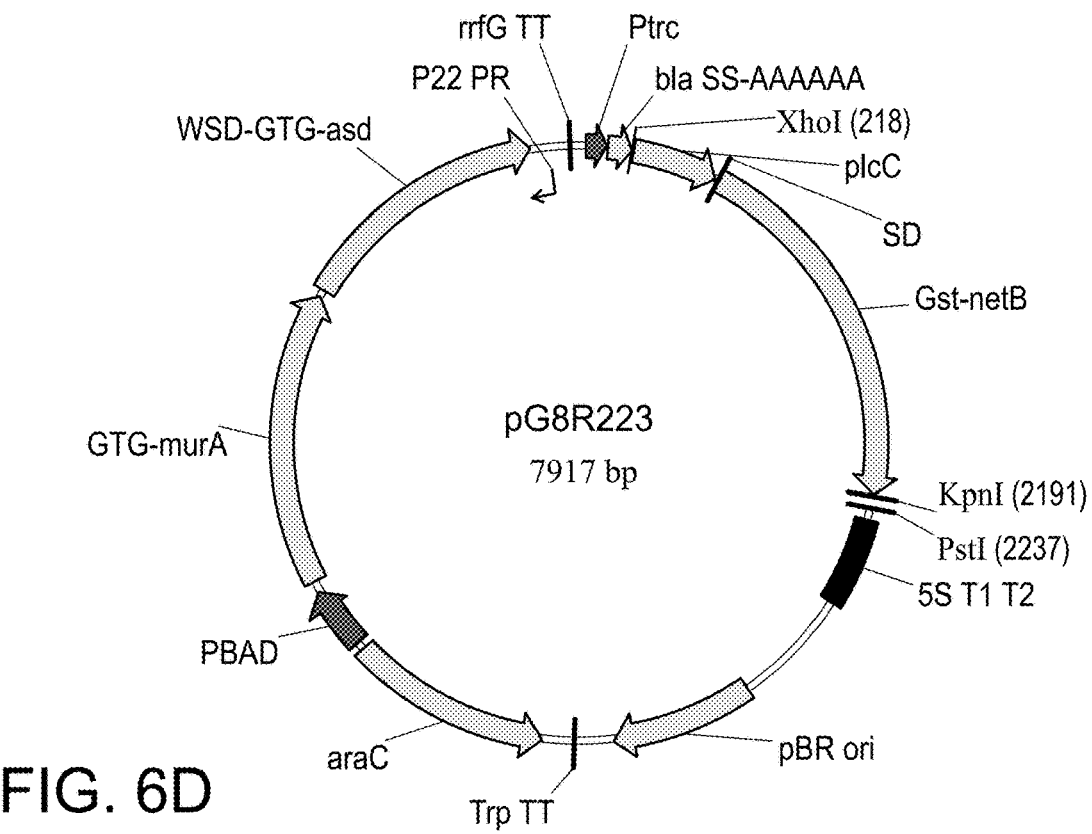
Figure 9B:
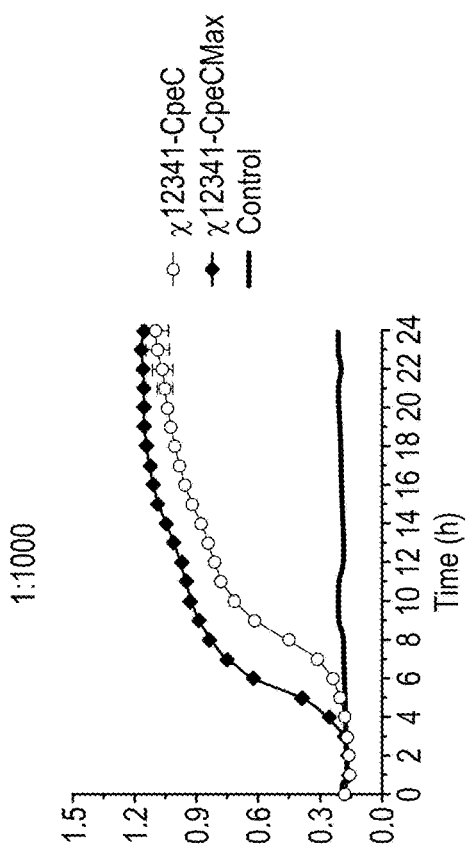
Figure 9C:
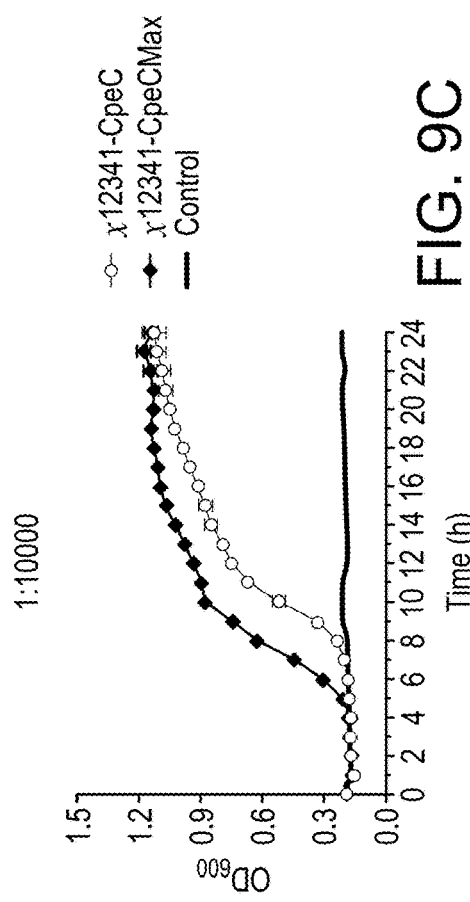
Figure 9A:
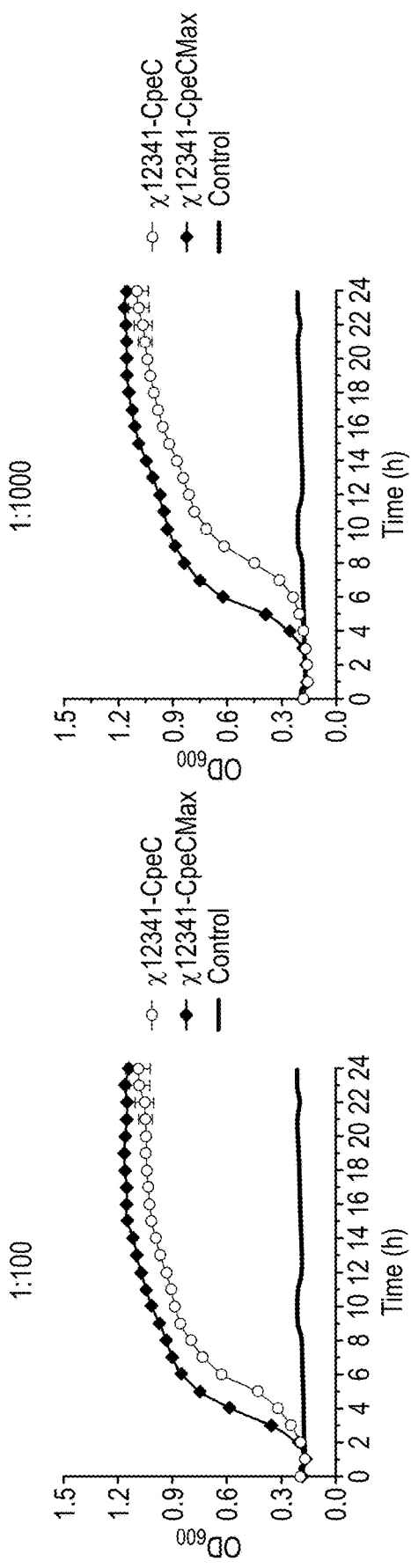
Figures 10A, 10B, 10C:
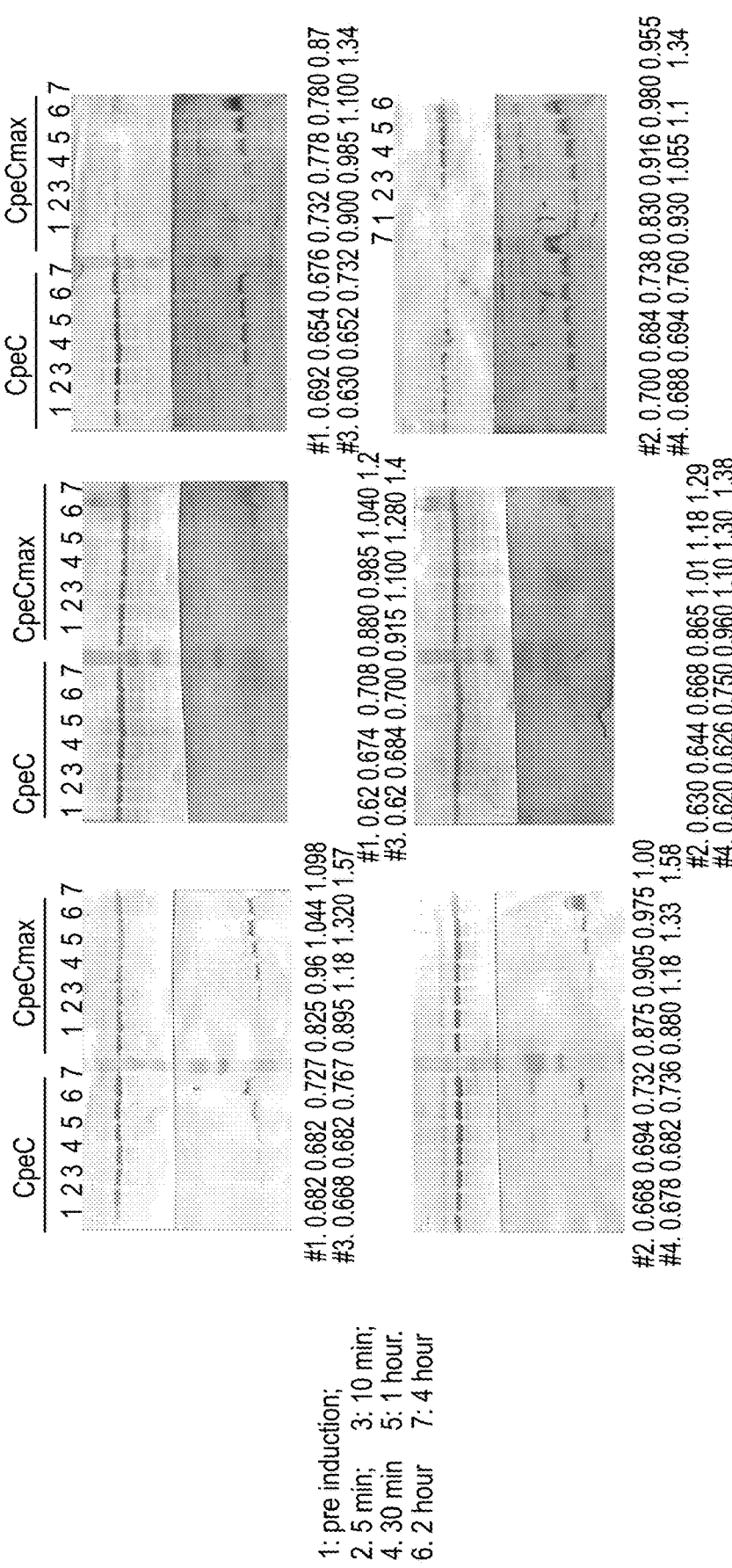
Figure 11A:
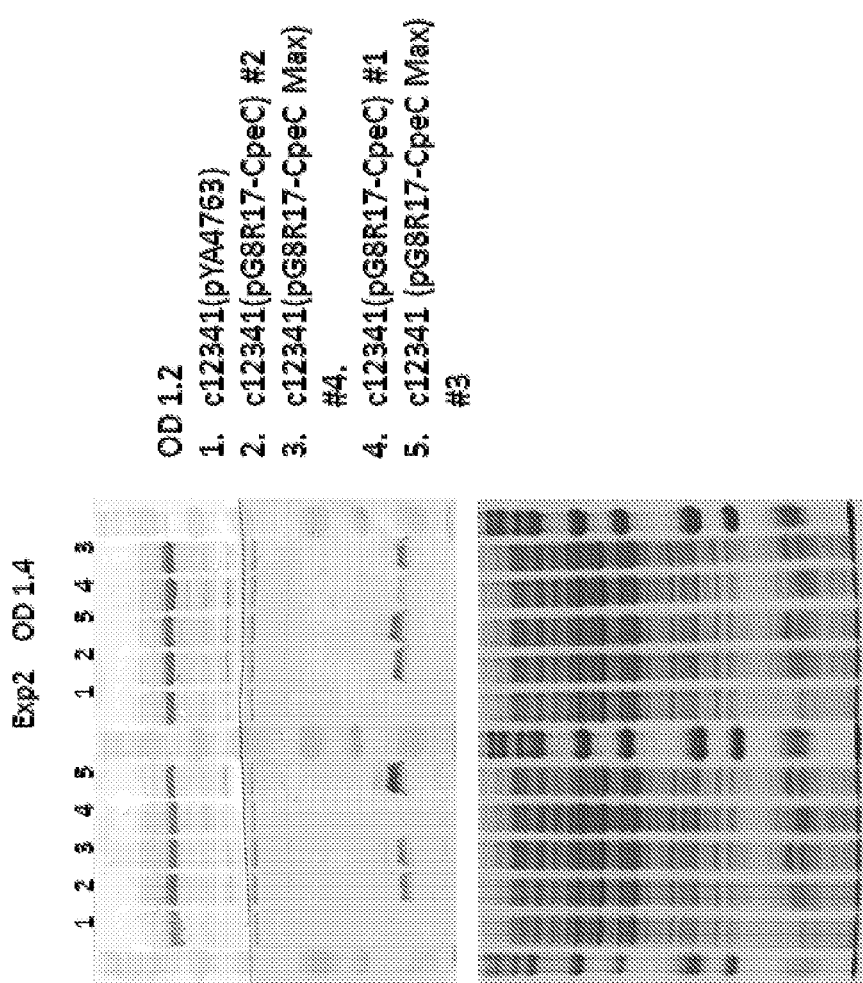
Figure 11B:
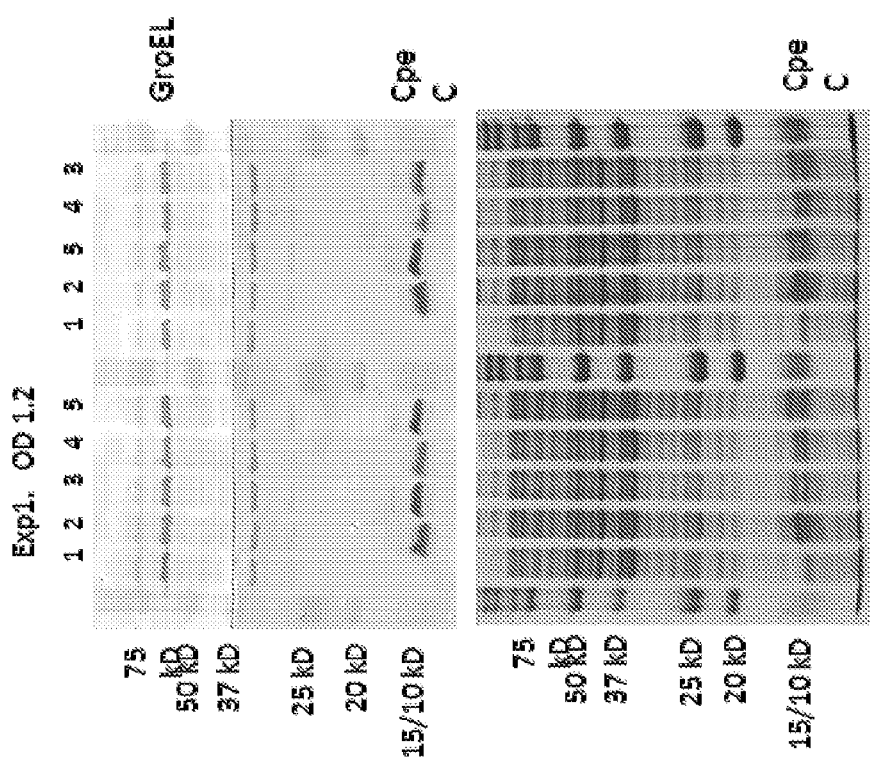
Figure 12A:
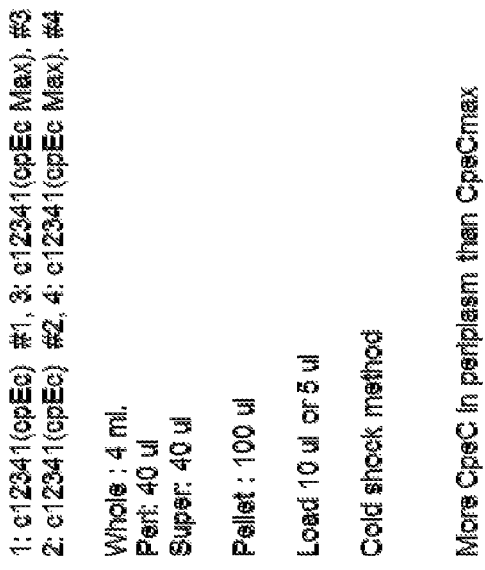
Figure 12B:
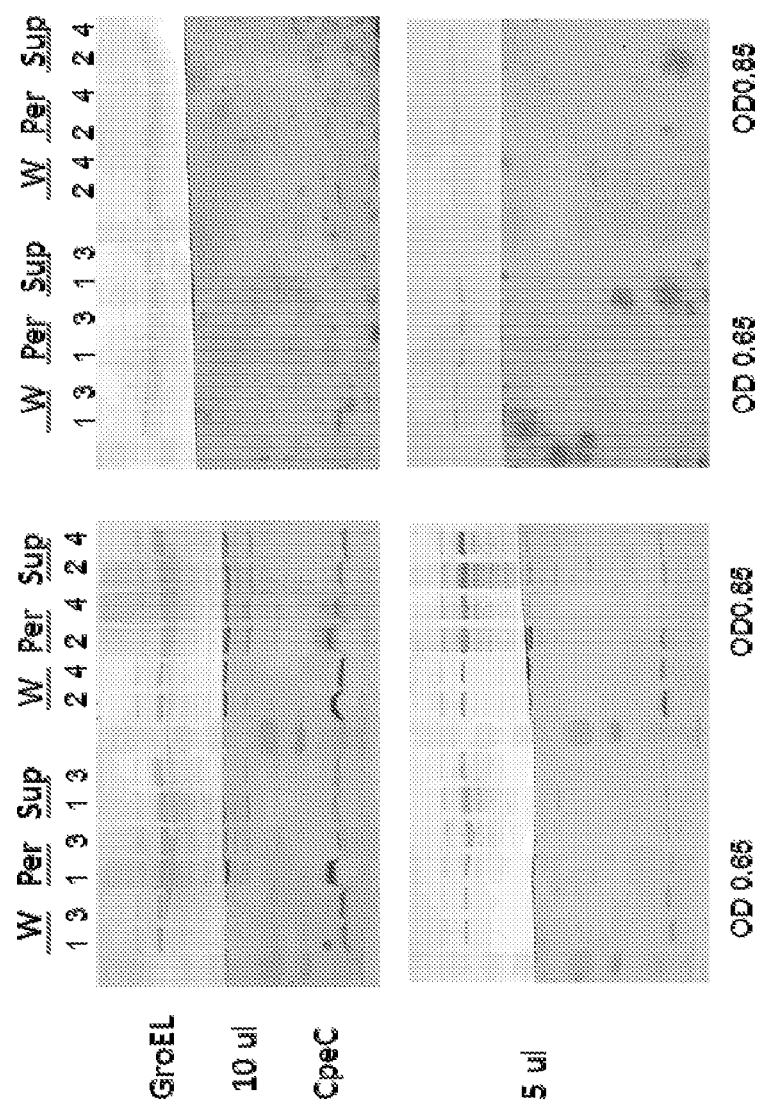

The two plasmids, pG8R78 and pG8R79, encode codon optimized cbh and cpeC genes synthesized by Genescript, respectively. The codons used less than 5% frequency in Salmonella in these two genes were optimized to highly used synonymous codons. The two genes were cloned into vector pG8R17 with KpnI/PstI sites to generate plasmids pG8R81 and pG8R82, respectively. Both plasmids were transformed strain χ12341. In observing pG8R82 encoding cpeC significantly retard the growth of strain χ12341 (FIG. 9), a new cpeC sequence, cpeCMax in plasmid pG8R80, with all codon optimized according to maximum codon usage in Salmonella was synthesized by Genescript and cloned into pG8R17 with KpnI/PstI sites to generate plasmid pG8R83. This further modified codon enables strain χ12341 (pG8R83) grows significantly better than strain χ12341 (pG8R82). The cbh and cpeCMax from pG8R78 and pG8R80 were further cloned into pG8R114 using KpnI/PstI sites to generate plasmid pG8R221(FIG. 6B) and pG8R222 (FIG. 6C), respectively. The gstnetB was amplified using primers PlcC-N-XhoI-s (5' ATATCTCGAGGACCCGTCCGTGGGCAACAAC 3') (SEQ ID NO:43) and GstNetB-C-KpnI-a(5' TGGCCGGTACCATTACAGATAATATTCGATTT-TATGGTC 3') (SEQ ID NO:44) with pG8R220 (FIG. 6A) as template and cloned into pG8R114 to generation plasmid pG8R223 (FIG. 6D).

Figure 6E:
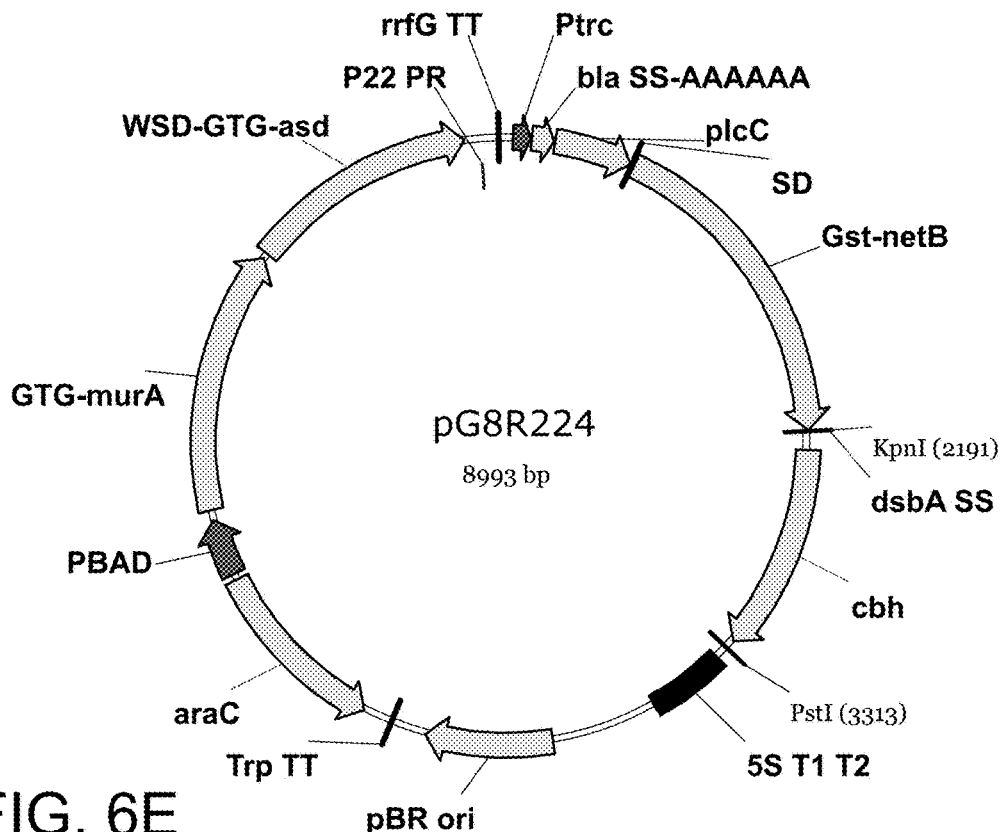
Figure 6F:
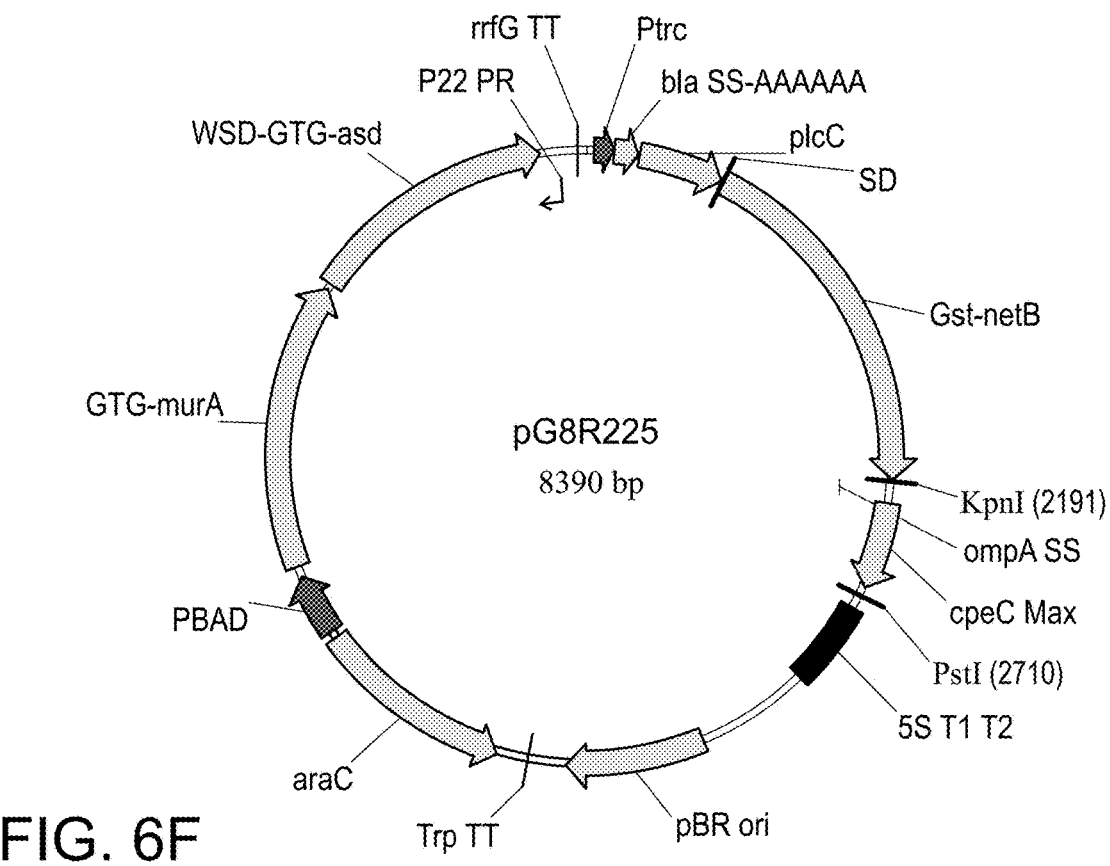
Figure 6G:
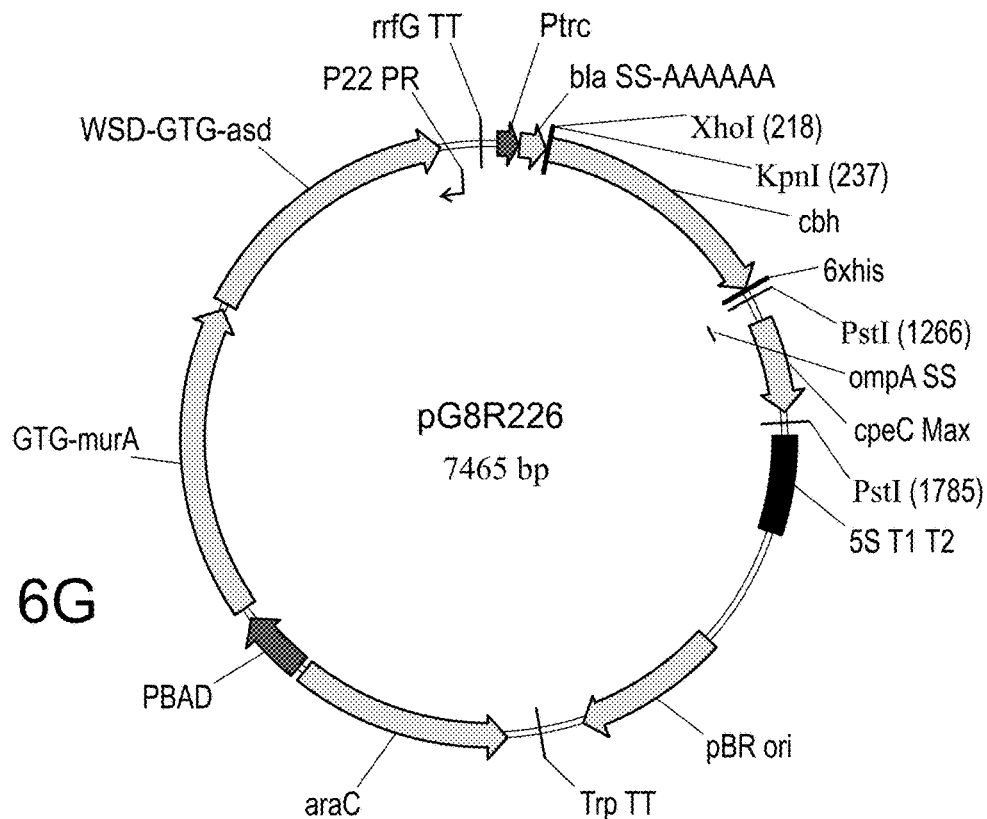
Figure 6H:
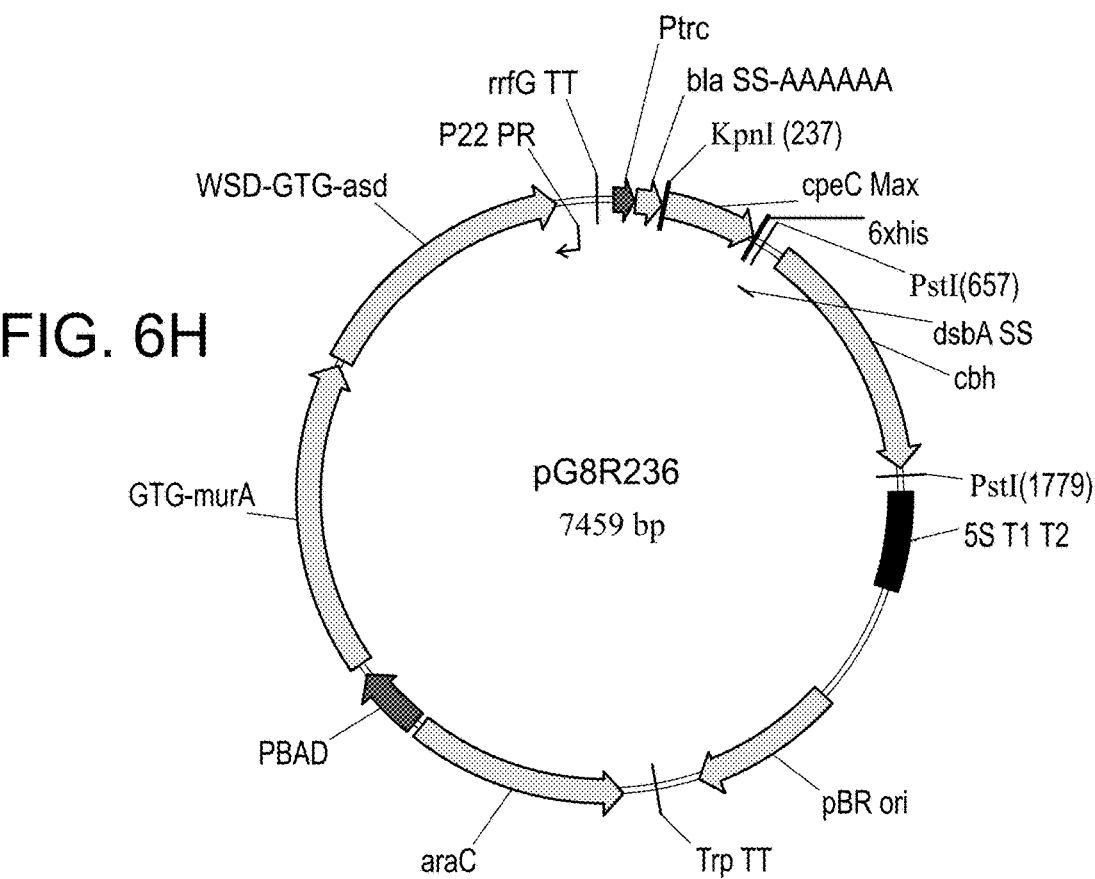

The dsbA SS was amplified with primers SDdsbASS-KpnIPstI-s (5' GCGCGGTACCTGCAGAGGAAGTTGAT-CATGAAAAAG 3') (SEQ ID NO:45) and dsbASS-XhoI-a (5' TATACtcgaGGTCGCTGATCTGTGCTGCCG 3') (SEQ ID NO:46) with strain χ3761 as template. The cbh gene was amplified with primers cbhN-XhoI-s (5' CTGACTCGAGATGTGCACAGGCCTGGCACTG 3') (SEQ ID NO:47) and cbhC-6×his-a1 (5' CATTACCGCG-GATGATGATGGTGGTGGTGCCGCGGGTT-CACGTGGTTGATGC 3') (SEQ ID NO:48) with pG8R78 as template. These two fragments were digested with XhoI and ligated. The SD dsbA SS-cbh was amplified with primers with SDdsbASS-KpnIPstI-s and cbhC-6×hisP-stIApaI-a2 (5' ATTACTGCAGGGCCCATTACCGCGGAT-GATGATG 3') (SEQ ID NO:49) and cloned into pG8R223 digested with KpnI/PstI to generate plasmid pG8R224 (FIG. 6E) or into pG8R222 digested with PstI to generate plasmid pG8R236 (FIG. 6H).

The ompA SS was amplified with primers SDompASS-KpnIPstI-s (5' ATATGGTACCTGCAGAGGACGCAAAAAAT-GAAAAAGACAGC 3') (SEQ ID NO:50) and ompASS-SacI-a (5' CTTAGAGCTCGTTATCTTTCG-GAGCGGCCTGC 3') (SEQ ID NO:51) with strain χ3761 as template. The cpeCMax gene was amplified with primers cpeCMax-SacI-s (5' GCCGGAGCTCGA-CATCGAAAAAGAAATCCTGGAC 3') (SEQ ID NO:52) and cpeCMax-6×his-a1 (5' ATTACCTAGGATGGTGGT-GATGATGGTGCCTAGGGAATTTCTGGAACAGGA-TAG 3') (SEQ ID NO:53) with pG8R80 as template. These two fragments were digested with SacI and ligated. The SD ompA SS-cpecMax was amplified with primers with SDom-pASS-KpnIPstI-s/cpeCMax-6×hisPstIApaI-a2 (5' GTGACTGCAGGGCCCATTACCTAGGATGGTGGTG 3') (SEQ ID NO:54) and cloned into pG8R223 digested with KpnI/PstI to generate plasmid pG8R225 ((FIG. 6F) or into pG8R221 digested with PstI to generate plasmid pG8R226 (FIG. 6G).

Figure 6I:
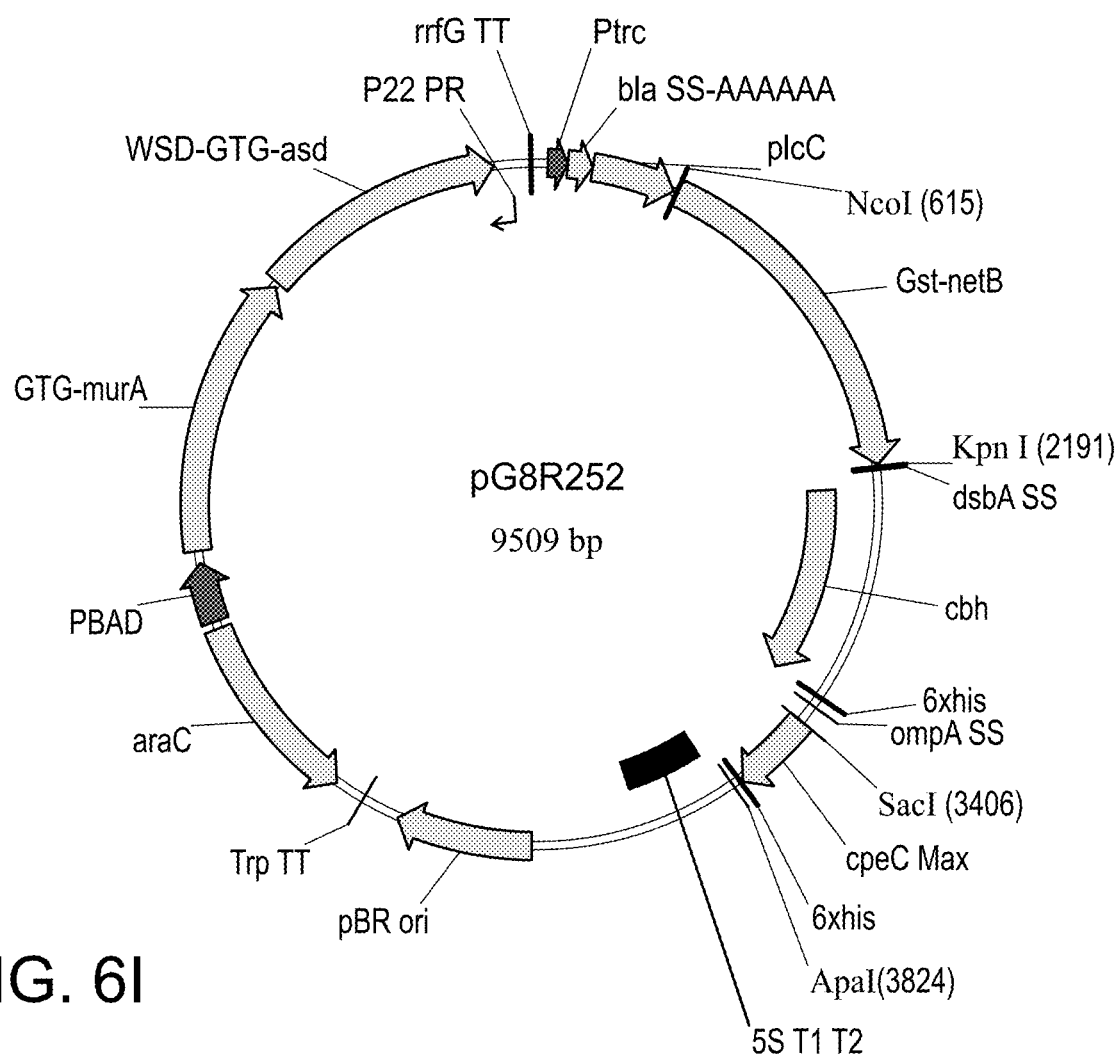
Figure 8A:
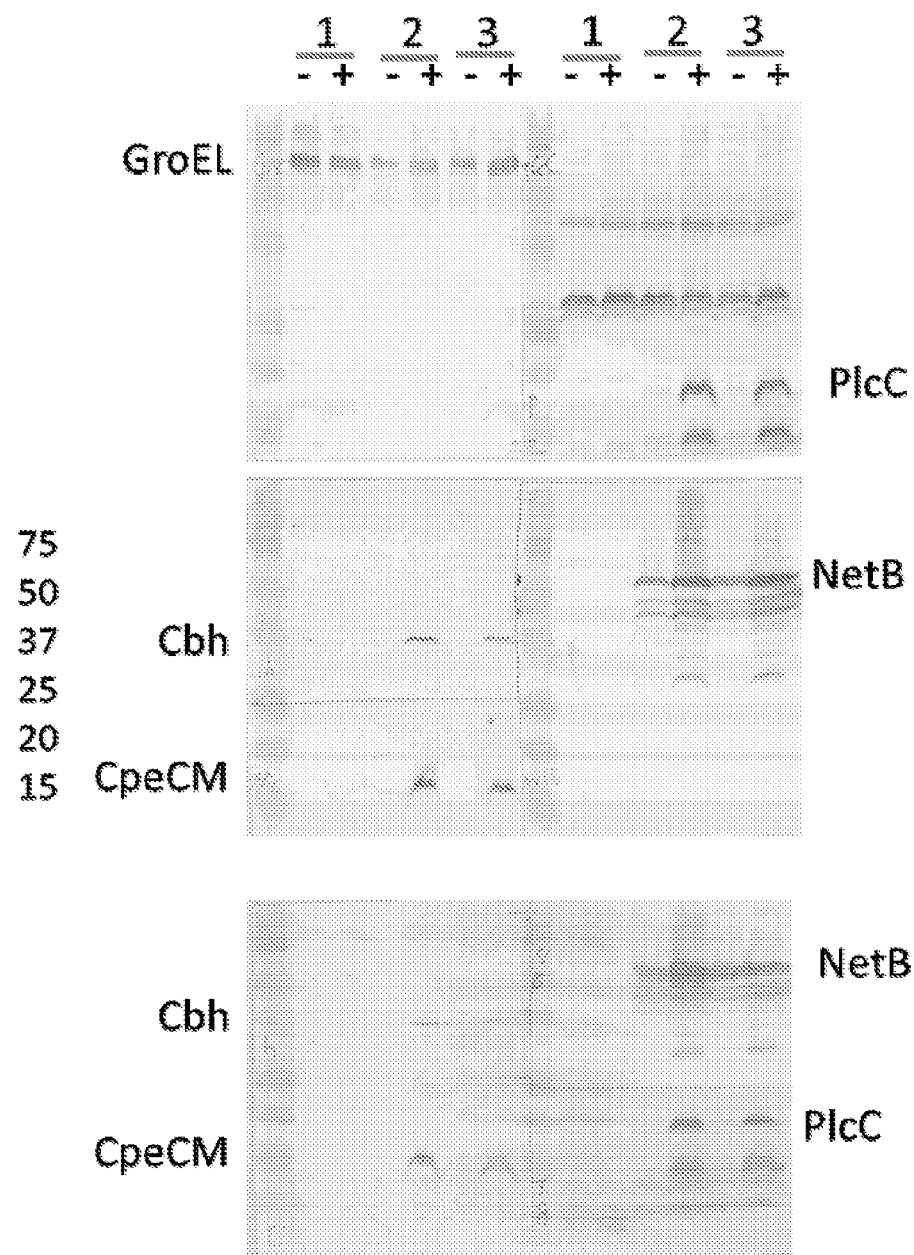

The fragment cbh-ompASS-cpeCMax was amplified using primers cbhN-XhoI-s (5' CTGACTCGAGATGTGCACAGGCCTGGCACTG 3') (SEQ ID NO:55) and cpeCMax-6×hisPstIApaI-a2 (5' GTGACTGCAGGGCCCATTACCTAGGATGGTGGTG 3') (SEQ ID NO:56) with pG8R226 as template. The dsbA SS was amplified with primers SDdsbASS-KpnIPstI-s (5' GCGCGGTACCTGCAGAGGAAGTTGATCAT-GAAAAAG 3') (SEQ ID NO:57) and dsbASS-XhoI-a (5' TATACtcgaGGTCGCTGATCTGTGCTGCCG 3') (SEQ ID NO:58) with strain χ3761 as template. These two fragments were cut with XhoI and ligated. The SD-dsbA SS-cbh-SD-ompA SS-cpecMax were amplified using primers SDds-bASS-KpnIPstI-s/cbhC-6×hisPstIApaI-a2 and cloned into pG8R223 digested with KpnI/ApaI to generate plasmid pG8R252 (FIG. 6I).

Figure 5A:
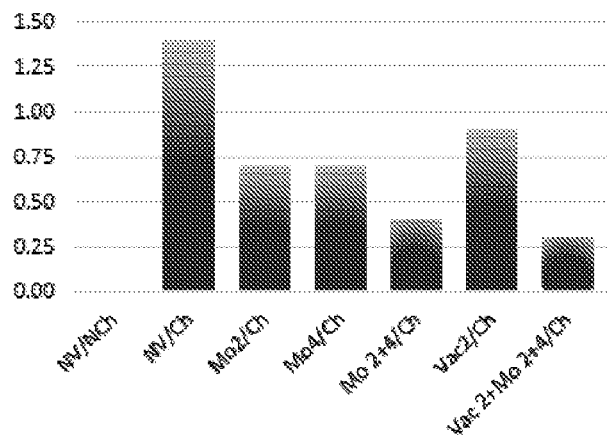
FIGS. 5A, 5B, and 5C depict that additional protective antigens alone and in combination induce protection against *C. perfringens* challenge. Shown are b as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function. The nucleic acid sequences of the promoters described herein are known in the art, and methods of operably-linking these promoters to a gene (e.g., a gene encoding a repressor) are known in the art.
Figure 5B:
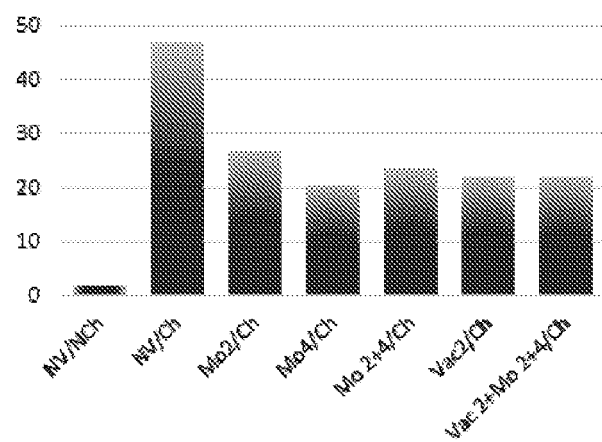
Figure 5C:
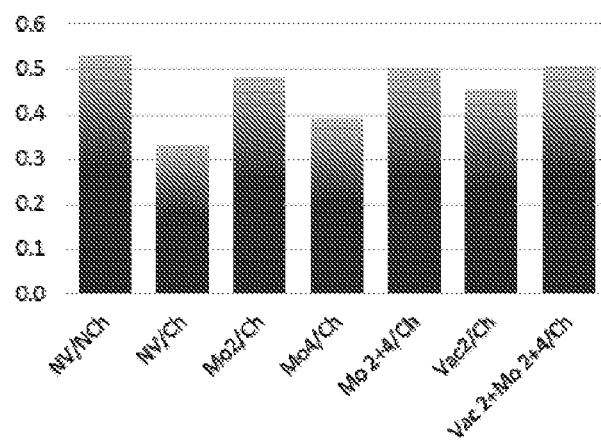

Similar C. perfringens challenge studies in which birds were vaccinated with host-vector strains expressing PlcC and NetB antigens also indicated the vaccines protection against C. perfringens as reflected in the average lesion scores, percent mortality and feed conversion ratios shown in FIGS. 5A, 5B and 5C, respectively. In these studies, Vaccine 2 (Vac2) is χ12341(pG8R220), Mo 2 is Cbh, and Mo 4 is CpeC. A mixture of these two χ12341-derived strains with χ12341(pG8R220) encoding the PlcC and NetB antigen genes yielded excellent results. All vaccine groups demonstrated biological effect, as feed conversation, mortality and lesion scores were all positive in favor of the various vaccine combinations. Challenge model resulted in targeted 40% mortality. These results indicated that the two additional antigens individually and combined provide significant reduction in lesion scores and mortality after C. perfringens challenge in E. maxima sensitized/stressed broiler chicks.

Thus, results in consecutive studies using a single oral vaccination of chicks with χ12341(pG8R220) on the day of hatch chicken indicated: (1) statistically significant protection from mortality in a "real world" C. perfringens-coccidia; (2) statistically significant protection from development of lesions from C. perfringens; (3) a dose dependent effect in protection; (4) improved body weights and feed conversion ratios comparable to the standard antibiotic treatment and better than vaccine 1, an earlier generation vaccine with evidence of protection; (5) effectiveness of multiple immunization routes, as regardless of the variables in E. maxima strain, C. perfringens strain, vaccine route and/or vaccine dose, χ12341(pG8R220) demonstrated consistent protection from the effects of C. perfringens challenge at a level equal or superior than BMD treatment; and (6) feed conversation at a lever similar to non-vaccinate/non challenge group.

Example 5: Host and Plasmid Constructs for Expressing C. perfringens Antigens as Vaccines pG8R220, a pYA5112 derived plasmid lacking the Pst I site of pYA5112, was used for constructing additional plasmids encoding C. perfringens antigens. These derivatives of pG8R220 are summarized in Table 1 below.

TABLE 1

| Plasmids derived from pYA5112 encoding *C. perfringens* antigens | |
|---|---|
| pG8R220 | pYA5112 without Pst I site |
| pG8R221 | pG8R114-cbh-his |
| pG8R222 | pG8R114-cpeCMax-his |
| pG8R223 | pG8R114-plcC-SD-GSTnetB |
| pG8R224 | pG8R114-plcC-SD-GSTnetB-SD-dsbASScbh-his |
| PG8R225 | pG8R114-plcC-SD-GSTnetB-SD-ompASScpecMax-his |
| pG8R226 | pG8R114-cbh-his-SD-ompASScpecMax-his |
| pG8R236 | pG8R114-cpeCMax-his-SD-dsbASScbh-his |
| pG8R252 | pG8R114 + plcC-SD GST-NetB+ SD dsbA cbh-his+ SD ompA-cpeCMax-His |

The structures of the plasmid constructs in Table 1 are illustrated in FIGS. 6A-6I. Nucleic acid sequences and their corresponding amino acid sequences for CpeC, Cbh, PlcC, GST and NetB are provided in FIGS. 7A-7J.

In the above constructs, the his sequence in cbh-his has the sequence: cac cac cac cat cat cat (SEQ ID NO: 30), and the his sequence in cpeC-his has the sequence: cac cat cat cac cac cat (SEQ ID NO: 31).

pYA3681 is a lysis plasmid originally described in Kong et al., Proc. Acad. Natl. Sci., 105(27):9361-9366, 2008. pYA3681 serves as the backbone with the addition of the optimized bla SS described by Jiang et al., Avian Diseases, 59(4):475-485, resulting in plasmid pG8R114. The difference between the native bla SS and the optimized blaSS is the change of the second and third codons to AAA for Lys. Having A-rich codons in the second and third codon increases translation efficiency of mRNA significantly. Therefore, in one embodiment of the invention, a signal sequence can be a blaSS signal sequence or an optimized blaSS signal sequence. In one embodiment, the codon-optimized fba sequence can be inserted into pG8R114 with an optimized bla SS.

Additional plasmids used in the studies are also disclosed in Table 2.

TABLE 2

| fba Plasmids | |
|---|---|
| pYA4756 | Codon optimized fba in pUC57, Genescript |
| pYA5020 | pYA3342-fba |
| pYA5129 | pYA3681-fba |
| pYA5023 | pYA3493- plcC -fba--gstnetB |
| pYA5130 | pYA3681-bla SS- plcC -fba-gstnetB |
| pYA5303 | pYA3681- blaSS opt-plcC -fba-gstnetB |
| pYA5107 | pET30a-fba |

Expression of *C. perfringens* antigens by three *Salmonella* host strains transformed with one of plasmid constructs were evaluated. The host strains and plasmid constructs evaluated are identified in Table 3.

TABLE 3

Combinations of host-plasmid constructs expressing *C. perfringens* antigens useful as vaccines

| Plasmid | Characterization $\chi$1* | $\chi$A* | $\chi$B* | |
|---|---|---|---|---|
| pG8R78 | | | | pUC57-cbh from Genescript |
| pG8R79 | | | | pUC57-cpeC from Genescript |
| pG8R80 | | | | pUC57-Kan-cpeCMax from Genescript |
| pG8R81 | X | | | pG8R17-cbh |
| pG8R82 | X | | | pG8R17-cpeC |
| pG8R83 | X | | | pG8R17-cpeCMax |
| pG8R220 | X | X | X | Rename pYA5112 to pG8R220, pY3681-plcC-SD-GSTnetB |
| pG8R81 | X | | | pG8R17-Cbh |
| pG8R82 | X | | | pG8R17-CpEc |
| pG8R83 | X | | | pG8R17-CpeC Max |
| pG8R221 | | X | | pG8R114-cbh-his |
| pG8R222 | | X | | pG8R114-cpeCMax-his |
| pG8R223 | | X | | pG8R114-plcC-SD-GSTnetB |
| pG8R224 | | X | | pG8R114-plcC-SD-GSTnetB-SD-dsbASScbh-his |
| pG8R225 | | X | | pG8R114-plcC-SD-GSTnetB-SD-ompASScpecMax-his |
| pG8R226 | | X | | pG8R114-cbh-his-SD-ompASScpecMax-his |
| pG8R236 | | X | | pG8R114-cpeCMax-his-SD-dsbASScbh-his |
| pG8R252 | | X | | pG8R114+ plcC-SD GST-NetB+ SD dsbA cbh-his+ SD ompA-cpeCMax-His |
| pYA5130 | | X | | pY3681 -plcC-fba-SD-GSTnetB |
| pYA5303 | | X | X | codon optimized bla pYA3681-plcC-fba-SD-GSTnetB |

*$\chi$1 is $\chi$12341,
$\chi$A and $\chi$B are two other *Salmonella* host isolates Evidence of expression of antigens PlcC, Fba, GST-NetB Cbh, and CpeC-max, by three *Salmonella* host-plasmid constructs are provided in FIGS. 8A, 8B, and 8C. In these results, 1 is a strain carrying pG8R114, while 2 and 3 are strains carrying pG8R252. Plasmid pG8R252 encodes four antigen genes, plcC, gstnetB, cbh, and cpeCMax, as an operon fusion. Strain $\chi$12341(pG8R252) can effectively produce these 4 antigens as expected (FIG. 8A). The strain $\chi$12341(pG8R252) also has complete O-antigen in the presence of 0.1% arabinose, 0.1% mannose, and 0.1% rhamanose (FIG. 8C).

Example 6: Growth of and CpeC Production by *Salmonella* $\chi$12341

FIGS. 9A, 9B, and 9C are three growth curves obtained for *Salmonella* strain $\chi$12341 expressing CpeC or CpeC-Max. Briefly, standing overnight cultures of the strain grown in LB/0.1% Ara/0.1% Man/0.1% rhamnose were normalized to same OD and diluted in the same media in a honeycomb plate. The growth curve was measured at 1 hour intervals for 24 hours. The CpeC change was only <5% frequency. CpeC-Max had all codons optimized according to maximum codon usage. $\chi$12341-cpeC, $\chi$12341(pG8R82); $\chi$12341-cpeCMax, $\chi$12341(pG8R83).

FIGS. 10A, 10B, and 10C are western blots obtained in three experiments that indicate CpeC and CpeC-max production in *Salmonella* vaccine strain $\chi$12341 at different times after induction.

FIGS. 11A-11B are SDS-PAGE gels demonstrating CpeC and CpeC-Max production in *Salmonella* vaccine strain $\chi$12341 with OD normalization at 4 hours after induction with IPTG. $\chi$12341(pG8R17-cpeC=pG8R82), $\chi$12341 (pG8R17-cpeC Max=pG8R83).

FIGS. 12A-12B are western blots demonstrating CpeC and CpeC-Max production in *Salmonella* vaccine strain χ12341 with $OD_{600}$ normalization 4 hours after induction with 1 mM IPTG. More CpeC was located in the periplasm than CpeC-Max.

Example 7: Isolation of *C. perfringens* Mutant Resistant to Nalidixic Acid

Multiple species of *Clostridium* strains occupy the intestinal microbiota in chickens. From this population, a mutant derivative of a wild-type virulent *C. perfringens* strain capable of causing necrotic enteritis was isolated. The isolate, a mutant derivative of the wild-type virulent *C. perfringens* CP4 strain, is resistant to the DNA synthesis inhibitor nalidixic acid. Nalidixic acid at 50 µg/mL is able to almost completely inhibit growth by all strains of bacteria present in the chicken intestinal tract. A spontaneous mutant of the CP4 strain was isolated by growing the CP4 culture in 100 mL of Tryptic Soy Broth (TSB) in a 250 mL flask at 37° C. for 24 hours in an anaerobic jar containing GasPak™ EZ Anaerobe Sachets with indicator. The culture was then placed in 50 mL centrifuge tubes with caps and then centrifuged in a Sorvall Legend RT refrigerated tabletop centrifuge using a swinging-bucket rotor at 3750 rpm for 18 minutes at room temperature. The supernatants were removed by aspiration and the pellet gently resuspended in 1 mL of sterile buffered saline with gelatin (BSG).

Tryptic Soy Agar II plates with 5% sheep blood and 50 ug/Nal/mL were inoculated with 100 uL (each) of the resuspended concentrated bacteria and incubated in a warm room at 37° C. for 24 hours in an anaerobic jar containing GasPak™ EZ Anaerobe Sachets with Indicator. Colonies appearing were picked with a sterile needle and streaked on selective plates to isolate pure mutant clones resistant to 50 µg nalidixic acid/mL. Multiple isolates were evaluated for growth with and without nalidixic acid and for hemolysis of red blood cells. Two representative strains that grew, with or without the presence of nalidixic acid, at nearly the same rates as the wild-type parent were saved and stocked in TSB+20% glycerol at −80° C.

One of these strain is used to inoculate chicks of different ages with fecal samples collected daily to quantitate the titers of the $Nal^R$ CP4 mutant. Subsequent studies will show that perturbations of the chicken microbial flora by addition of inflammatory agents such as by pretreatment with antibiotics such as streptomycin or *Eimeria oocysts* or by administering sodium dextran sulfate result in higher intestinal densities of the $Nal^R$ CP4 mutant.

These enable evaluation studies of day-of-hatch chicks immunized with various RASV strains delivering *C. perfringens* protective antigens such as the GST-NetB fusion, PlcC, CpeC-Max, Fba, and/or Cbh. The degree to which immune responses to the antigens alone or collectively reduce the intestinal titers of the $Nal^R$ CP4 mutant can be determined. Based on the fact that antibodies against the PlcC antigen coat the surface of *C. perfringens* cells, as revealed by indirect immunofluorescence assays, and reduce the growth of *C. perfringens* during growth in broth (Zekarias et al. 2008), reductions are expected in titers in immunized but not in unimmunized chicks. This allows for determining the effectiveness of vaccine constructs to reduce ability of *C. perfringens* strains from colonizing and persisting in the GI track of poultry and other animals such as dogs, horses and swine that are subject to diseases induced by *C. perfringens*

Example 8: Ability of Vaccine Constructions Delivering Synthesized Protective *C. perfringens* Antigens to Immunize Chickens to Reduce Colonization by *Salmonella enterica* Serotypes Many *Salmonella* serotypes colonize laying hens and broiler chickens to enable transmission of *Salmonella* in or on eggs or on contaminated broiler carcasses through the food chain to infect humans. Most recent estimates consider poultry to be the source of about half of the cases of human *Salmonella* infection, which total about 2 million infections and 500 deaths per year in the U.S. Effective immunization of chickens with vaccines to prevent or reduce colonization of chickens with *Salmonella* would thus enhance food safety by reducing the frequency of *Salmonella* transmission through the food chain to humans. It is thus expected that any of the vaccine constructs using the *S. Typhimurium* vaccine vector strain χ12341 to synthesize the *C. perfringens* protective antigens PlcC, GST-NetB, CpeC, Cbh and/or Fba encoded by the various pG8R and pYA plasmids listed in Tables 1 and 2, if used to immunize day-of-hatch chicks, would induce immune responses that would prevent or reduce colonization by *Salmonella* serotypes frequently found to colonize chickens.

In these regards, a diversity of recombinant attenuated *S. Typhimurium* vaccines with the regulated delayed lysis in vivo phenotype have induced significant antibody titers against *Salmonella* LPS and outer membrane proteins (SOMPs) when used to orally immunize mice (see Kong et al. PNAS 2008; Ameiss et al. Vaccine 2010; Juarez-Rodriquez et al. Infect Immun. 80:815 2012). It is thus logical that use of the χ12341-vectored vaccines described herein would stimulate such antibody responses after mucosal immunization of day-of-hatch chicks and as a consequence prevent or reduce colonization of immunized chicks after challenge with *Salmonella* serotypes.

Groups of ten day-of-hatch chicks are orally immunized with 50 to 100 µl of BSG suspensions of a χ12341 construct delivering one or more *C. perfringens* antigens and a group of 10 chicks with BSG with no vaccine cells as a control. Then at 3 weeks after immunization, each group of 10 immunized chicks and a group of BSG 'immunized' controls is orally inoculated with $1 \times 10^5$ CFU of *S. Enteritidis, S. Typhimurium, S. Newport, S. Infantis, S. Agona*, etc. as listed in the Materials and Methods section. Four days later, 5 birds in each group are euthanized and quantitative titers of the *Salmonella* strain in the bursa of Fabricius, liver and spleen and in intestinal and cecal contents are determined by plating on selective selenite agar as described in previous similar studies (Hassan and Curtiss, Infect. Immun. 1994). The remaining five birds in each group are euthanized 11 days after challenge and the titers of *Salmonella* determined. High titers of each *Salmonella* strain in BSG 'immunized' control birds are anticipated, but decreased titers of the B group *Salmonella S. Typhimurium* and *S. Heidelberg* and the D group *Salmonella S. Enteritidis* and *S. Dublin* challenge strains as observed in previous studies after immunization of chickens with *S. Typhimurium* derived vaccines (Hassan and Curtiss) are anticipated. However, the results in decreasing titers of C group *Salmonella* are more uncertain since attenuated *S. Typhimurium* vaccines that do not undergo lysis in vivo only poorly decreased colonization by C group *Salmonella* such as *S. Infantis, S. Newport* and *S. Kentucky* in previous studies. We predict, however, that using a vaccine that undergoes lysis in vivo should be superior to non-lysing strains in reducing colonization be C group *Salmonella*. This expectation will be determined by immunization of chicks with the $\chi$12341 strains delivering *C. perfringens* protective antigens.

REFERENCES

1. Lozano R, Naghavi M, Foreman K, Lim S, Shibuya K, Aboyans V, Abraham J, Adair T, Aggarwal R, Ahn S Y, Alvarado M, Anderson H R, Anderson L M, Andrews K G, Atkinson C, Baddour L M, Barker-Collo S, Bartels D H, Bell M L, Benjamin E J, Bennett D, Bhalla K, Bikbov B, Bin Abdulhak A, Birbeck G, Blyth F, Bolliger I, Boufous S, Bucello C, Burch M, Burney P, Carapetis J, Chen H, Chou D, Chugh S S, Coffeng L E, Colan S D, Colquhoun S, Colson K E, Condon J, Connor M D, Cooper L T, Corriere M, Cortinovis M, de Vaccaro K C, Couser W, Cowie B C, Criqui M H, Cross M, Dabhadkar K C, et al. 2012. Global and regional mortality from 235 causes of death for 20 age groups in 1990 and 2010: a systematic analysis for the Global Burden of Disease Study 2010. Lancet 380:2095-2128.
2. Tennant S M, Levine M M. 2015. Live attenuated vaccines for invasive *Salmonella* infections. Vaccine 33 Suppl 3:C36-C41.
3. Wain J, Hendriksen R S, Mikoleit M L, Keddy K H, Ochiai R L. 2015. Typhoid fever. Lancet 385:1136-1145.
4. Sahastrabuddhe S, Carbis R, Wierzba T F, Ochiai R L. 2013. Increasing rates of *Salmonella* Paratyphi A and the current status of its vaccine development. Expert Rev Vaccines 12:1021-1031.
5. Mogasale V, Maskery B, Ochiai R L, Lee J S, Mogasale V V, Ramani E, Kim Y E, Park J K, Wierzba T F. 2014. Burden of typhoid fever in low-income and middle-income countries: a systematic, literature-based update with risk-factor adjustment. Lancet Glob Health 2:e570-580.
6. Crump J A, Luby S P, Mintz E D. 2004. The global burden of typhoid fever. Bull World Health Organ 82:346-353.
7. Murray C J, Vos T, Lozano R, Naghavi M, Flaxman A D, Michaud C, Ezzati M, Shibuya K, Salomon J A, Abdalla S, Aboyans V, Abraham J, Ackerman I, Aggarwal R, Ahn S Y, Ali M K, Alvarado M, Anderson H R, Anderson L M, Andrews K G, Atkinson C, Baddour L M, Bahalim A N, Barker-Collo S, Barrero L H, Bartels D H, Basanez M G, Baxter A, Bell M L, Benjamin E J, Bennett D, Bernabe E, Bhalla K, Bhandari B, Bikbov B, Bin Abdulhak A, Birbeck G, Black J A, Blencowe H, Blore J D, Blyth F, Bolliger I, Bonaventure A, Boufous S, Bourne R, Boussinesq M, Braithwaite T, Brayne C, Bridgett L, Brooker 5, et al. 2012. Disability-adjusted life years (DALYs) for 291 diseases and injuries in 21 regions, 1990-2010: a systematic analysis for the Global Burden of Disease Study 2010. Lancet 380:2197-2223.
8. Feasey N A, Dougan G, Kingsley R A, Heyderman R S, Gordon M A. 2012. Invasive non-typhoidal *Salmonella* disease: an emerging and neglected tropical disease in Africa. Lancet 379:2489-2499.
9. Chiu C H, Su L H, Chu C. 2004. *Salmonella enterica* serotype Choleraesuis: epidemiology, pathogenesis, clinical disease, and treatment. Clin Microbiol Rev 17:311-322.
10. Ao T T, Feasey N A, Gordon M A, Keddy K H, Angulo F J, Crump J A. 2015. Global burden of invasive nontyphoidal *Salmonella* disease, 2010(1). Emerg Infect Dis 21.
11. Majowicz S E, Musto J, Scallan E, Angulo F J, Kirk M, O'Brien S J, Jones T F, Fazil A, Hoekstra R M, International Collaboration on Enteric Disease 'Burden of Illness S. 2010. The global burden of nontyphoidal *Salmonella* gastroenteritis. Clin Infect Dis 50:882-889.
12. Scallan E, Hoekstra R M, Mahon B E, Jones T F, Griffin P M. 2015. An assessment of the human health impact of seven leading foodborne pathogens in the United States using disability adjusted life years. Epidemiol Infect 143:2795-2804.
13. Scallan E, Hoekstra R M, Angulo F J, Tauxe R V, Widdowson M A, Roy S L, Jones J L, Griffin P M. 2011. Foodborne illness acquired in the United States—major pathogens. Emerg Infect Dis 17:7-15.
14. Hoffmann S, Batz M B, Morris J G, Jr. 2012. Annual cost of illness and quality-adjusted life year losses in the United States due to 14 foodborne pathogens. J Food Prot 75:1292-1302.
15. Scallan E, Mahon B E, Hoekstra R M, Griffin P M. 2013. Estimates of illnesses, hospitalizations and deaths caused by major bacterial enteric pathogens in young children in the United States. Pediatr Infect Dis J 32:217-221.
16. Olsen S J, Bishop R, Brenner F W, Roels T H, Bean N, Tauxe R V, Slutsker L. 2001. The changing epidemiology of *Salmonella*: trends in serotypes isolated from humans in the United States, 1987-1997. J Infect Dis 183:753-761.
17. Jackson B R, Griffin P M, Cole D, Walsh K A, Chai S J. 2013. Outbreak-associated *Salmonella enterica* serotypes and food Commodities, United States, 1998-2008. Emerg Infect Dis 19:1239-1244.
18. Gordon M A. 2008. *Salmonella* infections in immunocompromised adults. J Infect 56:413-422.
19. Preziosi M J, Kandel S M, Guiney D G, Browne S H. 2012. Microbiological analysis of nontyphoidal *Salmonella* strains causing distinct syndromes of bacteremia or enteritis in HIV/AIDS patients in San Diego, Calif. J Clin Microbiol 50:3598-3603.
20. MacLennan C A, Levine M M. 2013. Invasive nontyphoidal *Salmonella* disease in Africa: current status. Expert Rev Anti Infect Ther 11:443-446.
21. Graham S M, Molyneux E M, Walsh A L, Cheesbrough J S, Molyneux M E, Hart C A. 2000. Nontyphoidal *Salmonella* infections of children in tropical Africa. Pediatr Infect Dis J 19:1189-1196.
22. Crump J A, Medalla F M, Joyce K W, Krueger A L, Hoekstra R M, Whichard J M, Barzilay E J, Emerging Infections Program NWG. 2011. Antimicrobial resistance among invasive nontyphoidal *Salmonella* enterica isolates in the United States: National Antimicrobial Resistance Monitoring System, 1996 to 2007. Antimicrob Agents Chemother 55:1148-1154.
23. Bhutta Z A, Threlfall J. 2009. Addressing the global disease burden of typhoid fever. JAMA 302:898-899.
24. Jean S S, Hsueh P R. 2011. High burden of antimicrobial resistance in Asia. Int J Antimicrob Agents 37:291-295.
25. Crump J A, Mintz E D. 2010. Global trends in typhoid and paratyphoid Fever. Clin Infect Dis 50:241-246.
26. Martin L B. 2012. Vaccines for typhoid fever and other salmonelloses. Curr Opin Infect Dis 25:489-499.
27. MacLennan C A, Martin L B, Micoli F. 2014. Vaccines against invasive *Salmonella* disease: current status and future directions. Hum Vaccin Immunother 10:1478-1493.
28. Engels E A, Falagas M E, Lau J, Bennish M L. 1998. Typhoid fever vaccines: a meta-analysis of studies on efficacy and toxicity. BMJ 316:110-116.
29. Anwar E, Goldberg E, Fraser A, Acosta C J, Paul M, Leibovici L. 2014. Vaccines for preventing typhoid fever. Cochrane Database Syst Rev 1:CD001261.

30. Germanier R, Fuer E. 1975. Isolation and characterization of Gal E mutant Ty 21a of *Salmonella* typhi: a candidate strain for a live, oral typhoid vaccine. J Infect Dis 131:553-558.
31. Tacket C O, Ferreccio C, Robbins J B, Tsai C M, Schulz D, Cadoz M, Goudeau A, Levine M M. 1986. Safety and immunogenicity of two *Salmonella* typhi Vi capsular polysaccharide vaccines. J Infect Dis 154:342-345.
32. Desin T S, Koster W, Potter A A. 2013. *Salmonella* vaccines in poultry: past, present and future. Expert Rev Vaccines 12:87-96.
33. Gal-Mor O, Boyle E C, Grassi G A. 2014. Same species, different diseases: how and why typhoidal and nontyphoidal *Salmonella enterica* serovars differ. Front Microbiol 5:391.
34. Bhaysar A P, Zhao X, Brown E D. 2001. Development and characterization of a xylose-dependent system for expression of cloned genes in *Bacillus subtilis*: conditional complementation of a teichoic acid mutant. Appl Environ Microbiol 67:403-410.
35. Walder R Y, Walder J A. 1986. Oligodeoxynucleotide-directed mutagenesis using the yeast transformation system. Gene 42:133-139.
36. Bauer C E, Hesse S D, Waechter-Brulla D A, Lynn S P, Gumport R I, Gardner J F. 1985. A genetic enrichment for mutations constructed by oligodeoxynucleotide-directed mutagenesis. Gene 37:73-81.
37. Craik C S. 1985. Use Of Oligonucleotides For Site-specific Mutagenesis BIOTECHNIQUES 3:12-19.
38. Smith M, Gillam S. 1981. Constructed Mutants Using Synthetic Oligodeoxyribonucleotides as Site-Specific Mutagens, p 1-32. In Setlow J K, Hollaender A (ed), Genetic Engineering: Principles and Methods Volume 3 doi:10.1007/978-1-4615-7075-2_1. Springer US, Boston, Mass.
39. Giacalone M J, Gentile A M, Lovitt B T, Berkley N L, Gunderson C W, Surber M W. 2006. Toxic protein expression in *Escherichia coli* using a rhamnose-based tightly regulated and tunable promoter system. Biotechniques 40:355-364.
40. Elhenawy W, Bording-Jorgensen M, Valguarnera E, Haurat M F, Wine E, Feldman M F. 2016. LPS Remodeling Triggers Formation of Outer Membrane Vesicles in *Salmonella*. MBio 7:e00940-00916.
41. Man S M, Hopkins L J, Nugent E, Cox S, Gluck I M, Tourlomousis P, Wright J A, Cicuta P, Monie T P, Bryant C E. 2014. Inflammasome activation causes dual recruitment of NLRC4 and NLRP3 to the same macromolecular complex. Proc Natl Acad Sci USA 111:7403-7408.
42. Collins L V, Attridge S, Hackett J. 1991. Mutations at rfc or pmi attenuate *Salmonella typhimurium* virulence for mice. Infect Immun 59:1079-1085.
43. Curtiss R, III., Zhang X, Wanda S Y, Kang H Y, Konjufca V, Li Y, Gunn B, Wang S, Scarpellini G, Lee I S. 2007. Induction of host immune responses using *Salmonella*-vectored vaccines, p 297-313. In Brogden K A, Minion F C, Cornick N, Stanton T B, Zhang Q, Nolan L K, Wannemuehler M J (ed), Virulence mechanisms of bacterial pathogens, 4th ed. ASM Press, Washington D.C.
44. Raetz C R, Whitfield C. 2002. Lipopolysaccharide endotoxins. Annu Rev Biochem 71:635-700.
45. Frey P A. 1996. The Leloir pathway: a mechanistic imperative for three enzymes to change the stereochemical configuration of a single carbon in galactose. FASEB J 10:461-470

46. Leloir L F. 1951. The enzymatic transformation of uridine diphosphate glucose into a galactose derivative. Arch Biochem Biophys 33:186-190.
47. Germanier R, Furer E. 1971. Immunity in experimental salmonellosis. II. Basis for the avirulence and protective capacity of galE mutants of *Salmonella typhimurium*. Infect Immun 4:663-673.
48. Fukasawa T, Nikaido H. 1959. Galactose-sensitive mutants of *Salmonella*. Nature 184(Suppl 15):1168-1169.
49. Lee S J, Trostel A, Le P, Harinarayanan R, Fitzgerald P C, Adhya S. 2009. Cellular stress created by intermediary metabolite imbalances. Proc Natl Acad Sci USA 106: 19515-19520.
50. Hone D, Morona R, Attridge S, Hackett J. 1987. Construction of defined galE mutants of *Salmonella* for use as vaccines. J Infect Dis 156:167-174.
51. Cascales E, Buchanan S K, Duche D, Kleanthous C, Lloubes R, Postle K, Riley M, Slatin S, Cavard D. 2007. Colicin biology. Microbiol Mol Biol Rev 71:158-229.
52. Mastroeni P, Simmons C, Fowler R, Hormaeche C E, Dougan G. 2000. Igh-6$^{-/-}$ (B-cell-deficient) mice fail to mount solid acquired resistance to oral challenge with virulent *Salmonella enterica* serovar typhimurium and show impaired Th1 T-cell responses to *Salmonella* antigens. Infect Immun 68:46-53.
53. Ugrinovic S, Menager N, Goh N, Mastroeni P. 2003. Characterization and development of T-Cell immune responses in B-cell-deficient (Igh-6$^{-/-}$) mice with *Salmonella enterica* serovar Typhimurium infection. Infect Immun 71:6808-6819.
54. Mittrucker H W, Raupach B, Kohler A, Kaufmann S H. 2000. Cutting edge: role of B lymphocytes in protective immunity against *Salmonella typhimurium* infection. J Immunol 164:1648-1652.
55. Mastroeni P, Menager N. 2003. Development of acquired immunity to *Salmonella*. J Med Microbiol 52:453-459.
56. Pham O H, McSorley S J. 2015. Protective host immune responses to *Salmonella* infection. Future Microbiol 10:101-110.
57. Cunningham A F, Gaspal F, Serre K, Mohr E, Henderson I R, Scott-Tucker A, Kenny S M, Khan M, Toellner K M, Lane P J, MacLennan I C. 2007. *Salmonella* induces a switched antibody response without germinal centers that impedes the extracellular spread of infection. J Immunol 178:6200-6207.
58. MacLennan C A, Gondwe E N, Msefula C L, Kingsley R A, Thomson N R, White S A, Goodall M, Pickard D J, Graham S M, Dougan G, Hart C A, Molyneux M E, Drayson M T. 2008. The neglected role of antibody in protection against bacteremia caused by nontyphoidal strains of *Salmonella* in African children. J Clin Invest 118:1553-1562.
59. Guzman C A, Borsutzky S, Griot-Wenk M, Metcalfe I C, Pearman J, Collioud A, Favre D, Dietrich G. 2006. Vaccines against typhoid fever. Vaccine 24:3804-3811.
60. MacLennan C A. 2014. Antibodies and protection against invasive *Salmonella* disease. Front Immunol 5:635.
61. Isibasi A, Ortiz V, Vargas M, Paniagua J, Gonzalez C, Moreno J, Kumate J. 1988. Protection against *Salmonella typhi* infection in mice after immunization with outer membrane proteins isolated from *Salmonella typhi* 9,12,d, Vi. Infect Immun 56:2953-2959.
62. Klugman K P, Gilbertson I T, Koornhof H J, Robbins J B, Schneerson R, Schulz D, Cadoz M, Armand J. 1987.

Protective activity of Vi capsular polysaccharide vaccine against typhoid fever. Lancet 2:1165-1169.
63. Acharya I L, Lowe C U, Thapa R, Gurubacharya V L, Shrestha M B, Cadoz M, Schulz D, Armand J, Bryla D A, Trollfors B, et al. 1987. Prevention of typhoid fever in Nepal with the Vi capsular polysaccharide of *Salmonella typhi*. A preliminary report. N Engl J Med 317:1101-1104.
64. Szu S C. 2013. Development of Vi conjugate—a new generation of typhoid vaccine. Expert Rev Vaccines 12:1273-1286.
65. Jansson P E, Lindberg A A, Lindberg B, Wollin R. 1981. Structural studies on the hexose region of the core in lipopolysaccharides from Enterobacteriaceae. Eur J Biochem 115:571-577.
66. Lüderitz O, Westphal O, Staub A M, Nikaido H. 1971. Isolation and Chemical and Immunological Characterization of Bacterial Lipopolysaccharides, p 145-223. In Weinbaum G, Kadis S, Ajl S J (ed), Bacterial Endotoxins, vol 4. in Microbial Toxins. Academic Press, Inc, New York.
67. Kaniuk N A, Monteiro M A, Parker C T, Whitfield C. 2002. Molecular diversity of the genetic loci responsible for lipopolysaccharide core oligosaccharide assembly within the genus *Salmonella*. Mol Microbiol 46:1305-1318.
68. Olsthoorn M M, Petersen B O, Schlecht S, Haverkamp J, Bock K, Thomas-Oates J E, Holst O. 1998. Identification of a novel core type in *Salmonella* lipopolysaccharide. Complete structural analysis of the core region of the lipopolysaccharide from *Salmonella enterica* sv. Arizonae 062. J Biol Chem 273:3817-3829.
69. Malik M, Butchaiah G, Bansal M P, Siddiqui M Z, Bakshi C S, Singh R K. 2002. Antigenic relationships within the genus *Salmonella* as revealed by anti-*Salmonella enteritidis* monoclonal antibodies. Vet Res Commun 26:179-188.
70. Earhart C F. 1996. Uptake and metabolism of iron and molybdenum., p 1075-1090. In Neidhardt F C, Curtiss III R, Ingraham J L, Lin ECC, Low K B, Magasanik B, Reznikoff W S, Riley M, Schaechter M, Umbarger H E (ed), *Escherichia coli* and *Salmonella* Cellular and Molecular Biology, 2nd ed, vol 1. ASM Press, Washington, D.C.
71. Collins L V, Attridge S, Hackett J. 1991. Mutations at rfc or pmi attenuate *Salmonella typhimurium* virulence for mice. Infect Immun 59:1079-1085.
72. Rosen S M, Zeleznick L D, Fraenkel D, Wiener I M, Osborn M J, Horecker B L. 1965. Characterization of the cell wall lipopolysaccharide of a mutant of *Salmonella typhimurium* lacking phosphomannose isomerase. Biochem Z 342:375-386.
73. Mäkelä P H, Stocker BAD. 1969. Genetics of Polysaccharide Biosynthesis. Annual Review of Genetics 3:291-322.
74. Stocker BAD, Mäkelä P H. 1971. Genetic Aspects of Biosynthesis and Structure of *Salmonella* Lipopolysaccharide, p 369-438. In Weinbaum G, Kadis S, Ajl S J (ed), Bacterial Endotoxins, vol 4. in Microbial Toxins. Academic Press, Inc, New York.
75. Curtiss R, III, Wanda S Y, Gunn B M, Zhang X, Tinge S A, Ananthnarayan V, Mo H, Wang S, Kong W. 2009. *Salmonella enterica* serovar Typhimurium strains with regulated delayed attenuation in vivo. Infect Immun 77:1071-1082.
76. Curtiss R, III, Zhang X, Wanda S Y, Kang H Y, Konjufca V, Li H, Gunn B, Wang S, Scarpellini G, S. L I. 2007. Induction of host immune responses using *Salmonella*-vectored vaccines, p 297-313. In Brogden K A, Minion F C, Stanton T B, Zhang Q, Nolan L K, Wannemuehler M J (ed), Virulence Mechanisms of Bacterial Pathogens, 4th ed. ASM Press, Washington D.C.
77. Chamnongpol S, Dodson W, Cromie M J, Harris Z L, Groisman E A. 2002. Fe(III)-mediated cellular toxicity. Mol Microbiol 45:711-719.
78. Nnalue N A. 1999. All accessible epitopes in the *Salmonella* lipopolysaccharide core are associated with branch residues. Infect Immun 67:998-1003.
79. Stanislaysky E S, Makarenko T A, Kholodkova E V, Lugowski C. 1997. R-form lipopolysaccharides (LPS) of Gram-negative bacteria as possible vaccine antigens. FEMS Immunol Med Microbiol 18:139-145.
80. Muralinath M, Kuehn M J, Roland K L, Curtiss R, III. 2011. Immunization with *Salmonella enterica* serovar Typhimurium-derived outer membrane vesicles delivering the pneumococcal protein PspA confers protection against challenge with *Streptococcus pneumoniae*. Infect Immun 79:887-894.
81. Englesberg E, Irr J, Power J, Lee N. 1965. Positive control of enzyme synthesis by gene C in the L-arabinose system. J Bacteriol 90:946-957.
82. Guzman L M, Belin D, Carson M J, Beckwith J. 1995. Tight regulation, modulation, and high-level expression by vectors containing the arabinose $P_{BAD}$ promoter. J Bacteriol 177:4121-4130.
83. Bolin C A, Jensen A E. 1987. Passive immunization with antibodies against iron-regulated outer membrane proteins protects turkeys from *Escherichia coli* septicemia. Infect Immun 55:1239-1242.
84. Lin J, Hogan J S, Smith K L. 1999. Antigenic homology of the inducible ferric citrate receptor (FecA) of coliform bacteria isolated from herds with naturally occurring bovine intramammary infections. Clin Diagn Lab Immunol 6:966-969.
85. Clifton-Hadley F A, Breslin M, Venables L M, Sprigings K A, Cooles S W, Houghton S, Woodward M J. 2002. A laboratory study of an inactivated bivalent iron restricted *Salmonella enterica* serovars Enteritidis and Typhimurium dual vaccine against Typhimurium challenge in chickens. Vet Microbiol 89:167-179.
86. Woodward M J, Gettinby G, Breslin M F, Corkish J D, Houghton S. 2002. The efficacy of Salenvac, a *Salmonella enterica* subsp. *Enterica* serotype Enteritidis iron-restricted bacterin vaccine, in laying chickens. Avian Pathol 31:383-392.
87. Berlanda Scorza F, Colucci A M, Maggiore L, Sanzone S, Rossi O, Ferlenghi I, Pesce I, Caboni M, Norais N, Di Cioccio V, Saul A, Gerke C. 2012. High yield production process for Shigella outer membrane particles. PLoS One 7:e35616.
88. Clementz T, Bednarski J J, Raetz CR. 1996. Function of the htrB high temperature requirement gene of *Escherichia coli* in the acylation of lipid A: HtrB catalyzed incorporation of laurate. J Biol Chem 271:12095-12102.
89. Kulp A, Kuehn M J. 2010. Biological functions and biogenesis of secreted bacterial outer membrane vesicles. Annu Rev Microbiol 64:163-184.
90. Dowling J K, Mansell A. 2016. Toll-like receptors: the swiss army knife of immunity and vaccine development. Clin Transl Immunology 5:e85.
91. Duthie M S, Windish H P, Fox C B, Reed S G. 2011. Use of defined TLR ligands as adjuvants within human vaccines. Immunol Rev 239:178-196.
92. Steinhagen F, Kinjo T, Bode C, Klinman D M. 2011. TLR-based immune adjuvants. Vaccine 29:3341-3355.

93. Lahiri A, Das P, Chakravortty D. 2008. Engagement of TLR signaling as adjuvant: towards smarter vaccine and beyond. Vaccine 26:6777-6783.
94. Ishii K J, Akira S. 2007. Toll or toll-free adjuvant path toward the optimal vaccine development. J Clin Immunol 27:363-371.
95. Toussi D N, Massari P. 2014. Immune Adjuvant Effect of Molecularly-defined Toll-Like Receptor Ligands. Vaccines (Basel) 2:323-353.
96. Koeberling O, Delany I, Granoff D M. 2011. A critical threshold of meningococcal factor H binding protein expression is required for increased breadth of protective antibodies elicited by native outer membrane vesicle vaccines. Clin Vaccine Immunol 18:736-742.
97. Koeberling O, Seubert A, Granoff D M. 2008. Bactericidal antibody responses elicited by a meningococcal outer membrane vesicle vaccine with overexpressed factor H-binding protein and genetically attenuated endotoxin. J Infect Dis 198:262-270.
98. Pajon R, Fergus A M, Koeberling O, Caugant D A, Granoff D M. 2011. Meningococcal factor H binding proteins in epidemic strains from Africa: implications for vaccine development. PLoS Negl Trop Dis 5:e1302.
99. Zollinger W D, Babcock J G, Moran E E, Brandt B L, Matyas G R, Wassef N M, Alving C R. 2012. Phase I study of a *Neisseria meningitidis* liposomal vaccine containing purified outer membrane proteins and detoxified lipooligosaccharide. Vaccine 30:712-721.
100. Bernadac A, Gavioli M, Lazzaroni J C, Raina S, Lloubes R. 1998. *Escherichia coli* tol-pal mutants form outer membrane vesicles. J Bacteriol 180:4872-4878.
101. Henry T, Pommier S, Journet L, Bernadac A, Gorvel J P, Lloubes R. 2004. Improved methods for producing outer membrane vesicles in Gram-negative bacteria. Res Microbiol 155:437-446.
102. Berlanda Scorza F, Doro F, Rodriguez-Ortega M J, Stella M, Liberatori S, Taddei A R, Serino L, Gomes Moriel D, Nesta B, Fontana M R, Spagnuolo A, Pizza M, Norais N, Grandi G. 2008. Proteomics characterization of outer membrane vesicles from the extraintestinal pathogenic *Escherichia coli* DtolR IHE3034 mutant. Mol Cell Proteomics 7:473-485.
103. Clementz T, Zhou Z, Raetz C R. 1997. Function of the *Escherichia coli* msbB gene, a multicopy suppressor of htrB knockouts, in the acylation of lipid A. Acylation by MsbB follows laurate incorporation by HtrB. J Biol Chem 272:10353-10360.
104. Meloni E, Colucci A M, Micoli F, Sollai L, Gavini M, Saul A, Di Cioccio V, MacLennan C A. 2015. Simplified low-cost production of O-antigen from *Salmonella* Typhimurium Generalized Modules for Membrane Antigens (GMMA). J Biotechnol 198:46-52.
105. Gerke C, Colucci A M, Giannelli C, Sanzone S, Vitali C G, Sollai L, Rossi O, Martin L B, Auerbach J, Di Cioccio V, Saul A. 2015. Production of a *Shigella sonnei* Vaccine Based on Generalized Modules for Membrane Antigens (GMMA), 1790GAHB. PLoS One 10:e0134478.
106. Barat S, Willer Y, Rizos K, Claudi B, Maze A, Schemmer A K, Kirchhoff D, Schmidt A, Burton N, Bumann D. 2012. Immunity to intracellular *Salmonella* depends on surface-associated antigens. PLoS Pathog 8:e1002966.
107. Kurtz J R, Petersen H E, Frederick D R, Morici L A, McLachlan J B. 2014. Vaccination with a single CD4 T cell peptide epitope from a *Salmonella* type III-secreted effector protein provides protection against lethal infection. Infect Immun 82:2424-2433.
108. Rollenhagen C, Sorensen M, Rizos K, Hurvitz R, Bumann D. 2004. Antigen selection based on expression levels during infection facilitates vaccine development for an intracellular pathogen. Proc Natl Acad Sci USA 101: 8739-8744.
109. Lee S J, McLachlan J B, Kurtz J R, Fan D, Winter S E, Baumler A J, Jenkins M K, McSorley S J. 2012. Temporal expression of bacterial proteins instructs host CD4 T cell expansion and Th17 development. PLoS Pathog 8:e1002499.
110. McSorley S J, Cookson B T, Jenkins M K. 2000. Characterization of CD4+ T cell responses during natural infection with *Salmonella typhimurium*. J Immunol 164: 986-993.
111. Gil-Cruz C, Bobat S, Marshall J L, Kingsley R A, Ross E A, Henderson I R, Leyton D L, Coughlan R E, Khan M, Jensen K T, Buckley C D, Dougan G, MacLennan I C, Lopez-Macias C, Cunningham AF. 2009. The porin OmpD from nontyphoidal *Salmonella* is a key target for a protective B1b cell antibody response. Proc Natl Acad Sci USA 106:9803-9808.
112. Yang Y, Wan C, Xu H, Aguilar Z P, Tan Q, Xu F, Lai W, Xiong Y, Wei H. 2013. Identification of an outer membrane protein of *Salmonella enterica* serovar Typhimurium as a potential vaccine candidate for Salmonellosis in mice. Microbes Infect 15:388-398.
113. Goh Y S, Armour K L, Clark M R, Grant A J, Mastroeni P. 2016. Igg Subclasses Targeting the Flagella of *Salmonella enterica* Serovar Typhimurium Can Mediate Phagocytosis and Bacterial Killing. J Vaccines Vaccin 7.
114. Cummings L A, Wilkerson W D, Bergsbaken T, Cookson B T. 2006. In vivo, fliC expression by *Salmonella enterica* serovar Typhimurium is heterogeneous, regulated by ClpX, and anatomically restricted. Mol Microbiol 61:795-809.
115. Winter S E, Winter M G, Godinez I, Yang H J, Russmann H, Andrews-Polymenis H L, Baumler A J. 2010. A rapid change in virulence gene expression during the transition from the intestinal lumen into tissue promotes systemic dissemination of *Salmonella*. PLoS Pathog 6:e1001060.
116. Cummings L A, Barrett S L, Wilkerson W D, Fellnerova I, Cookson B T. 2005. FliC-specific CD4+ T cell responses are restricted by bacterial regulation of antigen expression. J Immunol 174:7929-7938.
117. Simon R, Tennant S M, Wang J Y, Schmidlein P J, Lees A, Ernst R K, Pasetti M F, Galen J E, Levine M M. 2011. *Salmonella enterica* serovar enteritidis core O polysaccharide conjugated to H:g,m flagellin as a candidate vaccine for protection against invasive infection with *S. Enteritidis*. Infect Immun 79:4240-4249.
118. Simon R, Wang J Y, Boyd M A, Tulapurkar M E, Ramachandran G, Tennant S M, Pasetti M, Galen J E, Levine M M. 2013. Sustained protection in mice immunized with fractional doses of *Salmonella* Enteritidis core and O polysaccharide-flagellin glycoconjugates. PLoS One 8:e64680.
119. Singh S P, Williams Y U, Benjamin W H, Klebba P E, Boyd D. 1996. Immunoprotection by monoclonal antibodies to the porins and lipopolysaccharide of *Salmonella typhimurium*. Microb Pathog 21:249-263.
120. Lee S J, Liang L, Juarez S, Nanton M R, Gondwe E N, Msefula C L, Kayala M A, Necchi F, Heath J N, Hart P, Tsolis R M, Heyderman R S, MacLennan C A, Feigner P L, Davies D H, McSorley S J. 2012. Identification of a 121. Secundino I, Lopez-Macias C, Cervantes-Barragan L, Gil-Cruz C, Rios-Sarabia N, Pastelin-Palacios R, Villasis-Keever M A, Becker I, Puente J L, Calva E, Isibasi A. 2006. *Salmonella* porins induce a sustained, lifelong specific bactericidal antibody memory response. Immunology 117:59-70.

122. Salazar-Gonzalez R M, Maldonado-Bernal C, Ramirez-Cruz N E, Rios-Sarabia N, Beltran-Nava J, Castanon-Gonzalez J, Castillo-Torres N, Palma-Aguirre J A, Carrera-Camargo M, Lopez-Macias C, Isibasi A. 2004. Induction of cellular immune response and anti-*Salmonella enterica* serovar Typhi bactericidal antibodies in healthy volunteers by immunization with a vaccine candidate against typhoid fever. Immunol Lett 93:115-122.

123. Santiviago C A, Toro C S, Bucarey S A, Mora G C. 2001. A chromosomal region surrounding the ompD porin gene marks a genetic difference between *Salmonella* typhi and the majority of *Salmonella* serovars. Microbiology 147:1897-1907.

124. Santiviago C A, Fuentes J A, Bueno S M, Trombert A N, Hildago A A, Socias L T, Youderian P, Mora G C. 2002. The *Salmonella enterica* sv. Typhimurium smvA, yddG and ompD (porin) genes are required for the efficient efflux of methyl viologen. Mol Microbio! 46:687-698.

125. Chakraborty S, Mizusaki H, Kenney L J. 2015. A FRET-based DNA biosensor tracks OmpR-dependent acidification of *Salmonella* during macrophage infection. PLoS Bio! 13:e1002116.

126. Reynolds C J, Jones C, Blohmke C J, Darton T C, Goudet A, Sergeant R, Maillere B, Pollard A J, Altmann D M, Boyton R J. 2014. The serodominant secreted effector protein of *Salmonella*, SseB, is a strong CD4 antigen containing an immunodominant epitope presented by diverse HLA class II alleles. Immunology 143:438-446.

127. McLaughlin L M, Govoni G R, Gerke C, Gopinath S, Peng K, Laidlaw G, Chien Y H, Jeong H W, Li Z, Brown M D, Sacks D B, Monack D. 2009. The *Salmonella* SPI2 effector SseI mediates long-term systemic infection by modulating host cell migration. PLoS Pathog 5:e 1000671.

128. Worley M J, Nieman G S, Geddes K, Heffron F. 2006. *Salmonella typhimurium* disseminates within its host by manipulating the motility of infected cells. Proc Natl Acad Sci USA 103:17915-17920.

129. McLaughlin L M, Xu H, Carden S E, Fisher S, Reyes M, Heilshorn S C, Monack D M. 2014. A microfluidic-based genetic screen to identify microbial virulence factors that inhibit dendritic cell migration. Integr Biol (Camb) 6:438-449.

130. Lawley T D, Chan K, Thompson L J, Kim C C, Govoni G R, Monack D M. 2006. Genome-wide screen for *Salmonella* genes required for long-term systemic infection of the mouse. PLoS Pathog 2:e 11.

131. Thornbrough J M, Worley M J. 2012. A naturally occurring single nucleotide polymorphism in the *Salmonella* SPI-2 type III effector srfH/sseI controls early extraintestinal dissemination. PLoS One 7:e45245.

132. Toobak H, Rasooli I, Talei D, Jahangiri A, Owlia P, Darvish Alipour Astaneh S. 2013. Immune response variations to *Salmonella enterica* serovar Typhi recombinant porin proteins in mice. Biologicals 41:224-230.

133. Pascual D W, Suo Z, Cao L, Avci R, Yang X. 2013. Attenuating gene expression (AGE) for vaccine development. Virulence 4:384-390.

134. Yang X, Suo Z, Thornburg T, Holderness K, Cao L, Lim T, Walters N, Kellerman L, Loetterle L, Avci R, Pascual D W. 2012. Expression of *Escherichia coli* virulence usher protein attenuates wild-type *Salmonella*. Virulence 3:29-42.

135. Yang X, Thornburg T, Suo Z, Jun S, Robison A, Li J, Lim T, Cao L, Hoyt T, Avci R, Pascual D W. 2012. Flagella overexpression attenuates *Salmonella* pathogenesis. PLoS One 7:e46828.

136. Kong Q, Liu Q, Roland K L, Curtiss R, III. 2009. Regulated delayed expression of rfaH in an attenuated *Salmonella enterica* serovar Typhimurium vaccine enhances immunogenicity of outer membrane proteins and a heterologous antigen. Infect Immun 77:5572-5582.

137. Curtiss R, III., Munson M. 1998. Cross-protective *Salmonella* vaccines.

138. Kelly S M, Bosecker B A, Curtiss R, III. 1992. Characterization and protective properties of attenuated mutants of *Salmonella* choleraesuis. Infect Immun 60:4881-4890.

139. Hassan J O, Curtiss R, III. 1994. Development and evaluation of an experimental vaccination program using a live avirulent *Salmonella typhimurium* strain to protect immunized chickens against challenge with homologous and heterologous *Salmonella* serotypes. Infect Immun 62:5519-5527.

140. Richardson E J, Limaye B, Inamdar H, Datta A, Manjari K S, Pullinger G D, Thomson N R, Joshi R R, Watson M, Stevens M P. 2011. Genome sequences of *Salmonella enterica* serovar Typhimurium, Choleraesuis, Dublin, and Gallinarum strains of well-defined virulence in food-producing animals. J Bacteriol 193:3162-3163.

141. Kong Q, Liu Q, Jansen A, Curtiss R, III. 2010. Regulated delayed expression of rfc enhances the immunogenicity and protective efficacy of a heterologous antigen delivered by live attenuated *Salmonella enterica* vaccines. Vaccine 28:6094-6103.

142. Bertani G. 1951. Studies on lysogenesis. I. The mode of phage liberation by lysogenic *Escherichia coli*. J Bacteriol 62:293-300.

143. Sambrook J, Russell D W. 2001. Molecular cloning: a laboratory manual, 3rd ed. Cold Spring Harbor Laboratory Press, Cold Spring Harbor, N.Y.

144. Edwards R A, Keller L H, Schifferli D M. 1998. Improved allelic exchange vectors and their use to analyze 987P fimbria gene expression. Gene 207:149-157.

145. Schmieger H, Backhaus H. 1976. Altered cotransduction frequencies exhibited by HT-mutants of *Salmonella*-phage P22. Mol Gen Genet 143:307-309.

146. Kang H Y, Dozois C M, Tinge S A, Lee T H, Curtiss R, III. 2002. Transduction-mediated transfer of unmarked deletion and point mutations through use of counterselectable suicide vectors. J Bacteriol 184:307-312.

147. Kang H Y, Srinivasan J, Curtiss R, III. 2002. Immune responses to recombinant pneumococcal PspA antigen delivered by live attenuated *Salmonella enterica* serovar Typhimurium vaccine. Infect Immun 70:1739-1749.

148. Hitchcock P J, Brown T M. 1983. Morphological heterogeneity among *Salmonella* lipopolysaccharide chemotypes in silver-stained polyacrylamide gels. J Bacteriol 154:269-277.

149. Chibber S, Bhardwaj S B. 2004. Protection in a mouse peritonitis model mediated by iron-regulated outer-membrane protein of *Salmonella* typhi coupled to its Vi antigen. J Med Microbiol 53:705-709.
150. Schertzer J W, Whiteley M. 2013. Bacterial outer membrane vesicles in trafficking, communication and the host-pathogen interaction. J Mol Microbiol Biotechnol 23:118-130.
151. Kuehn M J, Kesty N C. 2005. Bacterial outer membrane vesicles and the host-pathogen interaction. Genes Dev 19:2645-2655.
152. Ho D K, Jarva H, Meri S. 2010. Human complement factor H binds to outer membrane protein Rck of *Salmonella*. Journal of Immunology 185:1763-1769.
153. Gahring L C, Heffron F, Finlay B B, Falkow S. 1990. Invasion and replication of *Salmonella typhimurium* in animal cells. Infection and Immunity 58:443-448.
154. Galán J E, Curtiss R, III. 1989. Cloning and molecular characterization of genes whose products allow Salmonella typhimurium to penetrate tissue culture cells. Proc Natl Acad Sci USA 86:6383-6387.
155. Moser I, Hohmann A, Schmidt G, Rowley D. 1980. Salmonellosis in mice: studies on oral immunization with live avirulent vaccines. Med Microbiol Immunol 168: 119-128.
156. Nnalue N A, Stocker B A. 1987. Test of the virulence and live-vaccine efficacy of auxotrophic and galE derivatives of *Salmonella choleraesuis*. Infect Immun 55:955-962.
157. Germanier R. 1970. Immunity in Experimental Salmonellosis I. Protection Induced by Rough Mutants of *Salmonella typhimurium*. Infect Immun 2:309-315.
158. Kopecko D J, Sieber H, Ures J A, Furer A, Schlup J, Knof U, Collioud A, Xu D, Colburn K, Dietrich G. 2009. Genetic stability of vaccine strain *Salmonella* Typhi Ty21a over 25 years. Int J Med Microbiol 299:233-246.
159. Germanier R, Furer E. 1983. Characteristics of the attenuated oral vaccine strain "*S. typhi*" Ty 21a. Dev Biol Stand 53:3-7.
160. Edelman R, Levine M M. 1986. Summary of an international workshop on typhoid fever. Rev Infect Dis 8:329-349.
161. Wandan M H, Serie C, Cerisier Y, Sallam S, Germanier R. 1982. A controlled field trial of live *Salmonella typhi* strain Ty 21a oral vaccine against typhoid: three-year results. J Infect Dis 145:292-295.
162. Wandan M H, Serie C, Germanier R, Lackany A, Cerisier Y, Guerin N, Sallam S, Geoffroy P, el Tantawi A S, Guesry P. 1980. A controlled field trial of liver oral typhoid vaccine Ty21a. Bull World Health Organ 58:469-474.
163. Hone D M, Attridge S R, Forrest B, Morona R, Daniels D, LaBrooy J T, Bartholomeusz R C, Shearman D J, Hackett J. 1988. A galE via (Vi antigen-negative) mutant of *Salmonella typhi* Ty2 retains virulence in humans. Infect Immun 56:1326-1333.
164. Woodward T E, Woodward W E. 1982. A new oral vaccine against typhoid fever. J Infect Dis 145:289-291.
165. Nnalue N A, Stocker B A. 1986. Some galE mutants of *Salmonella choleraesuis* retain virulence. Infect Immun 54:635-640.
166. Fukasawa T, Nikaido H. 1961. Galactose-sensitive mutants of *Salmonella*. II. Bacteriolysis induced by galactose. Biochim Biophys Acta 48:470-483.
167. Nikaido H. 1961. Galactose-sensitive mutants of *Salmonella*. I. Metabolism of galactose. Biochim Biophys Acta 48:460-469.
168. Postma P W. 1977. Galactose transport in *Salmonella typhimurium*. J Bacteriol 129:630-639.
169. Müller N, Heine H G, Boos W. 1982. Cloning of mglB, the structural gene for the galactose-binding protein of *Salmonella typhimurium* and *Escherichia coli*. Mol Gen Genet 185:473-480.
170. Clarke R C, Gyles C L. 1986. Galactose epimeraseless mutants of *Salmonella typhimurium* as live vaccines for calves. Can J Vet Res 50:165-173.
171. Shuster C W, Rundell K. 1969. Resistance of *Salmonella typhimurium* mutants to galactose death. J Bacteriol 100:103-109.
172. Mulford C A, Osborn M J. 1983. An intermediate step in translocation of lipopolysaccharide to the outer membrane of *Salmonella typhimurium*. Proc Natl Acad Sci USA 80:1159-1163.
173. Nagy G, Palkovics T, Otto A, Kusch H, Kocsis B, Dobrindt U, Engelmann S, Hecker M, Emody L, Pal T, Hacker J. 2008. "Gently rough": the vaccine potential of a *Salmonella enterica* regulatory lipopolysaccharide mutant. J Infect Dis 198:1699-1706.
174. Merighi M, Ellermeier C D, Slauch J M, Gunn J S. 2005. Resolvase-in vivo expression technology analysis of the *Salmonella enterica* serovar Typhimurium PhoP and PmrA regulons in BALB/c mice. J Bacteriol 187: 7407-7416.
175. Brenneman K E, Willingham C, Kong W, Curtiss R, III, Roland K L. 2013. Low-pH rescue of acid-sensitive *Salmonella enterica* serovar Typhi strains by a Rhamnose-regulated arginine decarboxylase system. J Bacteriol 195:3062-3072.
176. Singh S P, Williams Y U, Klebba P E, Macchia P, Miller S. 2000. Immune recognition of porin and lipopolysaccharide epitopes of *Salmonella typhimurium* in mice. Microb Pathog 28:157-167.
177. Bentley A T, Klebba P E. 1988. Effect of lipopolysaccharide structure on reactivity of antiporin monoclonal antibodies with the bacterial cell surface. J Bacteriol 170:1063-1068.
178. Stevenson G, Andrianopoulos K, Hobbs M, Reeves P R. 1996. Organization of the *Escherichia coli* K-12 gene cluster responsible for production of the extracellular polysaccharide colanic acid. J Bacteriol 178:4885-4893.
179. Whitfield C. 2006. Biosynthesis and assembly of capsular polysaccharides in *Escherichia coli*. Annu Rev Biochem 75:39-68.
180. Wang S, Li Y, Scarpellini G, Kong W, Shi H, Baek C H, Gunn B, Wanda S Y, Roland K L, Zhang X, Senechal-Willis P, Curtiss R, III. 2010. *Salmonella* vaccine vectors displaying delayed antigen synthesis in vivo to enhance immunogenicity. Infect Immun 78:3969-3980.
181. Sun W, Wang S, Curtiss R, III. 2008. Highly efficient method for introducing successive multiple scarless gene deletions and markerless gene insertions into the *Yersinia pestis* chromosome. Applied and Environmental Microbiology 74:4241-4245.
182. Baek C H, Wang S, Roland K L, Curtiss R, III. 2009. Leucine-responsive regulatory protein (Lrp) acts as a virulence repressor in *Salmonella enterica* serovar Typhimurium. J Bacteriol 191:1278-1292.
183. Juárez-Rodríguez M D, Arteaga-Cortés L T, Kader R, Curtiss R, III, Clark-Curtiss J E. 2012. Live attenuated *Salmonella* vaccines against *Mycobacterium tuberculosis* with antigen delivery via the type III secretion system. Infect Immun 80:798-814.
184. Smith K D, Andersen-Nissen E, Hayashi F, Strobe K, Bergman M A, Barrett S L, Cookson B T, Aderem A. 2003. Toll-like receptor 5 recognizes a conserved site on 185. Murthy K G, Deb A, Goonesekera S, Szabo C, Salzman A L. 2004. Identification of conserved domains in *Salmonella muenchen* flagellin that are essential for its ability to activate TLR5 and to induce an inflammatory response in vitro. J Biol Chem 279:5667-5675.

186. Cookson B T, Bevan M J. 1997. Identification of a natural T cell epitope presented by Salmonella-infected macrophages and recognized by T cells from orally immunized mice. J Immunol 158:4310-4319.

187. Juárez-Rodriguez M D, Yang J, Kader R, Alamuri P, Curtiss R, III., Clark-Curtiss J E. 2012. Live attenuated *Salmonella* vaccines displaying regulated delayed lysis and delayed antigen synthesis to confer protection against *Mycobacterium tuberculosis*. Infect Immun 80:815-831.

188. Jiang Y, Mo H, Willingham C, Wang S, Park J Y, Kong W, Roland K L, Curtiss R, III. 2015. Protection Against Necrotic Enteritis in Broiler Chickens by Regulated Delayed Lysis Salmonella Vaccines. Avian Dis 59:475-485.

189. Xin W, Wanda S Y, Zhang X, Santander J, Scarpellini G, Ellis K, Alamuri P, Curtiss R, III. 2012. The Asd$^+$-DadB$^+$ dual-plasmid system offers a novel means to deliver multiple protective antigens by a recombinant attenuated *Salmonella* vaccine. Infect Immun 80:3621-3633.

190. Zhang X, Kong W, Ashraf S, Curtiss R, III. 2009. A one-plasmid system to generate influenza virus in cultured chicken cells for potential use in influenza vaccine. J Virol 83:9296-9303.

191. Zhang X, Curtiss R, III. 2015. Efficient generation of influenza virus with a mouse RNA polymerase I-driven all-in-one plasmid. Virol J 12:95.

192. Zhang X, Kong W, Wanda SY, Xin W, Alamuri P, Curtiss R, III. 2015. Generation of influenza virus from avian cells infected by *Salmonella* carrying the viral genome. PLoS One 10:e0119041.

193. Sanapala S, Rahav H, Patel H, Sun W, Curtiss R, III. 2016. Multiple antigens of Yersinia pestis delivered by live recombinant attenuated *Salmonella* vaccine strains elicit protective immunity against plague. Vaccine 34:2410-2416.

194. Zhang X, Wanda S Y, Brenneman K, Kong W, Roland K, Curtiss R, III. 2011. Improving *Salmonella* vector with rec mutation to stabilize the DNA cargoes. BMC Microbiol 11:31.

195. Marvin H J, ter Beest M B, Witholt B. 1989. Release of outer membrane fragments from wild-type *Escherichia coli* and from several *E. coli* lipopolysaccharide mutants by EDTA and heat shock treatments. J Bacteriol 171:5262-5267.

196. Witholt B, Boekhout M, Brock M, Kingma J, Heerikhuizen H V, Leij L D. 1976. An efficient and reproducible procedure for the formation of spheroplasts from variously grown *Escherichia coli*. Anal Biochem 74:160-170.

197. Juarez-Rodriguez M D, Arteaga-Cortes L T, Kader R, Curtiss R, III., Clark-Curtiss J E. 2012. Live attenuated *Salmonella* vaccines against *Mycobacterium tuberculosis* with antigen delivery via the type III secretion system. Infect Immun 80:798-814.

198. Konjufca V, Wanda S Y, Jenkins M C, Curtiss R, III. 2006. A recombinant attenuated *Salmonella enterica* serovar Typhimurium vaccine encoding *Eimeria acervulina* antigen offers protection against *E. acervulina* challenge. Infect Immun 74:6785-6796.

199. Konjufca V, Jenkins M, Wang S, Juárez-Rodriguez M D, Curtiss R, III. 2008. Immunogenicity of recombinant attenuated *Salmonella enterica* serovar Typhimurium vaccine strains carrying a gene that encodes *Eimeria tenella* antigen S07. Infect Immun 76:5745-5753.

200. Shi H, Santander J, Brenneman K E, Wanda S Y, Wang S, Senechal P, Sun W, Roland K L, Curtiss R, III. 2010. Live recombinant *Salmonella Typhi* vaccines constructed to investigate the role of rpoS in eliciting immunity to a heterologous antigen. PLoS One 5:e11142.

201. Czerkinsky C C, L. A. Nilsson, H. Nygren, O. Ouchterlony, and A. Tarkowski. 1983. A solid-phase enzyme-linked immunospot (ELISPOT) assay for enumeration of specific antibody-secreting cells. J Immunol Methods 65:109-121.

202. Li Y, Wang S, Scarpellini G, Gunn B, Xin W, Wanda S Y, Roland K L, Curtiss R, III. 2009. Evaluation of new generation *Salmonella enterica* serovar Typhimurium vaccines with regulated delayed attenuation to induce immune responses against PspA. Proc Natl Acad Sci USA 106:593-598.

203. Bonato V L D, V. M. F. Lima, R. E. Tascon, D. B. Lowrie, and C. L. Silva. 1998. Identification and characterization of protective T cells in hsp65 DNA-vaccinated and *Mycobacterium tuberculosis*-infected mice. Infect Immun 66:169-175.

204. Okamoto Y, H. Murakami, and M. Nishida. 1997. Detection of interleukin 6-producing cells among various organs in normal mice with an improved enzyme-linked immunospot (ELISPOT) assay. Endocr J 44:349-355.

205. Broz P, Newton K, Lamkanfi M, Mariathasan S, Dixit V M, Monack D M. 2010. Redundant roles for inflammasome receptors NLRP3 and NLRC4 in host defense against *Salmonella*. J Exp Med 207:1745-1755.

206. Rathinam V A, Vanaja S K, Waggoner L, Sokolovska A, Becker C, Stuart L M, Leong J M, Fitzgerald K A. 2012. TRIF licenses caspase-11-dependent NLRP3 inflammasome activation by gram-negative bacteria. Cell 150:606-619.

207. Riedemann N C, Guo R F, Sarma V J, Laudes I J, Huber-Lang M, Warner R L, Albrecht E A, Speyer C L, Ward P A. 2002. Expression and function of the C5a receptor in rat alveolar epithelial cells. J Immunol 168:1919-1925.

208. Montz H, Koch K C, Zierz R, Gotze O. 1991. The role of C5a in interleukin-6 production induced by lipopolysaccharide or interleukin-1. Immunology 74:373-379.

209. Buckner C M, Kardava L, Moir S. 2013. Evaluation of B cell function in patients with HIV. Curr Protoc Immunol Chapter 12:Unit 12 13.

210. Flores-Langarica A, Bobat S, Marshall J L, Yam-Puc J C, Cook C N, Serre K, Kingsley R A, Flores-Romo L, Uematsu S, Akira S, Henderson I R, Toellner K M, Cunningham A F. 2015. Soluble flagellin coimmunization attenuates Th1 priming to *Salmonella* and clearance by modulating dendritic cell activation and cytokine production. Eur J Immunol 45:2299-2311.

211. Quah B J, Wijesundara D K, Ranasinghe C, Parish C R. 2014. The use of fluorescent target arrays for assessment of T cell responses in vivo. J Vis Exp doi:10.3791/51627: e51627.

212. Quah B J, Wijesundara D K, Ranasinghe C, Parish C R. 2013. Fluorescent target array T helper assay: a multiplex flow cytometry assay to measure antigen-specific CD4+ T cell-mediated B cell help in vivo. J Immunol Methods 387:181-190.

213. Cretel E, Touchard D, Bongrand P, Pierres A. 2011. A new method for rapid detection of T lymphocyte decision to proliferate after encountering activating surfaces. J Immunol Methods 364:33-39.
214. Quah B J, Parish C R. 2010. The use of carboxyfluorescein diacetate succinimidyl ester (CFSE) to monitor lymphocyte proliferation. J Vis Exp doi:10.3791/2259.
215. Parish C R, Glidden M H, Quah B J, Warren H S. 2009. Use of the intracellular fluorescent dye CFSE to monitor lymphocyte migration and proliferation. Curr Protoc Immunol Chapter 4:Unit4 9.
216. Wallace P K, Tario J D, Jr., Fisher J L, Wallace S S, Ernstoff M S, Muirhead K A. 2008. Tracking antigen-driven responses by flow cytometry: monitoring proliferation by dye dilution. Cytometry A 73:1019-1034.
217. Hawkins E D, Hommel M, Turner M L, Battye F L, Markham J F, Hodgkin P D. 2007. Measuring lymphocyte proliferation, survival and differentiation using CFSE time-series data. Nat Protoc 2:2057-2067.
218. Brenchley J M, Douek D C. 2004. Flow cytometric analysis of human antigen-specific T-cell proliferation. Methods Cell Biol 75:481-496.
219. Tennant S M, Schmidlein P, Simon R, Pasetti M F, Galen J E, Levine M M. 2015. Refined live attenuated *Salmonella enterica* serovar Typhimurium and Enteritidis vaccines mediate homologous and heterologous serogroup protection in mice. Infect Immun 83:4504-4512.
220. Kong Q, Six D A, Roland K L, Liu Q, Gu L, Reynolds C M, Wang X, Raetz C R, Curtiss R, III. 2011. *Salmonella* synthesizing 1-dephosphorylated lipopolysaccharide exhibits low endotoxic activity while retaining its immunogenicity. J Immunol 187:412-423.
221. Kong Q, Six D A, Liu Q, Gu L, Wang S, Alamuri P, Raetz C R, Curtiss R, III. 2012. Phosphate groups of Lipid A are essential for *Salmonella enterica* serovar Typhimurium virulence and affect innate and adaptive immunity. Infect Immun 80:3215-3224.
222. Jiang Y, Mo H, Willingham C, Wang S, Park J Y, Kong W, Roland K L, Curtiss R III Protection Against Necrotic Enteritis in Broiler Chickens by Regulated Delayed Lysis Salmonella Vaccines. Avian Dis. 2015 December; 59(4): 475-85

What is claimed is:

1. A recombinant *Salmonella enterica* subsp. *Enterica* bacterium comprising a nucleic acid comprising: a sequence encoding a choloylglycine hydrolase (Cbh) antigen, or antigenic fragment thereof, and/or a sequence encoding a *Clostridium perfringens* enterotoxin (CpeC) antigen, or antigenic fragment thereof, wherein the recombinant bacteria further comprises:
   an araC $P_{araBAD}$-regulated murA gene;
   a deletion-insertion mutation that inactivates the expression of asdA gene and inserts a c2 gene;
   a deletion in a pmi gene;
   a deletion-insertion mutation that inactivates the expression of a RelA gene and inserts a lacI gene; and
   a deletion in a sifA gene.

2. The recombinant *Salmonella* bacterium of claim 1, wherein the nucleic acid comprising the sequence encoding the Cbh antigen, or antigenic fragment thereof, and/or the sequence encoding the CpeC antigen, or antigenic fragment thereof, are operably linked to a repressor-regulatable promoter.

3. The recombinant *Salmonella* bacterium of claim 2, wherein the repressor-regulatable promoter is selected from the group consisting of $P_{trc}$, $P_{lac}$, $P_{T7lac}$, $P_{tac}$, $P_{ompA\ lacO}$, and $P_{lpp\ lacO}$.

4. The recombinant *Salmonella* bacterium of claim 1,
   wherein the Cbh antigen, or antigenic fragment thereof, is a fusion protein, and/or
   wherein the CpeC antigen, or antigenic fragment thereof, is a fusion protein.

5. The recombinant *Salmonella* bacterium of claim 1,
   wherein the Cbh antigen, or antigenic fragment thereof, comprises a signal sequence, and/or
   wherein the CpeC antigen, or antigenic fragment thereof, comprises a signal sequence.

6. The recombinant *Salmonella* bacterium of claim 5, wherein the signal sequence is a bla, bla-opt, dsbA or ompA signal sequence.

7. The recombinant *Salmonella* bacterium of claim 1,
   wherein the sequence encoding the Cbh antigen is codon-optimized for expression in the bacterium, and/or
   wherein the sequence encoding the CpeC antigen is codon-optimized for expression in the bacterium.

8. The recombinant *Salmonella* bacterium of claim 1, wherein the CpeC antigen is encoded by a cpeC-max sequence.

9. The recombinant *Salmonella* bacterium of claim 1, further comprising a sequence encoding a C-terminal domain of *C. perfringens* alpha toxin (PlcC) antigen, or antigenic fragment thereof, and/or a sequence encoding a non-toxic necrotic enteritis B-like toxin (NetB) antigen, or antigenic fragment thereof.

10. The recombinant *Salmonella* bacterium of claim 9, wherein the sequence encoding the NetB antigen, or antigenic fragment thereof, is operably linked to one or more sequences encoding an antigen, or antigenic fragment thereof, selected from the group consisting of CpeC, CpeC-max, Cbh and Fba.

11. The recombinant *Salmonella* bacterium of claim 1, wherein the nucleic acid further comprises a sequence encoding a Fba antigen, or an antigenic fragment thereof.

12. The recombinant *Salmonella* bacterium of claim 1, wherein the nucleic acid is present in a plasmid in the bacterium, and/or in the chromosome of the bacterium.

13. The recombinant *Salmonella* bacterium of claim 1, wherein the bacterium further comprises a sequence for a *Clostridium perfringens* NetB antigen or antigenic fragment thereof, a PlcC antigen or antigenic fragment thereof, or a fusion protein comprising the NetB antigen or antigenic fragment thereof and the PlcC antigen or antigenic fragment thereof.

14. The recombinant *Salmonella* bacterium of claim 11, wherein the nucleic acid comprising the sequence encoding the Cbh antigen, or antigenic fragment thereof, the sequence encoding the CpeC antigen, or antigenic fragment thereof, and/or the sequence encoding the Fba antigen, or antigenic fragment thereof, are operably linked to a repressor-regulatable promoter.

15. The recombinant bacterium of claim 1, wherein:
   the araC $P_{araBAD}$-regulated murA gene is $\Delta P_{murA25}$::TT araC $P_{BAD}$ murA;
   the deletion-insertion mutation that inactivates the expression of asdA gene and inserts a c2 gene is $\Delta$asdA27::TT araC $P_{araBAD}$ c2;
   the deletion in a pmi gene is $\Delta$pmi-2426;
   the deletion-insertion mutation that inactivates the expression of a RelA gene and inserts a lacI gene is $\Delta$relA197::araC $P_{araBAD}$ lacI TT; and
   the deletion in a sifA gene is $\Delta$sifA26.

16. The recombinant bacterium of claim 1, further comprising one or more of the following:
   a rhaRS $P_{rhaBAD}$-regulated waaL gene;
   a deletion in a pagL gene;
   a deletion in a wza-wcaM gene; and/or
   a deletion in a recF gene.

17. The recombinant bacterium of claim 16, wherein:
   the deletion in a pagL gene and the rhaRS $P_{rhaBAD}$-regulated waaL gene are $\Delta$waaL46 $\Delta$pagL64::TT rhaRS $P_{rhaBAD}$ waaL;
   the deletion in a wza-wcaM gene is $\Delta$(wza-wcaM)-8; and
   the deletion in a recF gene is $\Delta$recF126.

* * * * *

UNITED STATES PATENT AND TRADEMARK OFFICE
CERTIFICATE OF CORRECTION

PATENT NO. : 11,596,677 B2
APPLICATION NO. : 16/636251
DATED : March 7, 2023
INVENTOR(S) : Roy Curtiss, III et al.

Page 1 of 1

It is certified that error appears in the above-identified patent and that said Letters Patent is hereby corrected as shown below:

In the Specification

At Column 1, Line numbers 15-20, delete the text and replace it with the following:
--This invention was made with government support under 2017-67017-26179 awarded by the United States Department of Agriculture, National Institute of Food and Agriculture. This invention was made with government support under AI126712 awarded by the National Institutes of Health. The government has certain rights in the invention.--

Signed and Sealed this
Twenty-fifth Day of July, 2023

Katherine Kelly Vidal
*Director of the United States Patent and Trademark Office*